(12) United States Patent
Meegalla et al.

(10) Patent No.: US 10,106,553 B2
(45) Date of Patent: Oct. 23, 2018

(54) SUBSTITUTED BENZOTHIOPHENYL DERIVATIVES AS GPR40 AGONISTS FOR THE TREATMENT OF TYPE II DIABETES

(71) Applicant: Janssen Pharmaceutica NV, Beerse (BE)

(72) Inventors: Sanath Meegalla, Garnet Valley, PA (US); Mark R. Player, Phoenixville, PA (US); Hui Huang, Blue Bell, PA (US); Michael P. Winters, Morgantown, PA (US)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 15/484,174

(22) Filed: Apr. 11, 2017

(65) Prior Publication Data

US 2017/0291908 A1    Oct. 12, 2017

Related U.S. Application Data

(60) Provisional application No. 62/320,828, filed on Apr. 11, 2016.

(51) Int. Cl.
*C07D 495/04* (2006.01)
*C07D 409/12* (2006.01)
*C07D 409/14* (2006.01)

(52) U.S. Cl.
CPC ......... *C07D 495/04* (2013.01); *C07D 409/12* (2013.01); *C07D 409/14* (2013.01)

(58) Field of Classification Search
CPC .................................................. C07D 495/04
See application file for complete search history.

(56) References Cited

U.S. PATENT DOCUMENTS

| | | |
|---|---|---|
| 7,384,965 B2 | 6/2008 | Conner et al. |
| 7,598,266 B2 | 10/2009 | Conner et al. |
| 7,816,367 B2 | 10/2010 | Akerman et al. |
| 2003/0220373 A1 | 11/2003 | Jaye et al. |
| 2006/0205744 A1 | 9/2006 | Conner et al. |
| 2007/0093476 A1 | 4/2007 | Debnath et al. |

FOREIGN PATENT DOCUMENTS

| | | |
|---|---|---|
| WO | WO 2001/66098 A2 | 9/2001 |
| WO | WO 2004/063155 A1 | 7/2004 |
| WO | WO 2005/086661 | 9/2005 |
| WO | WO 2014/073904 A1 | 5/2014 |
| WO | WO 2015/088868 A1 | 6/2015 |
| WO | WO 2016/057731 A1 | 4/2016 |

OTHER PUBLICATIONS

Eczema [online], retrieved from the internet on Jul. 21, 2017; URL http://www.mayoclinic.org/diseases-conditions/eczema/basics/definition/con-20032073?p=1.*
Abdul-Ghani et al., "Renal sodium-glucose cotransporter inhibition in the management of type 2 diabetes mellitus.", *American Journal of Physiology, Renal Physiol.*, 2015 pp. F869-900, vol. 309(11).
Briscoe et al., "The Orphan G Protein-coupled Receptor GPR40 Is Activated by Medium and Long Chain Fatty Acids.", J. Biol. Chem., 2003, pp. 11303-11311, vol. 278.
Edfalk et al., "Gpr40 is Expressed in Enteroendocrine Cells and Mediates Free Fatty Acid Stimulation of Incretin Secretion.", Diabetes, 2008, pp. 2280-2287, vol. 57.
Ferrannini et al., "SGLT2 Inhibition in diabetes mellitus: rationale and clinical prospects.", Nature Reviews Endocrinology, Aug. 2012, pp. 495-502, vol. 8.
Itoh et al., "Free fatty acids regulate insulin secretion from pancreatic β cells through GPR40", Nature, Mar. 13, 2003, pp. 173-176, vol. 422.
Kotarsky et al., "A human cell surface receptor activated by free fatty acids and thiazolidinedione drugs.", Biochem. Biophys. Res. Commun., 2003, pp. 406-410, vol. 301.
Murai et al., "Palladium-Catalyzed Direct Hydroxymethylation of Aryl Halides and Triflates with Potassium Acetoxymethyltrifluoroborate.", Organic Letters, 2012, pp. 1278-1281, vol. 14(5).
Wright et al., "Biology of Human Sodium Glucose Transporters.", Physiol. Rev., 2011, pp. 733-794, vol. 91.
Bharate et al., "Progress in the Discovery and Development of small-molecule modulators of G-protein-coupled receptor 40 (GPR40/FFA1/FFAR1): an emerging target for type 2 diabetes.", Expert Opinion on Therapeutic Patents, 2009, pp. 237-264, vol. 19(2), XP55279785.
Halder et al., "The therapeutic potential of GPR120: a patent review.", Expert Opinion on Therapeutic Patents, Oct. 6, 3013, pp. 1581-1590, vol. 23(12), XP55220975.
International Search Report relating to corresponding International Patent Application No. PCT/US2017/026924, filed Apr. 11, 2017. Date of Mailing of International Search Report: Jun. 29, 2017.
Written Opinion of the International Searching Authority relating to corresponding International Patent Application No. PCT/US2017/026924, filed Apr. 11, 2017. Date of Mailing of Written Opinion: Jun. 29, 2017.

* cited by examiner

*Primary Examiner* — Shawquia Jackson

(57) ABSTRACT

Disclosed are compounds, compositions and methods for treating of disorders that are affected by the modulation of the GPR40 receptor. Such compounds are represented by Formula (I) as follows:

Formula (I)

wherein $U_1$, $U_2$, $U_3$, $R_1$, $R_2$, Z, and W are defined herein.

19 Claims, No Drawings

SUBSTITUTED BENZOTHIOPHENYL DERIVATIVES AS GPR40 AGONISTS FOR THE TREATMENT OF TYPE II DIABETES

CROSS-REFERENCE TO RELATED APPLICATIONS

This application claims priority to U.S. Provisional Patent Application No. 62/320,828, filed Apr. 11, 2016 which is hereby incorporated by reference in its entirety.

FIELD OF THE INVENTION

The present invention relates to novel compounds which are GPR40 agonists and are useful for the treatment of disorders that are affected by the modulation of the GPR40 receptor. The invention also relates to pharmaceutical compositions comprising one or more of such compounds, to processes to prepare such compounds and compositions, and to the use of such compounds or pharmaceutical compositions for the treatment of various diseases, syndromes and disorders, including Type II diabetes mellitus, obesity, obesity-related disorders, impaired glucose tolerance, insulin resistance, metabolic syndrome, diabetic nephropathy, other cardiovascular risk factors such as hypertension and cardiovascular risk factors related to unmanaged cholesterol and/or lipid levels, osteoporosis, inflammation, and eczema, that are related to GPR40 modulation.

BACKGROUND OF THE INVENTION

According to WHO 2013 estimates, diabetes continues to present an increasing health risk to the global population, affecting 347 million individuals worldwide. There are two main types of diabetes. Type 1 diabetes, which affects ~10% of diabetic patients, is characterized by a depletion of pancreatic insulin supply, resulting from an autoimmune destruction of the insulin-producing beta-cells. Treatment requires the administration of exogenous insulin in order to meet energy demands. Type 2 diabetes, which affects the vast majority (~90%) of the diabetic population, occurs when the body cannot effectively utilize the insulin that is being produced. A number of factors may contribute to an impaired insulin response, including decreases in insulin production, insulin secretion or insulin sensitivity. In the initial stages of Type 2 diabetes, most patients' beta cells undergo a compensatory expansion of functional mass and insulin output. As the disease progresses, this compensatory response eventually fails and pharmaceutical intervention is required in order to adequately regulate glucose levels. However, with further disease progression, the effectiveness of initially prescribed therapeutics generally declines, thus requiring additional agents to be incorporated into the treatment regimen, each of which carries its own side-effect liability or risk.

Agents that reduce hepatic glucose production, the so-called biguanides, such as metformin or phenformin, are generally preferred as the first-line of treatment for newly-diagnosed patients. Glitazones, such as rosiglitazone and pioglitazone function as insulin sensitizers (i.e., enhance insulin action) through the activation of peroxisome proliferator-activated receptor-γ (PPAR-γ). These agents can provide the benefit of enhanced insulin action in tissues such as muscle, liver and adipose, but their use is frequently accompanied by increased weight and edema. In addition, rosiglitazone has recently been linked to heart attacks and its use has subsequently been more restricted. The insulin secretagogue sulfonylureas (such as tolbutamide, chlorpropamide, glipizide or glyburide) enhance insulin secretion from functional beta cells and are often combined with biguanide or glitazone therapy. However, because their effects on stimulating insulin release are independent of glucose levels, the sulfonylureas bear the risk of inducing incidences of hypoglycemia. Weight gain is also a common side-effect from this compound class.

More recently, agents capable of inducing insulin secretion from beta cells in a glucose-dependent fashion have been developed, based upon the mechanisms of incretin peptide hormones (ex., GLP-1, GIP). Importantly, because of their glucose-dependent mechanisms of action, these agents are able to provide glucose control while avoiding the risk of hypoglycemia. The direct GLP-1 receptor agonists, Exendin-4 (Byetta) and Liraglutide (Victoza®), which were engineered to provide enhanced metabolic stabilities in vivo, have been developed as marketed biological therapeutics. Dipeptidyl-peptidase-4 (DPP-4) inhibitors (the so-called, "gliptins" such as sitagliptin, saxagliptin, linagliptin, vildagliptin, anagliptin or alogliptin) inhibit the metabolic degradation of endogenous incretins and thereby provide indirect increases in insulin secretion in response to elevations in circulating glucose levels.

Most recently, the recognition of GPR40 as a receptor whose activation enhances glucose-dependent insulin secretion has led to the search for selective agonists for this putative therapeutic target. GPR40, also known as free fatty acid receptor 1 (FFR1), is one of a family of G-protein coupled receptors that, through receptor deorphanization studies, was shown to be endogenously activated by medium- to long-chain saturated and unsaturated fatty acids (~$C_{12-20}$) (Brisco, et al., 2003, J Biol Chem, 278: 11303-11311; Itoh, et al., 2003, Nature, 422: 173-176; Kotarsky et al., 2003, Biochem Biophys Res Commun, 301: 406-410). In humans and rodents, although present in brain and enteroendocrine cells, its expression is particularly high in pancreatic beta cells. Operating primarily through $G\alpha_{q/11}$ signaling, GPR40 activation of the beta cell leads to an increase in intracellular calcium levels, which in the presence of glucose, ultimately results in augmented insulin secretion. In enteroendocrine cells, GPR40 activation by fatty acids leads to stimulation of incretin secretion (Edfalk, et al., 2008, Diabetes, 57: 2280-2287). Thus, in addition to directly promoting GSIS from islet beta cells, GPR40 activation in enteroendocrine cells provides an indirect means of stimulating GSIS through the actions of released incretins.

Because of the hyperglycemic dependency of GPR40-mediated effects on insulin secretion, selective activation of this receptor provides a unique potential therapeutic mechanism by which to treat the diabetic state with minimal risk of hypoglycemic incidents. Given the relatively restricted tissue expression pattern of GPR40, selective GPR40 agonists may offer the additional advantage of providing an improved safety profile relative to the aforementioned therapeutic agents. Thus, GPR40 agonists of the present invention may provide therapeutic benefit for the treatment of diabetes (particularly Type 2 diabetes) and its associated conditions, including Type II diabetes mellitus, obesity, obesity-related disorders, impaired glucose tolerance, insulin resistance, metabolic syndrome, diabetic nephropathy, other cardiovascular risk factors such as hypertension and cardiovascular risk factors related to unmanaged cholesterol and/or lipid levels, osteoporosis, inflammation, and eczema, that are related to GPR40 modulation.

SUMMARY OF THE INVENTION

The present invention is directed to compounds of Formula (I)

Formula (I)

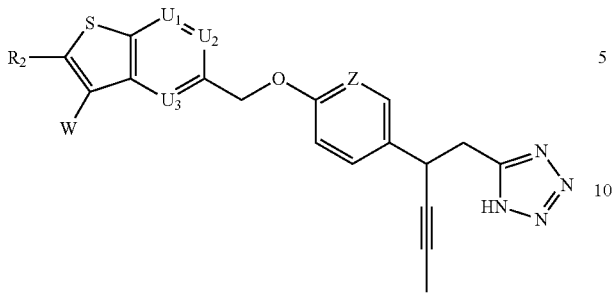

wherein
U$_1$ is N or C(R$_1$), wherein R$_1$ is hydrogen, fluoro, chloro, or methyl;
U$_2$ and U$_3$ are independently selected from CH or N, such that only up to one of U$_1$, U$_2$, and U$_3$ is N in any instance;
R$_2$ is selected from the group consisting of hydrogen, methyl, chloro, fluoro, bromo, iodo, trifluoromethyl, cyano, and C$_{1-4}$alkylsulfonyl;
W is selected from the group consisting of
i) hydrogen;

ii)

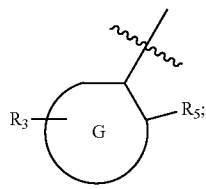

wherein ring G is selected from the group consisting of phenyl, pyridyl, pyrazinyl, and pyrimidinyl; and, when ring G is phenyl, substituents R$_3$ and R$_5$ are optionally taken together with the atoms to which they are attached to form an unsubstituted or substituted bicyclic ring system selected from dihydrobenzo[b][1,4]dioxin-5-yl, 2,2,-dimethylchroman-5-yl, or (1-ethylcarboxy-indolin-4-yl);
wherein R$_3$ is selected from the group consisting of hydrogen, chloro, C$_{1-4}$alkyl, 1,1-dioxidotetrahydro-2H-thiopyran-4-yl, 1,1-dioxido-3,6-dihydro-2H-thiopyran-4-yl, C$_{1-3}$alkylsulfonyl, C$_{1-3}$alkylsulfonylamino, and —OR$_4$; wherein R$_4$ is
i) C$_{1-8}$alkyl optionally independently substituted with one or two C$_{1-3}$alkoxy or hydroxy substituents;
ii) 4-hydroxy-1,1-dioxidotetrahydro-2H-thiopyran-4-ylmethyl;
iii) 1,1-dioxidotetrahydro-2H-thiopyran-4-yl;
iv) tetrahydro-2H-pyran-4-yl;
v) C$_{1-3}$alkylsulfonylpropyl;
or
vi) (3-methyl-1,1-dioxidothietan-3-yl)methyl;
wherein R$_5$ is methyl, bromo, chloro, or trifluoromethyl;
iii) C$_{3-8}$cycloalkyl;

iv)

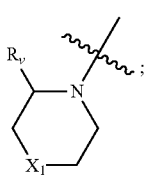

wherein X$_1$ is selected from the group consisting of CH$_2$, O, S, NH, and N(C$_{1-4}$alkyl); and wherein R$_v$ is hydrogen or methyl;

v)

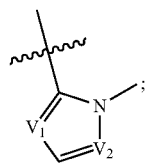

wherein V$_1$ and V$_2$ are independently selected from CH or N;
and
vi) C$_{1-6}$alkyl;
Z is CH or N;
or an enantiomer, diastereomer, or pharmaceutically acceptable salt form thereof.

The present invention also provides a pharmaceutical composition comprising, consisting of and/or consisting essentially of a pharmaceutically acceptable carrier, a pharmaceutically acceptable excipient, and/or a pharmaceutically acceptable diluent and a compound of Formula (I), or a pharmaceutically acceptable salt form thereof.

Also provided are processes for making a pharmaceutical composition comprising, consisting of, and/or consisting essentially of admixing a compound of Formula (I), and a pharmaceutically acceptable carrier, a pharmaceutically acceptable excipient, and/or a pharmaceutically acceptable diluent.

The present invention further provides methods for treating or ameliorating a disease, syndrome, or condition in a subject, including a mammal and/or human in which the disease, syndrome, or condition is affected by the agonism of GPR40, such as Type II diabetes mellitus, using a compound of Formula (I).

The present invention also is also directed to the use of any of the compounds described herein in the preparation of a medicament wherein the medicament is prepared for treating a disease or condition that is affected by the agonism of GPR40, selected from the group consisting of Type II diabetes mellitus, obesity, obesity-related disorders, impaired glucose tolerance, insulin resistance, metabolic syndrome, diabetic nephropathy, other cardiovascular risk factors such as hypertension and cardiovascular risk factors related to unmanaged cholesterol and/or lipid levels, osteoporosis, inflammation, and eczema, in a subject in need thereof.

The present invention is also directed to the preparation of substituted benzothiophenyl derivatives that act as selective agonists of the GPR40 receptor.

Exemplifying the invention are methods of treating a disorder modulated by GPR40 selected from the group consisting of Type II diabetes mellitus, obesity, obesity-related disorders, impaired glucose tolerance, insulin resistance, metabolic syndrome, diabetic nephropathy, other cardiovascular risk factors such as hypertension and cardiovascular risk factors related to unmanaged cholesterol and/or lipid levels, osteoporosis, inflammation, and eczema, comprising administering to a subject in need thereof a therapeutically effective amount of any of the compounds or pharmaceutical compositions described above.

In another embodiment, the present invention is directed to a compound of Formula (I) for use in the treatment of a disorder affected by the agonism of GPR40 selected from the group consisting of Type II diabetes mellitus, obesity, obesity-related disorders, impaired glucose tolerance, insulin resistance, metabolic syndrome, diabetic nephropathy other cardiovascular risk factors such as hypertension and cardiovascular risk factors related to unmanaged cholesterol and/or lipid levels, osteoporosis, inflammation, and eczema.

In another embodiment, the present invention is directed to a composition comprising a compound of Formula (I) for the treatment of a disorder affected by the agonism of GPR40 selected from the group consisting of Type II diabetes mellitus, obesity, obesity-related disorders, impaired glucose tolerance, insulin resistance, metabolic syndrome, diabetic nephropathy, other cardiovascular risk factors such as hypertension and cardiovascular risk factors related to unmanaged cholesterol and/or lipid levels, osteoporosis, inflammation, and eczema.

DETAILED DESCRIPTION OF THE INVENTION

With reference to substituents, the term "independently" refers to the situation where when more than one substituent is possible, the substituents may be the same or different from each other.

The term "alkyl" whether used alone or as part of a substituent group, refers to straight and branched carbon chains having 1 to 8 carbon atoms. Therefore, designated numbers of carbon atoms (e.g., $C_{1-8}$) refer independently to the number of carbon atoms in an alkyl moiety or to the alkyl portion of a larger alkyl-containing substituent. In substituent groups with multiple alkyl groups such as, $(C_{1-6}alkyl)_2$ amino-, the $C_{1-6}$alkyl groups of the dialkylamino may be the same or different.

The term "alkoxy" refers to an —O-alkyl group, wherein the term "alkyl" is as defined above.

The terms "alkenyl" and "alkynyl" refer to straight and branched carbon chains having 2 to 8 carbon atoms, wherein an alkenyl chain contains at least one double bond and an alkynyl chain contains at least one triple bond.

The term "cycloalkyl" refers to saturated or partially saturated, monocyclic or polycyclic hydrocarbon rings of 3 to 14 carbon atoms. Examples of such rings include cyclopropyl, cyclobutyl, cyclopentyl, cyclohexyl, cycloheptyl, and adamantyl.

The term "heterocyclyl" refers to a nonaromatic monocyclic or bicyclic ring system having 3 to 10 ring members that include at least 1 carbon atom and from 1 to 4 heteroatoms independently selected from N, O, and S. Included within the term heterocyclyl is a nonaromatic cyclic ring of 5 to 7 members in which 1 to 2 members are N, or a nonaromatic cyclic ring of 5 to 7 members in which 0, 1 or 2 members are N and up to 2 members are O or S and at least one member must be either N, O, or S; wherein, optionally, the ring contains 0 to 1 unsaturated bonds, and, optionally, when the ring is of 6 or 7 members, it contains up to 2 unsaturated bonds. The carbon atom ring members that form a heterocycle ring may be fully saturated or partially saturated. The term "heterocyclyl" also includes two 5 membered monocyclic heterocycloalkyl groups bridged to form a bicyclic ring. Such groups are not considered to be fully aromatic and are not referred to as heteroaryl groups. When a heterocycle is bicyclic, both rings of the heterocycle are non-aromatic and at least one of the rings contains a heteroatom ring member. Examples of heterocycle groups include, and are not limited to, pyrrolinyl (including 2H-pyrrole, 2-pyrrolinyl or 3-pyrrolinyl), pyrrolidinyl, imidazolinyl, imidazolidinyl, pyrazolinyl, pyrazolidinyl, piperidinyl, morpholinyl, thiomorpholinyl, and piperazinyl. Unless otherwise noted, the heterocycle is attached to its pendant group at any heteroatom or carbon atom that results in a stable structure.

The term "aryl" refers to an unsaturated, aromatic monocyclic or bicyclic ring of 6 to 10 carbon members. Examples of aryl rings include phenyl and naphthalenyl. The term "heteroaryl" refers to an aromatic monocyclic or bicyclic aromatic ring system having 5 to 10 ring members and which contains carbon atoms and from 1 to 4 heteroatoms independently selected from the group consisting of N, O, and S. Included within the term heteroaryl are aromatic rings of 5 or 6 members wherein the ring consists of carbon atoms and has at least one heteroatom member. Suitable heteroatoms include nitrogen, oxygen, and sulfur. In the case of 5 membered rings, the heteroaryl ring preferably contains one member of nitrogen, oxygen or sulfur and, in addition, up to 3 additional nitrogens. In the case of 6 membered rings, the heteroaryl ring preferably contains from 1 to 3 nitrogen atoms. For the case wherein the 6 membered ring has 3 nitrogens, at most 2 nitrogen atoms are adjacent. Examples of heteroaryl groups include furyl, thienyl, pyrrolyl, oxazolyl, thiazolyl, imidazolyl, pyrazolyl, isoxazolyl, isothiazolyl, oxadiazolyl, triazolyl, thiadiazolyl, pyridinyl, pyridazinyl, pyrimidinyl, pyrazinyl, indolyl, isoindolyl, benzofuryl, benzothienyl, indazolyl, benzimidazolyl, benzothiazolyl, benzoxazolyl, benzisoxazolyl, benzothiadiazolyl, benzotriazolyl, quinolinyl, isoquinolinyl and quinazolinyl. Unless otherwise noted, the heteroaryl is attached to its pendant group at any heteroatom or carbon atom that results in a stable structure.

The term "halogen" or "halo" refers to fluorine, chlorine, bromine and iodine atoms.

The term "carboxy" refers to the group —C(=O)OH.

The term "formyl" refers to the group —C(=O)H.

The term "oxo" or "oxido" refers to the group (=O).

Whenever the term "alkyl" or "aryl" or either of their prefix roots appear in a name of a substituent (e.g., arylalkyl, alkylamino) the name is to be interpreted as including those limitations given above for "alkyl" and "aryl." Designated numbers of carbon atoms (e.g., $C_1$-$C_6$) refer independently to the number of carbon atoms in an alkyl moiety, an aryl moiety, or in the alkyl portion of a larger substituent in which alkyl appears as its prefix root. For alkyl and alkoxy substituents, the designated number of carbon atoms includes all of the independent members included within a given range specified. For example $C_{1-6}$ alkyl would include methyl, ethyl, propyl, butyl, pentyl and hexyl individually as well as sub-combinations thereof (e.g., $C_{1-2}$, $C_{1-3}$, $C_{1-4}$, $C_{1-5}$, $C_{2-6}$, $C_{3-6}$, $C_{4-6}$, $C_{5-6}$, $C_{2-5}$, etc.).

In general, under standard nomenclature rules used throughout this disclosure, the terminal portion of the designated side chain is described first followed by the adjacent functionality toward the point of attachment. Thus, for example, a "$C_1$-$C_6$ alkylcarbonyl" substituent refers to a group of the formula:

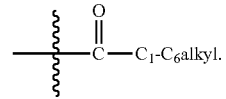

The term "R" at a stereocenter designates that the stereocenter is purely of the R-configuration as defined in the art; likewise, the term "S" means that the stereocenter is purely of the S-configuration. As used herein, the terms "*R" or "*S" at a stereocenter are used to designate that the stereocenter is of pure but unknown configuration. As used herein, the term "RS" refers to a stereocenter that exists as a mixture of the R- and S-configurations. Similarly, the terms "*RS" or "*SR" refer to a stereocenter that exists as a mixture of the R- and S-configurations and is of unknown configuration relative to another stereocenter within the molecule.

Compounds containing one stereocenter drawn without a stereo bond designation are a mixture of two enantiomers. Compounds containing two stereocenters both drawn without stereo bond designations are a mixture of four diastereomers. Compounds with two stereocenters both labeled "RS" and drawn with stereo bond designations are a two-component mixture with relative stereochemistry as drawn. Compounds with two stereocenters both labeled "*RS" and drawn with stereo bond designations are a two-component mixture with relative stereochemistry unknown. Unlabeled stereocenters drawn without stereo bond designations are a mixture of the R- and S-configurations. For unlabeled stereocenters drawn with stereo bond designations, the absolute stereochemistry is as depicted.

Unless otherwise noted, it is intended that the definition of any substituent or variable at a particular location in a molecule be independent of its definitions elsewhere in that molecule. It is understood that substituents and substitution patterns on the compounds of the present invention can be selected by one of ordinary skill in the art to provide compounds that are chemically stable and that can be readily synthesized by techniques known in the art as well as those methods set forth herein.

The term "subject" refers to an animal, preferably a mammal, most preferably a human, who has been the object of treatment, observation or experiment.

The term "therapeutically effective amount" refers to an amount of an active compound or pharmaceutical agent, including a compound of the present invention, which elicits the biological or medicinal response in a tissue system, animal or human that is being sought by a researcher, veterinarian, medical doctor or other clinician, which includes alleviation or partial alleviation of the symptoms of the disease, syndrome, condition, or disorder being treated.

The term "composition" refers to a product that includes the specified ingredients in therapeutically effective amounts, as well as any product that results, directly, or indirectly, from combinations of the specified ingredients in the specified amounts.

The term "GPR40 agonist" is intended to encompass a compound that interacts with GPR40 to substantially increase its downstream signaling, thereby resulting in physiologic effects such as, but not limited to, insulin secretion in the pancreas.

The term "GPR40 receptor-modulated" is used to refer to the condition of being affected by the modulation of the GPR40 receptor, including but not limited to, the state of being mediated by the GPR40 receptor, for the treatment of a disease or condition such as Type II diabetes or impaired glucose tolerance.

As used herein, unless otherwise noted, the term "disorder modulated by the GPR40 receptor" shall mean any disease, disorder or condition characterized in that at least one of its characteristic symptoms is alleviated or eliminated upon treatment with a GPR40 receptor agonist. Suitable examples include, but are not limited to Type II diabetes mellitus, obesity, obesity-related disorders, impaired glucose tolerance, insulin resistance, metabolic syndrome, diabetic nephropathy, other cardiovascular risk factors such as hypertension and cardiovascular risk factors related to unmanaged cholesterol and/or lipid levels, osteoporosis, inflammation, and eczema; more preferably, Type II diabetes mellitus and impaired glucose tolerance.

As used herein unless otherwise noted, the term "cardiovascular risk factors" shall mean any cardiovascular disease, disorder or condition in which obesity or diabetes (preferably, Type II diabetes) has a role in the initiation or exacerbation of said disorder or condition. Suitable examples include, but are not limited to, hypertension, atherosclerosis, diabetic nephropathy, and cardiac fibrosis.

As used herein, unless otherwise noted, the term "affect" or "affected" (when referring to a disease, syndrome, condition or disorder that is affected by agonism of GPR40) includes a reduction in the frequency and/or severity of one or more symptoms or manifestations of said disease, syndrome, condition or disorder; and/or include the prevention of the development of one or more symptoms or manifestations of said disease, syndrome, condition or disorder or the development of the disease, condition, syndrome or disorder.

The compounds of the instant invention are useful in methods for treating or ameliorating a disease, a syndrome, a condition or a disorder that is affected by the agonism of GPR40 receptor. Such methods comprise, consist of and/or consist essentially of administering to a subject, including an animal, a mammal, and a human in need of such treatment, amelioration and/or prevention, a therapeutically effective amount of a compound of Formula (I), or an enantiomer, diastereomer, solvate or pharmaceutically acceptable salt thereof.

In particular, the compounds of Formula (I), or an enantiomer, diastereomer, solvate or pharmaceutically acceptable salt form thereof are useful for treating or ameliorating diseases, syndromes, conditions, or disorders such as Type II diabetes mellitus, obesity, obesity-related disorders, impaired glucose tolerance, insulin resistance, metabolic syndrome, diabetic nephropathy, other cardiovascular risk factors such as hypertension and cardiovascular risk factors related to unmanaged cholesterol and/or lipid levels, osteoporosis, inflammation, and eczema.

More particularly, the compounds of Formula (I), or an enantiomer, diastereomer, solvate or pharmaceutically acceptable salt form thereof, are useful for treating or ameliorating Type II diabetes mellitus or impaired glucose tolerance, comprising administering to a subject in need thereof a therapeutically effective amount of a compound of Formula (I), or an enantiomer, diastereomer, solvate or pharmaceutically acceptable salt form thereof as herein defined.

Embodiments of the present invention include a compound of Formula (I)

Formula (I)

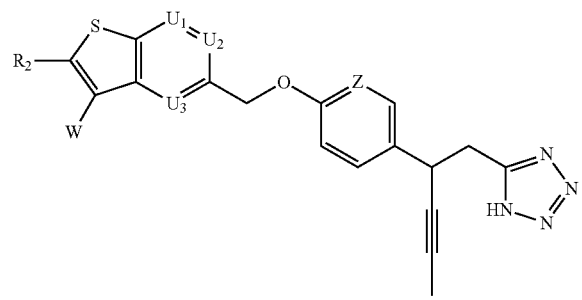

wherein
a) $U_1$ is N or $C(R_1)$, wherein $R_1$ is hydrogen, fluoro, or chloro;
b) $U_2$ and $U_3$ are independently selected from CH or N, such that only up to one of $U_1$, $U_2$, and $U_3$ is N in any instance;
c) $U_2$ is independently selected from CH or N; and $U_3$ is CH, such that only one of $U_1$ and $U_2$ is N in any instance;
d) $R_2$ is selected from the group consisting of hydrogen, methyl, chloro, fluoro, bromo, iodo, trifluoromethyl, and cyano;
e) $R_2$ is selected from the group consisting of hydrogen, chloro, fluoro, bromo, trifluoromethyl, and cyano;
f) $R_2$ is selected from the group consisting of hydrogen, chloro, fluoro, bromo, iodo, methyl, methanesulfonyl, trifluoromethyl, and cyano;
g) W is selected from the group consisting of

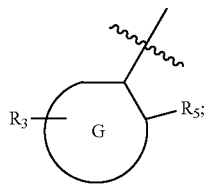
i)

wherein ring G is selected from the group consisting of phenyl, pyridyl, and pyrimidinyl; and, when ring G is phenyl, substituents $R_3$ and $R_5$ are optionally taken together with the atoms to which they are attached to form an unsubstituted or substituted bicyclic ring system selected from dihydrobenzo[b][1,4]dioxin-5-yl, or (1-ethylcarboxy-indolin-4-yl);

wherein $R_3$ is selected from the group consisting of hydrogen, chloro, $C_{1-4}$alkyl, 1,1-dioxido-3,6-dihydro-2H-thiopyran-4-yl, and —$OR_4$;

wherein $R_4$ is
i) $C_{1-8}$alkyl independently substituted with one or two $C_{1-3}$alkoxy or hydroxy substituents;
ii) 1,1-dioxidotetrahydro-2H-thiopyran-4-yl;
iii) $C_{1-3}$alkylsulfonylpropyl;
or
iv) (3-methyl-1,1-dioxidothietan-3-yl)methyl;
wherein $R_5$ is methyl, bromo, chloro, or trifluoromethyl;
ii) $C_{5-8}$cycloalkyl;

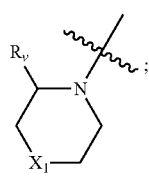
iii)

wherein $X_1$ is selected from the group consisting of $CH_2$, O, S, NH, and $N(C_{1-4}alkyl)$; and wherein $R_{\nu}$ is hydrogen or methyl;

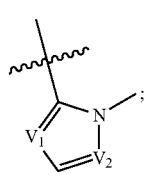
iv)

wherein $V_1$ and $V_2$ are independently selected from CH or N;
and
v) $C_{1-6}$alkyl;
h) W is selected from the group consisting of

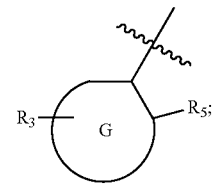
i)

wherein ring G is selected from the group consisting of phenyl, pyridyl, and pyrimidinyl; and, when ring G is phenyl, substituents $R_3$ and $R_5$ are optionally taken together with the atoms to which they are attached to form an unsubstituted or substituted bicyclic ring system selected from dihydrobenzo[b][1,4]dioxin-5-yl, or (1-ethylcarboxy-indolin-4-yl);

wherein $R_3$ is selected from the group consisting of hydrogen, chloro, $C_{1-4}$alkyl, 1,1-dioxido-3,6-dihydro-2H-thiopyran-4-yl, and —$OR_4$;

wherein $R_4$ is
i) $C_{1-6}$alkyl independently substituted with one or two $C_{1-3}$alkoxy substituents;
ii) 1,1-dioxidotetrahydro-2H-thiopyran-4-yl;
iii) $C_{1-3}$alkylsulfonylpropyl;
or
iv) (3-methyl-1,1-dioxidothietan-3-yl)methyl;
wherein $R_5$ is methyl, bromo, chloro, or trifluoromethyl;

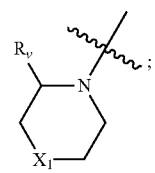
ii)

wherein $X_1$ is selected from the group consisting of $CH_2$, O, S, NH, and $N(C_{1-4}alkyl)$; and wherein $R_{\nu}$ is hydrogen or methyl;
and

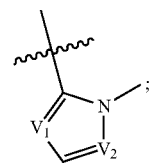
iii)

wherein $V_1$ is independently selected from CH or N, and $V_2$ is CH;

i) W is selected from the group consisting of

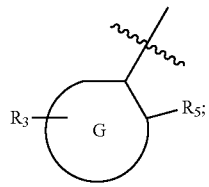

wherein ring G is selected from the group consisting of phenyl and pyridyl; and, when ring G is phenyl, substituents $R_3$ and $R_5$ are optionally taken together with the atoms to which they are attached to form (1-ethyl-carboxy-indolin-4-yl);
wherein $R_3$ is selected from the group consisting of hydrogen, and —$OR_4$;
wherein $R_4$ is
i) $C_{1-6}$alkyl independently substituted with one or two $C_{1-3}$alkoxy substituents;
ii) $C_{1-3}$alkylsulfonylpropyl;
or
iii) (3-methyl-1,1-dioxidothietan-3-yl)methyl;
wherein $R_5$ is methyl, bromo, chloro, or trifluoromethyl;
j) W is selected from the group consisting of 2-methylphenyl, 2-bromophenyl, 2-chloro-5-methylpyridin-4-yl, 2-methyl-4-(4-hydroxy-1,1-dioxidotetrahydro-2H-thiopyran-4-yl)methoxyphenyl, 2-methyl-4-(3-methyl-3-hydroxybutoxy)phenyl, 2-methyl-4-(2-methoxyethoxy)phenyl, 2-methyl-4-(tetrahydro-2H-pyran-4-yloxy)phenyl, 2-methyl-3-(2-methoxyethoxy)phenyl, 2-methylpyridin-3-yl, 2-methyl-4-(3-methyl-1,1-dioxidothietan-3-yl) methoxy)phenyl, 2-trifluoromethylphenyl, 2-methyl-4-(methyl sulfonyl)phenyl, 2-methyl-5-(2-methoxyethoxy) phenyl, 2-methyl-4-(3-methanesulfonylpropyloxy) phenyl, 2-methyl-4-(1,1-dioxidotetrahydro-2H-thiopyran-4-yl)phenyl, 2-methyl-4-(1,1-dioxidotetrahydro-2H-thiopyran-4-yloxy)phenyl, 2,6-dimethylphenyl, 2-(2-methoxyethoxy)-4-methylpyridin-5-yl, 1-methyl-1H-pyrazol-5-yl, 1-methyl-1H-1,2,4-triazol-5-yl, 4-methylpyrimidin-5-yl, 5-(2-methoxyethoxy)-3-methylpyridin-2-yl, dihydrobenzo[b] [1,4]dioxin-5-yl, 1-(ethylcarboxy)-indolin-4-yl, 2-methyl-5-(methanesulfonylamino)phenyl, 2,2,-dimethylchroman-5-yl, 2-methyl-4-(2,3-dihydroxy-propyloxy) phenyl, 2-chlorophenyl, 5-(2-methoxyethoxy)-2-methylpyridin-3-yl, cyclopropyl, cyclohexyl, cyclopentyl, isopropyl, 2-methylpiperidin-1-yl, 2-methyl-4-methoxyphenyl, n-propyl, hydrogen, and n-butyl;

and any combination of embodiments a) through j) above, provided that it is understood that combinations in which different embodiments of the same substituent would be combined are excluded; or an enantiomer, diastereomer, or pharmaceutically acceptable salt form thereof.

Embodiments of the present invention include a compound of Formula (I)

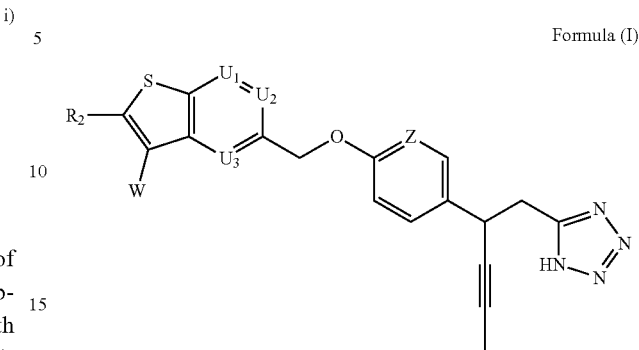

Formula (I)

wherein
$U_1$ is N or $C(R_1)$, wherein $R_1$ is hydrogen, fluoro, or chloro;
$U_2$ and $U_3$ are independently selected from CH or N, such that only up to one of $U_1$, $U_2$, and $U_3$ is N in any instance;
$R_2$ is selected from the group consisting of hydrogen, methyl, chloro, fluoro, bromo, iodo, trifluoromethyl, and cyano;
W is selected from the group consisting of i) 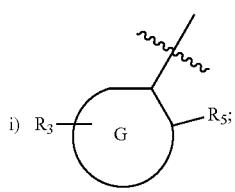

wherein ring G is selected from the group consisting of phenyl, pyridyl, and pyrimidinyl; and, when ring G is phenyl, substituents $R_3$ and $R_5$ are optionally taken together with the atoms to which they are attached to form an unsubstituted or substituted bicyclic ring system selected from dihydrobenzo[b][1,4]dioxin-5-yl, or (1-ethylcarboxy-indolin-4-yl);
wherein $R_3$ is selected from the group consisting of hydrogen, chloro, $C_{1-4}$alkyl, 1,1-dioxido-3,6-dihydro-2H-thiopyran-4-yl, and —$OR_4$;
wherein $R_4$ is
vii) $C_{1-8}$alkyl independently substituted with one or two $C_{1-3}$alkoxy or hydroxy substituents;
viii) 1,1-dioxidotetrahydro-2H-thiopyran-4-yl;
ix) $C_{1-3}$ alkylsulfonylpropyl;
or
x) (3-methyl-1,1-dioxidothietan-3-yl)methyl;
wherein $R_5$ is methyl, bromo, chloro, or trifluoromethyl;
ii) $C_{5-8}$cycloalkyl;

iii) 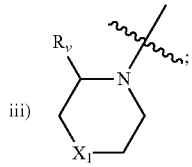

wherein $X_1$ is selected from the group consisting of $CH_2$, O, S, NH, and $N(C_{1-4}$alkyl); and wherein $R_v$ is hydrogen or methyl;

iv) 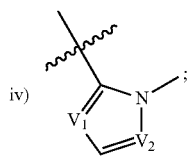

wherein $V_1$ and $V_2$ are independently selected from CH or N;

and v) $C_{1-6}$alkyl;

$Z$ is CH or N;

or an enantiomer, diastereomer, or pharmaceutically acceptable salt form thereof.

Embodiments of the present invention include a compound of Formula (I)

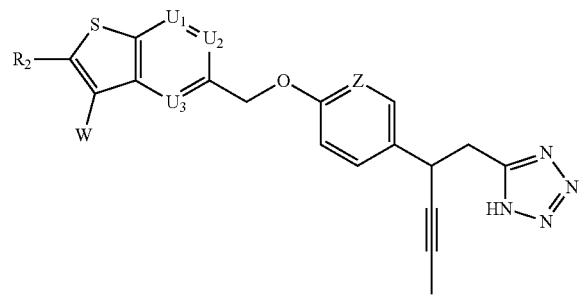

Formula (I)

wherein $U_1$ is N or $C(R_1)$, wherein $R_1$ is hydrogen, fluoro, or chloro;

$U_2$ is independently selected from CH or N;

$U_3$ is CH, such that only one of $U_1$ and $U_2$ is N in any instance;

$R_2$ is selected from the group consisting of hydrogen, methyl, chloro, fluoro, bromo, iodo, trifluoromethyl, and cyano;

W is selected from the group consisting of i) 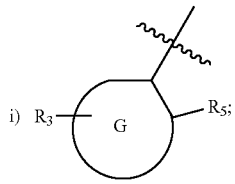

wherein ring G is selected from the group consisting of phenyl, pyridyl, and pyrimidinyl; and, when ring G is phenyl, substituents $R_3$ and $R_5$ are optionally taken together with the atoms to which they are attached to form an unsubstituted or substituted bicyclic ring system selected from dihydrobenzo[b][1,4]dioxin-5-yl, or (1-ethylcarboxy-indolin-4-yl);

wherein $R_3$ is selected from the group consisting of hydrogen, chloro, $C_{1-4}$alkyl 1,1-dioxido-3,6-dihydro-2H-thiopyran-4-yl, and —$OR_4$;

wherein $R_4$ is v) $C_{1-6}$alkyl independently substituted with one or two $C_{1-3}$alkoxy substituents;

vi) 1,1-dioxidotetrahydro-2H-thiopyran-4-yl;

vii) $C_{1-3}$alkylsulfonylpropyl;

or viii) (3-methyl-1,1-dioxidothietan-3-yl)methyl;

wherein $R_5$ is methyl, bromo, chloro, or trifluoromethyl;

ii) 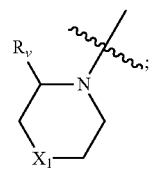

wherein $X_1$ is selected from the group consisting of $CH_2$, O, S, NH, and $N(C_{1-4}$alkyl); and wherein $R_v$ is hydrogen or methyl;

and iii) 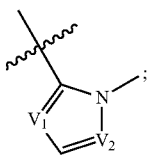

wherein $V_1$ is independently selected from CH or N, and $V_2$ is CH;

$Z$ is CH or N;

or an enantiomer, diastereomer, or pharmaceutically acceptable salt form thereof.

Embodiments of the present invention include a compound of Formula (I)

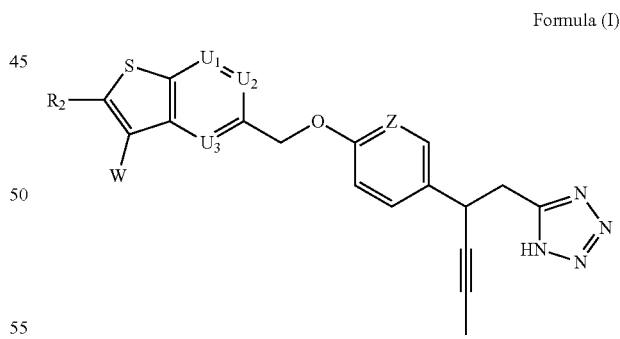

Formula (I)

wherein $U_1$ is N or $C(R_1)$, wherein $R_1$ is hydrogen, fluoro, or chloro;

$U_2$ is independently selected from CH or N;

$U_3$ is CH, such that only one of $U_1$ and $U_2$ is N in any instance;

$R_2$ is selected from the group consisting of hydrogen, chloro, fluoro, bromo, trifluoromethyl, and cyano;

W is selected from the group consisting of

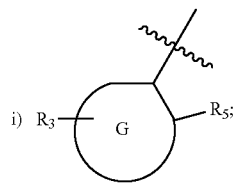

wherein ring G is selected from the group consisting of phenyl and pyridyl; and, when ring G is phenyl, substituents $R_3$ and $R_5$ are optionally taken together with the atoms to which they are attached to form (1-ethylcarboxy-indolin-4-yl);
wherein $R_3$ is selected from the group consisting of hydrogen, and —$OR_4$;
wherein $R_4$ is
i) $C_{1-6}$alkyl independently substituted with one or two $C_{1-3}$alkoxy substituents;
ii) $C_{1-3}$alkylsulfonylpropyl;
or
iii) (3-methyl-1,1-dioxidothietan-3-yl)methyl;
wherein $R_5$ is methyl, bromo, chloro, or trifluoromethyl;
Z is CH or N;
or an enantiomer, diastereomer, or pharmaceutically acceptable salt form thereof.

Embodiments of the present invention include a compound of Formula (I)

Formula (I)

wherein
$U_1$ is N or $C(R_1)$, wherein $R_1$ is hydrogen, methyl, fluoro, or chloro;
$U_2$ is independently selected from CH or N;
$U_3$ is CH or N, such that only one of $U_1$ and $U_2$ is N in any instance;
$R_2$ is selected from the group consisting of hydrogen, chloro, fluoro, bromo, iodo, methyl, methanesulfonyl, trifluoromethyl, and cyano;
W is selected from the group consisting of 2-methylphenyl, 2-bromophenyl, 2-chloro-5-methylpyridin-4-yl, 2-methyl-4-(4-hydroxy-1,1-dioxidotetrahydro-2H-thiopyran-4-yl)methoxyphenyl, 2-methyl-4-(3-methyl-3-hydroxybutoxy)phenyl, 2-methyl-4-(2-methoxyethoxy)phenyl, 2-methyl-4-(tetrahydro-2H-pyran-4-yloxy)phenyl, 2-methyl-3-(2-methoxyethoxy)phenyl, 2-methylpyridin-3-yl, 2-methyl-4-(3-methyl-1,1-dioxidothietan-3-yl)methoxy)phenyl, 2-trifluoromethylphenyl, 2-methyl-4-(methyl sulfonyl)phenyl, 2-methyl-5-(2-methoxyethoxy)phenyl, 2-methyl-4-(3-methanesulfonylpropyloxy)phenyl, 2-methyl-4-(1,1-dioxidotetrahydro-2H-thiopyran-4-yl)phenyl, 2-methyl-4-(1,1-dioxidotetrahydro-2H-thiopyran-4-yloxy)phenyl, 2,6-dimethylphenyl, 2-(2-methoxyethoxy)-4-methylpyridin-5-yl, 1-methyl-1H-pyrazol-5-yl, 1-methyl-1H-1,2,4-triazol-5-yl, 4-methylpyrimidin-5-yl, 5-(2-methoxyethoxy)-3-methylpyridin-2-yl, dihydrobenzo[b][1,4]dioxin-5-yl, 1-(ethylcarboxy)-indolin-4-yl, 2-methyl-5-(methanesulfonylamino)phenyl, 2,2,-dimethylchroman-5-yl, 2-methyl-4-(2,3-dihydroxy-propyloxy)phenyl, 2-chlorophenyl, 5-(2-methoxyethoxy)-2-methylpyridin-3-yl, cyclopropyl, cyclohexyl, cyclopentyl, isopropyl, 2-methylpiperidin-1-yl, 2-methyl-4-methoxyphenyl, n-propyl, hydrogen, and n-butyl;
Z is CH or N;
or an enantiomer, diastereomer, or pharmaceutically acceptable salt form thereof.

Additional embodiments of the present invention include compounds of Formula (I) as herein defined, or an enantiomer, diastereomer, solvate, or a pharmaceutically acceptable salt form thereof, as exemplified in the listing in Table 1, below.

TABLE 1

| Structure | Cpd No. | Cpd Name |
|---|---|---|
| 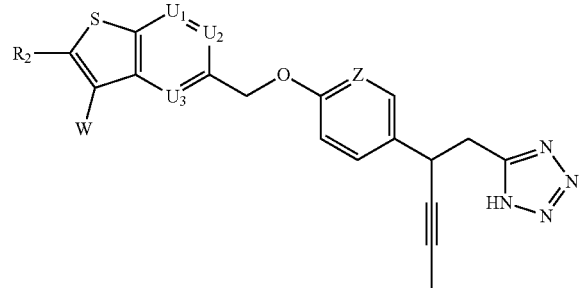 | 1 | (2S)-5-(2-(4-((3-(2-Methylphenyl)benzo[b]thiophen-5-yl)methoxy)phenyl)pent-3-yn-1-yl)-1H-tetrazole |

TABLE 1-continued

| Structure | Cpd No. | Cpd Name |
|---|---|---|
| 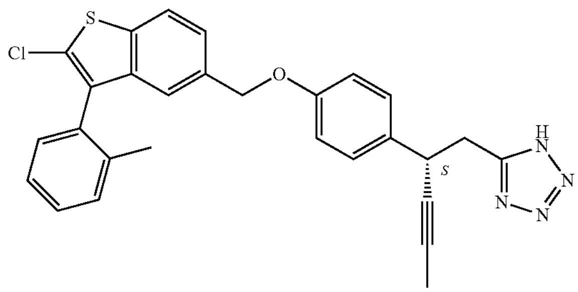 | 2 | 5-((2S)-2-(4-((2-Chloro-3-(2-methylphenyl)benzo[b]thiophen-5-yl)methoxy)phenyl)pent-3-ynyl)-1H-tetrazole |
| 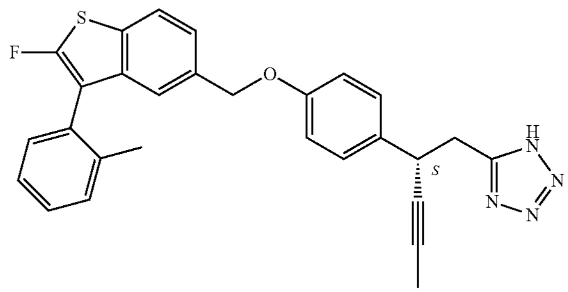 | 3 | 5-((2S)-2-(4-((2-Fluoro-3-(2-methylphenyl)benzo[b]thiophen-5-yl)methoxy)phenyl)pent-3-ynyl)-1H-tetrazole |
| 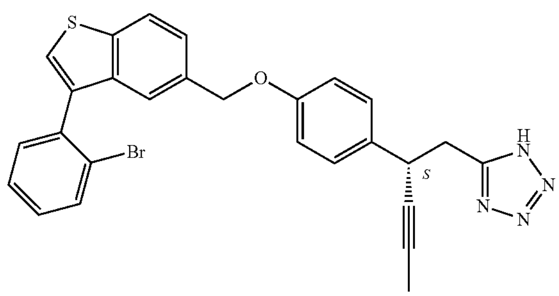 | 4 | (2S)-5-(2-(4-((3-(2-Bromophenyl)benzo[b]thiophen-5-yl)methoxy)phenyl)pent-3-yn-1-yl)-1H-tetrazole |
| 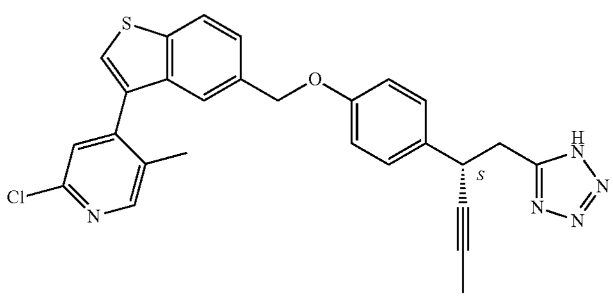 | 5 | (2S)-4-(5-((4-(1-(1H-tetrazol-5-yl)pent-3-yn-2-yl)phenoxy)methyl)benzo[b]thiophen-3-yl)-2-chloro-5-methylpyridine |
| 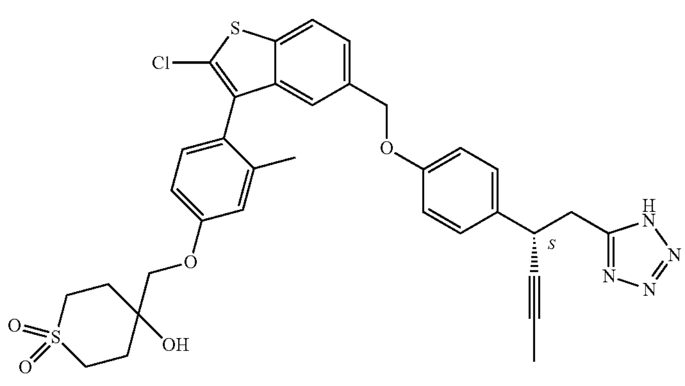 | 6 | (2S)-4-((4-(5-((4-(1-(1H-Tetrazol-5-yl)pent-3-yn-2-yl)phenoxy)methyl)benzo[b]thiophen-3-yl)-3-methylphenoxy)methyl)-4-hydroxytetrahydro-2H-thiopyran 1,1-dioxide |

TABLE 1-continued

| Structure | Cpd No. | Cpd Name |
|---|---|---|
| 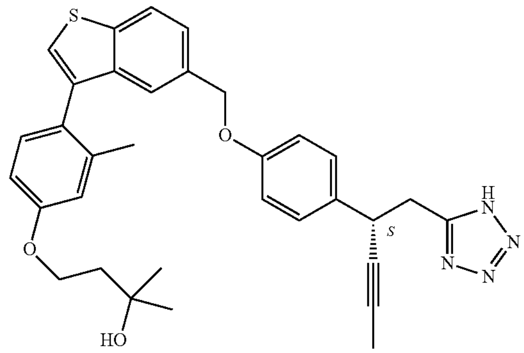 | 7 | (2S)-4-(4-(5-((4-(1-(1H-Tetrazol-5-yl)pent-3-yn-2-yl)phenoxy)methyl)benzo[b]thiophen-3-yl)-3-methylphenoxy)-2-methylbutan-2-ol |
| 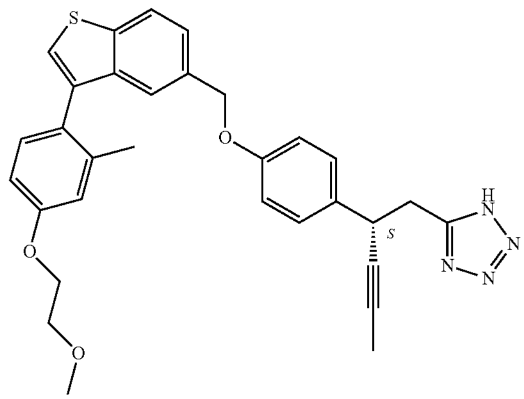 | 8 | (2S)-5-(2-(4-((3-(4-(2-Methoxyethoxy)-2-methylphenyl)benzo[b]thiophen-5-yl)methoxy)phenyl)pent-3-yn-1-yl)-1H-tetrazole |
| 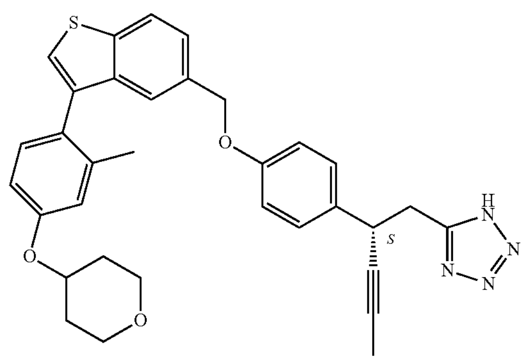 | 9 | (2S)-5-(2-(4-((3-(2-Methyl-4-((tetrahydro-2H-pyran-4-yl)oxy)phenyl)benzo[b]thiophen-5-yl)methoxy)phenyl)pent-3-yn-1-yl)-1H-tetrazole |
| 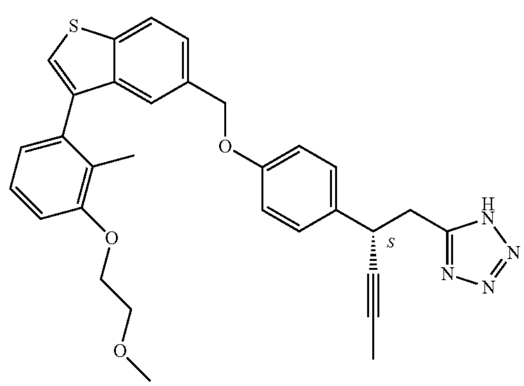 | 10 | (2S)-5-(2-(4-((3-(3-(2-Methoxyethoxy)-2-methylphenyl)benzo[b]thiophen-5-yl)methoxy)phenyl)pent-3-yn-1-yl)-1H-tetrazole |

TABLE 1-continued

| Structure | Cpd No. | Cpd Name |
|---|---|---|
| 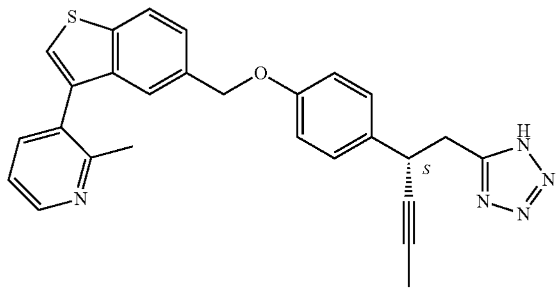 | 11 | (2S)-3-(5-((4-(1-(1H-Tetrazol-5-yl)pent-3-yn-2-yl)phenoxy)methyl)benzo[b]thiophen-3-yl)-2-methylpyridine |
| 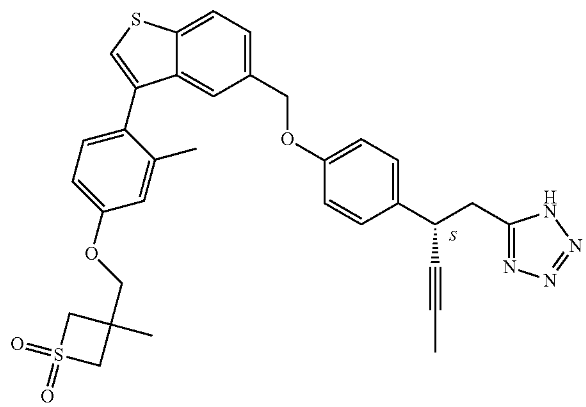 | 12 | (2S)-3-((4-(5-((4-(1-(1H-Tetrazol-5-yl)pent-3-yn-2-yl)phenoxy)methyl)benzo[b]thiophen-3-yl)-3-methylphenoxy)methyl)-3-methylthietane 1,1-dioxide |
| 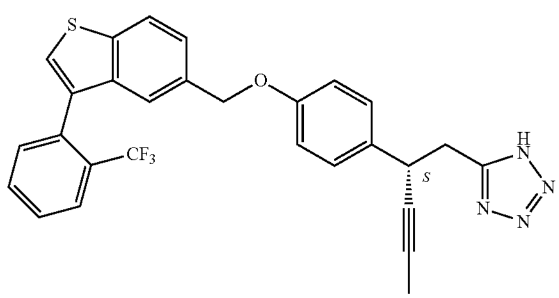 | 13 | (2S)-5-(2-(4-((3-(2-(Trifluoromethyl)phenyl)benzo[b]thiophen-5-yl)methoxy)phenyl)pent-3-yn-1-yl)-1H-tetrazole |
| 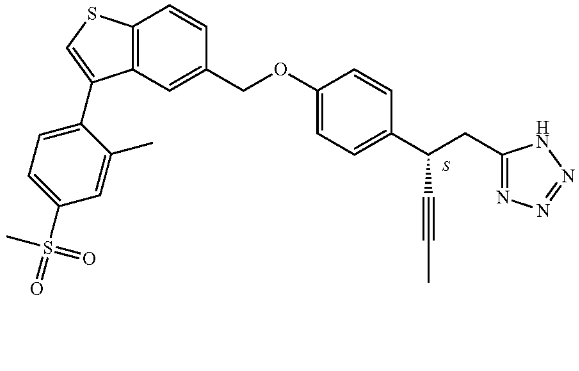 | 14 | (2S)-5-(2-(4-((3-(2-Methyl-4-(methylsulfonyl)phenyl)benzo[b]thiophen-5-yl)methoxy)phenyl)pent-3-yn-1-yl)-1H-tetrazole |

TABLE 1-continued

| Structure | Cpd No. | Cpd Name |
|---|---|---|
| 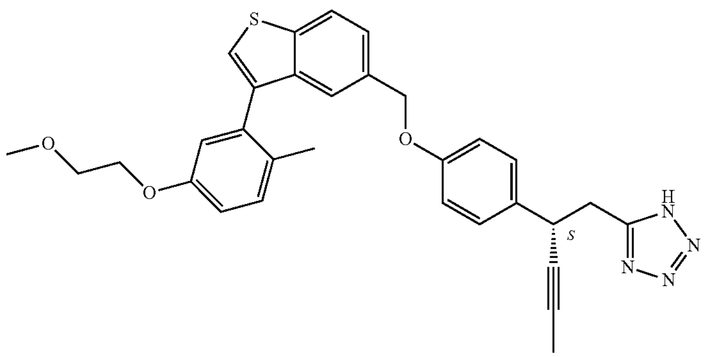 | 15 | (2S)-5-(2-(4-((3-(5-(2-Methoxyethoxy)-2-methylphenyl)benzo[b]thiophen-5-yl)methoxy)phenyl)pent-3-yn-1-yl)-1H-tetrazole |
| 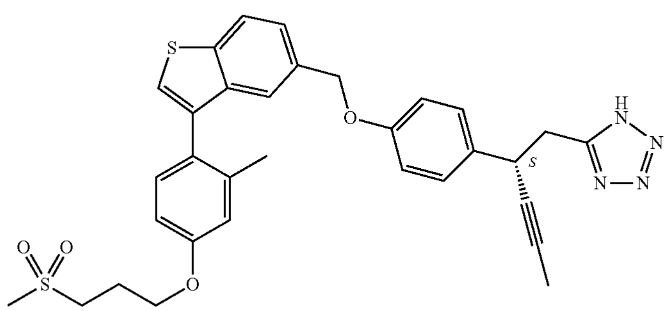 | 16 | (2S)-5-(2-(4-((3-(2-Methyl-4-(3-(methylsulfonyl)propoxy)phenyl)benzo[b]thiophen-5-yl)methoxy)phenyl)pent-3-yn-1-yl)-1H-tetrazole |
| 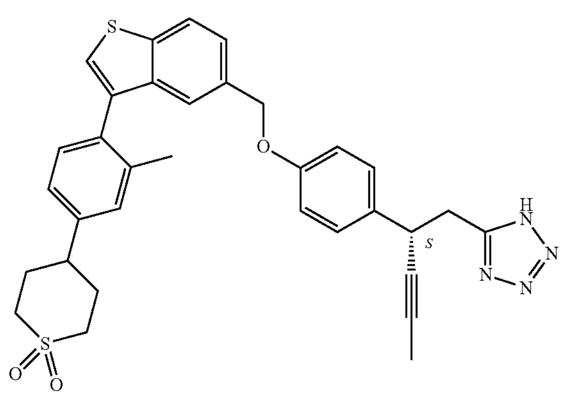 | 17 | (2S)-4-(4-(5-((4-(1-(1H-Tetrazol-5-yl)pent-3-yn-2-yl)phenoxy)methyl)benzo[b]thiophen-3-yl)-3-methylphenyl)tetrahydro-2H-thiopyran 1,1-dioxide |
| 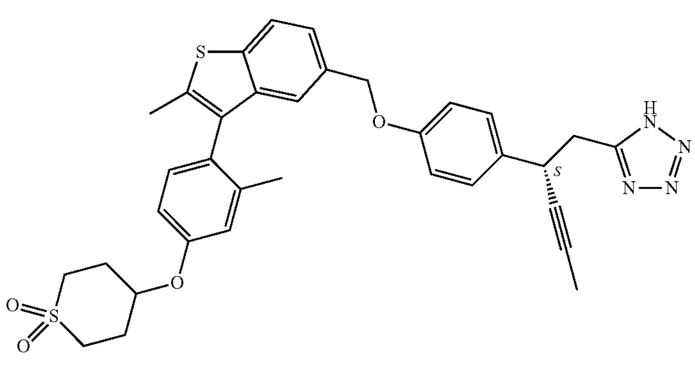 | 18 | 4-(4-(5-((4-((2S)-1-(1H-Tetrazol-5-yl)pent-3-yn-2-yl)phenoxy)methyl)-2-methylbenzo[b]thiophen-3-yl)-3-methylphenoxy)tetrahydro-2H-thiopyran 1,1-dioxide |

TABLE 1-continued

| Structure | Cpd No. | Cpd Name |
|---|---|---|
| 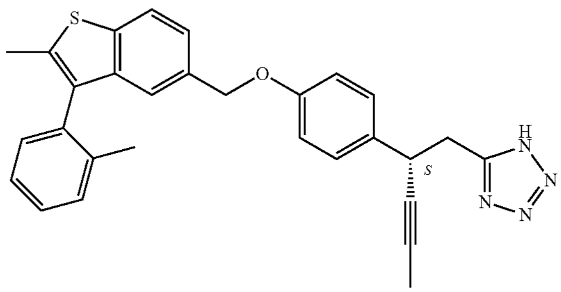 | 19 | 5-((2S)-2-(4-((2-Methyl-3-(2-methylphenyl)benzo[b]thiophen-5-yl)methoxy)phenyl)pent-3-ynyl)-1H-tetrazole |
| 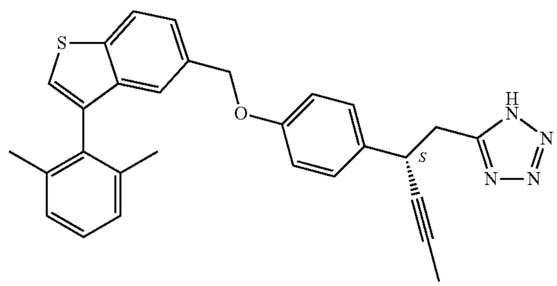 | 20 | (2S)-5-(2-(4-((3-(2,6-Dimethylphenyl)benzo[b]thiophen-5-yl)methoxy)phenyl)pent-3-yn-1-yl)-1H-tetrazole |
| 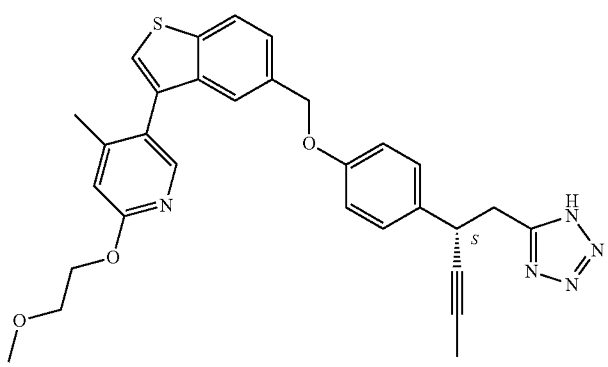 | 21 | (2S)-5-(5-((4-(1-(1H-Tetrazol-5-yl)pent-3-yn-2-yl)phenoxy)methyl)benzo[b]thiophen-3-yl)-2-(2-methoxyethoxy)-4-methylpyridine |
| 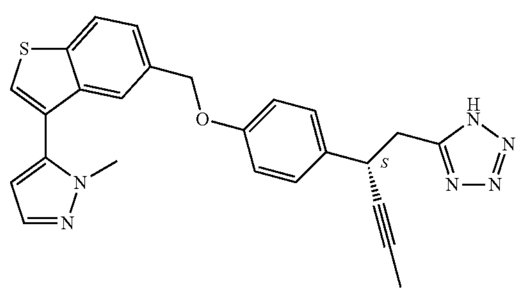 | 22 | (2S)-5-(2-(4-((3-(1-Methyl-1H-pyrazol-5-yl)benzo[b]thiophen-5-yl)methoxy)phenyl)pent-3-yn-1-yl)-1H-tetrazole |
| 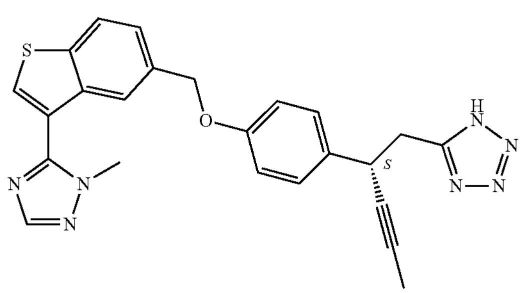 | 23 | (2S)-5-(2-(4-((3-(1-Methyl-1H-1,2,4-triazol-5-yl)benzo[b]thiophen-5-yl)methoxy)phenyl)pent-3-yn-1-yl)-1H-tetrazole |

TABLE 1-continued

| Structure | Cpd No. | Cpd Name |
|---|---|---|
| 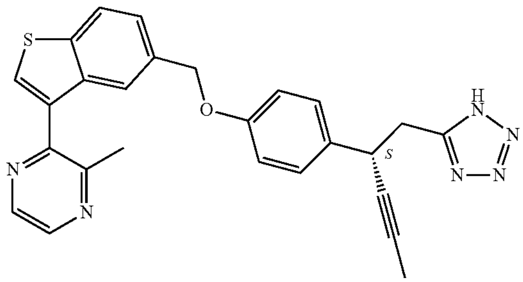 | 24 | (2S)-2-(5-((4-(1-(1H-Tetrazol-5-yl)pent-3-yn-2-yl)phenoxy)methyl)benzo[b]thiophen-3-yl)-3-methylpyrazine |
| 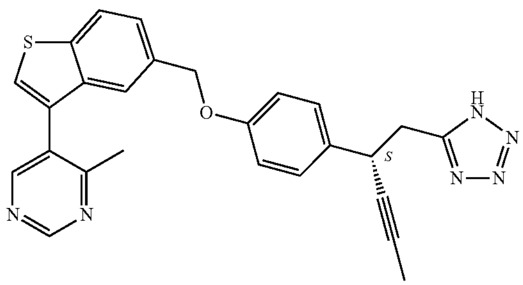 | 25 | (2S)-5-(5-((4-(1-(1H-Tetrazol-5-yl)pent-3-yn-2-yl)phenoxy)methyl)benzo[b]thiophen-3-yl)-4-methylpyrimidine |
| 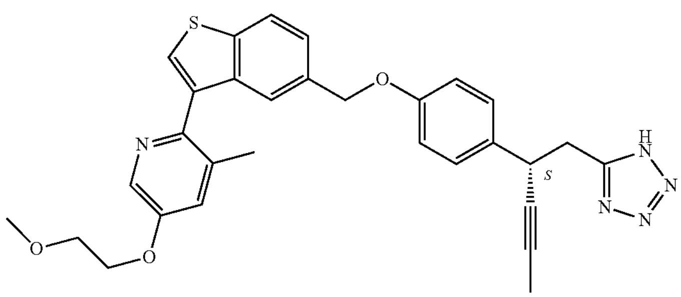 | 26 | (2S)-2-(5-((4-(1-(1H-Tetrazol-5-yl)pent-3-yn-2-yl)phenoxy)-methyl)benzo[b]thiophen-3-yl)-5-(2-methoxyethoxy)-3-methylpyridine |
| 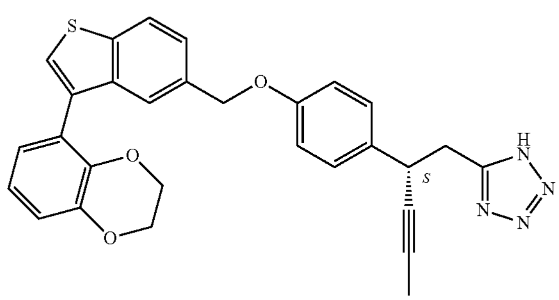 | 27 | (2S)-5-(2-(4-((3-(2,3-Dihydrobenzo[b][1,4]dioxin-5-yl)benzo[b]thiophen-5-yl)methoxy)phenyl)pent-3-yn-1-yl)-1H-tetrazole |
| 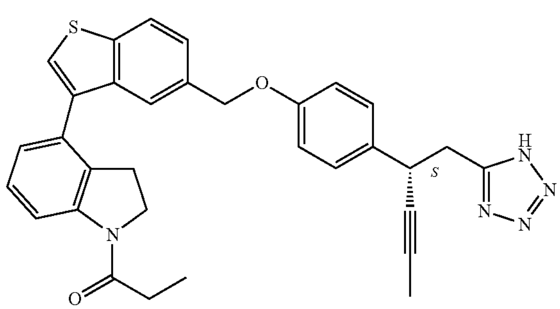 | 28 | (2S)-1-(4-(5-((4-(1-(1H-tetrazol-5-yl)pent-3-yn-2-yl)phenoxy)methyl)benzo[b]thiophen-3-yl)indolin-1-yl)propan-1-one |

TABLE 1-continued

| Structure | Cpd No. | Cpd Name |
|---|---|---|
| 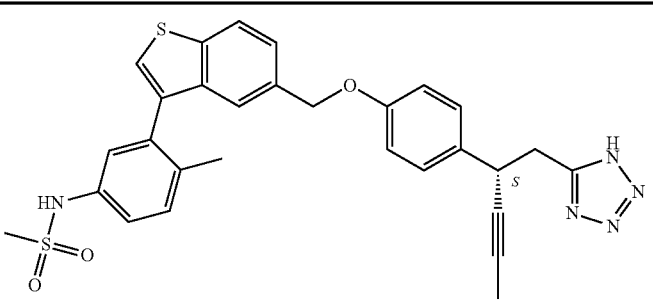 | 29 | (2S)-N-(3-(5-((4-(1-(1H-tetrazol-5-yl)pent-3-yn-2-yl)phenoxy)methyl)benzo[b]thiophen-3-yl)-4-methylphenyl)methanesulfonamide |
| 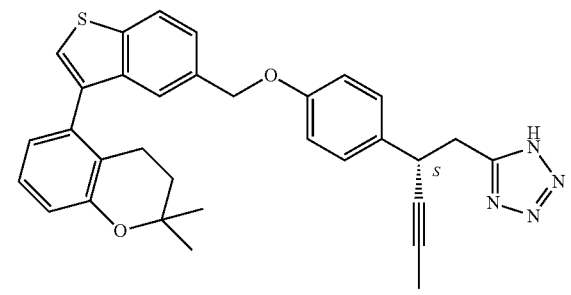 | 30 | (2S)-5-(2-(4-((3-(2,2-dimethylchroman-5-yl)benzo[b]thiophen-5-yl)methoxy)phenyl)pent-3-yn-1-yl)-1H-tetrazole |
| 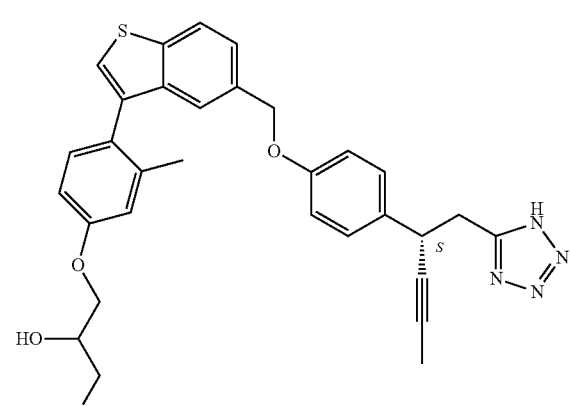 | 31 | 3-(4-(5-((4-((2S)-1-(1H-Tetrazol-5-yl)pent-3-yn-2-yl)phenoxy)methyl)benzo[b]thiophen-3-yl)-3-methylphenoxy)propane-1,2-diol |
| 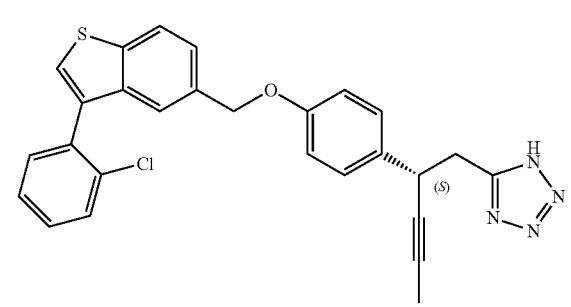 | 32 | (2S)-5-(2-(4-((3-(2-Chlorophenyl)benzo[b]thiophen-5-yl)methoxy)phenyl)pent-3-yn-1-yl)-1H-tetrazole |

TABLE 1-continued

| Structure | Cpd No. | Cpd Name |
|---|---|---|
| 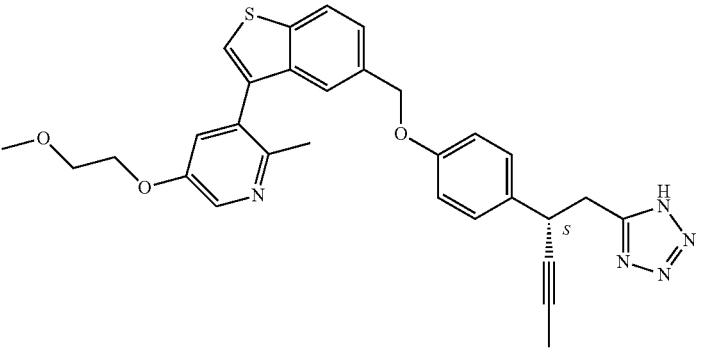 | 33 | (2S)-3-(5-((4-(1-(1H-Tetrazol-5-yl)pent-3-yn-2-yl)phenoxy)methyl)benzo[b]thiophen-3-yl)-5-(2-methoxyethoxy)-2-methylpyridine |
| 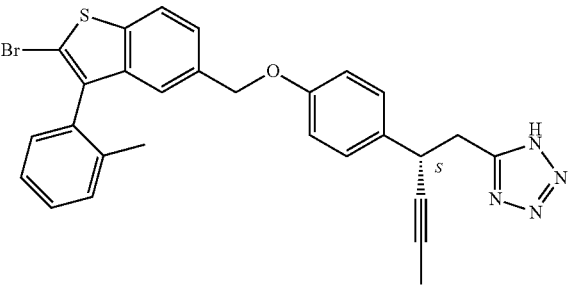 | 34 | 5-((2S)-2-(4-((2-Bromo-3-(2-methylphenyl)benzo[b]thiophen-5-yl)methoxy)phenyl)pent-3-ynyl)-1H-tetrazole |
| 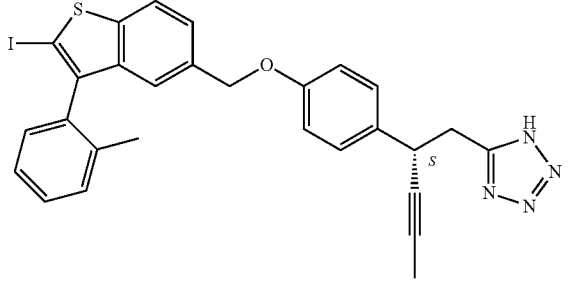 | 35 | 5-((2S)-2-(4-((2-Iodo-3-(2-methylphenyl)benzo[b]thiophen-5-yl)methoxy)phenyl)pent-3-ynyl)-1H-tetrazole |
| 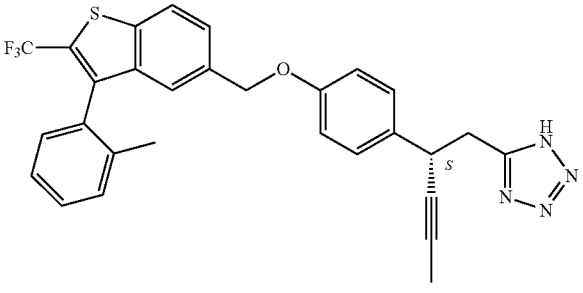 | 36 | 5-((2S)-2-(4-((2-Trifluoromethyl-3-(2-methylphenyl)benzo[b]thiophen-5-yl)methoxy)phenyl)pent-3-ynyl)-1H-tetrazole |
| 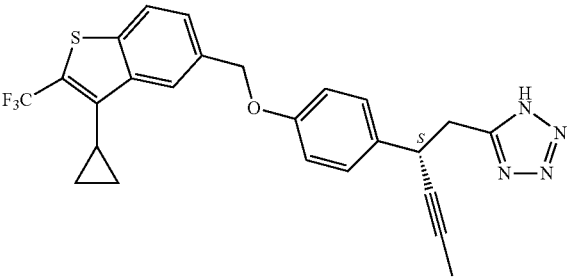 | 37 | (2S)-5-(2-(4-((3-Cyclopropyl-2-(trifluoromethyl)benzo[b]thiophen-5-yl)methoxy)phenyl)pent-3-yn-1-yl)-1H-tetrazole |

TABLE 1-continued

| Structure | Cpd No. | Cpd Name |
|---|---|---|
| 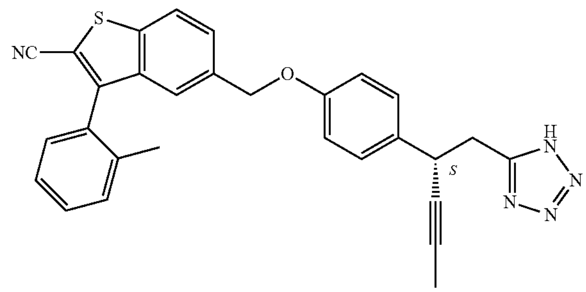 | 38 | 5-((2S)-2-(4-((2-Cyano-3-(2-methylphenyl)benzo[b]thiophen-5-yl)methoxy)phenyl)pent-3-yn-1-yl)-1H-tetrazole |
| 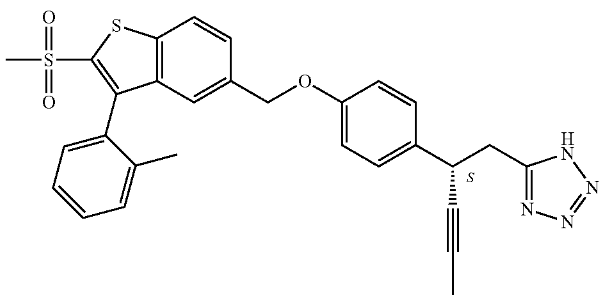 | 39 | (2S)-5-(2-(4-((2-(Methylsulfonyl)-3-(2-methylphenyl)benzo[b]thiophen-5-yl)methoxy)phenyl)pent-3-yn-1-yl)-1H-tetrazole |
| 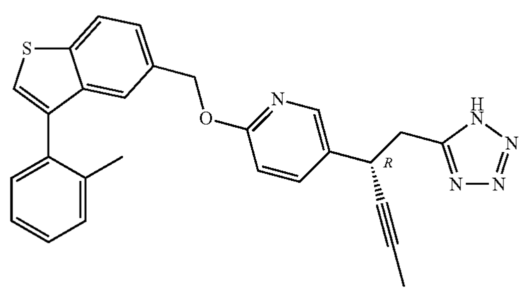 | 40 | (2S)-5-(1-(1H-Tetrazol-5-yl)pent-3-yn-2-yl)-2-((3-(2-methylphenyl)benzo[b]thiophen-5-yl)methoxy)pyridine |
| 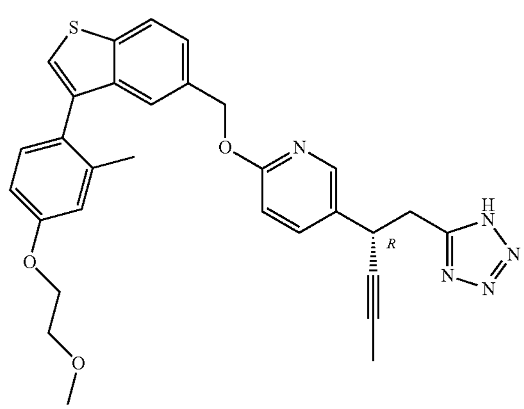 | 41 | (2S)-5-(1-(1H-Tetrazol-5-yl)pent-3-yn-2-yl)-2-((3-(4-(2-methoxyethoxy)-2-methylphenyl)benzo[b]thiophen-5-yl)methoxy)pyridine |

TABLE 1-continued

| Structure | Cpd No. | Cpd Name |
|---|---|---|
| 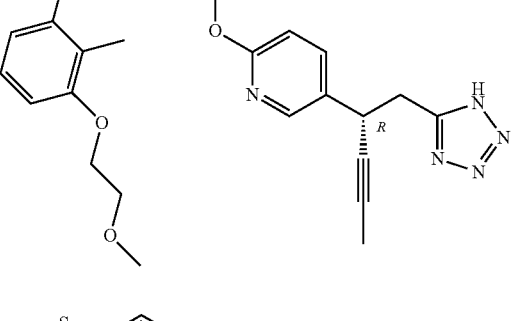 | 42 | (2S)-5-(1-(1H-Tetrazol-5-yl)pent-3-yn-2-yl)-2-((3-(3-(2-methoxyethoxy)-2-methylphenyl)benzo[b]thiophen-5-yl)methoxy)pyridine |
| 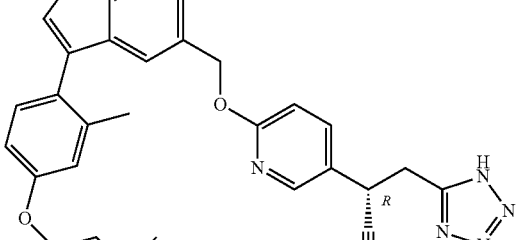 | 43 | (2S)-4-(4-(5-(((5-(1-(1H-Tetrazol-5-yl)pent-3-yn-2-yl)pyridin-2-yl)oxy)methyl)-benzo[b]thiophen-3-yl)-3-methylphenoxy)-2-methylbutan-2-ol |
| 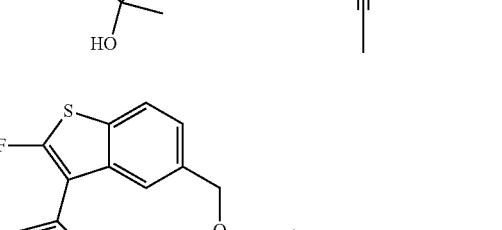 | 44 | (2S)-5-(2-(4-((2-Fluoro-3-(4-(2-methoxyethoxy)-2-methylphenyl)benzo[b]thiophen-5-yl)methoxy)phenyl)pent-3-yn-1-yl)-1H-tetrazole |
| 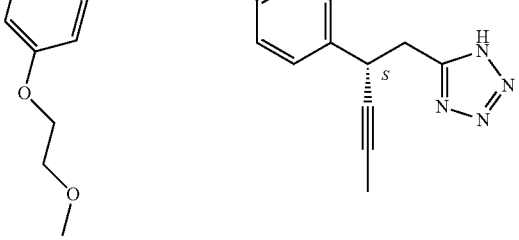 | 45 | (2S)-5-(2-(4-((2-Chloro-3-(4-(2-methoxyethoxy)-2-methylphenyl)benzo[b]thiophen-5-yl)methoxy)phenyl)pent-3-yn-1-yl)-1H-tetrazole |

TABLE 1-continued

| Structure | Cpd No. | Cpd Name |
|---|---|---|
| 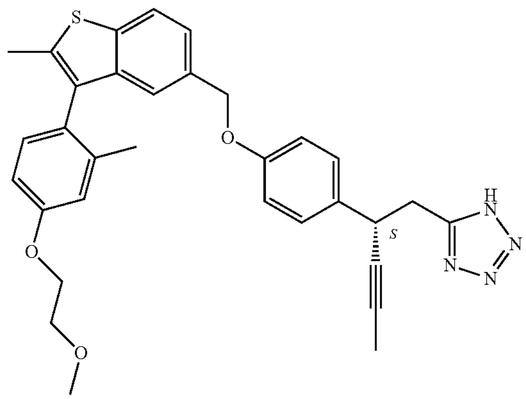 | 46 | (2S)-5-(2-(4-((3-(4-(2-Methoxyethoxy)-2-methylphenyl)-2-methylbenzo[b]thiophen-5-yl)methoxy)phenyl)pent-3-yn-1-yl)-1H-tetrazole |
| 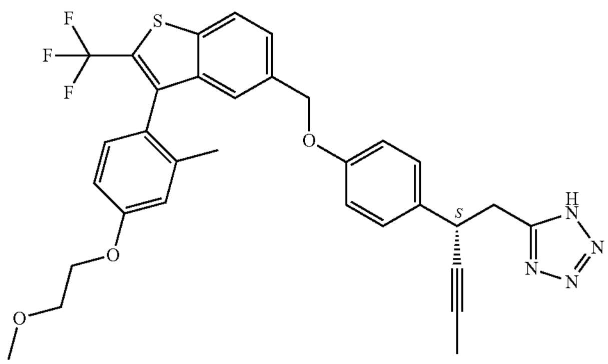 | 47 | 5-((2S)-2-(4-((3-(4-(2-Methoxyethoxy)-2-methylphenyl)-2-(trifluoromethyl)benzo[b]thiophen-5-yl)methoxy)phenyl)pent-3-yn-1-yl)-1H-tetrazole |
| 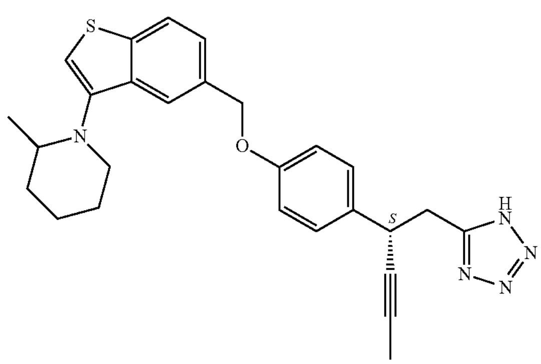 | 48 | 1-(5-((4-((2S)-1-(1H-Tetrazol-5-yl)pent-3-yn-2-yl)phenoxy)methyl)benzo[b]thiophen-3-yl)-2-methylpiperidine |
| 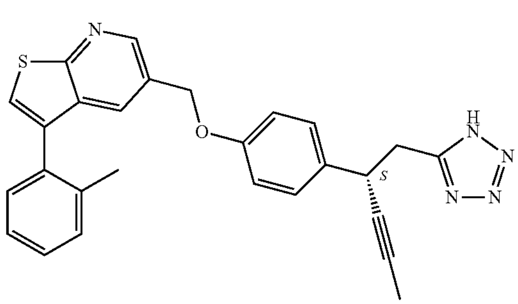 | 49 | (2S)-5-((4-(1-(1H-Tetrazol-5-yl)pent-3-yn-2-yl)phenoxy)methyl)-3-(2-methylphenyl)thieno[2,3-b]pyridine |

TABLE 1-continued

| Structure | Cpd No. | Cpd Name |
|---|---|---|
| 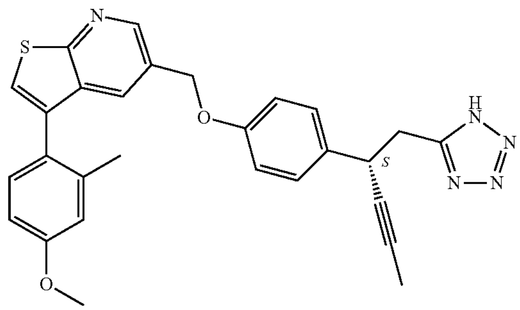 | 50 | (2S)-5-((4-(1-(1H-Tetrazol-5-yl)pent-3-yn-2-yl)phenoxy)methyl)-3-(4-methoxy-2-methylphenyl)thieno[2,3-b]pyridine |
| 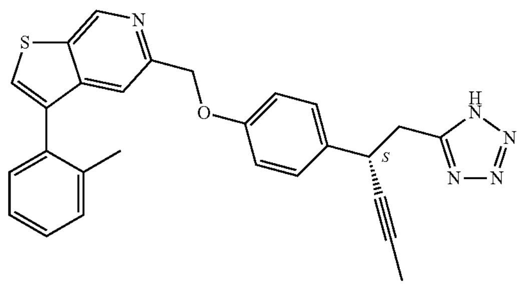 | 51 | (2S)-5-((4-(1-(1H-Tetrazol-5-yl)pent-3-yn-2-yl)phenoxy)methyl)-3-(2-methylphenyl)thieno[2,3-c]pyridine |
| 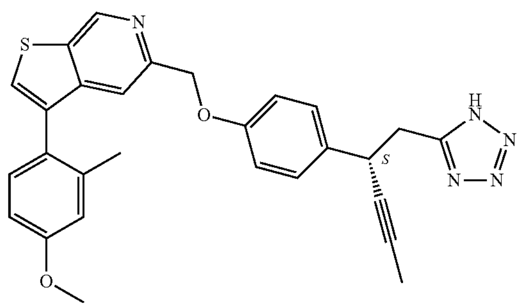 | 52 | (2S)-5-((4-(1-(1H-Tetrazol-5-yl)pent-3-yn-2-yl)phenoxy)methyl)-3-(4-methoxy-2-methylphenyl)thieno[2,3-c]pyridine |
| 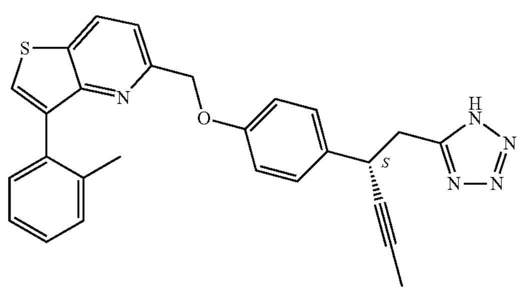 | 53 | (2S)-5-((4-(1-(1H-Tetrazol-5-yl)pent-3-yn-2-yl)phenoxy)methyl)-3-(2-methylphenyl)thieno[3,2-b]pyridine |
| 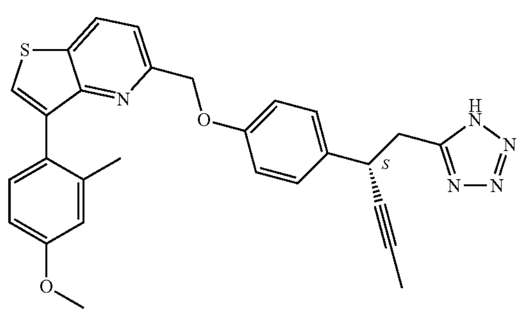 | 54 | (2S)-5-((4-(1-(1H-Tetrazol-5-yl)pent-3-yn-2-yl)phenoxy)methyl)-3-(4-methoxy-2-methylphenyl)thieno[3,2-b]pyridine |

TABLE 1-continued

| Structure | Cpd No. | Cpd Name |
|---|---|---|
| 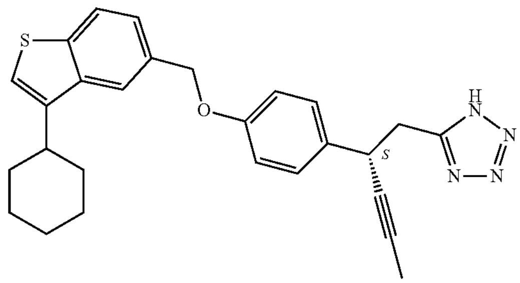 | 55 | (2S)-5-(2-(4-((3-Cyclohexylbenzo[b]thiophen-5-yl)methoxy)phenyl)pent-3-yn-1-yl)-1H-tetrazole |
| 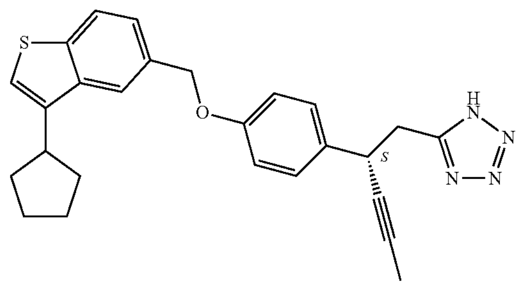 | 56 | (2S)-5-(2-(4-((3-Cyclopentylbenzo[b]thiophen-5-yl)methoxy)phenyl)pent-3-yn-1-yl)-1H-tetrazole |
| 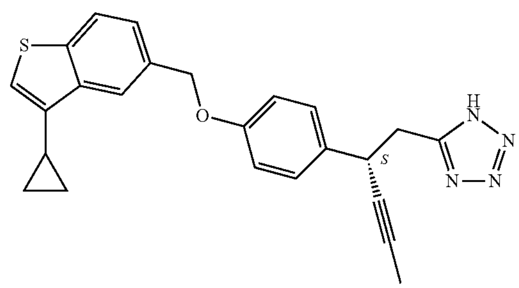 | 57 | (2S)-5-(2-(4-((3-Cyclopropylbenzo[b]thiophen-5-yl)methoxy)phenyl)pent-3-yn-1-yl)-1H-tetrazole |
| 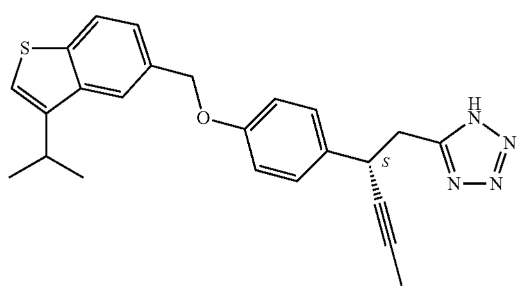 | 58 | (2S)-5-(2-(4-((3-Isopropylbenzo[b]thiophen-5-yl)methoxy)phenyl)pent-3-yn-1-yl)-1H-tetrazole |
| 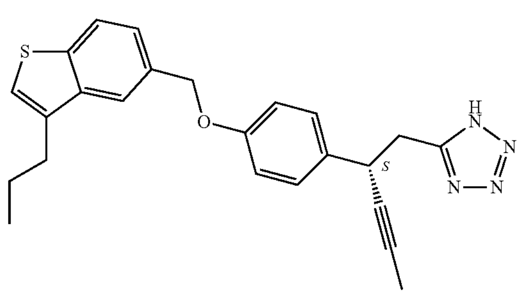 | 59 | (2S)-5-(2-(4-((3-Propylbenzo[b]thiophen-5-yl)methoxy)phenyl)pent-3-yn-1-yl)-1H-tetrazole |

TABLE 1-continued

| Structure | Cpd No. | Cpd Name |
|---|---|---|
| 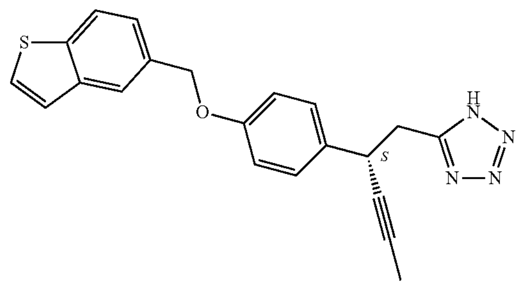 | 60 | (2S)-5-(2-(4-(Benzo[b]thiophen-5-ylmethoxy)phenyl)pent-3-yn-1-yl)-1H-tetrazole |
| 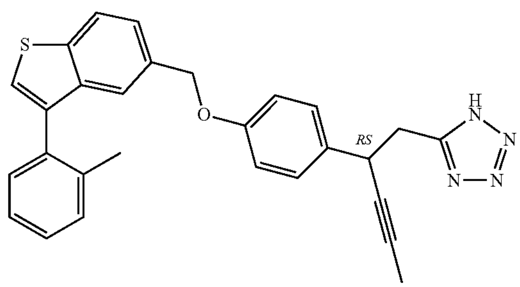 | 61 | (2S)-5-(2-(4-((3-(2-Methylphenyl)benzo[b]thiophen-5-yl)methoxy)phenyl)pent-3-yn-1-yl)-1H-tetrazole |
| 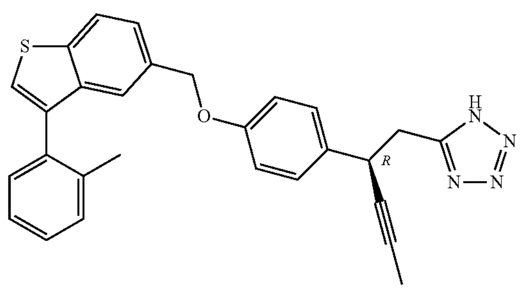 | 62 | (2S)-5-(2-(4-((3-(2-Methylphenyl)benzo[b]thiophen-5-yl)methoxy)phenyl)pent-3-yn-1-yl)-1H-tetrazole |
| 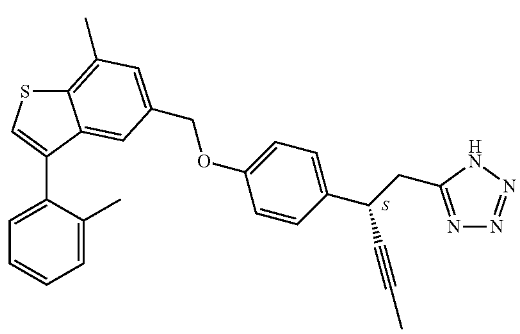 | 63 | (2S)-5-(2-(4-((7-Methyl-3-(2-methylphenyl)benzo[b]thiophen-5-yl)methoxy)phenyl)pent-3-yn-1-yl)-1H-tetrazole |
| 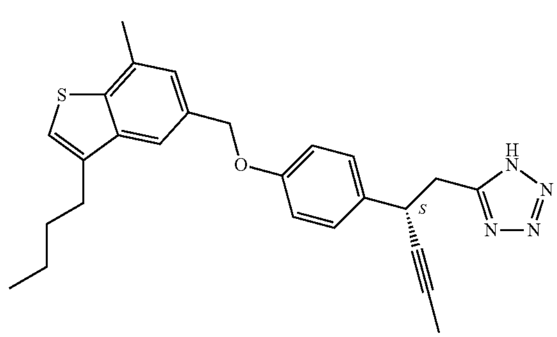 | 64 | (2S)-5-(2-(4-((3-Butyl-7-methylbenzo[b]thiophen-5-yl)methoxy)phenyl)pent-3-yn-1-yl)-1H-tetrazole |

TABLE 1-continued

| Structure | Cpd No. | Cpd Name |
|---|---|---|
| 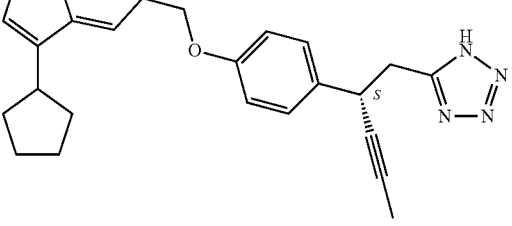 | 65 | (2S)-5-(2-(4-((3-Cyclopentyl-7-methylbenzo[b]thiophen-5-yl)methoxy)phenyl)pent-3-yn-1-yl)-1H-tetrazole |
| 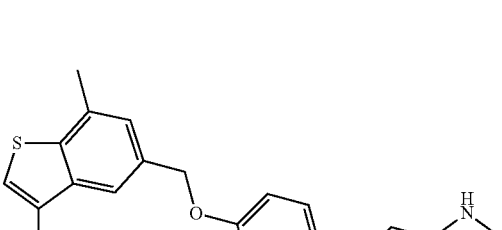 | 66 | (2S)-5-(2-(4-((3-Cyclohexyl-7-methylbenzo[b]thiophen-5-yl)methoxy)phenyl)pent-3-yn-1-yl)-1H-tetrazole |
| 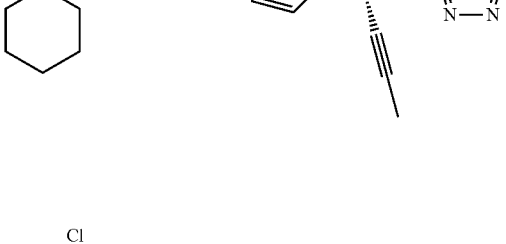 | 67 | (2S)-5-(2-(4-((7-Chloro-3-(2-methylphenyl)benzo[b]thiophen-5-yl)methoxy)phenyl)pent-3-yn-1-yl)-1H-tetrazole |
| 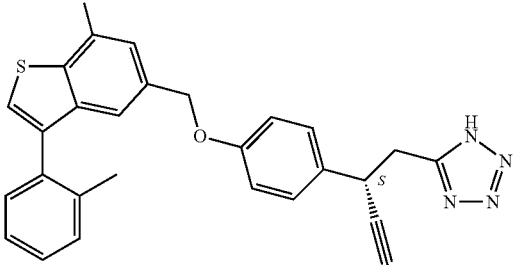 | 68 | (2S)-5-(2-(4-((7-Chloro-3-(4-methoxy-2-methylphenyl)benzo[b]thiophen-5-yl)methoxy)phenyl)pent-3-yn-1-yl)-1H-tetrazole |

TABLE 1-continued

| Structure | Cpd No. | Cpd Name |
|---|---|---|
| 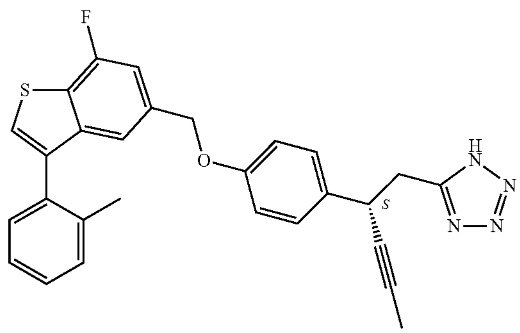 | 69 | (2S)-5-(2-(4-((7-Fluoro-3-(2-methylphenyl)benzo[b]thiophen-5-yl)methoxy)phenyl)pent-3-yn-1-yl)-1H-tetrazole |
| 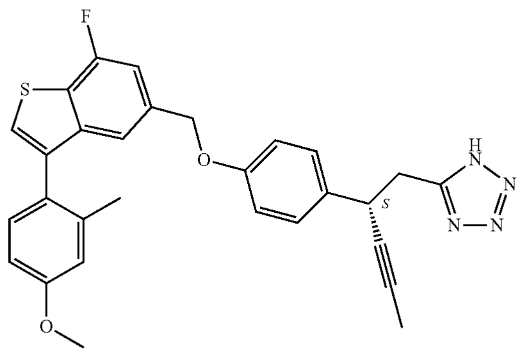 | 70 | (2S)-5-(2-(4-((7-Fluoro-3-(4-methoxy-2-methylphenyl)benzo[b]thiophen-5-yl)methoxy)phenyl)pent-3-yn-1-yl)-1H-tetrazole |

In a further embodiment, the invention is directed to a compound of Formula (I)

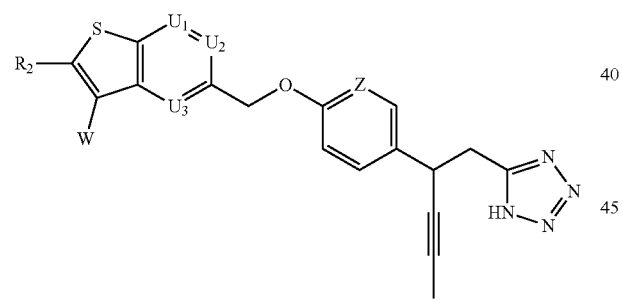

Formula (I)

selected from the group consisting of

Cpd 1, (2S)-5-(2-(4-((3-(2-Methylphenyl)benzo[b]thiophen-5-yl)methoxy)phenyl)pent-3-yn-1-yl)-1H-tetrazole;

Cpd 2, 5-((2S)-2-(4-((2-Chloro-3-(2-methylphenyl)benzo[b]thiophen-5-yl)methoxy)phenyl)pent-3-ynyl)-1H-tetrazole;

Cpd 3, 5-((2S)-2-(4-((2-Fluoro-3-(2-methylphenyl)benzo[b]thiophen-5-yl)methoxy)phenyl)pent-3-ynyl)-1H-tetrazole;

Cpd 4, (2S)-5-(2-(4-((3-(2-Bromophenyl)benzo[b]thiophen-5-yl)methoxy)phenyl)pent-3-yn-1-yl)-1H-tetrazole;

Cpd 5, (2S)-4-(5-((4-(1-(1H-tetrazol-5-yl)pent-3-yn-2-yl)phenoxy)methyl)benzo[b]thiophen-3-yl)-2-chloro-5-methylpyridine;

Cpd 6, (2S)-4-((4-(5-((4-(1-(1H-Tetrazol-5-yl)pent-3-yn-2-yl)phenoxy)methyl)benzo[b]thiophen-3-yl)-3-methylphenoxy)methyl)-4-hydroxytetrahydro-2H-thiopyran 1,1-dioxide;

Cpd 7, (2S)-4-(4-(5-((4-(1-(1H-Tetrazol-5-yl)pent-3-yn-2-yl)phenoxy)methyl)benzo[b]thiophen-3-yl)-3-methylphenoxy)-2-methylbutan-2-ol;

Cpd 8, (2S)-5-(2-(4-((3-(4-(2-Methoxyethoxy)-2-methylphenyl)benzo[b]thiophen-5-yl)methoxy)phenyl)pent-3-yn-1-yl)-1H-tetrazole;

Cpd 9, (2S)-5-(2-(4-((3-(2-Methyl-4-((tetrahydro-2H-pyran-4-yl)oxy)phenyl)benzo[b]thiophen-5-yl)methoxy)phenyl)pent-3-yn-1-yl)-1H-tetrazole;

Cpd 10, (2S)-5-(2-(4-((3-(3-(2-Methoxyethoxy)-2-methylphenyl)benzo[b]thiophen-5-yl)methoxy)phenyl)pent-3-yn-1-yl)-1H-tetrazole;

Cpd 11, (2S)-3-(5-((4-(1-(1H-Tetrazol-5-yl)pent-3-yn-2-yl)phenoxy)methyl)benzo[b]thiophen-3-yl)-2-methylpyridine;

Cpd 12, (2S)-3-((4-(5-((4-(1-(1H-Tetrazol-5-yl)pent-3-yn-2-yl)phenoxy)methyl)benzo[b]thiophen-3-yl)-3-methylphenoxy)methyl)-3-methylthietane 1,1-dioxide;

Cpd 13, (2S)-5-(2-(4-((3-(2-(Trifluoromethyl)phenyl)benzo[b]thiophen-5-yl)methoxy)phenyl)pent-3-yn-1-yl)-1H-tetrazole;

Cpd 14, (2S)-5-(2-(4-((3-(2-Methyl-4-(methylsulfonyl)phenyl)benzo[b]thiophen-5-yl)methoxy)phenyl)pent-3-yn-1-yl)-1H-tetrazole;

Cpd 15, (2S)-5-(2-(4-((3-(5-(2-Methoxyethoxy)-2-methylphenyl)benzo[b]thiophen-5-yl)methoxy)phenyl)pent-3-yn-1-yl)-1H-tetrazole;

Cpd 16, (2S)-5-(2-(4-((3-(2-Methyl-4-(3-(methyl sulfonyl)propoxy)phenyl)benzo[b]thiophen-5-yl)methoxy)phenyl)pent-3-yn-1-yl)-1H-tetrazole;

Cpd 17, (2S)-4-(4-(5-((4-(1-(1H-Tetrazol-5-yl)pent-3-yn-2-yl)phenoxy)methyl)benzo[b]thiophen-3-yl)-3-methylphenyl)tetrahydro-2H-thiopyran 1,1-dioxide;

Cpd 18, 4-(4-(5-((4-((2S)-1-(1H-Tetrazol-5-yl)pent-3-yn-2-yl)phenoxy)methyl)-2-methylbenzo[b]thiophen-3-yl)-3-methylphenoxy)tetrahydro-2H-thiopyran 1,1-dioxide;

Cpd 19, 5-(2S)-2-(4-((2-Methyl-3-(2-methylphenyl)benzo[b]thiophen-5-yl)methoxy)phenyl)pent-3-ynyl)-1H-tetrazole;

Cpd 20, (2S)-5-(2-(4-((3-(2,6-Dimethylphenyl)benzo[b]thiophen-5-yl)methoxy)phenyl)pent-3-yn-1-yl)-1H-tetrazole;

Cpd 21, (2S)-5-(5-(4-(1-(1H-Tetrazol-5-yl)pent-3-yn-2-yl)phenoxy)methyl)benzo[b]thiophen-3-yl)-2-(2-methoxyethoxy)-4-methylpyridine;

Cpd 22, (2S)-5-(2-(4-((3-(1-Methyl-1H-pyrazol-5-yl)benzo[b]thiophen-5-yl)methoxy)phenyl)pent-3-yn-1-yl)-1H-tetrazole;

Cpd 23, (2S)-5-(2-(4-((3-(1-Methyl-1H-1,2,4-triazol-5-yl)benzo[b]thiophen-5-yl)methoxy)phenyl)pent-3-yn-1-yl)-1H-tetrazole;

Cpd 24, (2S)-2-(5-((4-(1-(1H-Tetrazol-5-yl)pent-3-yn-2-yl)phenoxy)methyl)benzo[b]thiophen-3-yl)-3-methylpyrazine;

Cpd 25, (2S)-5-(5-((4-(1-(1H-Tetrazol-5-yl)pent-3-yn-2-yl)phenoxy)methyl)benzo[b]thiophen-3-yl)-4-methylpyrimidine;

Cpd 26, (2S)-2-(5-((4-(1-(1H-Tetrazol-5-yl)pent-3-yn-2-yl)phenoxy)-methyl)benzo[b]thiophen-3-yl)-5-(2-methoxyethoxy)-3-methylpyridine;

Cpd 27, (2S)-5-(2-(4-((3-(2,3-Dihydrobenzo[b][1,4]dioxin-5-yl)benzo[b]thiophen-5-yl)methoxy)phenyl)pent-3-yn-1-yl)-1H-tetrazole;

Cpd 28, (2S)-1-(4-(5-((4-(1-(1H-tetrazol-5-yl)pent-3-yn-2-yl)phenoxy)methyl)benzo[b]thiophen-3-yl)indolin-1-yl)propan-1-one;

Cpd 29, (2S)—N-(3-(5-((4-(1-(1H-tetrazol-5-yl)pent-3-yn-2-yl)phenoxy)methyl)benzo[b]thiophen-3-yl)-4-methylphenyl)methanesulfonamide;

Cpd 30, (2S)-5-(2-(4-((3-(2,2-dimethylchroman-5-yl)benzo[b]thiophen-5-yl)methoxy)phenyl)pent-3-yn-1-yl)-1H-tetrazole;

Cpd 31, 3-(4-(5-((4-(2S)-1-(1H-Tetrazol-5-yl)pent-3-yn-2-yl)phenoxy)methyl)benzo[b]thiophen-3-yl)-3-methylphenoxy)propane-1,2-diol;

Cpd 32, (2S)-5-(2-(4-((3-(2-Chlorophenyl)benzo[b]thiophen-5-yl)methoxy)phenyl)pent-3-yn-1-yl)-1H-tetrazole;

Cpd 33, (2S)-3-(5-((4-(1-(1H-Tetrazol-5-yl)pent-3-yn-2-yl)phenoxy)methyl)benzo[b]thiophen-3-yl)-5-(2-methoxyethoxy)-2-methylpyridine;

Cpd 34, 5-((2S)-2-(4-((2-Bromo-3-(2-methylphenyl)benzo[b]thiophen-5-yl)methoxy)phenyl)pent-3-ynyl)-1H-tetrazole;

Cpd 35, 5-((2S)-2-(4-((2-Iodo-3-(2-methylphenyl)benzo[b]thiophen-5-yl)methoxy)phenyl)pent-3-ynyl)-1H-tetrazole;

Cpd 36, 5-((2S)-2-(4-((2-Trifluoromethyl-3-(2-methylphenyl)benzo[b]thiophen-5-yl)methoxy)phenyl)pent-3-ynyl)-1H-tetrazole;

Cpd 37, (2S)-5-(2-(4-((3-Cyclopropyl-2-(trifluoromethyl)benzo[b]thiophen-5-yl)methoxy)phenyl)pent-3-yn-1-yl)-1H-tetrazole;

Cpd 38, 5-((2S)-2-(4-((2-Cyano-3-(2-methylphenyl)benzo[b]thiophen-5-yl)methoxy)phenyl)pent-3-yn-1-yl)-1H-tetrazole;

Cpd 39, 5-((2S)-2-(4-((2-(Methyl sulfonyl)-3-(2-methylphenyl)benzo[b]thiophen-5-yl)methoxy)phenyl)pent-3-yn-1-yl)-1H-tetrazole;

Cpd 40, (2R)-5-(1-(1H-Tetrazol-5-yl)pent-3-yn-2-yl)-2-((3-(2-methylphenyl)benzo[b]thiophen-5-yl)methoxy)pyridine;

Cpd 41, (2R)-5-(1-(1H-Tetrazol-5-yl)pent-3-yn-2-yl)-2-((3-(4-(2-methoxyethoxy)-2-methylphenyl)benzo[b]thiophen-5-yl)methoxy)pyridine;

Cpd 42, (2R)-5-(1-(1H-Tetrazol-5-yl)pent-3-yn-2-yl)-2-((3-(3-(2-methoxyethoxy)-2-methylphenyl)benzo[b]thiophen-5-yl)methoxy)pyridine;

Cpd 43, (2R)-4-(4-(5-(((5-(1-(1H-Tetrazol-5-yl)pent-3-yn-2-yl)pyridin-2-yl)oxy)methyl)-benzo[b]thiophen-3-yl)-3-methylphenoxy)-2-methylbutan-2-ol;

Cpd 44, (2S)-5-(2-(4-((2-Fluoro-3-(4-(2-methoxyethoxy)-2-methylphenyl)benzo[b]thiophen-5-yl)methoxy)phenyl)pent-3-yn-1-yl)-1H-tetrazole;

Cpd 45, (2S)-5-(2-(4-((2-Chloro-3-(4-(2-methoxyethoxy)-2-methylphenyl)benzo[b]thiophen-5-yl)methoxy)phenyl)pent-3-yn-1-yl)-1H-tetrazole;

Cpd 46, (2S)-5-(2-(4-((3-(4-(2-Methoxyethoxy)-2-methylphenyl)-2-methylbenzo[b]thiophen-5-yl)methoxy)phenyl)pent-3-yn-1-yl)-1H-tetrazole;

Cpd 47, 5-((2S)-2-(4-((3-(4-(2-Methoxyethoxy)-2-methylphenyl)-2-(trifluoromethyl)benzo[b]thiophen-5-yl)methoxy)phenyl)pent-3-yn-1-yl)-1H-tetrazole;

Cpd 48, 1-(5-((4-((2S)-1-(1H-Tetrazol-5-yl)pent-3-yn-2-yl)phenoxy)methyl)benzo[b]thiophen-3-yl)-2-methylpiperidine;

Cpd 49, (2S)-5-((4-(1-(1H-Tetrazol-5-yl)pent-3-yn-2-yl)phenoxy)methyl)-3-(2-methylphenyl)thieno[2,3-b]pyridine;

Cpd 50, (2S)-5-((4-(1-(1H-Tetrazol-5-yl)pent-3-yn-2-yl)phenoxy)methyl)-3-(4-methoxy-2-methylphenyl)thieno[2,3-b]pyridine;

Cpd 51, (2S)-5-((4-(1-(1H-Tetrazol-5-yl)pent-3-yn-2-yl)phenoxy)methyl)-3-(2-methylphenyl)thieno[2,3-c]pyridine;

Cpd 52, (2S)-5-((4-(1-(1H-Tetrazol-5-yl)pent-3-yn-2-yl)phenoxy)methyl)-3-(4-methoxy-2-methylphenyl)thieno[2,3-c]pyridine;

Cpd 53, (2S)-5-((4-(1-(1H-Tetrazol-5-yl)pent-3-yn-2-yl)phenoxy)methyl)-3-(2-methylphenyl)thieno[3,2-b]pyridine;

Cpd 54, (2S)-5-((4-(1-(1H-Tetrazol-5-yl)pent-3-yn-2-yl)phenoxy)methyl)-3-(4-methoxy-2-methylphenyl)thieno[3,2-b]pyridine;

Cpd 55, (2S)-5-(2-(4-((3-Cyclohexylbenzo[b]thiophen-5-yl)methoxy)phenyl)pent-3-yn-1-yl)-1H-tetrazole;

Cpd 56, (2S)-5-(2-(4-((3-Cyclopentylbenzo[b]thiophen-5-yl)methoxy)phenyl)pent-3-yn-1-yl)-1H-tetrazole;

Cpd 57, (2S)-5-(2-(4-((3-Cyclopropylbenzo[b]thiophen-5-yl)methoxy)phenyl)pent-3-yn-1-yl)-1H-tetrazole;

Cpd 58, (2S)-5-(2-(4-((3-Isopropylbenzo[b]thiophen-5-yl)methoxy)phenyl)pent-3-yn-1-yl)-1H-tetrazole;

Cpd 59, (2S)-5-(2-(4-((3-Propylbenzo[b]thiophen-5-yl)methoxy)phenyl)pent-3-yn-1-yl)-1H-tetrazole;

Cpd 60, (2S)-5-(2-(4-(Benzo[b]thiophen-5-ylmethoxy)phenyl)pent-3-yn-1-yl)-1H-tetrazole;

Cpd 61, (2RS)-5-(2-(4-((3-(2-Methylphenyl)benzo[b]thiophen-5-yl)methoxy)phenyl)pent-3-yn-1-yl)-1H-tetrazole;

Cpd 62, (2R)-5-(2-(4-((3-(2-Methylphenyl)benzo[b]thiophen-5-yl)methoxy)phenyl)pent-3-yn-1-yl)-1H-tetrazole;

Cpd 63, (2S)-5-(2-(4-((7-Methyl-3-(2-methylphenyl)benzo[b]thiophen-5-yl)methoxy)phenyl)pent-3-yn-1-yl)-1H-tetrazole;

Cpd 64, (2S)-5-(2-(4-((3-Butyl-7-methylbenzo[b]thiophen-5-yl)methoxy)phenyl)pent-3-yn-1-yl)-1H-tetrazole;

Cpd 65, (2S)-5-(2-(4-((3-Cyclopentyl-7-methylbenzo[b]thiophen-5-yl)methoxy)phenyl)pent-3-yn-1-yl)-1H-tetrazole;

Cpd 66, (2S)-5-(2-(4-((3-Cyclohexyl-7-methylbenzo[b]thiophen-5-yl)methoxy)phenyl)pent-3-yn-1-yl)-1H-tetrazole;

Cpd 67, (2S)-5-(2-(4-((7-Chloro-3-(2-methylphenyl)benzo[b]thiophen-5-yl)methoxy)phenyl)pent-3-yn-1-yl)-1H-tetrazole;

Cpd 68, (2S)-5-(2-(4-((7-Chloro-3-(4-methoxy-2-methylphenyl)benzo[b]thiophen-5-yl)methoxy)phenyl)pent-3-yn-1-yl)-1H-tetrazole;

Cpd 69, (2S)-5-(2-(4-((7-Fluoro-3-(2-methylphenyl)benzo[b]thiophen-5-yl)methoxy)phenyl)pent-3-yn-1-yl)-1H-tetrazole;

Cpd 70, (2S)-5-(2-(4-((7-Fluoro-3-(4-methoxy-2-methylphenyl)benzo[b]thiophen-5-yl)methoxy)phenyl)pent-3-yn-1-yl)-1H-tetrazole or a pharmaceutically acceptable salt form thereof.

For use in medicine, salts of compounds of Formula (I) refer to non-toxic "pharmaceutically acceptable salts." Other salts may, however, be useful in the preparation of compounds of Formula (I) or of their pharmaceutically acceptable salt forms thereof. Suitable pharmaceutically acceptable salts of compounds of Formula (I) include acid addition salts that can, for example, be formed by mixing a solution of the compound with a solution of a pharmaceutically acceptable acid such as, hydrochloric acid, sulfuric acid, fumaric acid, maleic acid, succinic acid, acetic acid, benzoic acid, citric acid, tartaric acid, carbonic acid or phosphoric acid. Furthermore, where the compounds of Formula (I) carry an acidic moiety, suitable pharmaceutically acceptable salts thereof may include alkali metal salts such as, sodium or potassium salts; alkaline earth metal salts such as, calcium or magnesium salts; and salts formed with suitable organic ligands such as, quaternary ammonium salts. Thus, representative pharmaceutically acceptable salts include acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide, and valerate.

Representative acids and bases that may be used in the preparation of pharmaceutically acceptable salts include acids including acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucoronic acid, L-glutamic acid, α-oxo-glutaric acid, glycolic acid, hippuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid and undecylenic acid; and bases including ammonia, L-arginine, benethamine, benzathine, calcium hydroxide, choline, deanol, diethanolamine, diethylamine, 2-(diethylamino)-ethanol, ethanolamine, ethylenediamine, N-methylglucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, sodium hydroxide, triethanolamine, tromethamine, and zinc hydroxide.

Embodiments of the present invention include prodrugs of compounds of Formula (I). In general, such prodrugs will be functional derivatives of the compounds that are readily convertible in vivo into the required compound. Thus, in the methods of treating or preventing embodiments of the present invention, the term "administering" encompasses the treatment or prevention of the various diseases, conditions, syndromes and disorders described with the compound specifically disclosed or with a compound that may not be specifically disclosed, but which converts to the specified compound in vivo after administration to a patient. Conventional procedures for the selection and preparation of suitable prodrug derivatives are described, for example, in "Design of Prodrugs", ed. H. Bundgaard, Elsevier, 1985.

Where the compounds according to embodiments of this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention. The skilled artisan will understand that the term compound as used herein, is meant to include solvated compounds of Formula (I).

Where the processes for the preparation of the compounds according to certain embodiments of the invention give rise to mixture of stereoisomers, these isomers may be separated by conventional techniques such as, preparative chromatography. The compounds may be prepared in racemic form, or individual enantiomers may be prepared either by enantiospecific synthesis or by resolution. The compounds may, for example, be resolved into their component enantiomers by standard techniques such as, the formation of diastereomeric pairs by salt formation with an optically active acid such as, (−)-di-p-toluoyl-d-tartaric acid and/or (+)-di-p-toluoyl-l-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

One embodiment of the present invention is directed to a composition, including a pharmaceutical composition, comprising, consisting of, and/or consisting essentially of the (+)-enantiomer of a compound of Formula (I) wherein said composition is substantially free from the (−)-isomer of said compound. In the present context, substantially free means less than about 25%, preferably less than about 10%, more preferably less than about 5%, even more preferably less than about 2% and even more preferably less than about 1% of the (−)-isomer calculated as $$\%(+)\text{-enantiomer} = \frac{(\text{mass}(+)\text{-enantiomer})}{(\text{mass}(+)\text{-enantiomer}) + (\text{mass}(-)\text{-enantiomer})} \times 100.$$

Another embodiment of the present invention is a composition, including a pharmaceutical composition, comprising, consisting of, and consisting essentially of the (−)-enantiomer of a compound of Formula (I) wherein said composition is substantially free from the (+)-isomer of said compound. In the present context, substantially free from means less than about 25%, preferably less than about 10%, more preferably less than about 5%, even more preferably less than about 2% and even more preferably less than about 1% of the (+)-isomer calculated as $$\%(-)\text{-enantiomer} = \frac{(\text{mass}(-)\text{-enantiomer})}{(\text{mass}(+)\text{-enantiomer}) + (\text{mass}(-)\text{-enantiomer})} \times 100.$$

During any of the processes for preparation of the compounds of the various embodiments of the present invention, it may be necessary and/or desirable to protect sensitive or reactive groups on any of the molecules concerned. This may be achieved by means of conventional protecting groups such as those described in *Protective Groups in Organic Chemistry*, Second Edition, J. F. W. McOmie, Plenum Press, 1973; T. W. Greene & P. G. M. Wuts, *Protective Groups in Organic Synthesis*, John Wiley & Sons, 1991; and T. W. Greene & P. G. M. Wuts, *Protective Groups in Organic Synthesis*, Third Edition, John Wiley & Sons, 1999. The protecting groups may be removed at a convenient subsequent stage using methods known from the art.

Even though the compounds of embodiments of the present invention (including their pharmaceutically acceptable salts and pharmaceutically acceptable solvates) can be administered alone, they will generally be administered in admixture with a pharmaceutically acceptable carrier, a pharmaceutically acceptable excipient and/or a pharmaceutically acceptable diluent selected with regard to the intended route of administration and standard pharmaceutical or veterinary practice. Thus, particular embodiments of the present invention are directed to pharmaceutical and veterinary compositions comprising compounds of Formula (I) and at least one pharmaceutically acceptable carrier, pharmaceutically acceptable excipient, and/or pharmaceutically acceptable diluent.

By way of example, in the pharmaceutical compositions of embodiments of the present invention, the compounds of Formula (I) may be admixed with any suitable binder(s), lubricant(s), suspending agent(s), coating agent(s), solubilizing agent(s), and combinations thereof.

Solid oral dosage forms such as, tablets or capsules, containing the compounds of the present invention may be administered in at least one dosage form at a time, as appropriate. It is also possible to administer the compounds in sustained release formulations.

Additional oral forms in which the present inventive compounds may be administered include elixirs, solutions, syrups, and suspensions; each optionally containing flavoring agents and coloring agents.

Alternatively, compounds of Formula (I) can be administered by inhalation (intratracheal or intranasal) or in the form of a suppository or pessary, or they may be applied topically in the form of a lotion, solution, cream, ointment or dusting powder. For example, they can be incorporated into a cream comprising, consisting of, and/or consisting essentially of an aqueous emulsion of polyethylene glycols or liquid paraffin. They can also be incorporated, at a concentration of between about 1% and about 10% by weight of the cream, into an ointment comprising, consisting of, and/or consisting essentially of a wax or soft paraffin base together with any stabilizers and preservatives as may be required. An alternative means of administration includes transdermal administration by using a skin or transdermal patch.

The pharmaceutical compositions of the present invention (as well as the compounds of the present invention alone) can also be injected parenterally, for example, intracavernosally, intravenously, intramuscularly, subcutaneously, intradermally, or intrathecally. In this case, the compositions will also include at least one of a suitable carrier, a suitable excipient, and a suitable diluent.

For parenteral administration, the pharmaceutical compositions of the present invention are best used in the form of a sterile aqueous solution that may contain other substances, for example, enough salts and monosaccharides to make the solution isotonic with blood.

For buccal or sublingual administration, the pharmaceutical compositions of the present invention may be administered in the form of tablets or lozenges, which can be formulated in a conventional manner.

By way of further example, pharmaceutical compositions containing at least one of the compounds of Formula (I) as the active ingredient can be prepared by mixing the compound(s) with a pharmaceutically acceptable carrier, a pharmaceutically acceptable diluent, and/or a pharmaceutically acceptable excipient according to conventional pharmaceutical compounding techniques. The carrier, excipient, and diluent may take a wide variety of forms depending upon the desired route of administration (e.g., oral, parenteral, etc.). Thus, for liquid oral preparations such as, suspensions, syrups, elixirs and solutions, suitable carriers, excipients and diluents include water, glycols, oils, alcohols, flavoring agents, preservatives, stabilizers, coloring agents and the like; for solid oral preparations such as, powders, capsules, and tablets, suitable carriers, excipients and diluents include starches, sugars, diluents, granulating agents, lubricants, binders, disintegrating agents and the like. Solid oral preparations also may be optionally coated with substances such as, sugars, or be enterically coated so as to modulate the major site of absorption and disintegration. For parenteral administration, the carrier, excipient and diluent will usually include sterile water, and other ingredients may be added to increase solubility and preservation of the composition. Injectable suspensions or solutions may also be prepared utilizing aqueous carriers along with appropriate additives such as, solubilizers and preservatives.

A therapeutically effective amount of a compound of Formula (I) or a pharmaceutical composition thereof includes a dose range from about 0.1 mg to about 3000 mg, or any particular amount or range therein, in particular from about 1 mg to about 1000 mg, or any particular amount or range therein, or, more particularly, from about 10 mg to about 500 mg, or any particular amount or range therein, of active ingredient in a regimen of about 1 to about 4 times per day for an average (70 kg) human; although, it is apparent to one skilled in the art that the therapeutically effective amount for a compound of Formula (I) will vary as will the diseases, syndromes, conditions, and disorders being treated.

For oral administration, a pharmaceutical composition is preferably provided in the form of tablets containing about 1.0, about 10, about 50, about 100, about 150, about 200, about 250, and about 500 milligrams of a compound of Formula (I).

Advantageously, a compound of Formula (I) may be administered in a single daily dose, or the total daily dosage may be administered in divided doses of two, three and four times daily.

Optimal dosages of a compound of Formula (I) to be administered may be readily determined and will vary with the particular compound used, the mode of administration, the strength of the preparation and the advancement of the disease, syndrome, condition or disorder. In addition, factors associated with the particular subject being treated, including subject gender, age, weight, diet and time of administration, will result in the need to adjust the dose to achieve an appropriate therapeutic level and desired therapeutic effect. The above dosages are thus exemplary of the average case. There can be, of course, individual instances wherein higher or lower dosage ranges are merited, and such are within the scope of this invention.

Compounds of Formula (I) may be administered in any of the foregoing compositions and dosage regimens or by means of those compositions and dosage regimens established in the art whenever use of a compound of Formula (I) is required for a subject in need thereof.

One embodiment of the present invention is directed to a pharmaceutical composition comprising 3-(4-((3-(2-Methylphenyl)benzo[b]thiophen-5-yl)methoxy)phenyl)hex-4-ynoic acid (compound 97) and at least one of a pharmaceutically acceptable carrier, a pharmaceutically acceptable excipient, and a pharmaceutically acceptable diluent.

Another embodiment of the present invention is directed to a pharmaceutical composition comprising (3S)-3-[4-[[3-(2-Methylphenyl)benzo[b]thiophen-5-yl]methoxy]phenyl]hex-4-ynoic acid (compound 2) and at least one of a pharmaceutically acceptable carrier, a pharmaceutically acceptable excipient, and a pharmaceutically acceptable diluent.

As GPR40 agonists, the compounds of Formula (I) are useful in methods for treating or preventing a disease, a syndrome, a condition or a disorder in a subject, including an animal, a mammal and a human in which the disease, the syndrome, the condition or the disorder is affected by the modulation, including agonism, of the GPR40 receptor. Such methods comprise, consist of and/or consist essentially of administering to a subject, including an animal, a mammal, and a human, in need of such treatment or prevention, a therapeutically effective amount of a compound, salt or solvate of Formula (I).

In another embodiment, the present invention is directed to a compound of Formula (I) for use in the treatment of a disorder affected by the agonism of GPR40 receptor selected from the group consisting of Type 2 diabetes mellitus, obesity, obesity related disorders, impaired glucose tolerance, insulin resistance, metabolic syndrome, diabetic nephropathy, other cardiovascular risk factors such as hypertension and cholesterol/lipids, osteoporosis, inflammation and eczema; preferably, Type II diabetes mellitus, metabolic syndrome, and impaired glucose tolerance; more preferably, Type II diabetes mellitus or impaired glucose tolerance.

In another embodiment, the present invention is directed to a compound of Formula (I) for use in the treatment of Type 2 diabetes mellitus.

General Synthetic Methods

Representative compounds of the present invention can be synthesized in accordance with the general synthetic methods described below and illustrated in the schemes and examples that follow. Since the schemes are an illustration, the invention should not be construed as being limited by the chemical reactions and conditions described in the schemes and examples. The various starting materials used in the schemes and examples are commercially available or may be prepared by methods well within the skill of persons versed in the art. The variables are as defined herein.

Abbreviations used in the instant specification, particularly the schemes and examples, are as follows:

ADDP azodicarboxylic acid dipiperidide
aq aqueous
Boc tert-butoxycarbonyl
DBAD di-tert-butyl azodicarboxylate
DBU 1,8-diazabicyclo[5.4.0]undec-7-ene
DCE 1,2-dichloroethane
DCM dichloromethane
DEA diethylamine
DEAD diethyl azodicarboxylate
DIAD diisopropyl azodicarboxylate
DIBAL-H diisobutylaluminum hydride
DIEA diisopropylethylamine
DMA dimethylacetamide
DMAP 4-dimethylaminopyridine
DME ethylene glycol dimethyl ether
DMF dimethylformamide
DMSO methyl sulfoxide
eq. equivalents
Et ethyl
EtOAc ethyl acetate
h hour(s)
HATU O-(7-azabenzotriazol-1-yl)-N,N,N',N'-tetramethyluronium hexafluorophosphate
HBTU 2-(1H-Benzotriazole-1-yl)-1,1,3,3-tetramethyluronium hexafluorophosphate)
HCl hydrochloric acid
HPLC high performance liquid chromatography
LAH lithium aluminum hydride
LC/MS high pressure liquid chromatography with mass spectrometry
mCPBA 3-chloroperbenzoic acid
Me methyl
MeCN acetonitrile
MeOH methyl alcohol
mg milligram
MOM methoxymethyl
MSCl methanesulfonyl chloride
NBS N-bromosuccinimide
NCS N-chlorosuccinimide
NIS N-iodosuccinimide
NMP N-methyl-2-pyrrolidone
$PdCl_2(dppf).CH_2Cl_2$ 1,1'-bis(diphenylphosphino)ferrocene-palladium(II)dichloride dichloromethane complex)
$Pd_2(dba)_3$ tris(dibenzylideneacetone)dipalladium(0)
rt room temperature
Ru-Phos 2-dicyclohexylphosphino-2',6'-diisopropoxybiphenyl
satd. saturated
S-Phos 2-dicyclohexylphosphino-2',6'-dimethoxybiphenyl
TBSCl tert-butyldimethylsilyl chloride
TEA triethylamine
TFA trifluoroacetic acid
THF tetrahydrofuran
THP tetrahydropyranyl
wt. weight Scheme A illustrates a method for the preparation of certain compounds of Formula (I) of the present invention.

Scheme A
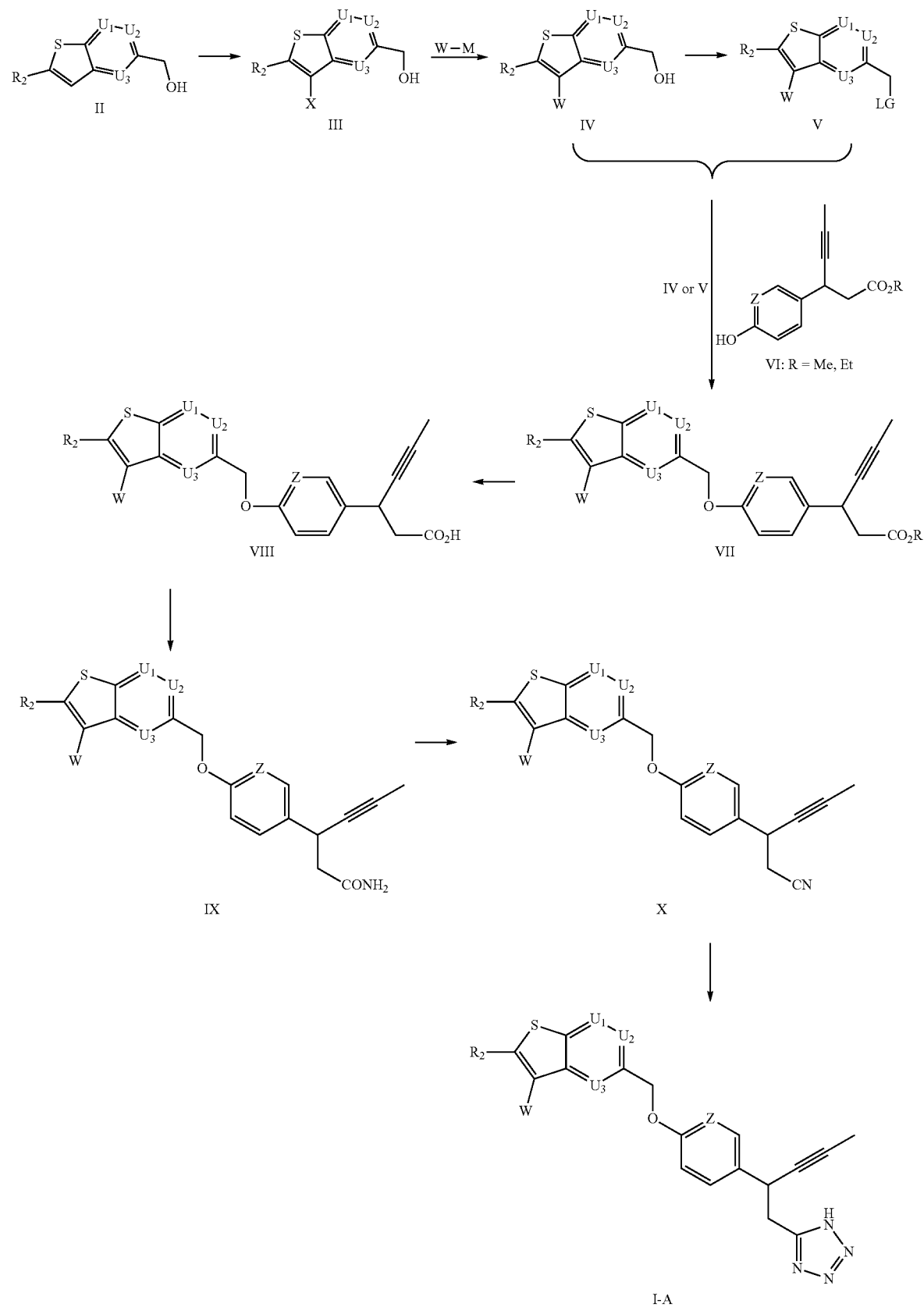

Certain compounds of Formula (I-A) may be synthesized as outlined by the general synthetic route illustrated in Scheme A. 5-Hydroxymethylbenzothiophene II may be treated with a halogenating reagent such as NBS, NIS in a suitable solvent such as DCM, DCE, $CCl_4$, THF, dioxane, DMF and the like, or, with $Br_2$ in HOAc, at a temperature preferably in the range of from about 0 and 50° C. to provide a 3-halogenated benzothiophene of formula III wherein X is bromo or iodo. The halogenated benzothiophene of formula III may be reacted with a compound of formula W-M wherein W is as defined herein, under suitable coupling conditions, to yield the corresponding coupling product of formula IV. A compound of formula W-M is chosen wherein W may be substituted aryl groups such as $(R_3)(R_5)$-G, heteroaryl groups as defined above or alkyl or cycloalkyl groups and M may be (a) a boronic acid to form a compound of formula W—$B(OH)_2$; (b) a suitably selected boronic ester such as pinacolatoboryl, neopentylglycolatoboryl, or the like; (c) a suitably selected trialkylstannyl such as tri(n-butyl)tin, or the like; (d) a suitably selected trialkylsilyl such as triallylsilyl, or the like; (e) a suitably selected aryldialkylsilyl such as 2-(hydroxymethyl)phenyldimethylsilyl, or the like; or (f) a suitably selected organo zinc reagent such as W—ZnX wherein X is a halogen such as chloro, bromo, or iodo.

For example, a compound of formula W-M, wherein M is preferably —$B(OH)_2$ or a suitably selected boronic ester, may be reacted with a compound of formula III under Suzuki coupling conditions, more particularly in the presence of a suitably selected palladium catalyst selected from palladium (II) acetate, palladium (II) chloride, bis(acetonitrile)-dichloro-palladium(II), allylpalladium (II) chloride dimer, tris(dibenzylidineacetone)dipalladium (0) ($Pd_2(dba)_3$), 2-(di-tert-butylphosphino)biphenyl, dichloro-bis(di-tert-butylphenylphosphine)-palladium (II), [1,1'-bis-(diphenylphosphino)-ferrocene]-palladium (II) dichloride dichloromethane adduct ($PdCl_2$(dppf).DCM), tetrakis(triphenylphosphine) palladium(0) ($Pd(PPh_3)_4$), (1,1'-bis(di-tert-butylphosphino)ferrocene palladium (II) chloride, and the like; optionally in the presence of a suitably selected ligand such as triphenylphosphine, tri-o-tolylphosphine, tributylphosphine, tri(tert-butyl)-phosphine, tricyclohexylphosphine, 1,1'-bis(diphenylphosphino)-ferrocene, 2-(dicyclohexylphosphino)-2',4',6'-tri-i-propyl-1,1'-biphenyl, S-Phos, Ru-Phos, bis[2-(diphenyl-phosphino)phenyl]ether, 2-dicyclohexylphosphino-2',6'-dimethoxybiphenyl, tris(2-furyl)phosphine, 1-butyl-3-methylimidazolium hexafluorophosphate, or the like; in the presence of a suitably selected inorganic base such as cesium carbonate, potassium carbonate, sodium carbonate, cesium fluoride, potassium fluoride, tetrabutylammonium fluoride, potassium tert-butoxide, sodium tert-butoxide, sodium hydroxide, sodium bicarbonate; or potassium phosphate; preferably, sodium carbonate; in a suitably selected solvent such as ethanol, THF, DMF, toluene, benzene, DME, $H_2O$, 1,4-dioxane, and the like, or a combination thereof; at a temperature ranging from about rt to about 180° C.

A compound of formula IV may be reacted under Mitsunobu conditions (for a review, see: Mitsunobu, O. *Synthesis* (1981), 1-28) with compounds of formula VI in the presence of triphenylphosphine, tri-n-butylphosphine, tri-tert-butylphosphine, or a resin-bound triphenylphosphine equivalent such as PS-$PPh_3$; and an azido coupling reagent such as DIAD, ADDP, DBAD, DEAD, or the like; in an organic solvent such as THF, MeCN, toluene, N,N-DMA, or the like; at a temperature preferably in the range of from about 25 to 100° C., to yield a compound of formula VII.

Alternatively, the alcoholic function of a compound of formula IV may be converted to a suitable leaving group (LG) such as chloro, bromo, iodo, tosylate, mesylate, nosylate, or the like, (March, J. *Advanced Organic Chemistry. Reactions, Mechanisms and Structure*, $2^{nd}$ ed.; McGraw-Hill Co.: New York, 1977; pp 326) to form a compound of formula V, which may then react with a compound of formula VI in the presence of a suitable base to provide a compound of formula VII. For example, treatment of a compound of formula IV with a halogenating agent such as oxalyl chloride, oxalyl bromide, thionyl chloride, thionyl bromide, $Ph_3P.Br_2$, $PBr_3$, or the like; or with a sulfonyl halide such as tosyl chloride, mesyl chloride, nosyl chloride, or the like; in the presence of a base such as $K_2CO_3$, $Cs_2CO_3$, KOH, NaH, or the like; in a solvent such as NMP, DMF, THF, or the like; at a temperature preferably in the range of from about 25 to 150° C. may provide a compound of formula V. Reaction of a compound of formula V with a compound of formula VI in the presence of a suitable base such as $K_2CO_3$, $Cs_2CO_3$, KOH, NaH, or the like, in a solvent such as NMP, DMF, THF, or the like; at a temperature preferably in the range of from about 25 to 150° C.; may provide a compound of formula VII.

One skilled in the art will recognize that for the preparation of certain compounds of the present invention, the order in which the above transformations are carried out to provide compounds of formula VII may be reversed. For example, a compound of formula VI may be reacted with a compound of formula III or a derivative thereof, and subsequently reacted with a compound of formula W-M to provide a compound of formula VII.

Hydrolysis of the ester functionality of a compound of formula VII may be effected under a variety of conditions to provide a compound of formula VIII (such as described in T. W. Greene & P. G. M. Wuts, *Protective Groups in Organic Synthesis*, $3^{rd}$ ed.; John Wiley & Sons, Inc.: New York, 1999). For example, treatment of a compound of formula VII with a base such as NaOH, LiOH, KOH, CsOH, or the like; in a solvent such as THF, EtOH, MeOH, a dioxane and water mixture, or the like, or mixtures thereof; at a temperature in the range of from about 25 to 100° C.; may provide a compound of formula VIII. The preferred method for this transformation includes the treatment of a compound of formula VII with an aqueous base such as NaOH or LiOH; in a solvent mixture such as THF/MeOH; at about room temperature.

A carboxylic acid of formula VIII may be converted to its corresponding nitrile of formula X following conventional methods available in the scientific literature. A preferred method for this transformation includes conversion of an acid of formula VIII to its corresponding primary amide of formula IX, followed by the dehydration of the latter to the corresponding nitrile of formula X. The conversion of an acid of formula VIII to the corresponding primary amide of formula IX includes, but is not limited to, reaction with ammonia or an ammonia equivalent under suitable coupling conditions, in the presence of one or more suitable catalysts or activators. A preferred method for this transformation is reaction of a carboxylic acid with ammonium chloride, in the presence of a coupling agent such as HBTU, HATU, or the like; in a solvent such as THF, DCM, DMF, or the like; at a temperature in the range of from about −20 to 50° C. Alternatively, in a two-stage process, a carboxylic acid of formula VIII may be converted to its corresponding acid chloride by treatment with oxalyl chloride, thionyl chloride, or the like, followed by treatment with ammonia, to provide the corresponding amide of formula IX. One of ordinary skill in the art will recognize that there are a variety of reagents and reaction conditions available for the dehydration of the primary amides to corresponding nitriles. A preferred method for this transformation includes treatment of a compound of formula IX with triflic anhydride as a dehydrating reagent, in the presence of a base, such as TEA, DIEA, or the like; in a solvent such as DCM, DCE, or the like; at a temperature in the range of from about −20 to 50° C., preferably at a temperature in the range of from about 0° C. to 5° C. The addition of azide ion to the nitrile is a convenient way to obtain a desired tetrazole of Formula I-A from a compound of formula X.

It is understood that the chemical literature is replete with methods and protocols to perform this transformation. The addition of a silyl azide, such as $Me_3SiN_3$, in the presence of a suitable catalyst such as $Bu_2SnO$; in a solvent such as toluene or xylene; at an elevated temperature, preferably in the range of from about 70 to 130° C.; is a preferred method for carrying out this conversion. It should be understood that certain compounds of formulas W-M, IV, V, or VII, W may contain functionalities that may optionally bear a suitable functional protecting group (P) (see *Protective Groups in Organic Chemistry*, J. F. W. McOmie, Ed.; Plenum Press: 1973; and T. W. Greene & P. G. M. Wuts, *Protective Groups in Organic Synthesis*, 3$^{rd}$ ed.; John Wiley & Sons, Inc.: New York, 1999). In such cases where the $R_3$ substituent contains one or more amino groups, suitable protecting groups such as Boc, Cbz, or the like, may be incorporated, which may subsequently be removed under appropriate conditions known to those skilled in the art. For example, Boc-protected amines may be deprotected under acidic conditions using reagents such as HCl, TFA, and the like. Likewise, Cbz-protected amines may be deprotected under acidic conditions or hydrogenolysis. In the case where an $R_3$ substituent contains one or more carboxyl groups, suitable protecting groups such as methyl, ethyl and t-butyl esters, or the like, may be incorporated, which may subsequently be removed under acidic conditions using HCl, TFA, or the like. In the case where $R_3$ is substituted with one or more hydroxy groups, suitable protecting groups such as MOM, THP, t-butyl ethers, acetonides (for 1,2-dihydroxylated substituents), or the like, may be incorporated, and subsequently removed under acidic conditions such as HCl, TFA, or the like. The unmasked functionalities generated by deprotection may be subjected to further chemical transformations according to methods known in the art, to provide additional derivatives of Formula I-A.

Compounds of formula X may be obtained by an alternate route, as illustrated in general Scheme B, by the incorporation of a hydroxyarylpropionitrile of formula XI in place of a hydroxyarylpropionic ester of formula VI. Thus, compounds of formula X may be obtained directly by suitable reaction with a compound of formulas IV or V, using methods described in Scheme A. Alternatively, incorporation of a hydroxyarylpropionitrile of formula XI may precede the incorporation of a compound of formula W-M. Thus, reaction of a hydroxyarylpropionitrile of formula XI with a compound of formula III under Mitsunobu conditions, as described above, may provide a compound of formula XII. These, in turn, may be reacted with a compound of formula W-M to provide a compound of formula X.

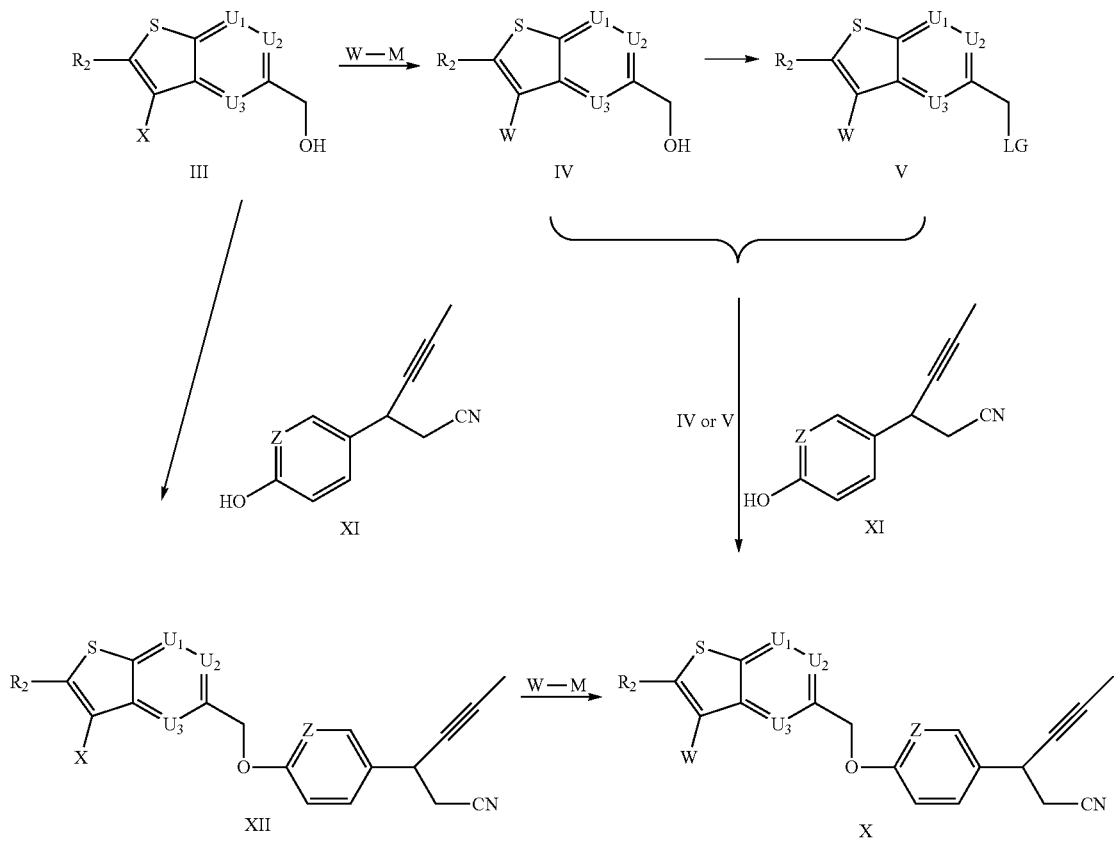

Scheme B

In certain cases, a compound of formula IV of the present invention may be prepared from an alternative starting material, wherein either an aldehyde or an ester functionality may serve as a precursor for the hydroxymethyl group, as illustrated in Scheme C.

LAH, $B_2H_6$, DIBAL-H, $NaCNBH_3$, $AlH_3$, $LiAlH(O\text{-}t\text{-}Bu)_3$, $KBH(O\text{-}i\text{-}Pr)_3$, or the like; preferably $NaBH_4$ or $B_2H_6$, in a solvent such as THF, ether, dioxane, MeOH, EtOH, or the like; at a temperature preferably in the range of from about 0 to 75° C.; to provide the corresponding benzylic alcohol of Scheme C

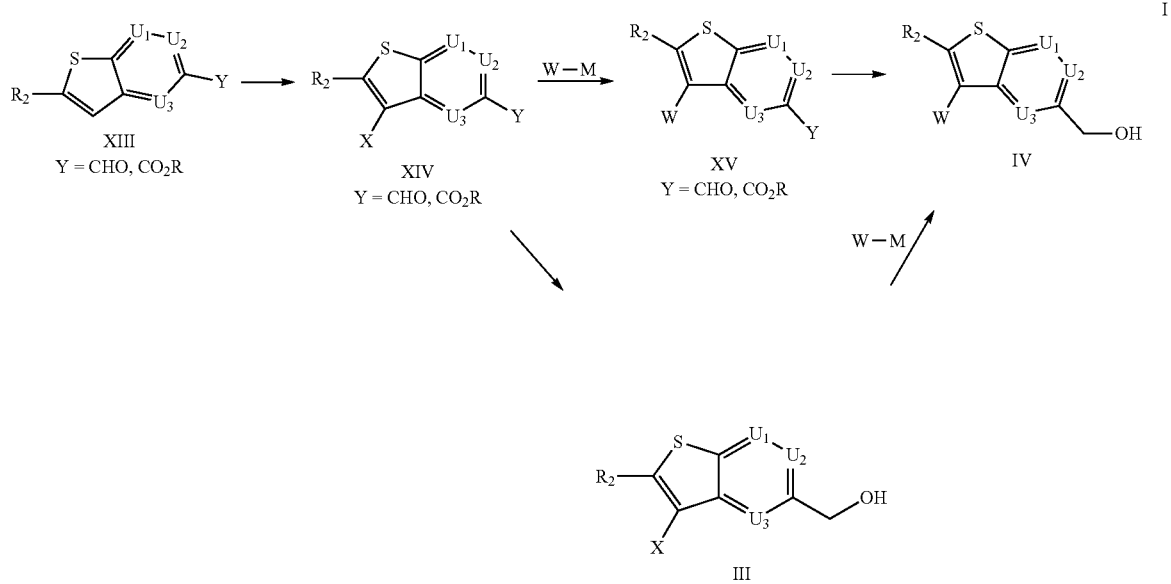

In such cases, a compound of formula XIII may be halogenated to provide a compound of formula XIV, which in turn may be converted to a compound of formula XV via a coupling reaction with a compound of formula W-M, using the methods outlined in Scheme A. The ester or aldehyde functionality of a compound of formula XV may be reduced upon treatment with a suitably selected reducing agent (as described in Larock, R. C. *Comprehensive Organic Transformations. A Guide to Functional Group Preparations*, 2$^{nd}$ ed.; Wiley-VCH: New York, 1999; pp 61), such as $NaBH_4$, formula IV. In certain cases, the order of these transformations may be reversed, such that the reduction of a compound of formula XIV to afford a compound of formula III precedes the coupling reaction with a compound of formula W-M.

In certain cases, a compound of formula IV of the present invention may be prepared by an alternative cross-coupling strategy, as illustrated in Scheme D.

Scheme D

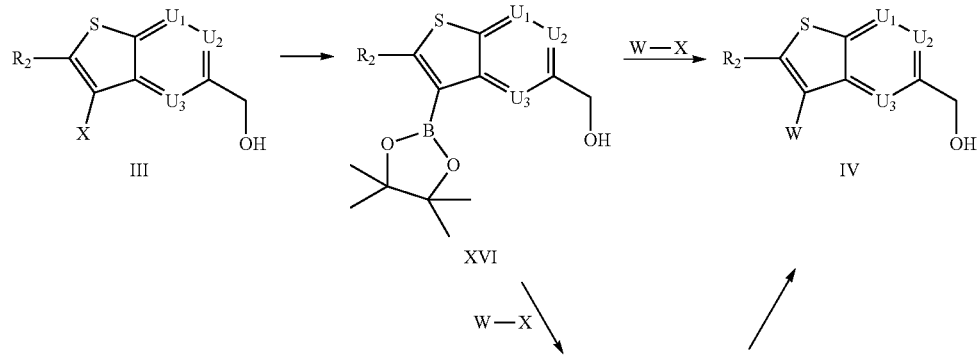

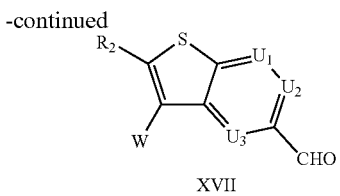

XVII

Under Suzuki coupling conditions as previously described in Scheme A, a compound of formula III may be reacted with bis(pinacolato)diboron to provide the corresponding borolane of formula XVI. A compound of formula XVI may, in turn, be reacted with an aromatic halide of formula W—X, wherein W is substituted aryl or heteroaryl and X is as defined in Scheme A, to provide a compound of formula IV directly. In certain cases, this coupling reaction may afford the corresponding aldehydic compound of formula XVII, which upon treatment with a suitable reducing agent, using methods described in Scheme C, may provide an alcohol of formula IV.

Certain compounds of formula IV of the present invention in which W is $(R_3)(R_5)G$ and $R_3$ is —$OR_{4e}$ may be prepared as illustrated in Scheme E. As defined herein, $R_{4e}$ is $R_4$ wherein the hydroxy-substituted $R_4$ substituents are suitably protected with a conventional hydroxy protecting group.

Treatment of a compound of formula III with a compound of formula $(R_{4e}O)(R_5)G$-M, where G is phenyl or pyridyl, $R_5$ is methyl and M is as defined in Scheme A, under coupling conditions previously described may provide a compound of formula IVe directly. Alternatively, a compound of formula III may be reacted with a compound of formula $(HO)(R_5)G_e$-M wherein $G_e$ is phenyl or pyridyl, and M is preferably a boronic acid or boronic ester, under suitable coupling conditions as previously described, to provide the corresponding coupling product of formula IVb. Alkylation of a compound of formula IVb with a compound of formula $R_{4e}$-LG, where LG is a suitable leaving group as previously described, in the presence of a base such as $K_2CO_3$, $Cs_2CO_3$, KOH, NaH, or the like; in a solvent such as NMP, DMF, THF, or the like; at a temperature preferably in the range of from about 25 to 150° C.; may provide a compound of formula IVe.

Scheme E

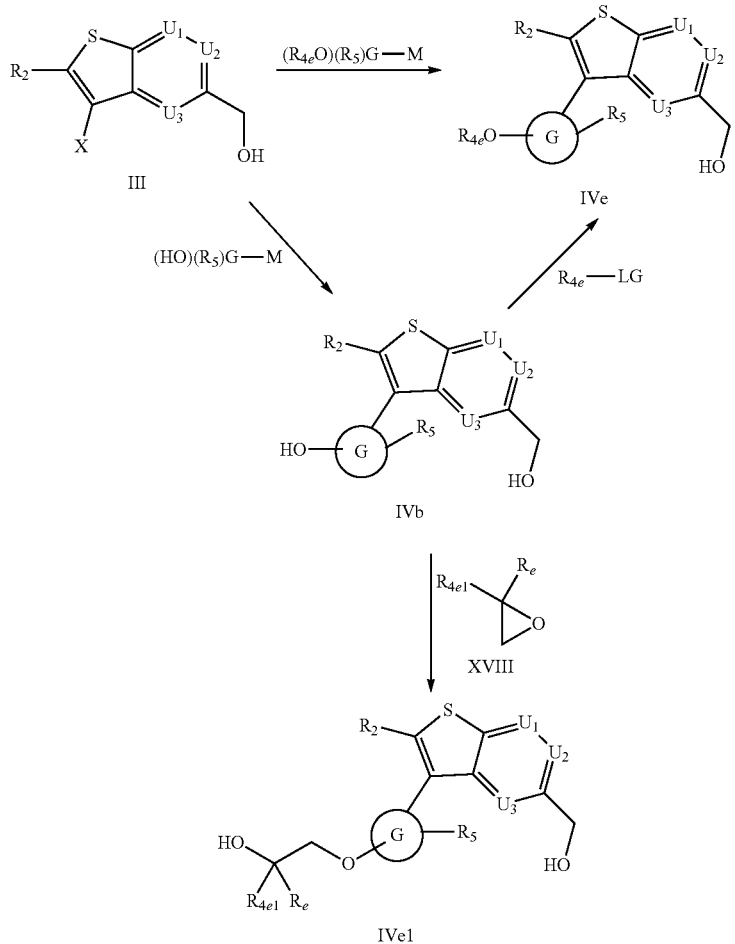

Alternatively, a compound of formula IVb may be alkylated by reaction with an epoxide of formula XVIII, wherein $R_e$ is hydrogen and $R_{4e1}$ is defined as $C_{1-6}$alkyl, $C_{3-7}$cycloalkyl, or $C_{1-3}$alkoxy($C_{1-8}$)alkyl, to provide a compound of formula IVe1. Similarly, a compound of formula IVb may be alkylated by reaction with an epoxide of formula XVIII, wherein $R_e$ and $R_{4e1}$ may be taken together to form a spirofused 1,1-dioxidotetrahydro-2H-thiopyran-4-yl, to provide additional compounds of formula IVe1. The reaction with an epoxide of formula XVIII is preferably carried out in the presence of a base such as $K_2CO_3$, $Cs_2CO_3$, KOH, or the like; in a solvent such as NMP, DMF, THF, or the like; at a temperature preferably in the range of from about 25 to 125° C.

Alternatively, certain compounds of formula IV of the present invention in which W is $(R_3)(R_5)G$, G is phenyl or pyridyl, $R_3$ is —$OR_{4f}$ and $R_5$ is Me or $CF_3$ may be prepared as illustrated in Scheme F. As defined herein, $R_{4f}$ is $R_4$ wherein the hydroxy-substituted $R_4$ substituents are suitably protected with a conventional hydroxy protecting group.

Scheme F

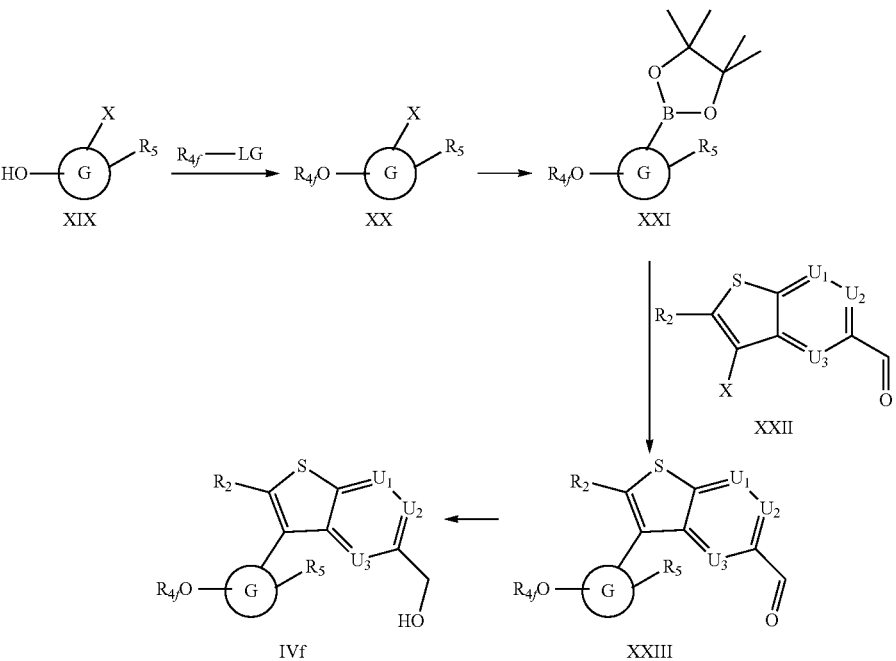

Alkylation of a phenolic compound of formula XIX with a compound of formula $R_{4f}$-LG, where LG is a suitable leaving group as previously described, in the presence of a base such as $K_2CO_3$, $Cs_2CO_3$, KOH, NaH, or the like; in a solvent such as NMP, DMF, THF, or the like; at a temperature preferably in the range of from about 25° C. to 150° C.; may provide a compound of formula XX. Treatment of a compound of formula XX with bis(pinacolato)diboron under Suzuki coupling conditions, as defined in Scheme A, may provide the corresponding borolane of formula XXI. A borolane of formula XXI may be reacted with a benzothiophene aldehyde of formula XXII under Suzuki coupling conditions, as defined in Scheme A, to provide an arylated benzothiophene aldehyde of formula XXIII, which in turn may be reduced upon treatment with a suitably selected reducing agent, as described in Scheme C, to provide the corresponding benzylic alcohol of formula IVf.

Certain compounds of formula VII of the present invention in which W is $(R_3)(R_5)G$, G is phenyl, pyrazolyl or pyridyl and $R_3$ is —OH, $CF_3$ or —$OR_4$ may be prepared as illustrated in Scheme G.

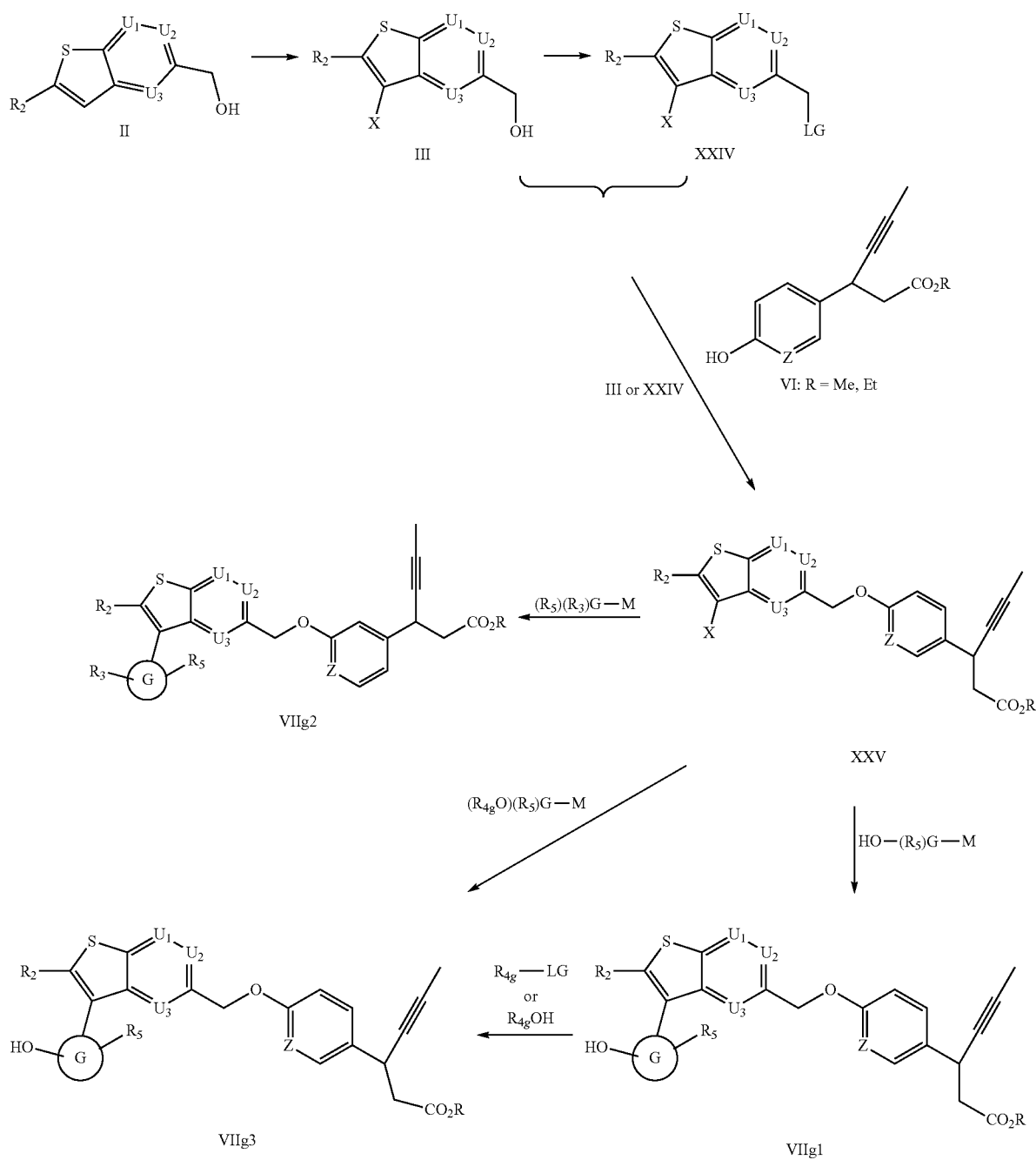

Scheme G

A compound of formula III may be reacted with a compound of formula VI directly under Mitsunobu conditions, as defined in Scheme A to provide a compound of formula XXV. Alternatively, a compound of formula III may be converted to a compound of formula XXIV, wherein LG is a suitable leaving group as previously described, and reacted with a phenol of formula VI in the presence of a suitable base as previously described to provide a compound of formula XXV. Reaction of a compound of formula XXV with a compound of formula $(R_5)(R_3)G$—M, using the methods described in Scheme A, provides a compound of formula VIIg2. In instances wherein $R_3$ is hydroxy, this reaction provides a compound of formula VIIg1. A compound of formula VIIg1 may be reacted under Mitsunobu conditions as previously described with a compound of formula $R_4OH$, or may be reacted with a compound of formula $R_4$-LG in the presence of a suitable base as previously described, to provide a compound of formula VIIg3. Alternatively, a compound of formula XXV may be reacted with a compound of formula $(R_4O)(R_5)G$-M to provide a compound of formula VIIg3 directly.

Certain compounds of formula IV in which $R_2$ is chloro, bromo, fluoro, iodo, trifluoromethyl, cyano, or methanesulfonyl may be prepared by the general route illustrated in Scheme H.

Scheme H

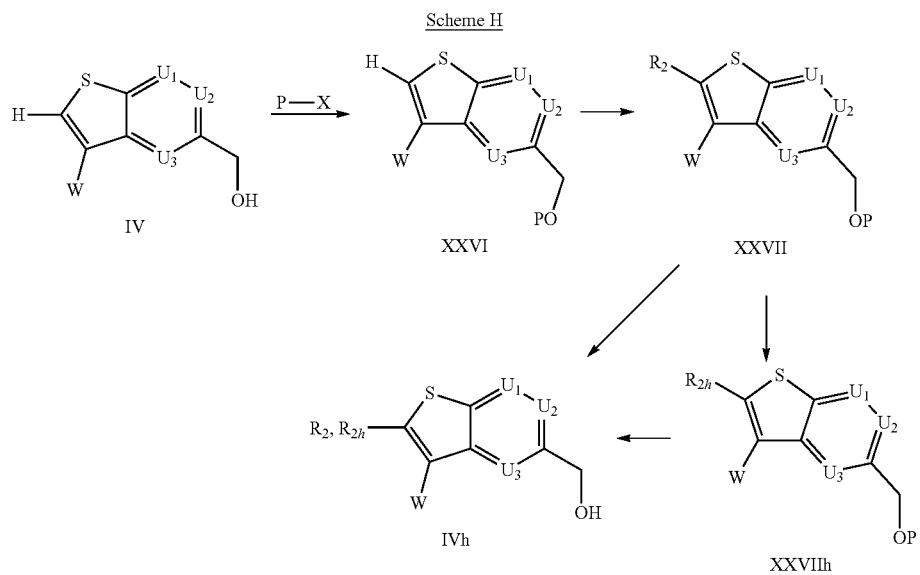

Protection of the hydroxy functionality of a compound of formula IV with a suitable protecting group, preferably a silyl protecting group such as tert-butyldimethylsilyl, may provide a compound of formula XXVI. Lithiation of a compound of formula XXVI, using an alkyl lithium reagent such as n-BuLi, or a lithium amide such as LDA, in an ethereal solvent such as THF, at a temperature at less than 0° C., preferably at about −78° C., followed by treatment with a suitable electrophile, such as iodomethane, NCS, NBS, I$_2$, N-fluoro-N-(phenylsulfonyl)benzenesulfonamide, or triisopropoxyborane, may provide a compound of formula XXVII, wherein R$_2$ is Me, Cl, Br, I, F and B(OH)$_2$, respectively. Deprotection of a compound of formula XXVII provides the corresponding compound of formula IVg. In some instances, using methods known in the art, a compound of formula XXVII may be further transposed to a compound of formula XXVIIh. For example, a compound of formula XXVII, wherein R$_2$ is bromo, may be converted to a compound of formula XXVIIh, where R$_{2h}$ is CN, CF$_3$ or SO$_2$Me. Similarly, a compound of formula XXVII, wherein R$_2$ is B(OH)$_2$ may also be converted to a compound of formula XXVIIh, where R$_{2h}$ is CF$_3$.

Certain compounds of formula IV wherein W is

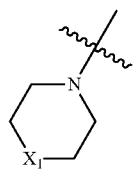

may be prepared by the general route illustrated in Scheme I.

Scheme I

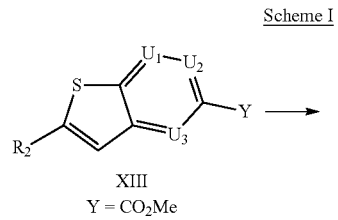

XIII
Y = CO$_2$Me

-continued

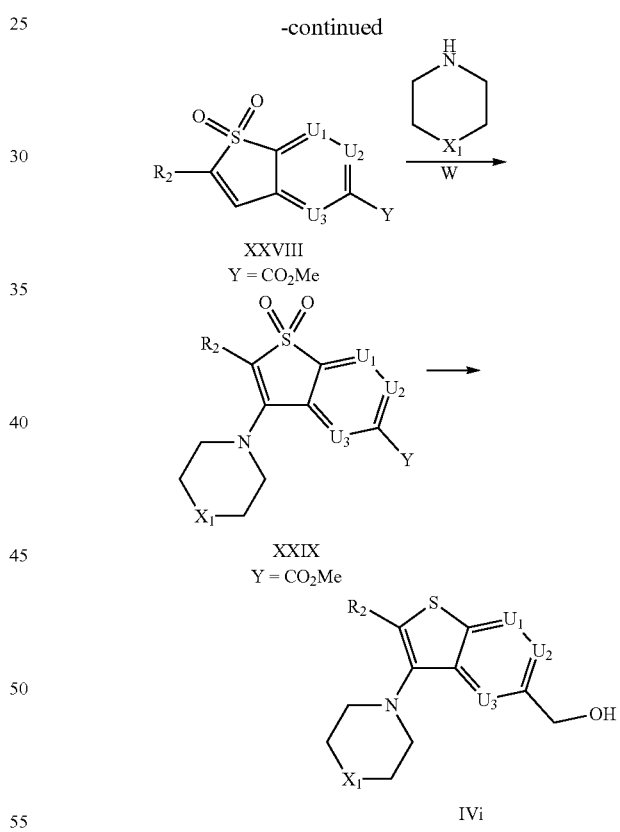

Oxidation of a compound of formula XIII, using methods well known in the art, may provide a compound of formula XXVIII. Preferably, this oxidation is carried out with aqueous hydrogen peroxide in a suitable co-solvent such as DCM or the like, in the presence of an acid, such as TFA, at ambient temperature. Reaction of a compound of formula XXVIII with a secondary amine of formula Wi, in a solvent such as toluene or the like, at an elevated temperature, preferably at about 120° C., may provide a compound of formula XXIX. Dual reduction of the sulfone and ester functionalities of a compound of formula XXIX may be effected using a suitable reducing agent as described in Scheme C, to provide a compound of formula IVi. Preferably, this reduction is carried out using DIBAL-H, in a solvent or solvent combination selected from THF or DCM, or the like, at a reaction temperature in the range of from about −20 to 40° C., preferably in the range of from about 0° C. to rt.

Certain compounds of Formula I-A may be synthesized as outlined by the general synthetic route illustrated in Scheme J.

in the presence of a suitable base, such as DIEA, in a suitable reaction solvent, such as DMF at a temperature in the range of from about 0 to 100° C., preferably at ambient temperature. A compound of formula XXXII may be converted to the corresponding tetrazole compound of formula XXXIII in a two-stage process by way of the in situ-generated iminochloride. For example, treatment of a compound of formula XXXII with a chlorinating agent such as $PCl_5$ in the presence of an amine such as pyridine, in a suitable solvent

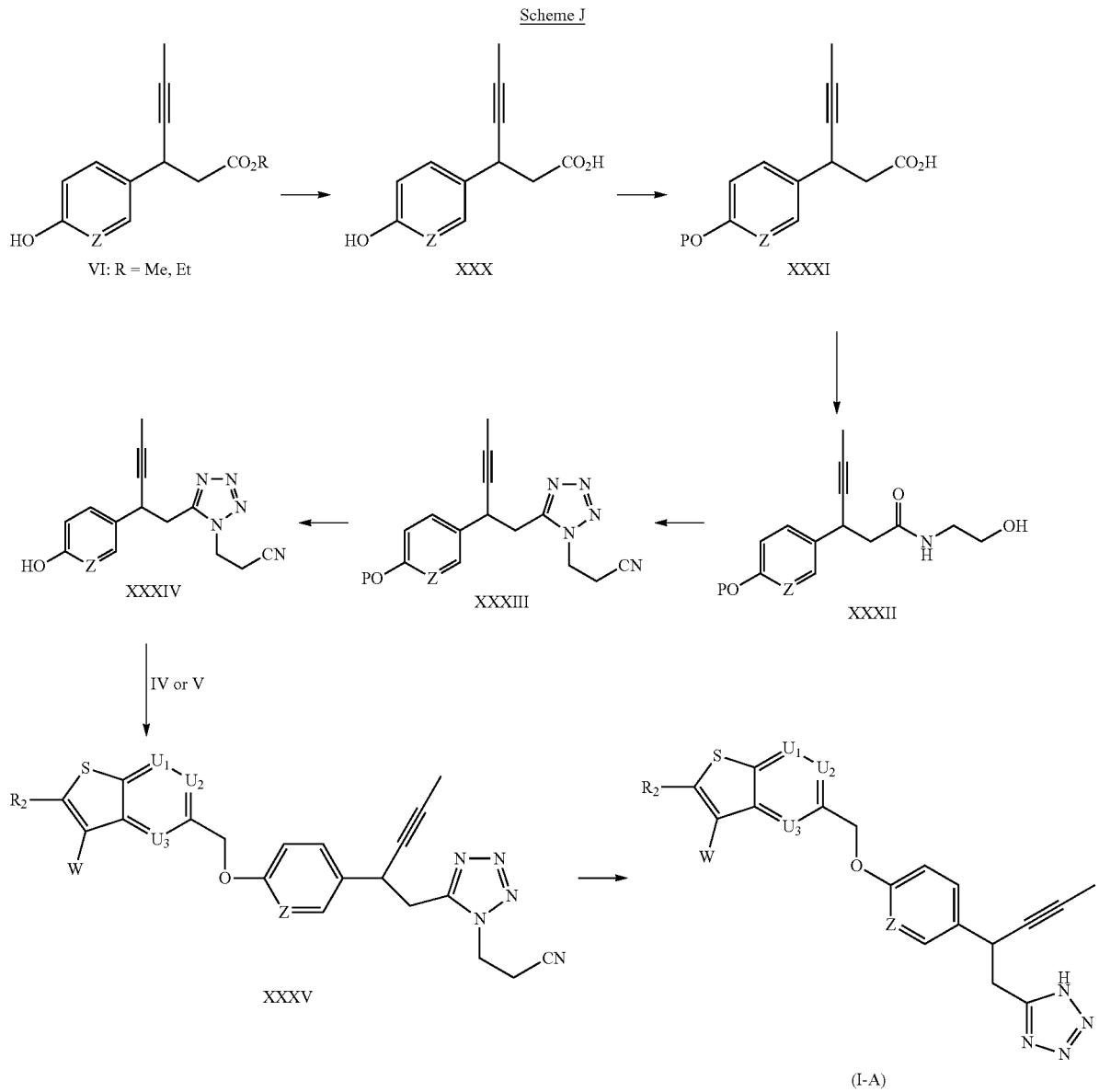

Hydrolysis of a hydroxyphenylpropanoate of formula VI may provide the corresponding hydroxyphenylpropionic acid or formula XXX. Protection of the phenolic hydroxy group with a suitable protecting group as defined in Scheme A, preferably with a 4-methoxybenzyl group, may provide a compound of formula XXXI. Coupling of a compound of formula XXXI with a suitably protected amine, such as 2-cyanoethylamine, may be effected under a variety of conditions known in the art to provide compounds of formula XXXII. For example, this transformation may be conveniently carried out using HATU as the coupling agent such as DCM at a temperature of about 40° C. provides the corresponding imidoyl chloride, which upon treatment with a silyl azide, such as trimethylsilyl azide, provides a compound of formula XXXIII Deprotection of the phenolic protecting group of a compound of formula XXXIII provides compound XXXIV. When a 4-methoxybenzyl protecting group has been used, its removal may be conveniently carried out upon treatment with TFA in a solvent such as DCM, or the like, at a concentration of about 25 to 50% (v/v). Treatment of a compound of formulas IV or V with a compound of formula XXXIV, using the methods described in Scheme A for its reaction with a compound of formula VI, may provide a compound of formula XXXV. Treatment of a compound of formula XXXV with an aqueous solution of a metal hydroxide, such as NaOH or LiOH, in a protic co-solvent such as MeOH, EtOH, i-PrOH, or the like, along with an ethereal co-solvent such as THF or dioxane, may provide the corresponding tetrazole of formula I-A.

In a related manner, certain compounds of Formula I-A may be synthesized as outlined by the general synthetic route illustrated in Scheme K. Reaction of a compound of formula XXXIV with a compound of formula III or XXIV, using methods described in Scheme G, may provide a compound of formula XXXVI. A compound of formula XXXVI, in turn, may be cross-coupled with a compound of formula W-M, as described in Scheme A, to provide a compound of formula XXXVII. Reaction of a compound of formula XXXVII with a metal hydroxide solution, as described in Scheme J, may provide a compound of formula I-A.

Scheme K

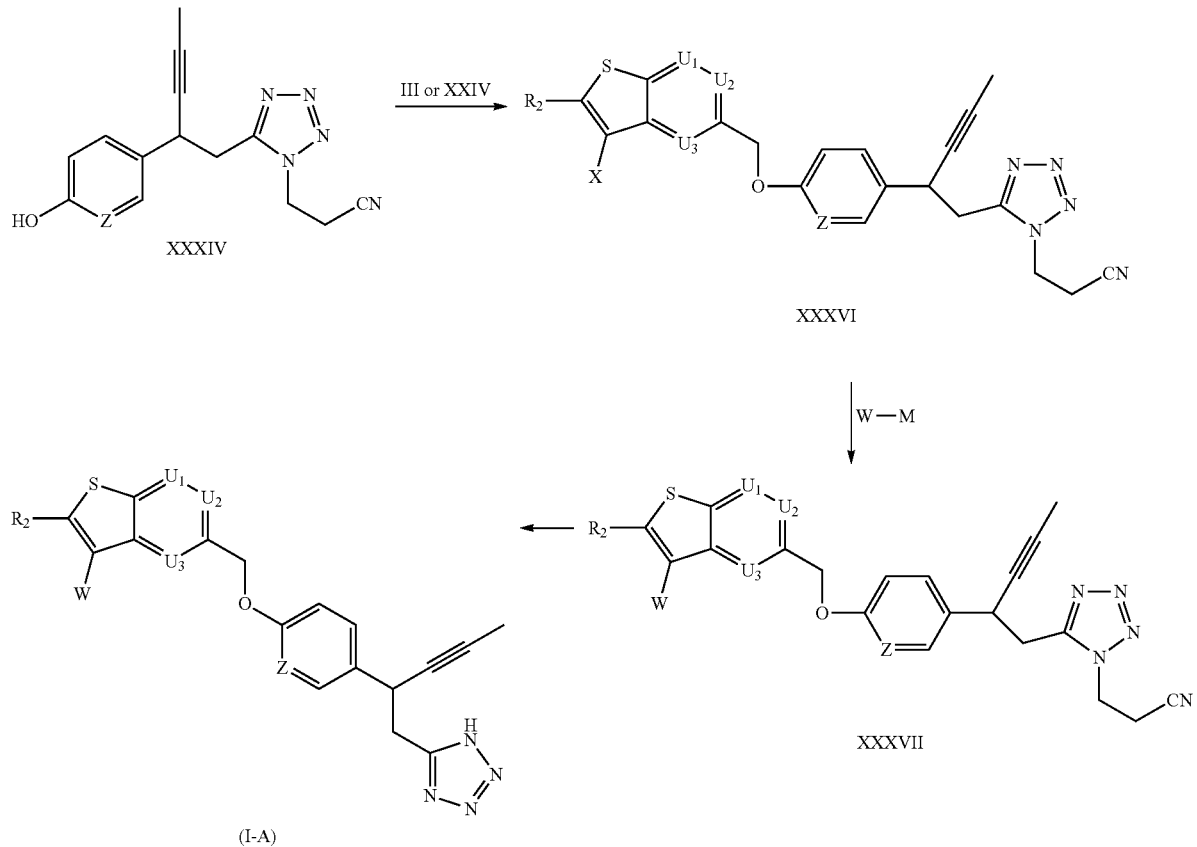

Certain compounds of formula I-A may be prepared as illustrated in general Scheme L.

Scheme L

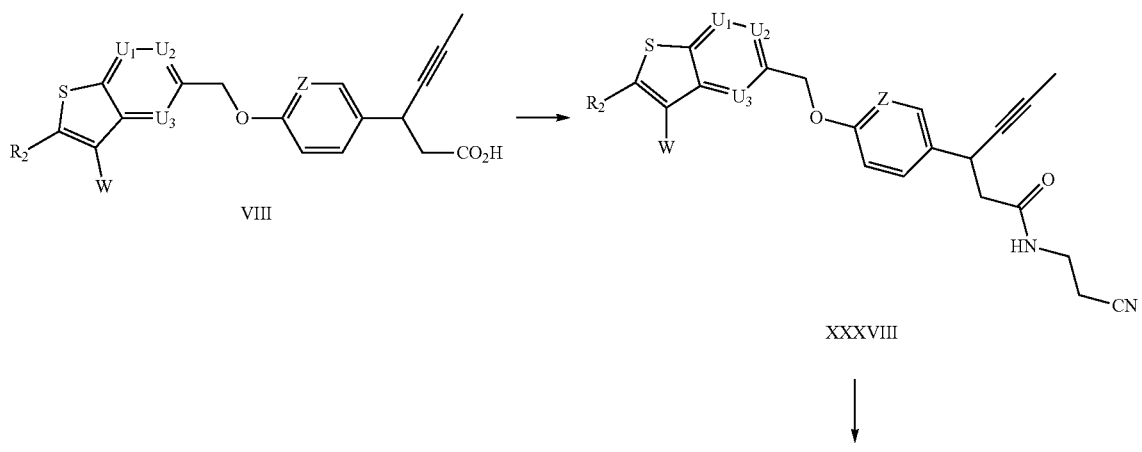

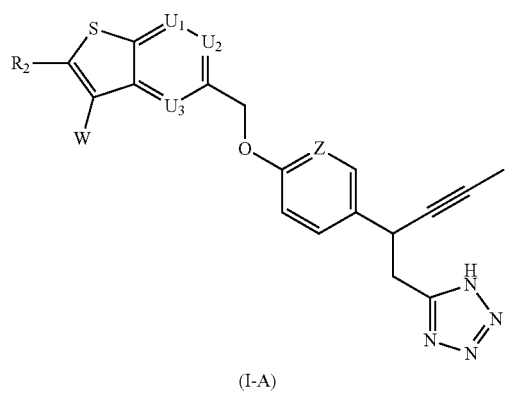

(I-A)

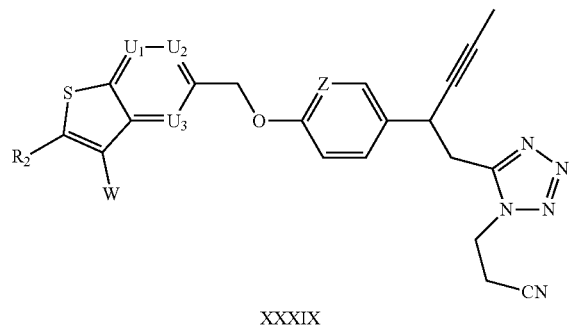

XXXIX

Using methods similar to those described in Scheme J, a carboxylate of formula VIII may be converted to an amide of formula XXXVIII, which in turn, may be converted to a protected tetrazole of formula XXXIX. Deprotection of the tetrazole of formula XXXIX, as described in Scheme J, may provide the corresponding tetrazole of formula I-A.

SPECIFIC EXAMPLES

General Procedure A:

A mixture of an arylbromide or aryliodide (1 mmol), an arylboronic acid, aryldioxaborolane or bis(pinacolato)diboron (1.5 mmol), a palladium catalyst (0.1 mmol) and $K_2CO_3$ (2-3 mmol) was placed in a reaction vessel which was then thoroughly purged with argon. Dioxane (3 mL) and water (1.5 mL) were added, and the mixture was stirred at 80-95° C. for 1 to 4 h. After cooling to rt, the mixture was poured into EtOAc/$H_2O$ (1:1, 10 mL) and the aqueous layer was extracted with EtOAc (5 mL×2). The combined organic extracts were dried ($Na_2SO_4$), filtered and concentrated under reduced pressure. Purification of the resultant residue by silica gel chromatography (EtOAc/heptanes) afforded the desired biaryl product.

General Procedure B:

To a mixture of the alcohol (0.2 mmol) and the phenol (0.3 mmol) in dry THF (1 mL) was added a mixture of the phosphine ($Ph_3P$, $Bu_3P$ or t-$Bu_3P$; 0.3 mmol) and the azidodicarboxylate (DEAD, DIAD, DBAD or ADDP; 0.3 mmol), and the resultant solution was stirred under argon for 1-16 h. The mixture was then either worked up by an extractive process (ex., quenching with satd. aq. $NH_4Cl$ and extraction with EtOAc) or concentrated directly under reduced pressure and the resultant residue was purified by silica gel chromatography (EtOAc/heptanes) or EtOAc/petroleum ether to afford the desired phenolic ether.

General Procedure C:

To a solution of the ester (0.16 mmol) in THF (1 mL) and MeOH (0.5 mL) was added the hydroxide base (1N LiOH (aq) or 1N NaOH (aq)) (1 mL) and the resultant mixture was stirred at rt for 1-3 h, or until hydrolysis was complete. The reaction was then acidified to pH 3-4 with either 1-2N HCl or 2M citric acid and poured into a 1:1 mixture of EtOAc/$H_2O$ (10 mL). The aqueous layer was extracted with EtOAc (5 mL×2) and the combined organic extract was dried ($Na_2SO_4$), filtered and concentrated under reduced pressure. The residue was dissolved in DCM (1 mL) and the product was precipitated with heptanes to afford the pure carboxylic acid.

General Procedure D:

To an ice-cooled solution of the benzylic alcohol (0.22 mmol) in DCM (5 mL) was added thionyl chloride (0.45 mmol) in drop-wise fashion. After stirring at 0-5° C. for 2 h, the reaction was quenched by the addition of water (~10 mL) followed by DCM (50 mL). After partitioning the two phases, the organic layer was successively washed with water, satd. $NaHCO_3$ and brine, then dried ($Na_2SO_4$), filtered and concentrated to afford the corresponding benzylic chloride which was used without further purification.

General Procedure E:

A mixture of the benzylic chloride (0.11 mmol), the phenol (0.14 mmol) and $Cs_2CO_3$ (0.17 mmol) in MeCN (2 mL) was stirred at rt for 16 h. EtOAc (50 mL) was then added and the organic layer was successively washed with water and brine, dried ($Na_2SO_4$), filtered and concentrated to afford the crude corresponding benzylic phenyl ether, which was purified by silica gel chromatography (EtOAc/heptanes).

General Procedure F:

To an ice-cooled solution of the benzothiophenyl aldehyde (1.02 mmol) in THF (4 mL) and MeOH (0.5 mL) was added $NaBH_4$ (2.09 mmol) in a portion-wise fashion. After stirring for 30 min, the reaction was quenched by the addition of satd. $NH_4Cl$ (10 mL). The mixture was extracted with EtOAc (3×20 mL) and the combined organic extracts were dried ($Na_2SO_4$) and concentrated under reduced pressure. Purification of the resultant residue by silica gel chromatography (EtOAc/petroleum ether) afforded the corresponding benzylic alcohol.

General Procedure G:

To a cooled (0° C.) solution of the arylalkanoic acid (1 mmol) and DMF (10 µL) in DCM (25 mL) was added either thionyl chloride (3 mmol) or oxalyl chloride (2 mmol) in drop-wise fashion. After stirring at 0° C. for 1 h, the reaction was quenched by the addition of satd. aq. $NaHCO_3$ (3 mL) and the resulting mixture was extracted with DCM (3×5 mL). The combined organic extracts were dried ($Na_2SO_4$) and concentrated under reduced pressure to afford the crude arylalkanoyl chloride, which was used directly without further purification.

General Procedure Ha:

To a cold (0° C.) solution of the crude arylalkanoyl chloride (6 mmol) in THF (1 mL) was added aq. $NH_4OH$ (28-30%, w/w; 5 mL) in drop-wise fashion. Alternatively, the reaction solution could be prepared by a drop-wise addition of a solution of the arylalkanoyl chloride in THF to cold aq. $NH_4OH$ (inverse addition). After stirring at 0° C. for 1 h, the resulting mixture was extracted with EtOAc (3×20 mL) and the combined organic extracts were dried ($Na_2SO_4$) and concentrated under reduced pressure to afford the corresponding crude arylalkanoyl amide, which was used directly without further purification.

General Procedure Hb:

To a solution of the crude arylalkanoyl chloride (2.2 mmol) in diethyl ether (100 mL) was bubbled ammonia gas at rt for 10 min. The mixture was then concentrated under reduced pressure to afford the corresponding arylalkanoyl amide, which was used directly without further purification.

General Procedure I:

To a cold (0° C.) solution of the arylalkanoyl amide (1 mmol) and TEA (3 mmol) in DCM (4 mL) was added trifluoroacetic anhydride (1 mmol) in drop-wise fashion. After stirring at 0° C. for 0.5 h, the reaction was quenched by the addition of sat' d aq. NaHCO$_3$ (3 mL) and the resulting mixture was extracted with EtOAc (3×3 mL). The combined organic extracts were dried (Na$_2$SO$_4$) and concentrated under reduced pressure and the residue thus obtained was purified by silica gel chromatography (EtOAc/petroleum ether) to afford the corresponding arylalkylnitrile.

General Procedure J:

A mixture of the nitrile (0.32 mmol), azidotrimethylsilane (3 eq.) and Bis(tri-n-butyltin)oxide (0.2 eq.) in toluene (2 mL) was stirred overnight at 110° C. in a sealed tube. The reaction was then quenched by the addition of water (10 mL) and the mixture was extracted with EtOAc (3×10 mL). The combined organic extracts were dried (Na$_2$SO$_4$), concentrated under reduced pressure and the residue thus obtained was purified by reverse-phase flash chromatography using Flash Spherical C18 columns (120 g, 20-35 μm, 100 Å; Agela Technologies), eluting with a gradient of MeCN/H$_2$O (0.05% NH$_4$HCO$_3$) (Workup 1). Alternatively, the crude reaction was concentrated under reduced pressure and the residue was directly purified by silica gel chromatography eluting with DCM/MeOH or EtOAc/petroleum ether mixtures (Workup 2).

Example 1

(2S)-5-(2-(4-((3-(2-Methylphenyl)benzo[b]thiophen-5-yl)methoxy)phenyl)pent-3-yn-1-yl)-1H-tetrazole, Cpd 1

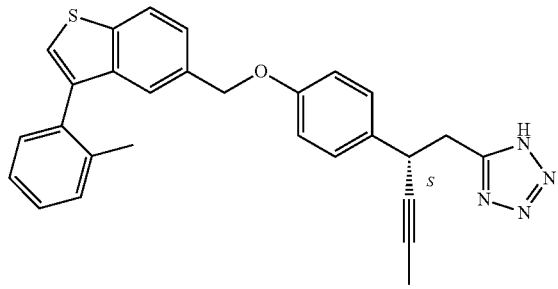

(A) To an ice-cooled solution of 5-hydroxymethylbenzothiophene (1.45 g; 8.83 mmol) in THF (15 mL) was added NBS (1.73 g; 9.71 mmol) under an argon atmosphere. The resulting solution was allowed to warm to rt, with stirring continued for another 3 h. The reaction was then concentrated under reduced pressure and the residue was purified by silica gel chromatography eluting with 0-20% EtOAc in heptanes to afford 3-bromo-5-hydroxymethylbenzothiophene (968 mg, 45%) as a white solid. $^1$H NMR (CDCl$_3$) δ: 7.78-7.88 (m, 2H), 7.46 (s, 1H), 7.43 (d, J=9.6 Hz, 1H), 4.86 (d, J=5.8 Hz, 2H), 1.84 (t, J=5.8 Hz, 1H).

(B) 5-Hydroxymethyl-3-(2-methylphenyl)benzo[b]thiophene was prepared from 3-bromo-5-hydroxymethylbenzothiophene and 2-methylphenylboronic acid following General Procedure A, using PdCl$_2$(dppf).CH$_2$Cl$_2$ as the palladium catalyst. LC/MS: mass calcd. for C$_{16}$H$_{14}$OS: 254.35, found 277.1 [M+Na]$^+$.

(C) (3S)-Methyl 3-(4-((3-(2-methylphenyl)benzo[b]thiophen-5-yl)methoxy)phenyl)-hex-4-ynoate was prepared from 5-hydroxymethyl-3-(2-methylphenyl)benzo[b]-thiophene and (3S)-methyl 3-(4-hydroxyphenyl)hex-4-ynoate (prepared as described in WO 2005086661) following General Procedure B using PPh$_3$ and DBAD. LC/MS: mass calcd. for C$_{29}$H$_{26}$O$_3$S: 454.59, found 455.1 [M]$^+$, 477.0 [M+Na]$^+$.

(D) (3S)-3-[4-[[3-(2-Methylphenyl)benzo[b]thiophen-5-yl]methoxy]phenyl]hex-4-ynoic acid was prepared from (3S)-methyl 3-(4-((3-(2-methylphenyl)benzo[b]thiophen-5-yl)methoxy)phenyl)hex-4-ynoate following General Procedure C using LiOH as base 2N HCl for reaction acidification. $^1$H NMR (400 MHz, CDCl$_3$) δ 7.93 (d, J=9.09 Hz, 1H), 7.41-7.50 (m, 2H), 7.27-7.38 (m, 7H), 6.89 (d, J=8.59 Hz, 2H), 5.08 (s, 2H), 3.97-4.10 (m, 1H), 2.78 (dd, J=8.59, 15.66 Hz, 1H), 2.69 (dd, J=6.57, 15.66 Hz, 1H), 2.15 (s, 3H), 1.82 (d, J=2.02 Hz, 3H). LC/MS: mass calcd. for C$_{28}$H$_{24}$O$_3$S: 440.56, found 463.1 [M+Na]$^+$.

(E) (3S)-Methyl 3-(4-((3-(2-methylphenyl)benzo[b]thiophen-5-yl)methoxy)phenyl)hex-4-ynoyl chloride was prepared from (3S)-3-[4-[[3-(2-methylphenyl)benzo[b]thiophen-5-yl]methoxy]phenyl]hex-4-ynoic acid following General Procedure G.

(F) (3S)-3-(4-((3-(2-Methylphenyl)benzo[b]thiophen-5-yl)methoxy)phenyl)hex-4-ynamide was prepared from (3S)-3-[4-[[3-(2-methylphenyl)benzo[b]thiophen-5-yl]methoxy] phenyl]hex-4-ynoyl chloride following General Procedure Hb. LC/MS: mass calcd. for C$_{28}$H$_{25}$NO$_2$S: 439.16, found: 440.1 [M+H]$^+$.

(G) (3S)-3-(4-((3-(2-Methylphenyl)benzo[b]thiophen-5-yl)methoxy)phenyl)hex-4-ynenitrile was prepared from (3S)-3-[4-[[3-(2-methylphenyl)benzo[b]thiophen-5-yl] methoxy]phenyl]hex-4-ynoic acid following General Procedure I. LC/MS: mass calcd. for C$_{28}$H$_{23}$NOS: 421.15, found: 444.1 [M+Na]$^+$.

(H) (2S)-5-(2-(4-((3-(2-Methylphenyl)benzo[b]thiophen-5-yl)methoxy)phenyl)pent-3-yn-1-yl)-1H-tetrazole (Cpd 1) was prepared from (3S)-3-(4-((3-(2-methylphenyl)benzo[b] thiophen-5-yl)methoxy)phenyl)hex-4-ynenitrile following the General Procedure J, using Workup 2. $^1$H NMR (DMSO-d$_6$) δ 8.08 (d, J=8.1 Hz, 1H), 7.72 (s, 1H), 7.48 (d, J=8.6 Hz, 1H), 7.41 (s, 1H), 7.37 (d, J=4.0 Hz, 2H), 7.19-7.35 (m, 4H), 6.92 (d, J=8.6 Hz, 2H), 5.17 (s, 2H), 4.06-4.13 (m, 1H), 3.23 (d, J=8.1 Hz, 2H), 2.08 (s, 3H), 1.74 (d, J=2.5 Hz, 3H). LC/MS: mass calcd. for C$_{28}$H$_{24}$N$_4$OS: 464.17, found: 465.1 [M+H]$^+$.

Example 2

5-((2S)-2-(4-((2-Chloro-3-(2-methylphenyl)benzo[b]thiophen-5-yl)methoxy)phenyl)pent-3-ynyl)-1H-tetrazole, Cpd 2

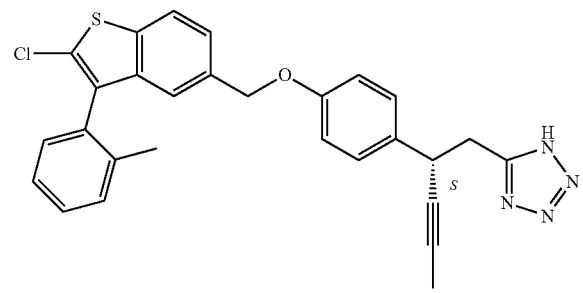

(A) To a solution of 5-Hydroxymethyl-3-(2-methylphenyl)benzo[b]thiophene (from Example 1B) (2.54 g, 9.99 mmol), TBSCl (1.8 g, 11.94 mmol) and DMAP (122 mg, 1 mmol) in DCM (50 mL) was added TEA (2.02 g, 20 mmol) and the resultant solution was stirred at rt for 2 h. Water (100 mL) was then added and the mixture was extracted with DCM (3×50 mL) and the combined organic extracts were dried (Na$_2$SO$_4$) and concentrated under reduced pressure. Purification of the resultant residue by silica gel chromatography (0-5% EtOAc/petroleum ether) afforded tert-butyldimethyl-((3-(2-methylphenyl)benzo[b]thiophen-5-yl)methoxy)silane (3.5 g, 95%) as colorless oil. LC/MS: mass calcd. for C$_{22}$H$_{28}$OSSi: 368.16, found: 391.1 [M+Na]$^+$.

(B) To a cooled (−78° C.) solution of tert-butyldimethyl-((3-(2-methylphenyl)benzo[b]thiophen-5-yl)methoxy)silane (300 mg, 0.81 mmol) in anhydrous THF (4 mL), maintained under a nitrogen atmosphere was added n-BuLi (2.5 M in hexanes; 0.65 mL, 1.625 mmol) in drop-wise fashion. After stirring at −78° C. for 10 min, a solution of NCS (163 mg, 1.22 mmol) in THF (2 mL) was added in drop-wise fashion and the mixture was stirred for an additional 0.5 h. The reaction was then quenched by the addition of aq. NH$_4$Cl (15 mL) and the resultant mixture was extracted with EtOAc (3×15 mL). The combined organic extracts were dried (Na$_2$SO$_4$) and concentrated under reduced pressure. Purification of the resultant residue by silica gel chromatography (0-5% EtOAc/petroleum ether) afforded tert-butyl-((2-chloro-3-(2-methylphenyl)benzo[b]thiophen-5-yl)methoxy)dimethylsilane (250 mg, 76%) as yellow oil. LC/MS: mass calcd. for C$_{22}$H$_{27}$ClOSSi: 402.12, found: 371.1 [M−OTBS]$^+$.

(C) To a solution of tert-butyl-((2-chloro-3-(2-methylphenyl)benzo[b]thiophen-5-yl)methoxy)dimethylsilane (250 mg, 0.62 mmol) in THF (10 mL) was added TBAF (1M in THF; 0.75 mL, 0.75 mmol) and the resultant solution was stirred at rt for 0.5 h. Water (15 mL) was then added and the mixture was extracted with EtOAc (3×15 mL). The combined organic extracts were dried (Na$_2$SO$_4$) and concentrated under reduced pressure. Purification of the resultant residue by silica gel chromatography (0-15% EtOAc/petroleum ether) afforded (2-chloro-3-(2-methylphenyl)benzo[b]thiophen-5-yl)methanol (130 mg, 73%) as yellow oil. LC/MS: mass calcd. for C$_{16}$H$_{13}$ClOS: 288.04, found: 271.1 [M−OH]$^+$.

(D) 2-Chloro-5-(chloromethyl)-3-(2-methylphenyl)benzo[b]thiophene was prepared from (2-chloro-3-(2-methylphenyl)benzo[b]thiophen-5-yl)methanol following General Procedure D.

(E) (3S)-3-(4-Hydroxyphenyl)hex-4-ynoyl chloride was prepared from (3S)-3-(4-hydroxyphenyl)hex-4-ynoic acid (available from Synnovator, Inc., Research Triangle Park, N.C.; Cat. # PB05592) following General Procedure G, using thionyl chloride with DMF as the chlorinating agent.

(F) (3S)-3-(4-Hydroxyphenyl)hex-4-ynamide was prepared from (3S)-3-(4-hydroxyphenyl)hex-4-ynoyl chloride following General Procedure Ha. LC/MS: mass calcd. for C$_{12}$H$_{13}$NO$_2$: 203.24, found: 204.0 [M+H]$^+$.

(G) (3S)-3-(4-Hydroxyphenyl)hex-4-ynenitrile was prepared from (3S)-3-(4-hydroxyphenyl)hex-4-ynamide following General Procedure I. $^1$H NMR (DMSO-d$_6$) δ 9.40 (s, 1H), 7.14-7.33 (m, 2H), 6.60-6.85 (m, 2H), 3.91-4.15 (m, 1H), 2.74-3.00 (m, 2H), 1.85 (d, J=2.4 Hz, 3H).

(H) (3S)-3-(4-((2-Chloro-3-(2-methylphenyl)benzo[b]thiophen-5-yl)methoxy)phenyl)hex-4-ynenitrile was prepared from 2-chloro-5-(chloromethyl)-3-(2-methylphenyl)benzo[b]thiophene and (3S)-3-(4-hydroxyphenyl)hex-4-ynenitrile following General Procedure E, at a reaction temperature of 60° C. overnight. LC/MS: mass calcd. for C$_{28}$H$_{22}$ClNOS: 455.11, found: 478.2 [M+Na]$^+$.

(I) 5-((2S)-2-(4-((2-Chloro-3-(2-methylphenyl)benzo[b]thiophen-5-yl)methoxy)phenyl)pent-3-ynyl)-1H-tetrazole (Cpd 2) was prepared from (3S)-3-(4-((2-chloro-3-(2-methylphenyl)benzo[b]thiophen-5-yl)methoxy)phenyl)hex-4-ynenitrile following General Procedure J, using Workup 2. Additional purification of the product was carried out by preparative HPLC on a Waters SunFire™ Prep C18, 5μ column (19×100 mm) using an acetonitrile/water (0.05% TFA) gradient (45-95%). $^1$H NMR (DMSO-d$_6$) δ 8.04 (d, J=8.4 Hz, 1H), 7.21-7.52 (m, 8H), 6.88-6.94 (m, 2H), 5.13 (s, 2H), 4.10-4.18 (m, 1H), 3.23 (d, J=7.8 Hz, 2H), 2.02 (s, 3H), 1.74 (d, J=2.1 Hz, 3H). LC/MS: mass calcd. for C$_{28}$H$_{23}$ClN$_4$OS: 498.13, found: 499.0 [M+H]$^+$.

Example 3

5-((2S)-2-(4-((2-Fluoro-3-(2-methylphenyl)benzo[b]thiophen-5-yl)methoxy)phenyl)pent-3-ynyl)-1H-tetrazole, Cpd 3

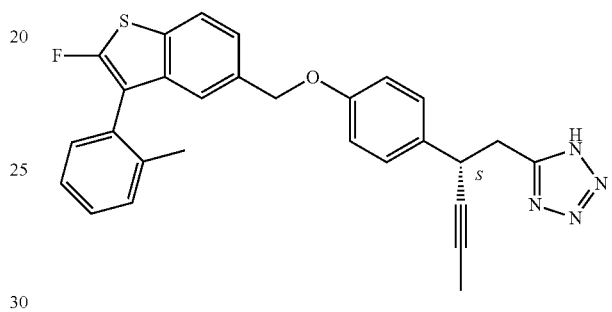

(A) To a cooled (−78° C.) solution of tert-butyldimethyl((3-(2-methylphenyl)benzo[b]thiophen-5-yl)methoxy)silane (from Example 2A; 1.0 g, 2.71 mmol) in THF (25 mL) was added n-BuLi (2.5 M in hexanes; 0.65 mL, 1.625 mmol) in drop-wise fashion. After stirring for 10 min, a solution of N-fluoro-N-(phenylsulfonyl)benzenesulfonamide (1027 mg, 3.257 mmol) in THF (5 mL) was added in drop-wise fashion and stirring was continued at −78° C. for 30 min. The reaction was then quenched by the addition of aq. NH$_4$Cl (15 mL) and the resultant mixture was extracted with EtOAc (3×15 mL). The combined organic extracts were dried (Na$_2$SO$_4$) and concentrated under reduced pressure. Purification of the resultant residue by silica gel chromatography (0-5% EtOAc/petroleum ether) afforded tert-butyldimethyl-((2-fluoro-3-(2-methylphenyl)benzo[b]thiophen-5-yl)methoxy)silane (800 mg, 76%) as a yellow oil. LC/MS: mass calcd. for C$_{22}$H$_{27}$FOSSi: 386.15, found: 254.9 [M−OTBS]$^+$.

(B) (2-Fluoro-3-(2-methylphenyl)benzo[b]thiophen-5-yl)methanol was prepared from tert-butyldimethyl-((2-fluoro-3-(2-methylphenyl)benzo[b]thiophen-5-yl)methoxy)silane following the procedure described in Example 2C. LC/MS: mass calcd. for C$_{16}$H$_{13}$FOS: 272.07, found: 254.9 [M−OH]$^+$.

(C) 2-Fluoro-5-(chloromethyl)-3-(2-methylphenyl)benzo[b]thiophene was prepared from (2-fluoro-3-(2-methylphenyl)benzo[b]thiophen-5-yl)methanol following General Procedure D.

(D) (3S)-3-(4-((2-Fluoro-3-(2-methylphenyl)benzo[b]thiophen-5-yl)methoxy)phenyl)hex-4-ynenitrile was prepared from 2-fluoro-5-(fluoromethyl)-3-(2-methylphenyl)benzo[b]thiophene and (3S)-3-(4-hydroxyphenyl)hex-4-ynenitrile (from Example 2G) following General Procedure E, at a reaction temperature of 60° C. overnight. LC/MS: mass calcd. for C$_{28}$H$_{22}$ClNOS: 439.14, found: 457.0 [M+NH$_4$]$^+$.

(E) 5-((2S)-2-(4-((2-Fluoro-3-(2-methylphenyl)benzo[b]thiophen-5-yl)methoxy)phenyl)pent-3-ynyl)-1H-tetrazole (Cpd 3) was prepared from (3S)-3-(4-((2-fluoro-3-(2-methylphenyl)benzo[b]thiophen-5-yl)methoxy)phenyl)hex-4-ynenitrile following General Procedure J, using Workup 2. Additional purification of the product was carried out by preparative HPLC on a Waters SunFire™ Prep C18, 5μ column (19×100 mm) using an acetonitrile/water (0.05% TFA) gradient (45-95%). $^1$H NMR (DMSO-$d_6$) δ 8.01 (d, J=8.4 Hz, 1H), 7.30-7.50 (m, 6H), 7.25 (d, J=8.4 Hz, 2H), 6.91 (d, J=8.4 Hz, 2H), 5.13 (s, 2H), 4.07-4.10 (m, 1H), 3.23 (d, J=7.8 Hz, 2H), 2.11 (s, 3H), 1.74 (d, J=2.1 Hz, 3H). LC/MS: mass calcd. for $C_{28}H_{23}FN_4OS$: 482.16, found: 483.0 $[M+H]^+$.

Example 4

(2S)-5-(2-(4-((3-(2-Bromophenyl)benzo[b]thiophen-5-yl)methoxy)phenyl)pent-3-yn-1-yl)-1H-tetrazole, Cpd 4

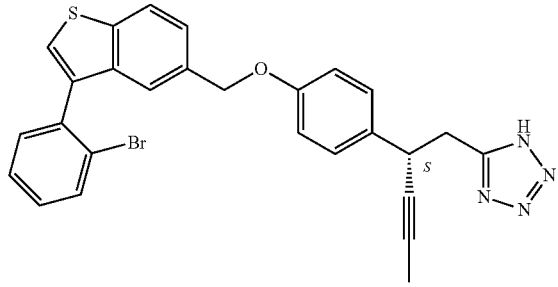

(A) To a cooled (15° C.) solution of benzo[b]thiophene-5-carbaldehyde (6.9 g, 52.54 mmol) in HOAc (80 mL) was added a solution of bromine (10.5 g, 65.7 mmol) in HOAc (20 mL) in drop-wise fashion. After stirring at 15° C. for 2 h, water (500 mL) was added, whereupon the solid product precipitated from the mixture. The precipitate was collected by filtration and dried under vacuum to provide 3-bromobenzo[b]thiophene-5-carbaldehyde (7.8 g, 38% yield) as a yellow solid. $^1$H NMR (CDCl$_3$) δ 10.17 (s, 1H), 8.32 (s, 1H), 7.93-7.98 (m, 2H), 7.78 (s, 1H).

(B) 3-(2-Bromophenyl)benzo[b]thiophene-5-carbaldehyde was prepared from 3-bromobenzo[b]thiophene-5-carbaldehyde and 2-bromophenylboronic acid following General Procedure A, using $PdCl_2(dppf)CH_2Cl_2$ as the palladium catalyst and $Cs_2CO_3$ in place of $K_2CO_3$. LC/MS: mass calcd. for $C_{15}H_9BrOS$: 317.20, found: 317.0 $[M]^+$, 319.0 $[M+2]^+$.

(C) (3-(2-Bromophenyl)benzo[b]thiophen-5-yl)methanol was prepared from 3-(2-bromophenyl)benzo[b]thiophene-5-carbaldehyde following General Procedure F. LC/MS: mass calcd. for $C_{15}H_{11}BrOS$: 319.22, found: 319.0 $[M]^+$, 321.0 $[M+2]^+$.

(D) 3-(2-Bromophenyl)-5-(chloromethyl)benzo[b]thiophene was prepared from (3-(2-bromophenyl)benzo[b]thiophen-5-yl)methanol following General Procedure D.

(E) (3S)-Ethyl 3-(4-((3-(2-bromophenyl)benzo[b]thiophen-5-yl)methoxy)phenyl)hex-4-ynoate was prepared from 3-(2-bromophenyl)-5-(chloromethyl)benzo[b]thiophene and (3S)-ethyl 3-(4-hydroxyphenyl)hex-4-ynoate (available from Synnovator, Inc., Research Triangle Park, N.C.; Cat. # PB05708) following General Procedure E, at a reaction temperature of 50° C. for 2 h. LC/MS: mass calcd. for $C_{29}H_{25}BrO_3S$: 533.48, found: 533.1 $[M]^-$, 535.1 $[M+H]^+$.

(F) (3S)-3-(4-((3-(2-Bromophenyl)benzo[b]thiophen-5-yl)methoxy)phenyl)hex-4-ynoic acid was prepared from (3S)-ethyl 3-(4-((3-(2-bromophenyl)benzo[b]thiophen-5-yl)methoxy)phenyl)hex-4-ynoate following General Procedure C using LiOH as base, EtOH in place of MeOH and 2N HCl for reaction acidification. $^1$H NMR (DMSO-$d_6$) δ 8.08 (d, J=8.1 Hz, 1H), 7.80-7.85 (m, 2H), 7.40-7.56 (m, 5H), 7.24 (d, J=8.7 Hz, 2H), 6.92 (d, J=8.4 Hz, 2H), 5.16 (s, 2H), 3.89-3.94 (m, 1H), 2.58 (d, J=7.5 Hz, 2H), 1.77 (s, 3H). LC/MS: mass calcd. for $C_{27}H_{21}BrO_3S$: 505.42, found: 505.0 $[M]^-$, 507.0 $[M+^2]^-$.

(G) (3S)-3-(4-((3-(2-Bromophenyl)benzo[b]thiophen-5-yl)methoxy)phenyl)hex-4-ynoyl chloride was prepared from (3S)-3-(4-((3-(2-Bromophenyl)benzo[b]thiophen-5-yl)methoxy)phenyl)hex-4-ynoic acid following General Procedure G, using oxalyl chloride as the chlorinating agent.

(H) (3S)-3-(4-((3-(2-Bromophenyl)benzo[b]thiophen-5-yl)methoxy)phenyl)hex-4-ynamide was prepared from (3S)-3-(4-((3-(2-Bromophenyl)benzo[b]thiophen-5-yl)methoxy)phenyl)hex-4-ynoyl chloride following General Procedure Ha (inverse addition), and used directly without further characterization.

(I) (3S)-3-(4-((3-(2-Bromophenyl)benzo[b]thiophen-5-yl)methoxy)phenyl)hex-4-ynenitrile was prepared from (3S)-3-(4-((3-(2-Bromophenyl)benzo[b]thiophen-5-yl)methoxy)phenyl)hex-4-ynamide following General Procedure I. LC/MS: mass calcd. for $C_{27}H_{20}BrNOS$: 485.05, found: 508.0, 509.9 $[M+Na]^+$, $[M+Na+2]^+$.

(J) (2S)-5-(2-(4-((3-(2-Bromophenyl)benzo[b]thiophen-5-yl)methoxy)phenyl)pent-3-yn-1-yl)-1H-tetrazole (Cpd 4) was prepared from (3S)-3-(4-((3-(2-Bromophenyl)benzo[b]thiophen-5-yl)methoxy)phenyl)hex-4-ynenitrile following General Procedure J, using Workup 2. Additional purification of the product was carried out by preparative HPLC on a Waters SunFire™ Prep C18, 5μ column (19×100 mm) using an acetonitrile/water (0.05% TFA) gradient (20-50%). $^1$H NMR (CD$_3$OD) δ 7.96 (d, J=8.7 Hz, 1H), 7.75-7.78 (m, 1H), 7.56 (s, 1H), 7.33-7.50 (m, 5H), 7.22 (d, J=8.4 Hz, 2H), 6.92 (d, J=8.7 Hz, 2H), 5.14 (s, 2H), 4.03-4.08 (m, 1H), 3.25-3.28 (m, 2H), 1.78 (s, 3H). LC/MS: mass calcd. for $C_{27}H_{21}BrN_4OS$: 428.06, found: 528.8, 530.8 $[M+H]^+$, $[M+H+2]^+$.

Example 5

(2S)-4-(5-((4-(1-(1H-Tetrazol-5-yl)pent-3-yn-2-yl)phenoxy)methyl)benzo[b]thiophen-3-yl)-2-chloro-5-methylpyridine, Cpd 5

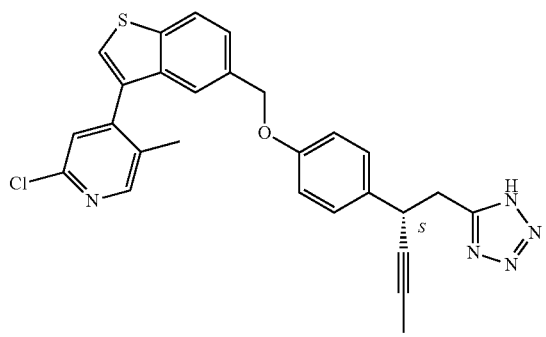

(A) (3-(4,4,5,5-Tetramethyl-1,3,2-dioxaborolan-2-yl)benzo[b]thiophen-5-yl)methanol was prepared from 3-bromo-5-hydroxymethylbenzothiophene (from Example 1A) and bis(pinacolato)diboron following General Procedure A, using PdCl$_2$(dppf).CH$_2$Cl$_2$ as the palladium catalyst and KOAc in place of K$_2$CO$_3$. LC/MS: mass calcd. for C$_{15}$H$_{19}$BO$_3$S: 290.19, found: 273.1[M–OH]$^+$.

(B) (3-(2-Chloro-5-methylpyridin-4-yl)benzo[b]thiophen-5-yl)methanol was prepared from 4-bromo-2-chloro-5-methylpyridine and (3-(4,4,5,5-tetramethyl-1,3,2-dioxaborolan-2-yl)benzo[b]thiophen-5-yl)methanol following General Procedure A, using PdCl$_2$(dppf).CH$_2$Cl$_2$ as the palladium catalyst and Cs$_2$CO$_3$ in place of K$_2$CO$_3$. LC/MS: mass calcd. for C$_{15}$H$_{12}$ClNOS: 289.78, found: 290.0 [M]$^+$, 292.0 [M+2]$^+$.

(C) (3S)-Ethyl 3-(4-((3-(2-chloro-5-methylpyridin-4-yl)benzo[b]thiophen-5-yl)methoxy)phenyl)hex-4-ynoate was prepared from (3-(2-chloro-5-methylpyridin-4-yl)benzo[b]thiophen-5-yl)methanol and (3S)-ethyl 3-(4-hydroxyphenyl)hex-4-ynoate (available from Synnovator, Inc., Research Triangle Park, N.C.; Cat. # PB05708) following General Procedure B, using Bu$_3$P and ADDP at a reaction temperature of 60° C. in toluene overnight. LC/MS: mass calcd. for C$_{29}$H$_{26}$ClNO$_3$S: 504.04, found: 504.1 [M]$^+$, 506.1 [M+2]$^+$.

(D) (3S)-3-(4-((3-(2-Chloro-5-methylpyridin-4-yl)benzo[b]thiophen-5-yl)methoxy)phenyl)hex-4-ynoic acid was prepared (3S)-ethyl 3-(4-((3-(2-chloro-5-methylpyridin-4-yl)benzo[b]thiophen-5-yl)methoxy)phenyl)hex-4-ynoate following General Procedure C, using NaOH as base, MeOH as solvent and a reaction temperature of 60° C. for 2 h. For workup, the reaction mixture was filtered and concentrated, then purified directly by preparative HPLC on a Waters SunFire™ Prep C18, 5µ column (19×100 mm) using an acetonitrile/water (0.5% NH$_4$HCO$_3$) gradient (65-75%). $^1$H NMR (CD$_3$OD) δ 8.31 (s, 1H), 7.97 (d, J=8.4 Hz, 1H), 7.66 (s, 1H), 7.49 (d, J=8.7 Hz, 1H), 7.41 (s, 1H), 7.36 (s, 1H), 7.24 (d, J=8.4 Hz, 2H), 6.86 (d, J=8.4 Hz, 2H), 5.16 (s, 2H), 3.90-3.98 (m, 1H), 2.48-2.63 (m, 2H), 2.05 (s, 3H), 1.76 (s, 3H). LC/MS: mass calcd. for C$_{27}$H$_{22}$ClNO$_3$S: 475.99, found: 476.1 [M]$^+$, 478.1 [M+2]$^+$.

(E) (3S)-3-(4-((3-(2-Chloro-5-methylpyridin-4-yl)benzo[b]thiophen-5-yl)methoxy)phenyl)hex-4-ynoyl chloride was prepared from (3S)-3-(4-((3-(2-chloro-5-methylpyridin-4-yl)benzo[b]thiophen-5-yl)methoxy)phenyl)hex-4-ynoic acid following General Procedure G, using oxalyl chloride as the chlorinating agent.

(F) (3S)-3-(4-((3-(2-Chloro-5-methylpyridin-4-yl)benzo[b]thiophen-5-yl)methoxy)phenyl)hex-4-ynamide was prepared from (3S)-3-(4-((3-(2-chloro-5-methylpyridin-4-yl)benzo[b]thiophen-5-yl)methoxy)phenyl)hex-4-ynoyl chloride following General Procedure Ha. LC/MS: mass calcd. for C$_{27}$H$_{23}$ClN$_2$O$_2$S: 474.12, found: 475.0 [M+H]$^+$.

(G) (3S)-3-(4-((3-(2-Chloro-5-methylpyridin-4-yl)benzo[b]thiophen-5-yl)methoxy)phenyl)hex-4-ynenitrile was prepared from (3S)-3-(4-((3-(2-chloro-5-methylpyridin-4-yl)benzo[b]thiophen-5-yl)methoxy)phenyl)hex-4-ynamide following General Procedure I. LC/MS: mass calcd. for C$_{27}$H$_{21}$ClN$_2$OS: 456.11, found: 457.2 [M+H]$^+$.

(H) (2S)-4-(5-((4-(1-(1H-Tetrazol-5-yl)pent-3-yn-2-yl)phenoxy)methyl)benzo[b]thiophen-3-yl)-2-chloro-5-methylpyridine (Cpd 5) was prepared from (3S)-3-(4-((3-(2-chloro-5-methylpyridin-4-yl)benzo[b]thiophen-5-yl)methoxy)phenyl)hex-4-ynenitrile following General Procedure J, using Workup 2. $^1$H NMR (CD$_3$OD) δ 8.31 (s, 1H), 7.97 (d, J=8.4 Hz, 1H), 7.66 (s, 1H), 7.48 (d, J=8.4 Hz, 1H), 7.42 (s, 1H), 7.35 (s, 1H), 7.19 (d, J=8.7 Hz, 2H), 6.88 (d, J=8.7 Hz, 2H), 5.15 (s, 2H), 3.97-4.06 (m, 1H), 3.17-3.29 (m, 2H), 2.06 (s, 3H), 1.75 (s, 3H). LC/MS: mass calcd. for C$_{27}$H$_{22}$ClN$_5$OS: 499.12, found: 500.0 [M+H]$^+$.

Example 6

(2S)-4-((4-(5-((4-(1-(1H-Tetrazol-5-yl)pent-3-yn-2-yl)phenoxy)methyl)benzo[b]thiophen-3-yl)-3-methylphenoxy)methyl)-4-hydroxytetrahydro-2H-thiopyran 1,1-dioxide, Cpd 6

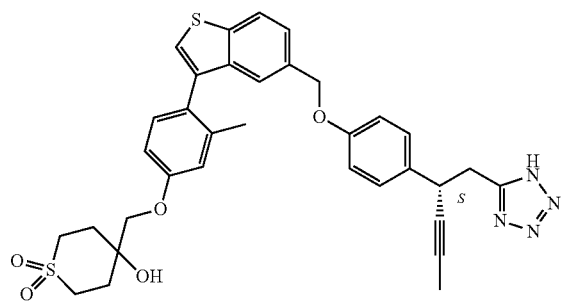

(A) 5-Hydroxymethyl-3-(4-hydroxy-2-methylphenyl)benzo[b]thiophene was prepared from 3-bromo-5-hydroxymethylbenzothiophene (from Example 1A) and 4-hydroxy-2-methylphenylboronic acid following General Procedure A, using PdCl$_2$(dppf).CH$_2$Cl$_2$ as the palladium catalyst. LC/MS: mass calcd. for C$_{16}$H$_{14}$O$_2$S: 270.35, found 293.0 [M+Na]$^+$.

(B) A mixture of 5-hydroxymethyl-3-(4-hydroxy-2-methylphenyl)benzo[b]thiophene (162 mg; 0.6 mmol), 1-oxa-6-thiaspiro[2.5]octane 6,6-dioxide (107 mg; 0.66 mmol) and K$_2$CO$_3$ (138 mg; 1 mmol) in DMF (1.5 mL) was stirred at 90° C. for 6 h. After cooling to rt, the reaction was partitioned between EtOAc and aq NH$_4$Cl and the aqueous layer was extracted with EtOAc (2×). The combined organic layers were washed with brine, dried (Na$_2$SO$_4$), filtered and concentrated under reduced pressure. The residue was purified by silica gel chromatography eluting with 5-80% EtOAc in heptanes to afford 4-hydroxy-4-((4-(5-(hydroxymethyl)benzo[b]thiophen-3-yl)-3-methylphenoxy)methyl)tetrahydro-2H-thiopyran 1,1-dioxide (245 mg, 94%). LC/MS: mass calcd. for C$_{22}$H$_{24}$O$_5$S$_2$: 432.56, found 455.0 [M+Na]$^+$.

(C) (3S)-Methyl 3-(4-((3-(4-((4-hydroxy-1,1-dioxidotetrahydro-2H-thiopyran-4-yl)methoxy)-2-methylphenyl)benzo[b]thiophen-5-yl)methoxy)phenyl)hex-4-ynoate was prepared from 4-hydroxy-4-((4-(5-(hydroxymethyl)benzo[b]thiophen-3-yl)-3-methylphenoxy)methyl)tetrahydro-2H-thiopyran 1,1-dioxide and (3S)-methyl 3-(4-hydroxyphenyl)hex-4-ynoate (prepared as described in WO 2005086661) following General Procedure B using PPh$_3$ and DBAD. MS: mass calcd. for C$_{35}$H$_{36}$O$_7$S$_2$: 632.8, found 633.2 [M]$^-$, 655.2 [M+Na]$^+$.

(D) (3S)-3-[4-[[3-[4-[(4-Hydroxy-1,1-dioxothian-4-yl)methoxy]-2-methylphenyl]-benzo[b]thiophen-5-yl]methoxy]phenyl]hex-4-ynoic acid was prepared from (3S)-methyl 3-(4-((3-(4-((4-hydroxy-1,1-dioxidotetrahydro-2H-thiopyran-4-yl)methoxy)-2-methylphenyl)benzo[b]thiophen-5-yl)methoxy)phenyl)hex-4-ynoate following General Procedure C using LiOH as base and 2N HCl for reaction acidification. $^1$H NMR (CDCl$_3$) δ 7.92 (d, J=8.1 Hz, 1H), 7.37-7.49 (m, 2H), 7.27-7.32 (m, 3H), 7.22 (d, J=8.1 Hz, 1H), 6.89 (d, J=8.6 Hz, 3H), 6.82 (dd, J=8.1, 2.5 Hz, 1H), 5.09 (s, 2H), 3.98-4.10 (m, 1H), 3.93 (s, 2H), 3.42-3.59 (m, 2H), 2.92-3.02 (m, 2H), 2.80 (dd, J=15.7, 8.1 Hz, 1H), 2.70 (dd, J=15.7, 7.1 Hz, 1H), 2.13 (s, 3H), 1.83 (d, J=2.53 Hz, 3H). LC/MS: mass calcd. for $C_{34}H_{34}O_7S_2$: 618.8, found 619.0 [M]$^+$.

(E) A solution of (3S)-3-[4-[[3-[4-[(4-hydroxy-1,1-dioxothian-4-yl)methoxy]-2-methylphenyl]-benzo[b]thiophen-5-yl]methoxy]phenyl]hex-4-ynoic acid (30 mg, 0.048 mmol), HATU (55 mg, 0.145 mmol), NH$_4$Cl (26 mg, 0.49 mmol) and DIEA (19 mg, 0.15 mmol) in DMF (2 mL) was stirred at rt for 1 h. The reaction was then quenched by the addition of satd. aq NH$_4$Cl (5 mL) and the mixture was extracted with EtOAc (3×5 mL). The combined organic extracts were dried (Na$_2$SO$_4$) and concentrated under reduced pressure to afford (3S)-3-[4-[[3-[4-[(4-hydroxy-1,1-dioxothian-4-yl)methoxy]-2-methylphenyl]-benzo[b]thiophen-5-yl]methoxy]phenyl]hex-4-ynamide (20 mg, 67%) as a light yellow oil, which was used directly without purification. LC/MS: mass calcd. for $C_{34}H_{35}NO_6S_2$: 617.19, found 618.0 [M+H]$^+$.

(F) (3S)-3-[4-[[3-[4-[(4-hydroxy-1,1-dioxothian-4-yl)methoxy]-2-methylphenyl]-benzo[b]thiophen-5-yl]methoxy]phenyl]hex-4-ynenitrile was prepared from (3S)-3-[4-[[3-[4-[(4-hydroxy-1,1-dioxothian-4-yl)methoxy]-2-methylphenyl]-benzo[b]thiophen-5-yl]methoxy]phenyl]hex-4-ynamide following General Procedure I. LC/MS: mass calcd. for $C_{34}H_{33}NO_5S_2$: 599.18, found 617.1 [M+NH$_4$]$^+$.

(G) (2S)-4-((4-(5-((4-(1-(1H-Tetrazol-5-yl)pent-3-yn-2-yl)phenoxy)methyl)benzo[b]thiophen-3-yl)-3-methylphenoxy)methyl)-4-hydroxytetrahydro-2H-thiopyran 1,1-dioxide (Cpd 6) was prepared from (3S)-3-[4-[[3-[4-[(4-hydroxy-1,1-dioxothian-4-yl)methoxy]-2-methylphenyl]-benzo[b]thiophen-5-yl]methoxy]phenyl]hex-4-ynenitrile following General Procedure J, using Workup 2. Additional purification of the product was carried out by preparative HPLC on a Waters SunFire™ Prep C18, 5μ column (19×100 mm) using an acetonitrile/water (0.05% NH$_4$HCO$_3$) gradient (30-85%). $^1$H NMR (CDCl$_3$) δ 7.92 (d, J=8.7 Hz, 1H), 7.41-7.43 (m, 2H), 7.20-7.27 (m, 4H), 6.79-6.89 (m, 4H), 5.07 (s, 2H), 4.05-4.09 (m, 1H), 3.94 (s, 2H), 3.49-3.52 (m, 2H), 3.36-3.39 (m, 2H), 2.87-3.11 (m, 2H), 2.22-2.30 (m, 4H), 2.12 (s, 3H), 1.85 (d, J=2.4 Hz, 3H). LC/MS: mass calcd. for $C_{34}H_{34}N_4O_5S_2$: 642.20, found 643.0 [M+H]$^+$.

Example 7

(2S)-4-(4-(5-((4-(1-(1H-Tetrazol-5-yl)pent-3-yn-2-yl)phenoxy)methyl)benzo[b]thiophen-3-yl)-3-methylphenoxy)-2-methylbutan-2-ol, Cpd 7

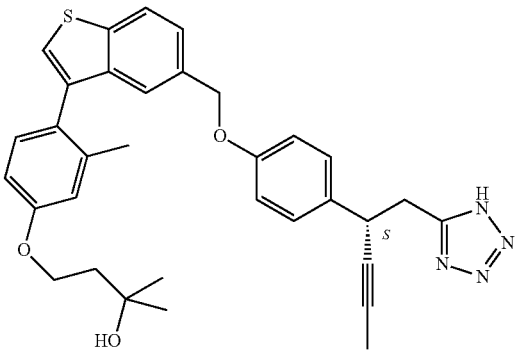

(A) 3-Bromo-5-(chloromethyl)benzo[b]-thiophene was prepared from 3-bromo-5-hydroxymethylbenzothiophene (from Example 1A) following General Procedure D.

(B) A mixture of 3-bromo-5-(chloromethyl)-1-benzothiophene (200 mg, 0.76 mmol), (3S)-ethyl 3-(4-hydroxyphenyl)hex-4-ynoate (180 mg, 0.77 mmol) (available from Synnovator, Inc., Research Triangle Park, N.C.; Cat. # PB05708) and K$_2$CO$_3$ (420 mg, 1.29 mmol) in MeCN (20 mL) was stirred overnight at 50° C. The reaction was then quenched by the addition of satd. aq. NH$_4$Cl (40 mL) and the resulting solution was extracted with ethyl acetate (3×40 mL) and the combined organic extracts were concentrated under reduced pressure. The resultant residue was purified by silica gel chromatography (0-20% EtOAC/petroleum ether) to provide (3S)-ethyl 3-(4-((3-bromobenzo[b]thiophen-5-yl)methoxy)phenyl)hex-4-ynoate as a colorless oil (300 mg, 86% yield). LC/MS: mass calcd. for $C_{23}H_{21}BrO_3S$: 457.38, found: 459.0 [M+H]$^+$.

(C) (3S)-Ethyl 3-(4-((3-(4-hydroxy-2-methylphenyl)benzo[b]thiophen-5-yl)methoxy)phenyl)hex-4-ynoate was prepared from (3S)-ethyl 3-(4-((3-bromobenzo[b]thiophen-5-yl)methoxy)phenyl)hex-4-ynoate and 4-hydroxy-2-methylphenylboronic acid following General Procedure A using PdCl$_2$(dppf).CH$_2$Cl$_2$ as the palladium catalyst and Cs$_2$CO$_3$ in place of K$_2$CO$_3$. LC/MS: mass calcd. for $C_{30}H_{28}O_4S$: 484.61, found: 485.2 [M+H]$^+$.

(D) (3S)-Ethyl 3-(4-((3-(4-(3-hydroxy-3-methylbutoxy)-2-methylphenyl)benzo[b]thiophen-5-yl)methoxy)phenyl)hex-4-ynoate was prepared from 3-(4-((3-(4-hydroxy-2-methylphenyl)benzo[b]thiophen-5-yl)methoxy)phenyl)hex-4-ynoate and 3-methylbutane-1,3-diol following General Procedure B using PPh$_3$ and ADDP. LC/MS: mass calcd. for $C_{35}H_{38}O_5S$: 570.74, found: 571.2 [M+H]$^+$.

(E) (3S)-3-(4-((3-(4-(3-Hydroxy-3-methylbutoxy)-2-methylphenyl)benzo[b]thiophen-5-yl)methoxy)phenyl)hex-4-ynoic acid was prepared from (3S)-ethyl 3-(4-((3-(4-(3-hydroxy-3-methylbutoxy)-2-methylphenyl)benzo[b]thiophen-5-yl)methoxy)phenyl)hex-4-ynoate following General Procedure C using LiOH as base, EtOH in place of MeOH and 1N HCl for reaction acidification. $^1$H NMR (CD$_3$OD) δ 7.96 (m, 1H), 7.48 (m, 1H), 7.38 (s, 2H), 7.22-7.28 (m, 2H), 7.13-7.16 (m, 1H), 6.81-6.95 (m, 4H), 5.16 (s, 2H), 4.19-4.22 (m, 2H), 3.39-4.01 (m, 1H), 2.62-2.67 (m, 2H), 2.01-2.08 (m, 5H), 1.82 (s, 3H), 1.38 (s, 6H). LC/MS: mass calcd. for $C_{33}H_{34}O_5S$: 542.69, found: 543.2 [M+H]$^+$.

(F) (3S)-3-(4-((3-(4-(3-Hydroxy-3-methylbutoxy)-2-methylphenyl)benzo[b]thiophen-5-yl)methoxy)phenyl)hex-4-ynoamide was prepared by the HATU-mediated coupling of (3S)-3-(4-((3-(4-(3-hydroxy-3-methylbutoxy)-2-methylphenyl)benzo[b]thiophen-5-yl)methoxy)phenyl)hex-4-ynoic acid and NH$_4$Cl following the procedure described in Example 6E. LC/MS: mass calcd. for $C_{33}H_{35}NO_4S$: 541.23, found: 542.1 [M+H]$^+$.

(G) (3S)-3-(4-((3-(4-(3-Trifluoroacetoxy-3-methylbutoxy)-2-methylphenyl)benzo[b]thiophen-5-yl)methoxy)phenyl)hex-4-ynenitrile was prepared from (3S)-3-(4-((3-(4-(3-hydroxy-3-methylbutoxy)-2-methylphenyl)benzo[b]thiophen-5-yl)methoxy)phenyl)hex-4-ynoamide following General Procedure I. LC/MS: mass calcd. for $C_{35}H_{32}F_3NO_4S$: 619.20, found 506.0 [M−CF$_3$COO]$^+$.

(H) (3S)-4-(4-(5-((4-(1-(1H-Tetrazol-5-yl)pent-3-yn-2-yl)phenoxy)methyl)benzo[b]thiophen-3-yl)-3-methylphenoxy)-2-methylbutan-2-yl 2,2,2-trifluoroacetate was prepared from (3S)-3-(4-((3-(4-(3-Trifluoroacetoxy-3-methylbutoxy)-2-methylphenyl)benzo[b]thiophen-5-yl)methoxy)phenyl)hex-4-ynenitrile following General Procedure J, using Workup 2. LC/MS: mass calcd. for $C_{35}H_{33}F_3N_4O_4S$: 662.22, found 549.1 [M−CF$_3$COO]$^+$.

(I) A solution of (3S)-4-(4-(5-((4-(1-(1H-tetrazol-5-yl)pent-3-yn-2-yl)phenoxy)methyl)benzo[b]thiophen-3-yl)-3-methylphenoxy)-2-methylbutan-2-yl 2,2,2-trifluoroacetate (10 mg, 0.015 mmol), LiOH (20 mg, 0.48 mmol), THF (2 mL) and water (1 mL) was stirred at rt overnight. The mixture was concentrated under reduced pressure and then diluted with water (5 mL). The pH of the solution was adjusted to 4-5 with 1 M HCl and the solids that formed were collected by filtration and dried to afford (2S)-4-(4-(5-((4-(1-(1H-tetrazol-5-yl)pent-3-yn-2-yl)phenoxy)methyl)benzo[b]thiophen-3-yl)-3-methylphenoxy)-2-methylbutan-2-ol (Cpd 7) (2.7 mg, 33%) as a white solid. $^1$H NMR (CD$_3$OD+D$_2$O) δ 7.90 (d, J=8.4 Hz, 1H), 7.41 (d, J=8.7 Hz, 1H), 7.34 (d, J=5.1 Hz, 2H), 7.18 (d, J=8.4 Hz, 2H), 7.11 (d, J=8.1 Hz, 1H), 6.80-6.84 (m, 4H), 5.09 (s, 2H), 4.16 (t, J=6.6 Hz, 2H), 4.02 (br. s, 1H), 3.07-3.15 (m, 2H), 1.95-2.00 (m, 5H), 1.71 (s, 3H), 1.28 (s, 6H). LC/MS: mass calcd. for C$_{33}$H$_{34}$N$_4$O$_3$S: 566.24, found: 567.1 [M+H]$^+$.

Example 8

(2S)-5-(2-(4-((3-(4-(2-Methoxyethoxy)-2-methylphenyl)benzo[b]thiophen-5-yl)methoxy)phenyl)pent-3-yn-1-yl)-1H-tetrazole, Cpd 8

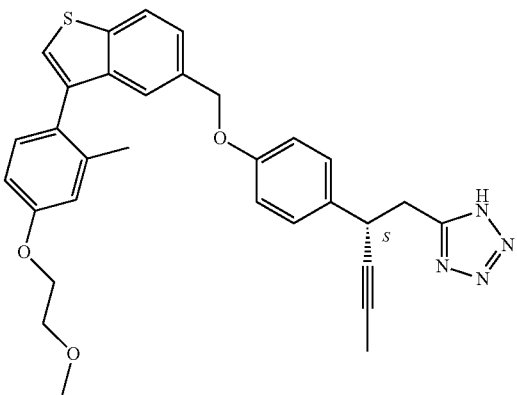

(A) A mixture of 4-bromo-3-methylphenol (5 g, 26.7 mmol), 1-bromo-2-methoxyethane (4.4 g, 31.7 mmol) and K$_2$CO$_3$ (15 g, 108.5 mmol) in MeCN (100 mL) was stirred overnight at 80° C. After cooling to rt, the reaction was filtered and the filtrate was concentrated under reduced pressure to afford 1-bromo-4-(2-methoxyethoxy)-2-methylbenzene as a yellow oil. $^1$H NMR (CDCl$_3$) δ 7.38 (d, J=8.8 Hz, 1H), 6.81 (d, J=2.8 Hz, 1H), 6.63 (dd, J=8.4, 2.8 Hz, 1H), 4.06 (t, J=4.8 Hz, 2H), 3.72 (t, J=4.8 Hz, 2H), 3.43 (s, 3H), 2.34 (s, 3H).

(B) 2-(4-(2-Methoxyethoxy)-2-methylphenyl)-4,4,5,5-tetramethyl-1,3,2-dioxaborolane was prepared from 1-bromo-4-(2-methoxyethoxy)-2-methylbenzene and bis(pinacolato)diboron following General Procedure A, using PdCl$_2$(dppf).CH$_2$Cl$_2$ as the palladium catalyst and Cs$_2$CO$_3$ in place of K$_2$CO$_3$. LC/MS: mass calcd. for C$_{16}$H$_{25}$BO$_4$: 292.18, found: 293.2 [M+H]$^+$.

(C) 3-(4-(2-Methoxyethoxy)-2-methylphenyl)benzo[b]thiophene-5-carbaldehyde was prepared from 2-(4-(2-methoxyethoxy)-2-methylphenyl)-4,4,5,5-tetramethyl-1,3,2-dioxaborolane and 3-bromobenzo[b]thiophene-5-carbaldehyde (from Example 4A) following General Procedure A, using PdCl$_2$(dppf).CH$_2$Cl$_2$ as the palladium catalyst and Cs$_2$CO$_3$ in place of K$_2$CO$_3$. $^1$H NMR (CDCl$_3$) δ 10.02 (s, 1H), 8.02-8.04 (m, 1H), 7.88-7.90 (m, 2H), 7.37 (s, 1H), 7.20-7.26 (m, 1H), 6.83-6.94 (m, 2H), 4.19-4.21 (m, 2H), 3.37-3.82 (m, 2H), 3.49 (s, 3H), 2.14 (s, 3H).

(D) (3-(4-(2-Methoxyethoxy)-2-methylphenyl)benzo[b]thiophen-5-yl)methanol was prepared 3-(4-(2-methoxyethoxy)-2-methylphenyl)benzo[b]thiophene-5-carbaldehyde following General Procedure F. LC/MS: mass calcd. for C$_{19}$H$_{20}$O$_3$S: 328.43, found: 311.0 [M-OH]$^+$.

(E) 5-(Chloromethyl)-3-(4-(2-methoxyethoxy)-2-methylphenyl)benzo[b]thiophene was prepared from (3-(4-(2-methoxyethoxy)-2-methylphenyl)benzo[b]thiophen-5-yl)methanol following General Procedure D. LC/MS: mass calcd. for C$_{19}$H$_{19}$ClO$_2$S: 346.87, found: 347.1 [M]$^+$.

(F) (3S)-Ethyl 3-(4-((3-(4-(2-methoxyethoxy)-2-methylphenyl)benzo[b]thiophen-5-yl)methoxy)phenyl)hex-4-ynoate was prepared from 5-(chloromethyl)-3-(4-(2-methoxyethoxy)-2-methylphenyl)benzo[b]thiophene and (3S)-ethyl 3-(4-hydroxyphenyl)hex-4-ynoate (available from Synnovator, Inc., Research Triangle Park, N.C.; Cat. # PB05708) following General Procedure E. LC/MS: mass calcd. for C$_{33}$H$_{34}$O$_5$S: 542.69, found: 543.2 [M+H]$^+$.

(G) (3S)-3-(4-((3-(4-(2-Methoxyethoxy)-2-methylphenyl)benzo[b]thiophen-5-yl)methoxy)phenyl)hex-4-ynoic acid was prepared from (3S)-ethyl 3-(4-((3-(4-(2-methoxyethoxy)-2-methylphenyl)benzo[b]thiophen-5-yl)methoxy)phenyl)hex-4-ynoate following General Procedure C using LiOH as base, EtOH in place of MeOH and 1N HCl for reaction acidification. $^1$H NMR (DMSO-d$_6$) δ 8.06 (d, J=8.4 Hz, 1H), 7.65 (s, 1H), 7.47 (d, J=8.4 Hz, 1H), 7.41 (s, 1H), 7.23-7.25 (m, 2H), 7.16 (d, J=8.0 Hz, 1H), 6.86-6.96 (m, 4H), 5.17 (s, 2H), 4.13-4.16 (m, 2H), 3.90-3.95 (m, 1H), 3.68-3.70 (m, 2H), 3.33 (s, 3H), 2.54-2.58 (m, 2H), 2.05 (s, 3H), 1.76 (s, 3H). LC/MS: mass calcd. for C$_{31}$H$_{30}$O$_5$S: 514.63, found: 515.2 [M+H]$^+$.

(H) (3S)-3-(4-((3-(4-(2-methoxyethoxy)-2-methylphenyl)benzo[b]thiophen-5-yl)methoxy)phenyl)hex-4-ynoyl chloride was prepared from (3S)-3-(4-((3-(4-(2-Methoxyethoxy)-2-methylphenyl)benzo[b]thiophen-5-yl)methoxy)phenyl)hex-4-ynoic acid following General Procedure G, using oxalyl chloride as the chlorinating agent.

(I) (3S)-3-(4-((3-(4-(2-Methoxyethoxy)-2-methylphenyl)benzo[b]thiophen-5-yl)methoxy)phenyl)hex-4-ynamide was prepared from (3S)-3-(4-((3-(4-(2-methoxyethoxy)-2-methylphenyl)benzo[b]thiophen-5-yl)methoxy)phenyl)hex-4-ynoyl chloride following General Procedure Ha. LC/MS: mass calcd. for C$_{31}$H$_{31}$NO$_4$S: 513.20, found: 514.3 [M+H]$^+$.

(J) (3S)-3-(4-((3-(4-(2-Methoxyethoxy)-2-methylphenyl)benzo[b]thiophen-5-yl)methoxy)phenyl)hex-4-ynenitrile was prepared from (3S)-3-(4-((3-(4-(2-methoxyethoxy)-2-methylphenyl)benzo[b]thiophen-5-yl)methoxy)phenyl)hex-4-ynamide following General Procedure I. LC/MS: mass calcd. for C$_3$H$_{29}$NO$_3$S: 495.19, found: 513.1 [M+NH$_4$]$^+$.

(K) (2S)-5-(2-(4-((3-(4-(2-Methoxyethoxy)-2-methylphenyl)benzo[b]thiophen-5-yl)methoxy)phenyl)pent-3-yn-1-yl)-1H-tetrazole, (Cpd 8) was prepared from (3S)-3-(4-((3-(4-(2-methoxyethoxy)-2-methylphenyl)benzo[b]thiophen-5-yl)methoxy)phenyl)hex-4-ynenitrile following General Procedure J, using Workup 2. $^1$H NMR (CD$_3$OD) δ 7.92 (d, J=8.4 Hz, 1H), 7.43 (d, J=8.4 Hz, 1H), 7.38 (d, J=8.8 Hz, 2H), 7.21 (d, J=8.4 Hz, 2H), 7.14 (d, J=8.4 Hz, 1H), 6.84-6.91 (m, 4H), 5.12 (s, 2H), 4.15-4.17 (m, 2H), 4.02-4.07 (m, 1H), 3.76-3.78 (m, 2H), 3.45 (s, 3H), 3.25 (d, J=7.6 Hz, 2H), 2.05 (s, 3H), 1.77 (s, 3H). LC/MS: mass calcd. for C$_3$H$_{30}$N$_4$O$_3$S: 538.20, found: 539.1[M+H]$^+$.

Example 9

(2S)-5-(2-(4-((3-(2-Methyl-4-((tetrahydro-2H-pyran-4-yl)oxy)phenyl)benzo[b]thiophen-5-yl)methoxy)phenyl)pent-3-yn-1-yl)-1H-tetrazole, Cpd 9

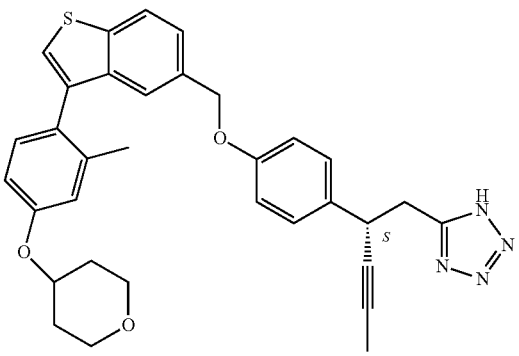

(A) 4-(4-Bromo-3-methylphenoxy)-tetrahydro-2H-pyran was prepared from 4-bromo-3-methylphenol and oxan-4-ol following General Procedure B using PPh$_3$ and DBAD at a reaction temperature of 50° C. overnight. $^1$H NMR (CDCl$_3$) δ 7.41 (d, J=8.6 Hz, 1H), 6.81 (d, J=3.0 Hz, 1H), 6.62 (dd, J=8.7, 3.0 Hz, 1H), 4.39-4.47 (m, 1H), 3.93-4.00 (m, 2H), 3.53-3.60 (m, 2H), 2.35 (s, 3H), 1.95-2.03 (m, 2H), 1.70-1.82 (m, 2H); LC/MS: Calcd. for C$_{12}$H$_{15}$BrO$_2$: 271.2, found: 271.0 [M]$^+$, 273.0 [M+2]$^+$.

(B) 4,4,5,5-Tetramethyl-2-(2-methyl-4-(tetrahydro-2H-pyran-4-yloxy)phenyl)-1,3,2-dioxaborolane was prepared from 4-(4-bromo-3-methylphenoxy)-tetrahydro-2H-pyran and bis(pinacolato)diboron following General Procedure A, using PdCl$_2$(dppf).CH$_2$Cl$_2$ as the palladium catalyst, KOAc in place of K$_2$CO$_3$ and a reaction temperature of 70° C. overnight. LC/MS: mass calcd. for C$_{18}$H$_{27}$BO$_4$: 318.2, found: 319.2 [M]$^+$.

(C) 3-(2-Methyl-4-(tetrahydro-2H-pyran-4-yloxy)phenyl)benzo[b]thiophene-5-carbaldehyde was prepared from 3-bromobenzo[b]thiophene-5-carbaldehyde (from Example 4A) and 4,4,5,5-tetramethyl-2-[2-methyl-4-(oxan-4-yloxy)phenyl]-1,3,2-dioxaborolane following General Procedure A using PdCl$_2$(dppf).CH$_2$Cl$_2$ as the palladium catalyst and Cs$_2$CO$_3$ in place of K$_2$CO$_3$. LC/MS: mass calcd. for C$_{21}$H$_{20}$O$_3$S: 352.45, found: 353.1 [M+H]$^+$.

(D) (3-(2-Methyl-4-(tetrahydro-2H-pyran-4-yloxy)phenyl)benzo[b]thiophen-5-yl)methanol was prepared from 3-(2-methyl-4-(tetrahydro-2H-pyran-4-yloxy)phenyl)benzo[b]thiophene-5-carbaldehyde following General Procedure F. LC/MS: mass calcd. for C$_{21}$H$_{22}$O$_3$S: 354.46, found: 355.1 [M+H]$^+$.

(E) 4-(4-(5-(Chloromethyl)benzo[b]thiophen-3-yl)-3-methylphenoxy)-tetrahydro-2H-pyran was prepared from (3-(2-methyl-4-(tetrahydro-2H-pyran-4-yloxy)phenyl) benzo[b]thiophen-5-yl)methanol following General Procedure D.

(F) (3S)-Ethyl 3-(4-((3-(2-methyl-4-(tetrahydro-2H-pyran-4-yloxy)phenyl)benzo[b]thiophen-5-yl)methoxy)phenyl)hex-4-ynoate was prepared from 4-(4-(5-(chloromethyl)benzo[b]thiophen-3-yl)-3-methylphenoxy)-tetrahydro-2H-pyran and (3S)-ethyl 3-(4-hydroxyphenyl)hex-4-ynoate (available from Synnovator, Inc., Research Triangle Park, N.C.; Cat. # PB05708) following General Procedure E using DMF as solvent at a reaction temperature of 60° C. for 1 h. LC/MS: mass calcd. for C$_{35}$H$_{36}$O$_5$S: 568.72, found: 569.2 [M]$^+$.

(G) (3S)-3-(4-((3-(2-Methyl-4-(tetrahydro-2H-pyran-4-yloxy)phenyl)benzo[b]thiophen-5-yl)methoxy)phenyl)hex-4-ynoic acid was prepared from (3S)ethyl 3-(4-((3-(2-methyl-4-(tetrahydro-2H-pyran-4-yloxy)phenyl)benzo[b]thiophen-5-yl)methoxy)phenyl)hex-4-ynoate following General Procedure C using LiOH as base and 1N HCl for reaction acidification. $^1$H NMR (DMSO-d$_6$) δ 12.35 (br. s, 1H), 8.00-8.04 (m, 1H), 7.65 (s, 1H), 7.42-7.49 (m, 2H), 7.23-7.26 (m, 2H), 7.14-7.17 (m, 1H), 6.98-6.99 (m, 1H), 6.90-6.93 (m, 3H), 5.17 (s, 2H), 4.60-4.66 (m, 1H), 3.84-3.95 (m, 3H), 3.47-3.55 (m, 2H), 2.56-2.59 (m, 2H), 1.99-2.05 (m, 5H), 1.76 (s, 3H), 1.56-1.68 (m, 2H). LC/MS: mass calcd. for C$_{33}$H$_{32}$O$_5$S: 540.67, found: 541.2 [M+H]$^+$.

(H) (3S)-3-(4-((3-(2-Methyl-4-(tetrahydro-2H-pyran-4-yloxy)phenyl)benzo[b]thiophen-5-yloxy)methyl)phenyl) hex-4-ynoyl chloride was prepared from (3S)-3-(4-((3-(2-methyl-4-(tetrahydro-2H-pyran-4-yloxy)phenyl)benzo[b]thiophen-5-yl)methoxy)phenyl)hex-4-ynoic acid following General Procedure G, using oxalyl chloride as the chlorinating agent.

(I) (3S)-3-(4-((3-(2-Methyl-4-(tetrahydro-2H-pyran-4-yloxy)phenyl)benzo[b]thiophen-5-yloxy)methyl)phenyl) hex-4-ynamide was prepared from (3S)-3-(4-((3-(2-methyl-4-(tetrahydro-2H-pyran-4-yloxy)phenyl)benzo[b]thiophen-5-yloxy)methyl)phenyl)hex-4-ynoyl chloride following General Procedure Ha and was used directly without characterization.

(J) (3S)-3-(4-((3-(2-Methyl-4-(tetrahydro-2H-pyran-4-yloxy)phenyl)benzo[b]thiophen-5-yloxy)methyl)phenyl) hex-4-ynenitrile was prepared from (3S)-3-(4-((3-(2-methyl-4-(tetrahydro-2H-pyran-4-yloxy)phenyl)benzo[b]thiophen-5-yloxy)methyl)phenyl)hex-4-ynamide following General Procedure I and was used directly without characterization.

(K) (2S)-5-(2-(4-((3-(2-Methyl-4-((tetrahydro-2H-pyran-4-yl)oxy)phenyl)benzo[b]thiophen-5-yl)methoxy)phenyl) pent-3-yn-1-yl)-1H-tetrazole, (Cpd 9) was prepared from (3S)-3-(4-((3-(2-methyl-4-(tetrahydro-2H-pyran-4-yloxy) phenyl)benzo[b]thiophen-5-yloxy)methyl)phenyl)hex-4-ynenitrile following General Procedure J, using Workup 2. $^1$H NMR (CD$_3$OD) δ 7.78 (d, J=8.8 Hz, 1H), 7.30-7.33 (m, 5H), 7.02-7.14 (m, 2H), 6.78-6.95 (m, 3H), 5.01 (s, 2H), 4.62-4.64 (m, 1H), 4.10-4.15 (m, 1H), 3.96-4.02 (m, 2H), 3.60-3.67 (m, 2H), 3.30-3.33 (m, 2H), 2.05-2.16 (m, 2H), 1.94 (s, 3H), 1.68-1.86 (m, 5H). LC/MS: mass calcd. for C$_{33}$H$_{32}$N$_4$O$_3$S: 564.22, found: 565.3 [M+H]$^+$.

Example 10

(2S)-5-(2-(4-((3-(3-(2-Methoxyethoxy)-2-methylphenyl)benzo[b]thiophen-5-yl)methoxy)phenyl)pent-3-yn-1-yl)-1H-tetrazole, Cpd 10

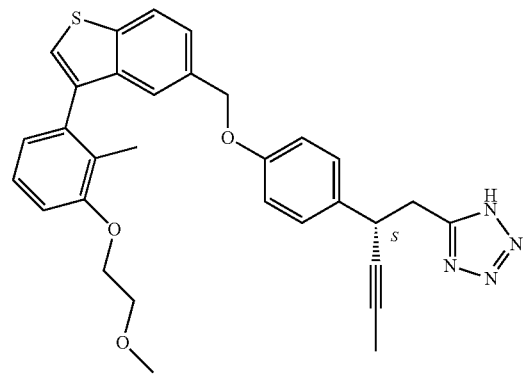

(A) 1-Bromo-3-(2-methoxyethoxy)-2-methylbenzene was prepared from 3-bromo-2-methylphenol and 1-bromo-2-methoxyethane following the procedure described in Example 8A. GC/MS: mass calcd. for C₁H₁₃BrO₂: 244.01, found: 244.0 [M]⁺, 246.0 [M+2]⁺.

(B) 2-[3-(2-Methoxyethoxy)-2-methylphenyl]-4,4,5,5-tetramethyl-1,3,2-dioxaborolane was prepared from 1-bromo-3-(2-methoxyethoxy)-2-methylbenzene and bis(pinacolato)diboron following General Procedure A, using PdCl₂(dppf)CH₂Cl₂ as the palladium catalyst, KOAc in place of K₂CO₃ and DMSO as solvent at a reaction temperature of 90° C. overnight. ¹H NMR (CDCl₃) δ 7.35 (dd, J=7.5, 1.2 Hz, 1H), 7.13 (t, J=7.5 Hz, 1H), 6.91-6.93 (m, 1H), 4.09-4.12 (m, 2H), 3.75-3.78 (m, 2H), 3.46 (s, 3H), 2.44 (s, 3H), 1.34 (s, 12H).

(C) Ethyl (3S)-3-[4-([3-[3-(methoxyethoxy)-2-methylphenyl]-1-benzothiophen-5-yl]methoxy)phenyl]hex-4-ynoate was prepared from 2-[3-(2-methoxyethoxy)-2-methylphenyl]-4,4,5,5-tetramethyl-1,3,2-dioxaborolane and ethyl (3S)-3-[4-[(3-bromo-1-benzothiophen-5-yl)methoxy]phenyl]hex-4-ynoate (from Example 22C) following General Procedure A, using PdCl₂(dppf).CH₂Cl₂ as the palladium catalyst and Cs₂CO₃ in place of K₂CO₃. LC/MS: mass calcd. for C₃₃H₃₄O₅S: 542.69, found: 543.2 [M+H]⁺.

(D) (3S)-3-[4-([3-[3-(2-Methoxyethoxy)-2-methylphenyl]-1-benzothiophen-5-yl]methoxy)phenyl]hex-4-ynoic acid was prepared from ethyl (3S)-3-[4-([3-[3-(methoxymethoxy)-2-methylphenyl]-1-benzothiophen-5-yl]methoxy)phenyl]hex-4-ynoate following General Procedure C, using LiOH as base, EtOH in place of MeOH and 1N HCl for reaction acidification. ¹H NMR (300 MHz, DMSO-d₆) δ 8.06 (d, J=8.1 Hz, 1H), 7.67 (s, 1H), 7.47 (d, J=8.4 Hz, 1H), 7.39-7.40 (m, 1H), 7.21-7.28 (m, 3H), 7.04-7.07 (m, 1H), 6.85-6.90 (m, 3H), 5.15 (s, 2H), 4.15-4.18 (m, 2H), 3.89-3.95 (m, 1H), 3.71-3.74 (m, 2H), 3.35 (s, 3H), 2.36-2.44 (m, 2H), 1.92 (s, 3H), 1.75 (s, 3H). LC/MS: mass calcd. for C₃₁H₃₀O₅S: 514.63, found: 515.2 [M+H]⁺, 537.2 [M+Na]⁺.

(E) (3S)-3-(4-((3-(3-(2-methoxyethoxy)-2-methylphenyl)benzo[b]thiophen-5-yl)methoxy)phenyl)hex-4-ynoyl chloride was prepared from (3S)-3-[4-([3-[3-(2-methoxyethoxy)-2-methylphenyl]-1-benzothiophen-5-yl]methoxy)phenyl]hex-4-ynoic acid following General Procedure G, using oxalyl chloride as the chlorinating agent.

(F) (3S)-3-(4-((3-(3-(2-methoxyethoxy)-2-methylphenyl)benzo[b]thiophen-5-yl)methoxy)phenyl)hex-4-ynamide was prepared from (3S)-3-(4-((3-(3-(2-methoxyethoxy)-2-methylphenyl)benzo[b]thiophen-5-yl)methoxy)phenyl)hex-4-ynoyl chloride following General Procedure Ha and was used directly without characterization.

(G) (3S)-3-(4-((3-(3-(2-methoxyethoxy)-2-methylphenyl)benzo[b]thiophen-5-yl)methoxy)phenyl)hex-4-ynenitrile was prepared from (3S)-3-(4-((3-(3-(2-methoxyethoxy)-2-methylphenyl)benzo[b]thiophen-5-yl)methoxy)phenyl)hex-4-ynamide following General Procedure I and was used directly without characterization.

(H) (2S)-5-(2-(4-((3-(3-(2-Methoxyethoxy)-2-methylphenyl)benzo[b]thiophen-5-yl)methoxy)phenyl)pent-3-yn-1-yl)-1H-tetrazole (Cpd 10) was prepared from (3S)-3-(4-((3-(3-(2-methoxyethoxy)-2-methylphenyl)benzo[b]thiophen-5-yl)methoxy)phenyl)hex-4-ynenitrile following General Procedure J, using Workup 2. ¹H NMR (CD₃OD) δ 7.96 (d, J=8.3 Hz, 1H), 7.50-7.54 (m, 1H), 7.36-7.38 (m, 2H), 7.18-7.29 (m, 3H), 6.99-7.06 (m, 1H), 6.88-6.92 (m, 3H), 5.13 (s, 2H), 4.17-4.25 (m, 2H), 4.07-4.10 (m, 1H), 3.79-3.84 (m, 2H), 3.47 (s, 3H), 3.26 (d, J=7.7 Hz, 2H), 1.97 (s, 3H), 1.79 (s, 3H). LC/MS: mass calcd. for C₃H₃₀N₄O₃S: 538.20, found: 539.3 [M+H]⁺.

Example 11

(2S)-3-(5-((4-(1-(1H-Tetrazol-5-yl)pent-3-yn-2-yl)phenoxy)methyl)benzo[b]thiophen-3-yl)-2-methylpyridine, Cpd 11

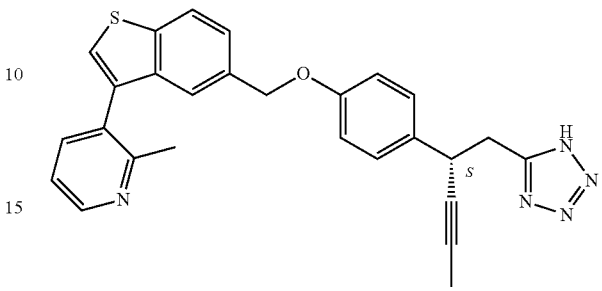

(A) (3S)-Ethyl 3-(4-((3-(2-methylpyridin-3-yl)benzo[b]thiophen-5-yl)methoxy)phenyl)hex-4-ynoate was prepared from (3S)-ethyl 3-(4-((3-bromobenzo[b]thiophen-5-yl)methoxy)phenyl)hex-4-ynoate (from Example 7B) and (2-methylpyridin-3-yl)boronic acid following General Procedure A, using PdCl₂(dppf).CH₂Cl₂ as the palladium catalyst and Cs₂CO₃ in place of K₂CO₃. LC/MS: mass calcd. for C₂₉H₂₇NO₃S: 469.59, found: 470.2 [M+H]⁺.

(B) (3S)-3-(4-((3-(2-Methylpyridin-3-yl)benzo[b]thiophen-5-yl)methoxy)phenyl)hex-4-ynoic acid was prepared from (3S)-ethyl 3-(4-((3-(2-methylpyridin-3-yl)benzo[b]thiophen-5-yl)methoxy)phenyl)hex-4-ynoate following General Procedure C using LiOH as base, EtOH in place of MeOH and 2N HCl for reaction acidification. ¹H NMR (DMSO-d₆) δ 12.24 (s, 1H), 8.56 (dd, J=1.6, 4.8 Hz, 1H), 8.11 (d, J=8.4 Hz, 1H), 7.85 (s, 1H), 7.68 (dd, J=1.6, 7.6 Hz, 1H), 7.51 (d, J=8.4 Hz, 1H), 7.44 (s, 1H), 7.34-7.38 (m, 1H), 7.24 (d, J=8.4 Hz, 2H), 6.91 (d, J=8.8 Hz, 2H), 5.18 (s, 2H), 3.90-3.92 (m, 1H), 2.56 (d, J=7.6 Hz, 2H), 2.29 (s, 3H), 1.77 (s, 3H). LC/MS: mass calcd. for C₂₇H₂₃NO₃S: 441.54, found: 442.1 [M+H]⁺.

(C) (3S)-3-(4-((3-(2-Methylpyridin-3-yl)benzo[b]thiophen-5-yl)methoxy)phenyl)hex-4-ynoyl chloride was prepared from (3S)-3-(4-((3-(2-methylpyridin-3-yl)benzo[b]thiophen-5-yl)methoxy)phenyl)hex-4-ynoic acid following General Procedure G, using oxalyl chloride as the chlorinating agent.

(D) (3S)-3-(4-((3-(2-Methylpyridin-3-yl)benzo[b]thiophen-5-yl)methoxy)phenyl)hex-4-ynamide was prepared from (3S)-3-(4-((3-(2-methylpyridin-3-yl)benzo[b]thiophen-5-yl)methoxy)phenyl)hex-4-ynoyl chloride following General Procedure Ha (inverse addition). LC/MS: mass calcd. for C₂₇H₂₄N₂O₂S: 440.16, found: 441.1 [M+H]⁺.

(E) (3S)-3-(4-((3-(2-Methylpyridin-3-yl)benzo[b]thiophen-5-yl)methoxy)phenyl)hex-4-ynenitrile was prepared from (3S)-3-(4-((3-(2-methylpyridin-3-yl)benzo[b]thiophen-5-yl)methoxy)phenyl)hex-4-ynamide following General Procedure I. LC/MS: mass calcd. for C₂₇H₂₂N₂OS: 422.15, found: 423.2 [M+H]⁺.

(F) (2S)-3-(5-((4-(1-(1H-Tetrazol-5-yl)pent-3-yn-2-yl)phenoxy)methyl)benzo[b]thiophen-3-yl)-2-methylpyridine (Cpd 11) was prepared from (3S)-3-(4-((3-(2-methylpyridin-3-yl)benzo[b]thiophen-5-yl)methoxy)phenyl)hex-4-ynenitrile following General Procedure J, using Workup 2. ¹H NMR (CD₃OD) δ 8.73-8.75 (m, 1H), 8.34-8.37 (m, 1H), 8.06 (d, J=8.1 Hz, 1H), 7.84-7.91 (m, 2H), 7.52-7.58 (m, 2H), 7.21 (d, J=8.4 Hz, 2H), 6.91 (d, J=8.7 Hz, 2H), 5.19 (s, 2H), 4.04-4.10 (m, 1H), 3.22-3.23 (m, 2H), 2.54 (s, 3H), 1.79 (s, 3H). LC/MS: mass calcd. for $C_{27}H_{23}N_5OS$: 465.16, found: 466.2 $[M+H]^+$.

Example 12

(2S)-3-((4-(5-((4-(1-(1H-Tetrazol-5-yl)pent-3-yn-2-yl)phenoxy)methyl)benzo[b]thiophen-3-yl)-3-methylphenoxy)methyl)-3-methylthietane 1,1-dioxide, Cpd 12

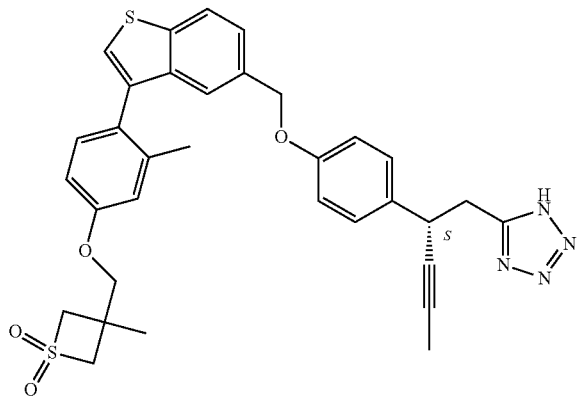

(A) To an ice-cooled solution of 4-bromo-3-methylphenol (300 mg, 1.60 mmol), (3-methylthietan-3-yl)methanol (300 mg, 2.54 mmol) and (n-Bu)$_3$P (810 mg, 4.02 mmol) in toluene (10 mL) was added ADDP (1020 mg, 4.07 mmol). Upon completion of addition, the reaction mixture was warmed to 60° C. and stirred for 2 h. The reaction was treated with satd. aq. NH$_4$Cl (50 mL), extracted with EtOAc (2×50 mL) and the combined organic extracts were concentrated under reduced pressure. Purification of the resultant residue by silica gel chromatography (0-2% EtOAc/petroleum ether) afforded 3-((4-bromo-3-methylphenoxy)methyl)-3-methylthietane (0.67 g, crude) as a white solid. $^1$H NMR (CDCl$_3$) δ 7.36-7.42 (m, 1H), 6.84-6.85 (m, 1H), 6.63-6.67 (m, 1H), 3.90 (s, 2H), 3.18 (d, J=6.3 Hz, 2H), 2.95 (d, J=6.3 Hz, 2H), 2.37 (s, 3H), 1.46 (s, 3H).

(B) To a solution of 3-((4-bromo-3-methylphenoxy)methyl)-3-methylthietane (570 mg, 1.37 mmol) and Na$_2$WO$_4$.2H$_2$O (110 mg, 0.35 mmol) in MeOH (50 mL) was added 30% H$_2$O$_2$ (1.92 g, 16.94 mmol) in drop-wise fashion, and the resulting mixture was stirred at rt for 2 h. The mixture was then concentrated under reduced pressure and purified directly by silica gel chromatography (0-10% EtOAc/petroleum ether) to afford 3-(4-bromo-3-methylphenoxymethyl)-3-methylthietane-1,1-dioxide (412 mg, 94% yield) as a colorless oil. $^1$H NMR (CDCl$_3$) δ 7.41-7.44 (m, 1H), 6.82-6.83 (m, 1H), 6.61-6.65 (m, 1H), 4.20-4.25 (m, 2H), 3.97 (s, 2H), 3.83-3.88 (m, 2H), 2.37 (s, 3H), 1.60 (s, 3H).

(C) 3-Methyl-3-[3-methyl-4-(tetramethyl-1,3,2-dioxaborolan-2-yl)phenoxymethyl]-thietane-1,1-dioxide was prepared from 3-(4-bromo-3-methylphenoxymethyl)-3-methyl-thietane-1,1-dioxide and bis(pinacolato)diboron following General Procedure A, using PdCl$_2$(dppf).CH$_2$Cl$_2$ as the palladium catalyst, dioxane as solvent and Cs$_2$CO$_3$ in place of K$_2$CO$_3$ at a reaction temperature of 80° C. overnight. $^1$H NMR (CDCl$_3$) δ 7.44-7.46 (m, 1H), 6.85-6.86 (m, 1H), 6.64-6.67 (m, 1H), 4.23-4.29 (m, 2H), 3.99 (s, 2H), 3.85-3.90 (m, 2H), 2.37 (s, 3H), 1.63 (s, 3H), 1.35 (s, 12H).

(D) 3-{2-Methyl-4-[(3 oxo-thietan-3-yl)methoxy]phenyl}-1-benzothiophene-5-carbaldehyde was prepared from 3-methyl-3-[3-methyl-4-(tetramethyl-1,3,2-dioxaborolan-2-yl)phenoxymethyl]-thietane-1,1-dioxide and 3-bromobenzo[b]thiophene-5-carbaldehyde (from Example 4A) following General Procedure A, using PdCl$_2$(dppf).CH$_2$Cl$_2$ as the palladium catalyst and Cs$_2$CO$_3$ in place of K$_2$CO$_3$ at a reaction temperature of 80° C. overnight. $^1$H NMR (CDCl$_3$) δ 7.44-7.46 (m, 1H), 6.85-6.86 (m, 1H), 6.64-6.67 (m, 1H), 4.23-4.29 (m, 2H), 3.99 (s, 2H), 3.85-3.90 (m, 2H), 2.37 (s, 3H), 1.63 (s, 3H), 1.35 (s, 12H).

(E) 3-{4-[5-(Hydroxymethyl)-1-benzothiophen-3-yl]-3-methylphenoxymethyl}-3-methyl-thietane-1,1-dione was prepared from 3-{2-methyl-4-[(3-methyl-1,1-dioxo-thietan-3-yl)methoxy]phenyl}-1-benzothiophene-5-carbaldehyde following General Procedure F. LC/MS: mass calcd. for $C_{21}H_{22}O_4S_2$: 402.53, found: 403.1 $[M+H]^+$.

(F) 3-{4-[5-(Chloromethyl)-1-benzothiophen-3-yl]-3-methylphenoxymethyl}-3-methyl-thietane-1,1-dione was prepared from 3-{4-[5-(hydroxymethyl)-1-benzothiophen-3-yl]-3-methylphenoxymethyl}-3-methyl-thietane-1,1-dione following General Procedure D. LC/MS: mass calcd. for $C_{21}H_{21}ClO_3S_2$: 420.97; found: 421.1 $[M]^+$.

(G) (3S)-3-(4-((3-(2-Methyl-4-((3-methyl-1,1-dioxidothietan-3-yl)methoxy)phenyl)benzo[b]thiophen-5-yl)methoxy)phenyl)hex-4-ynenitrile was prepared from 3-{4-[5-(chloromethyl)-1-benzothiophen-3-yl]-3-methylphenoxymethyl}-3-methyl-thietane-1,1-dione and (3S)-3-(4-hydroxyphenyl)hex-4-ynenitrile (from Example 2G) following General Procedure E, at a reaction temperature of 60° C. overnight. LC/MS: mass calcd. for $C_{33}H_{31}NO_4S_2$: 569.17, found: 587.0 $[M+NH_4]^+$.

(H) (2S)-3-((4-(5-((4-(1-(1H-Tetrazol-5-yl)pent-3-yn-2-yl)phenoxy)methyl)benzo[b]thiophen-3-yl)-3-methylphenoxy)methyl)-3-methylthietane 1,1-dioxide (Cpd 12) was prepared from (3S)-3-(4-((3-(2-methyl-4-((3-methyl-1,1-dioxidothietan-3-yl)methoxy)phenyl)benzo[b]thiophen-5-yl)methoxy)phenyl)hex-4-ynenitrile following General Procedure J, using Workup 2. $^1$H NMR (CD$_3$OD) δ 7.90 (d, J=8.4 Hz, 1H), 7.35-7.42 (m, 3H), 7.12-7.19 (m, 3H), 6.84-6.94 (m, 4H), 5.08 (s, 2H), 4.22-4.27 (m, 2H), 4.08 (s, 2H), 3.99-4.05 (m, 1H), 3.84-3.89 (m, 2H), 3.21-3.24 (m, 2H), 2.03 (s, 3H), 1.74 (d, J=2.4 Hz, 3H), 1.57 (s, 3H). LC/MS: mass calcd. for $C_{33}H_{32}N_4O_4S_2$: 612.19, found: 613.0 $[M+H]^+$.

Example 13

(2S)-5-(2-(4-((3-(2-(Trifluoromethyl)phenyl)benzo[b]thiophen-5-yl)methoxy)phenyl)pent-3-yn-1-yl)-1H-tetrazole, Cpd 13

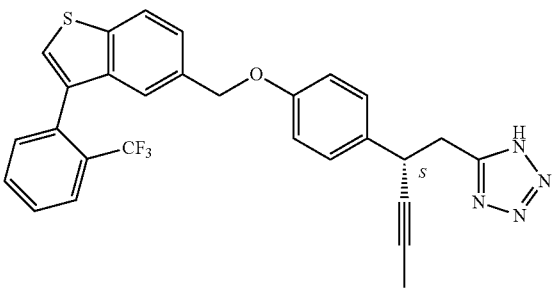

(A) (3S)-Ethyl 3-(4-((3-(2-(trifluoromethyl)phenyl)benzo[b]thiophen-5-yl)methoxy)phenyl)hex-4-ynoate was prepared from 2-(trifluoromethyl)phenylboronic acid and (3S)- ethyl 3-(4-((3-bromobenzo[b]thiophen-5-yl)methoxy)phenyl)hex-4-ynoate (from Example 7B) following General Procedure A, using PdCl$_2$(dppf).CH$_2$Cl$_2$ as the palladium catalyst and Cs$_2$CO$_3$ in place of K$_2$CO$_3$. LC/MS: mass calcd. for C$_{30}$H$_{25}$F$_3$O$_3$S: 522.58, found: 523.1 [M+H]$^+$.

(B) (3S)-3-(4-((3-(2-(Trifluoromethyl)phenyl)benzo[b]thiophen-5-yl)methoxy)phenyl)hex-4-ynoic acid was prepared from (3S)-ethyl 3-(4-((3-(2-(trifluoromethyl)phenyl)benzo[b]thiophen-5-yl)methoxy)phenyl)hex-4-ynoate following General Procedure C using LiOH as base, EtOH in place of MeOH, 2N HCl for reaction acidification and a reaction temperature of 30° C. overnight. $^1$H NMR (DMSO-d$_6$) δ 8.08 (d, J=8.4 Hz, 1H), 7.93 (d, J=7.6 Hz, 1H), 7.69-7.82 (m, 3H), 7.48-7.51 (m, 2H), 7.43 (s, 1H), 7.24 (d, J=8.8 Hz, 2H), 6.89 (d, J=8.4 Hz, 2H), 5.13 (s, 2H), 3.91-3.93 (m, 1H), 2.58-2.67 (m, 2H), 1.77 (s, 3H). LC/MS: mass calcd. for C$_{28}$H$_{21}$F$_3$O$_3$S: 494.52, found: 493.1 [M−H]$^-$.

(C) (3S)-3-(4-((3-(2-(Trifluoromethyl)phenyl)benzo[b]thiophen-5-yl)methoxy)phenyl)hex-4-ynoyl chloride was prepared from (3S)-3-(4-((3-(2-(Trifluoromethyl)phenyl)benzo[b]thiophen-5-yl)methoxy)phenyl)hex-4-ynoic acid following General Procedure G, using oxalyl chloride as the chlorinating agent.

(D) (3S)-3-(4-((3-(2-(Trifluoromethyl)phenyl)benzo[b]thiophen-5-yl)methoxy)phenyl)hex-4-ynamide was prepared from (3S)-3-(4-((3-(2-(trifluoromethyl)phenyl)benzo[b]thiophen-5-yl)methoxy)phenyl)hex-4-ynoyl chloride following General Procedure Ha (inverse addition). LC/MS: mass calcd. for C$_{28}$H$_{22}$F$_3$NO$_2$S: 493.13, found: 494.2 [M+H]$^+$.

(E) (3S)-3-(4-((3-(2-(Trifluoromethyl)phenyl)benzo[b]thiophen-5-yl)methoxy)phenyl)hex-4-ynenitrile was prepared from (3S)-3-(4-((3-(2-(trifluoromethyl)phenyl)benzo[b]thiophen-5-yl)methoxy)phenyl)hex-4-ynamide following General Procedure I. LC/MS: mass calcd. for C$_{28}$H$_{20}$F$_3$NOS: 475.12, found: 498.1 [M+Na]$^+$.

(F) (2S)-5-(2-(4-((3-(2-(Trifluoromethyl)phenyl)benzo[b]thiophen-5-yl)methoxy)phenyl)pent-3-yn-1-yl)-1H-tetrazole (Cpd 13) was prepared from (3S)-3-(4-((3-(2-(trifluoromethyl)phenyl)benzo[b]thiophen-5-yl)methoxy)phenyl)hex-4-ynenitrile following General Procedure J, using Workup 2. Additional purification of the product was carried out by preparative HPLC on a Waters SunFire™ Prep C18, 5μ column (19×100 mm) using an acetonitrile/water (0.05% TFA) gradient (20-50%). $^1$H NMR (CD$_3$OD) δ 7.96 (d, J=8.1 Hz, 1H), 7.88 (d, J=7.5 Hz, 1H), 7.61-7.75 (m, 2H), 7.36-7.52 (m, 4H), 7.22 (d, J=8.7 Hz, 2H), 6.89 (d, J=8.7 Hz, 2H), 5.12 (s, 2H), 4.03-4.09 (m, 1H), 3.25-3.28 (m, 2H), 1.78 (s, 3H). LC/MS: mass calcd. for C$_{28}$H$_{21}$F$_3$N$_4$OS: 518.14, found: 519.2 [M+H]$^+$.

Example 14

(2S)-5-(2-(4-((3-(2-Methyl-4-(methylsulfonyl)phenyl)benzo[b]thiophen-5-yl)methoxy)phenyl)pent-3-yn-1-yl)-1H-tetrazole, Cpd 14

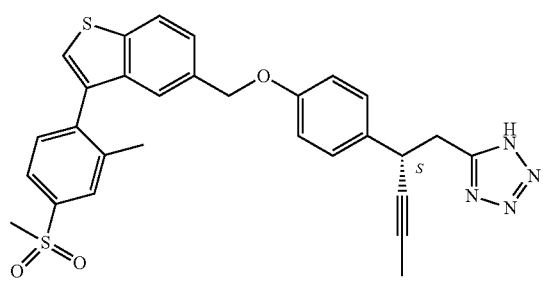

(A) 3-(2-Methyl-4-(methylsulfonyl)phenyl)benzo[b]thiophene-5-carbaldehyde was prepared from (3-(4,4,5,5-tetramethyl-1,3,2-dioxaborolan-2-yl)benzo[b]thiophen-5-yl)methanol (from Example 5A) and 1-bromo-4-methanesulfonyl-2-methylbenzene following General Procedure A, using PdCl$_2$(dppf).CH$_2$Cl$_2$ as the palladium catalyst, Cs$_2$CO$_3$ in place of K$_2$CO$_3$. LC/MS: mass calcd. for C$_{17}$H$_{14}$O$_3$S$_2$: 330.42, found: 331.1 [M+H]$^+$.

(B) (3-(2-Methyl-4-(methylsulfonyl)phenyl)benzo[b]thiophen-5-yl)methanol was prepared from 3-(2-methyl-4-(methylsulfonyl)phenyl)benzo[b]thiophene-5-carbaldehyde and NaBH$_4$, following General Procedure F. LC/MS: mass calcd. for C$_{17}$H$_{16}$O$_3$S$_2$: 332.44, found: 314.9 [M−OH]$^+$.

(C) (3S)-Ethyl 3-(4-((3-(2-methyl-4-(methylsulfonyl)phenyl)benzo[b]thiophen-5-yl)methoxy)phenyl)hex-4-ynoate was prepared from (3-(2-methyl-5-(methylsulfonyl)phenyl)benzo[b]-thiophen-5-yl)methanol and (3S)-ethyl 3-(4-hydroxyphenyl)hex-4-ynoate (available from Synnovator, Inc., Research Triangle Park, N.C.; Cat. # PB05708) following General Procedure B, using Bu$_3$P and ADDP at a reaction temperature of 60° C. overnight. LC/MS: mass calcd. for C$_{31}$H$_{30}$O$_5$S$_2$: 546.70, found: 547.2 [M]$^+$.

(D) (3S)-3-(4-((3-(2-Methyl-4-(methyl sulfonyl)phenyl)benzo[b]thiophen-5-yl)methoxy)phenyl)hex-4-ynoic acid was prepared from (3S)-ethyl 3-(4-((3-(2-methyl-4-(methyl sulfonyl)phenyl)benzo[b]thiophen-5-yl)methoxy)phenyl)hex-4-ynoate following General Procedure C, using LiOH as base, EtOH in place of MeOH and 1N HCl for reaction acidification. $^1$H NMR (DMSO-d$_6$) δ 12.23 (br. s, 1H), 8.11 (d, J=8.4 Hz, 1H), 7.96 (s, 1H), 7.85-7.87 (m, 2H), 7.51-7.57 (m, 2H), 7.45 (s, 1H), 7.24 (d, J=8.4 Hz, 2H), 6.92 (d, J=8.4 Hz, 2H), 5.17 (s, 2H), 3.90-3.95 (m, 1H), 3.29 (s, 3H), 2.54-2.59 (m, 2H), 2.21 (s, 3H), 1.76 (s, 3H). LC/MS: mass calcd. for C$_{29}$H$_{26}$O$_5$S$_2$: 518.64, found: 519.0 [M]$^+$.

(E) (3S)-3-(4-((3-(2-Methyl-4-(methylsulfonyl)phenyl)benzo[b]thiophen-5-yl)methoxy)phenyl)hex-4-ynoyl chloride was prepared from (3S)-3-(4-((3-(2-Methyl-4-(methylsulfonyl)phenyl)benzo[b]thiophen-5-yl)methoxy)phenyl)hex-4-ynoic acid following General Procedure G, using oxalyl chloride as the chlorinating agent.

(F) (3S)-3-(4-((3-(2-Methyl-4-(methylsulfonyl)phenyl)benzo[b]thiophen-5-yl)methoxy)phenyl)hex-4-ynamide was prepared from (3S)-3-(4-((3-(2-methyl-4-(methylsulfonyl)phenyl)benzo[b]thiophen-5-yl)methoxy)phenyl)hex-4-ynoyl chloride following General Procedure Ha. LC/MS: mass calcd. for C$_{29}$H$_{27}$NO$_4$S$_2$: 517.14, found: 518.0 [M+H]$^+$.

(G) (3S)-3-(4-((3-(2-Methyl-4-(methylsulfonyl)phenyl)benzo[b]thiophen-5-yl)methoxy)phenyl)hex-4-ynenitrile was prepared from (3S)-3-(4-((3-(2-methyl-4-(methylsulfonyl)phenyl)benzo[b]thiophen-5-yl)methoxy)phenyl)hex-4-ynamide following General Procedure I. LC/MS: mass calcd. for C$_{29}$H$_{25}$NO$_3$S$_2$: 499.13, found: 517.0 [M+NH$_4$]$^+$.

(H) (2S)-5-(2-(4-((3-(2-Methyl-4-(methylsulfonyl)phenyl)benzo[b]thiophen-5-yl)methoxy)phenyl)pent-3-yn-1-yl)-1H-tetrazole (Cpd 14) was prepared from (3S)-3-(4-((3-(2-methyl-4-(methylsulfonyl)phenyl)benzo[b]thiophen-5-yl)methoxy)phenyl)hex-4-ynenitrile following General Procedure J, using Workup 2. $^1$H NMR (CD$_3$OD) δ 7.95 (t, J=8.1 Hz, 2H), 7.84 (d, J=8.1 Hz, 1H), 7.55 (s, 1H), 7.48 (t, J=8.4 Hz, 2H), 7.35 (s, 1H), 7.18 (d, J=8.4 Hz, 2H), 6.86 (d, J=8.7 Hz, 2H), 5.12 (s, 2H), 4.02-4.08 (m, 1H), 3.21-3.28 (m, 2H), 3.16 (s, 3H), 2.17 (s, 3H), 1.75 (s, 3H). LC/MS: mass calcd. for C$_{29}$H$_{26}$N$_4$O$_3$S$_2$: 542.15, found: 543.0 [M+H]$^+$.

Example 15

(2S)-5-(2-(4-((3-(5-(2-Methoxyethoxy)-2-methylphenyl)benzo[b]thiophen-5-yl)methoxy)phenyl)pent-3-yn-1-yl)-1H-tetrazole, Cpd 15

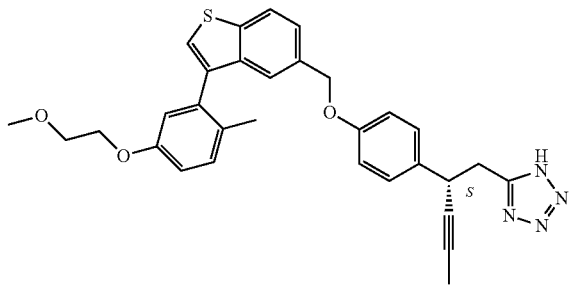

(A) 2-Bromo-4-(2-methoxyethoxy)-1-methylbenzene was prepared from 3-bromo-4-methylphenol and 1-bromo-2-methoxyethane following the procedure described in Example 8A. GC/MS: mass calcd. for $C_{10}H_nBrO_2$: 244.01, found: 244.1 [M]$^+$, 246.1 [M+2]$^+$.

(B) 2-[5-(2-Methoxyethoxy)-2-methylphenyl]-4,4,5,5-tetramethyl-1,3,2-dioxaborolane was prepared from 2-bromo-4-(2-methoxyethoxy)-1-methylbenzene and bis(pinacolato)diboron following General Procedure A, using PdCl$_2$(dppf).CH$_2$Cl$_2$ as the palladium catalyst, KOAc in place of K$_2$CO$_3$ and DMSO as solvent. $^1$H NMR (CDCl$_3$) δ 7.31-7.32 (m, 1H), 7.05-7.10 (m, 1H), 6.88-6.93 (m, 1H), 4.11-4.14 (m, 2H), 3.72-3.75 (m, 2H), 3.44 (s, 3H), 2.46 (s, 3H), 1.33 (s, 12H).

(C) Ethyl (3S)-3-[4-([3-[5-(2-methoxyethoxy)-2-methylphenyl]-1-benzothiophen-5-yl]methoxy)phenyl]hex-4-ynoate was prepared from ethyl (3S)-3-[4-[(3-bromo-1-benzothiophen-5-yl)methoxy]phenyl]hex-4-ynoate and 2-[5-(2-methoxyethoxy)-2-methylphenyl]-4,4,5,5-tetramethyl-1,3,2-dioxaborolane following General Procedure A, using PdCl$_2$(dppf).CH$_2$Cl$_2$ as the palladium catalyst and Cs$_2$CO$_3$ in place of K$_2$CO$_3$. $^1$H NMR (CDCl$_3$) δ 7.80-7.90 (m, 1H), 7.45-7.58 (m, 2H), 7.30-7.35 (m, 2H), 7.13-7.20 (m, 2H), 6.86-6.90 (m, 4H), 5.08 (s, 2H), 4.05-4.13 (m, 4H), 3.73-3.76 (m, 2H), 3.44 (s, 3H), 2.63-2.71 (m, 2H), 2.06 (s, 3H), 1.81 (s, 3H), 1.15-1.25 (m, 3H).

(D) (3S)-3-[4-([3-[5-(2-Methoxyethoxy)-2-methylphenyl]-1-benzothiophen-5-yl]methoxy)phenyl]hex-4-ynoic acid was prepared from ethyl (3S)-3-[4-([3-[5-(2-methoxyethoxy)-2-methylphenyl]-1-benzothiophen-5-yl]methoxy)phenyl]hex-4-ynoate following General Procedure C, using LiOH as base, EtOH in place of MeOH, a reaction temperature of 30° C. overnight and 1N HCl for reaction acidification. Additional product purification was carried out by silica gel chromatography [EtOAc/petroleum ether (1:1)]. $^1$H NMR (DMSO-d$_6$) δ 8.07 (d, J=8.4 Hz, 1H), 7.71 (s, 1H), 7.45-7.49 (m, 2H), 7.23-7.28 (m, 3H), 6.90-6.96 (m, 3H), 6.82 (d, J=2.8 Hz, 1H), 5.18 (s, 2H), 4.07-4.09 (m, 2H), 3.90-3.94 (m, 1H), 3.64 (t, J=4.4 Hz, 2H), 3.29 (s, 3H), 2.56 (d, J=8.4 Hz, 2H), 1.99 (s, 3H), 1.76 (s, 3H). LC/MS: mass calcd for $C_{31}H_{30}O_5S$: 514.63, found 515.2 [M+H]$^+$, 537.2 [M+Na]$^+$.

(E) (3S)-3-(4-((3-(5-(2-Methoxyethoxy)-2-methylphenyl)benzo[b]thiophen-5-yl)methoxy)phenyl)hex-4-ynoyl chloride was prepared from (3S)-3-[4-([3-[5-(2-methoxyethoxy)-2-methylphenyl]-1-benzothiophen-5-yl]methoxy)phenyl]hex-4-ynoic acid following General Procedure G, using oxalyl chloride as the chlorinating agent.

(F) (3S)-3-(4-((3-(5-(2-Methoxyethoxy)-2-methylphenyl)benzo[b]thiophen-5-yl)methoxy)phenyl)hex-4-ynamide was prepared from (3S)-3-(4-((3-(5-(2-methoxyethoxy)-2-methylphenyl)benzo[b]thiophen-5-yl)methoxy)phenyl)hex-4-ynoyl chloride following General Procedure Ha. LC/MS: mass calcd. for $C_{31}H_{31}NO_4S$: 513.20, found: 514.1 [M+H]$^+$.

(G) (3S)-3-(4-((3-(5-(2-Methoxyethoxy)-2-methylphenyl)benzo[b]thiophen-5-yl)methoxy)phenyl)hex-4-ynenitrile was prepared from (3S)-3-(4-((3-(5-(2-methoxyethoxy)-2-methylphenyl)benzo[b]thiophen-5-yl)methoxy)phenyl)hex-4-ynamide following General Procedure I. LC/MS: mass calcd. for $C_3H_{29}NO_3S$: 495.19, found: 513.1 [M+NH$_4$]$^+$.

(H) (2S)-5-(2-(4-((3-(5-(2-Methoxyethoxy)-2-methylphenyl)benzo[b]thiophen-5-yl)methoxy)phenyl)pent-3-yn-1-yl)-1H-tetrazole (Cpd 15) was prepared from (3S)-3-(4-((3-(5-(2-methoxyethoxy)-2-methylphenyl)benzo[b]thiophen-5-yl)methoxy)phenyl)hex-4-ynenitrile following General Procedure J, using Workup 2. $^1$H NMR (CD$_3$OD) δ 7.92 (d, J=8.1 Hz, 1H), 7.40-7.44 (m, 3H), 7.17-7.22 (m, 3H), 6.80-6.92 (m, 4H), 5.11 (s, 2H), 4.00-4.08 (m, 3H), 3.69-3.72 (m, 2H), 3.38 (s, 3H), 3.21-3.29 (m, 2H), 1.98 (s, 3H), 1.75 (s, 3H). LC/MS: mass calcd. for $C_{31}H_{30}N_4O_3S$: 538.20, found: 539.1 [M+H]$^+$.

Example 16

(2S)-5-(2-(4-((3-(2-Methyl-4-(3-(methylsulfonyl)propoxy)phenyl)benzo[b]thiophen-5-yl)methoxy)phenyl)pent-3-yn-1-yl)-1H-tetrazole, Cpd 16

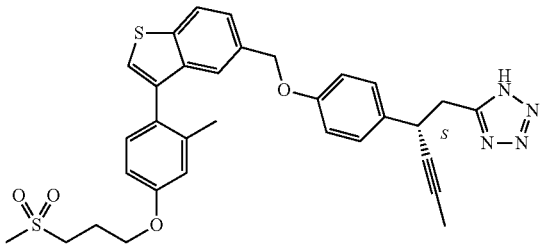

(A) To a solution of 3-methylthiopropanol (1.6 g; 15.07 mmol) and tosyl chloride (3.16 g; 16.57 mmol) in DCM (10 mL) was added pyridine (1.46 mL; 18.08 mmol) in dropwise fashion, and the resultant mixture was stirred at rt for 1 h. The mixture was then concentrated under reduced pressure and the residue thus obtained was purified by silica gel chromatography eluting with 0-50% EtOAc in hexanes to afford 3-(methylthio)propyl 4-methylbenzenesulfonate (3.6 g; 92%) as a colorless oil. LC/MS: mass calcd. for $C_{11}H_{16}O_3S_2$: 260.38, found 283.1 [M+Na]$^+$.

(B) To an ice-cooled solution of 3-(methylthio)propyl 4-methylbenzenesulfonate (3.6 g; 13.8 mmol) in MeOH (70 mL) was added a suspension of monopersulfate compound (17 g; 27.4 mmol) in water (70 mL) in a portion-wise fashion. Upon completion of the addition, the mixture was allowed to warm to rt, and stirring was continued for 20 h. The reaction was partially concentrated to remove the MeOH and the mixture was further diluted with water and extracted with EtOAc (2×). The combined organic extracts were dried (Na$_2$SO$_4$), filtered and concentrated under reduced pressure. The residue was purified by silica gel chromatography eluting with 0-67% EtOAc in hexanes to afford 3-(methylsulfonyl)propyl 4-methylbenzene-sulfonate (3.72 g, 92%) as a white solid. LC/MS: mass calcd. for $C_{11}H_{16}O_5S_2$: 292.38, found 315.1 [M+Na]+.

(C) A mixture of 5-hydroxymethyl-3-(4-hydroxy-2-methylphenyl)benzo[b]thiophene (from Example 6A) (108 mg; 0.4 mmol), 3-(methylsulfonyl)propyl 4-methylbenzenesulfonate (292 mg; 1.0 mmol) and $K_2CO_3$ (82 mg; 0.6 mmol) in DMF (1.0 mL) was stirred at 90° C. for 6 h. After cooling to rt, the reaction was partitioned between EtOAc and aq $NH_4Cl$ and the aqueous layer was extracted with EtOAc (2×). The combined organic layers were washed with brine, dried ($Na_2SO_4$), filtered and concentrated under reduced pressure. The residue was purified by silica gel chromatography eluting with 5-60% EtOAc in heptanes to afford 5-hydroxymethyl-3-(2-methyl-4-(3-(methylsulfonyl) propoxy)phenyl)benzo[b]thiophene (87 mg, 56%). LC/MS: mass calcd. for $C_{20}H_{20}O_4S_2$: 390.52, found 413.1 [M+Na]+.

(D) (3S)-Methyl 3-(4-((3-(2-methyl-4-(3-(methyl sulfonyl)propoxy)phenyl)benzo-[b]thiophen-5-yl)methoxy)phenyl)hex-4-ynoate was prepared from 5-hydroxymethyl-3-(2-methyl-4-(3-(methylsulfonyl)propoxy)phenyl)benzo[b] thiophene and (3S)-methyl 3-(4-hydroxyphenyl)hex-4-ynoate (prepared as described in WO 2005086661) following General Procedure B using $PPh_3$ and DBAD. LC/MS: mass calcd. for $C_{33}H_{34}O_6S_2$: 590.76, found 591.0 [M]+, 613.0 [M+Na]+.

(E) (3S)-3-[4-[[3-[2-Methyl-4-(3-methylsulfonylpropoxy)phenyl]benzo[b]thiophen-5-yl]methoxy]phenyl] hex-4-ynoic acid was prepared from (3S)-methyl 3-(4-((3-(2-methyl-4-(3-(methylsulfonyl)propoxy)phenyl)benzo[b] thiophen-5-yl)methoxy)phenyl)hex-4-ynoate following General Procedure C using LiOH as base and 2N HCl for reaction acidification. $^1$H NMR ($CDCl_3$) δ 7.92 (d, J=9.1 Hz, 1H), 7.40-7.48 (m, 2H), 7.27-7.32 (m, 3H), 7.20 (d, J=8.1 Hz, 1H), 6.83-6.95 (m, 3H), 6.80 (dd, J=8.6, 2.5 Hz, 1H), 5.08 (s, 2H), 4.17 (t, J=5.6 Hz, 2H), 3.98-4.09 (m, 1H), 3.25-3.35 (m, 2H), 2.98 (s, 3H), 2.79 (dd, J=15.7, 8.1 Hz, 1H), 2.69 (dd, J=15.7, 7.1 Hz, 1H), 2.12 (s, 3H), 1.82 (d, J=2.5 Hz, 3H). LC/MS: mass calcd. for $C_{32}H_{32}O_6S_2$: 576.73, found 577.0 [M]+.

(F) (3S)-3-[4-[[3-[2-Methyl-4-(3-methylsulfonylpropoxy)phenyl]benzo[b]thiophen-5-yl]methoxy]phenyl] hex-4-ynoyl chloride was prepared from (3S)-3-[4-[[3-[2-methyl-4-(3-methylsulfonylpropoxy)phenyl]benzo[b] thiophen-5-yl]methoxy]phenyl]hex-4-ynoic acid following General Procedure G, using thionyl chloride as the chlorinating agent.

(G) (3S)-3-[4-[[3-[2-Methyl-4-(3-methylsulfonylpropoxy)phenyl]benzo[b]thiophen-5-yl]methoxy]phenyl] hex-4-ynamide was prepared from (3S)-3-[4-[[3-[2-methyl-4-(3-methylsulfonylpropoxy)phenyl]benzo[b]thiophen-5-yl]methoxy]phenyl]hex-4-ynoyl chloride following General Procedure Ha. LC/MS: mass calcd. for $C_{32}H_{33}NO_5S_2$: 575.18, found 576.0 [M+H]+.

(H) (3S)-3-[4-[[3-[2-Methyl-4-(3-methylsulfonylpropoxy)phenyl]benzo[b]thiophen-5-yl]methoxy]phenyl] hex-4-ynenitrile was prepared from (3S)-3-[4-[[3-[2-methyl-4-(3-methylsulfonylpropoxy)phenyl]benzo[b] thiophen-5-yl]methoxy]phenyl]hex-4-ynamide following General Procedure I. LC/MS: mass calcd. for $C_{32}H_{31}NO_4S_2$: 557.72, found 575.1 [M+NH_4]+.

(I) (2S)-5-(2-(4-((3-(2-Methyl-4-(3-(methylsulfonyl) propoxy)phenyl)benzo[b]thiophen-5-yl)methoxy)phenyl) pent-3-yn-1-yl)-1H-tetrazole (Cpd 16) was prepared from (3S)-3-[4-[[3-[2-methyl-4-(3-methylsulfonylpropoxy)phenyl]benzo[b]thiophen-5-yl]methoxy]phenyl]hex-4-ynenitrile following General Procedure J, using Workup 2. Additional purification of the product was carried out by preparative HPLC on a Waters SunFire™ Prep C18, 5μ column (19×100 mm) using an acetonitrile/water (0.05% $NH_4CO_3$) gradient (30-85%). $^1$H NMR ($CD_3OD$) δ 7.92 (d, J=8.4 Hz, 1H), 7.43 (d, J=8.0 Hz, 1H), 7.36-7.37 (m, 2H), 7.13-7.19 (m, 3H), 6.91-6.92 (m, 1H), 6.83-6.87 (m, 3H), 4.03-4.05 (m, 1H), 3.12-3.37 (m, 4H), 3.02 (s, 3H), 2.28-2.30 (m, 2H), 2.04 (s, 3H), 1.74 (d, J=2.4 Hz, 3H). LC/MS: mass calcd. for $C_{32}H_{32}N_4O_4S_2$: 600.19, found: 601.3 [M+H]+.

Example 17

(2S)-4-(4-(5-((4-(1-(1H-Tetrazol-5-yl)pent-3-yn-2-yl)phenoxy)methyl)benzo[b]thiophen-3-yl)-3-methylphenyl)tetrahydro-2H-thiopyran 1,1-dioxide, Cpd 17

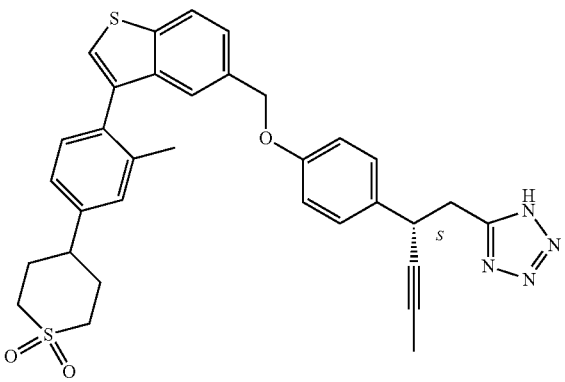

(A) 4-(4-Bromo-3-methylphenyl)-3,6-dihydro-2H-thiopyran was prepared from 2-bromo-5-iodotoluene and 2-(3,6-dihydro-2H-thiopyran-4-yl)-4,4,5,5-tetramethyl-1,3,2-dioxaborolane following General Procedure A, using $PdCl_2$(dppf)$\cdot CH_2Cl_2$ as the palladium catalyst. LC/MS: mass calcd. for $C_{12}H_{13}BrS$: 269.21, found 269.0 [M]+.

(B) To an ice-cooled solution of 4-(4-bromo-3-methylphenyl)-3,6-dihydro-2H-thiopyran (1.12 g; 4.16 mmol) in DCM (15 mL) was added a solution of mCPBA (1.865 g; 8.32 mmol) in DCM (15 mL) in drop-wise fashion. After stirring at 0° C. for 0.5 h, the reaction mixture was poured into a mixture of DCM (30 mL) and satd. aq. $Na_2CO_3$ (60 mL). The aqueous layer was extracted with DCM and the combined organic extracts were washed with satd. aq. $Na_2CO_3$, dried ($Na_2SO_4$), filtered and concentrated under reduced pressure. The resultant residue was purified by silica gel chromatography eluting with 5-40% EtOAc in DCM to afford 4-(4-bromo-3-methylphenyl)-3,6-dihydro-2H-thiopyran 1,1-dioxide (815 mg, 65%). MS: mass calcd. for $C_{12}H_{13}BrO_2S$: 301.20, found 323.0 [M+Na]+, 325.0 [M+2+Na]+.

(C) 4-(3-Methyl-4-(4,4,5,5-tetramethyl-1,3,2-dioxaborolan-2-yl)phenyl)-3,6-dihydro-2H-thiopyran 1,1-dioxide was prepared from 4-(4-bromo-3-methylphenyl)-3,6-dihydro-2H-thiopyran 1,1-dioxide and bis(pinacolato)diboron following General Procedure A, using $PdCl_2$(dppf)$\cdot CH_2Cl_2$ as the palladium catalyst and KOAc in place of $K_2CO_3$. LC/MS: mass calcd. for $C_{18}H_{25}BO_4S$: 348.27, found 349.2 [M+H]+.

(D) 4-(4-(5-(Hydroxymethyl)benzo[b]thiophen-3-yl)-3-methylphenyl)-3,6-dihydro-2H-thiopyran 1,1-dioxide was prepared from 4-(3-methyl-4-(4,4,5,5-tetramethyl-1,3,2-dioxaborolan-2-yl)phenyl)-3,6-dihydro-2H-thiopyran 1,1-dioxide and 3-bromo-5-hydroxymethylbenzothiophene (from Example 1A) following General Procedure A, using $PdCl_2$(dppf).$CH_2Cl_2$ as the palladium catalyst. LC/MS: mass calcd. for $C_{21}H_{20}O_3S_2$: 384.52, found 407.0 $[M+Na]^+$.

(E) A mixture of 4-(4-(5-(hydroxymethyl)benzo[b]thiophen-3-yl)-3-methylphenyl)-3,6-dihydro-2H-thiopyran 1,1-dioxide (from Example 6) (192 mg; 0.5 mmol) and 10% Pd/C (80 mg) in EtOH (6 mL) was prepared under an inert $N_2$ atmosphere and warmed to 45-50° C. A solution of ammonium formate (472 mg, 7.5 mmol) in water (1 mL) was added and the mixture was stirred for 5 h. After cooling to rt, the mixture was diluted with EtOAc (10 mL), filtered and concentrated under reduced pressure. The residue was treated with a mixture of EtOAc/water (2/20 mL), followed by heptanes (30 mL), and the resulting solid product was filtered and washed successively with water and heptanes to afford pure 4-(4-(5-(hydroxymethyl)benzo[b]thiophen-3-yl)-3-methylphenyl)tetrahydro-2H-thiopyran 1,1-dioxide (136 mg, 70%). LC/MS: mass calcd. for $C_{21}H_{22}O_3S_2$: 386.54, found 409.0 $[M+Na]^+$.

(F) (3S)-Methyl 3-(4-((3-(4-(1,1-dioxidotetrahydro-2H-thiopyran-4-yl)-2-methylphenyl)benzo[b]thiophen-5-yl)methoxy)phenyl)hex-4-ynoate was prepared from 4-(4-(5-(hydroxymethyl)benzo[b]thiophen-3-yl)-3-methylphenyl)tetrahydro-2H-thiopyran 1,1-dioxide and (3S)-methyl 3-(4-hydroxyphenyl)hex-4-ynoate (prepared as described in WO 2005086661) following General Procedure B using $PPh_3$ and DBAD. LC/MS: mass calcd. for $C_{34}H_{34}O_5S_2$: 486.77, found 587.3 $[M]^+$; 609.2 $[M+Na]^+$.

(G) (3S)-3-[4-[[3-[4-(1,1-Dioxothian-4-yl)-2-methylphenyl]benzo[b]thiophen-5-yl]methoxy]phenyl]hex-4-ynoic acid was prepared from (3S)-methyl 3-(4-((3-(4-(1,1-dioxidotetrahydro-2H-thiopyran-4-yl)-2-methylphenyl)benzo[b]thiophen-5-yl)methoxy)phenyl)hex-4-ynoate following General Procedure C, using NaOH as base and 2M citric acid for reaction acidification. $^1$H NMR ($CDCl_3$) δ 7.92 (d, J=8.6 Hz, 1H), 7.42-7.48 (m, 2H), 7.22-7.32 (m, 4H), 7.19 (s, 1H), 7.13 (d, J=7.6 Hz, 1H), 6.89 (d, J=9.1 Hz, 2H), 5.08 (s, 2H), 4.00-4.08 (m, 1H), 3.14-3.23 (m, 4H), 2.74-2.87 (m, 2H), 2.64-2.73 (m, 1H), 2.40-2.57 (m, 2H), 2.29 (d, J=14.7 Hz, 2H), 2.14 (s, 3H), 1.82 (d, J=2.5 Hz, 3H). LC/MS: mass calcd. for $C_{33}H_{32}O_5S_2$: 572.75, found 595.3 $[M+Na]^+$.

(H) (3S)-3-[4-[[3-[4-(1,1-Dioxothian-4-yl)-2-methylphenyl]benzo[b]thiophen-5-yl]methoxy]phenyl]hex-4-ynoyl chloride was prepared from (3S)-3-[4-[[3-[4-(1,1-dioxothian-4-yl)-2-methylphenyl]benzo[b]thiophen-5-yl]methoxy]phenyl]hex-4-ynoic acid following General Procedure G, using thionyl chloride as the chlorinating agent.

(I) (3S)-3-[4-[[3-[4-(1,1-Dioxothian-4-yl)-2-methylphenyl]benzo[b]thiophen-5-yl]methoxy]phenyl]hex-4-ynamide was prepared from (3S)-3-[4-[[3-[4-(1,1-dioxothian-4-yl)-2-methylphenyl]benzo[b]thiophen-5-yl]methoxy]phenyl]hex-4-ynoyl chloride following General Procedure Ha. LC/MS: mass calcd. for $C_{33}H_{33}NO_4S_2$: 571.19, found: 572.0 $[M+H]^+$.

(J) (3S)-3-[4-[[3-[4-(1,1-Dioxothian-4-yl)-2-methylphenyl]benzo[b]thiophen-5-yl]methoxy]phenyl]hex-4-ynenitrile was prepared from (3S)-3-[4-[[3-[4-(1,1-dioxothian-4-yl)-2-methylphenyl]benzo[b]thiophen-5-yl]methoxy]phenyl]hex-4-ynamide following General Procedure I. LC/MS: mass calcd. for $C_{33}H_{31}NO_3S_2$: 553.18, found: 571.1 $[M+NH_4]^+$.

(K) (2S)-4-(4-(5-((4-(1-(1H-Tetrazol-5-yl)pent-3-yn-2-yl)phenoxy)methyl)benzo[b]thiophen-3-yl)-3-methylphenyl)tetrahydro-2H-thiopyran 1,1-dioxide (Cpd 17) was prepared from (3S)-3-[4-[[3-[4-(1,1-Dioxothian-4-yl)-2-methylphenyl]benzo[b]thiophen-5-yl]methoxy]phenyl]hex-4-ynenitrile following General Procedure J, using Workup 2. Additional purification of the product was carried out by preparative HPLC on a Waters SunFire™ Prep C18, 5μ column (19×100 mm) using an acetonitrile/water (0.05% $NH_4CO_3$) gradient (30-85%). $^1$H NMR ($CD_3OD$) δ 7.91 (d, J=8.1 Hz, 1H), 7.42 (d, J=8.1 Hz, 1H), 7.35 (d, J=7.8 Hz, 2H), 7.14-7.23 (m, 5H), 6.81 (d, J=8.7 Hz, 2H), 5.08 (s, 2H), 3.99-4.02 (m, 1H), 3.34-3.37 (m, 2H), 3.05-3.21 (m, 4H), 2.91-2.95 (m, 1H), 2.21-2.36 (m, 4H), 2.05 (s, 3H), 1.72 (d, J=2.4 Hz, 3H). LC/MS: mass calcd. for $C_{33}H_{32}N_4O_3S_2$: 596.19, found: 597.3 $[M+H]^+$.

Example 18

4-(4-(5-((4-((2S)-1-(1H-Tetrazol-5-yl)pent-3-yn-2-yl)phenoxy)methyl)-2-methylbenzo[b]thiophen-3-yl)-3-methylphenoxy)tetrahydro-2H-thiopyran 1,1-dioxide, Cpd 18

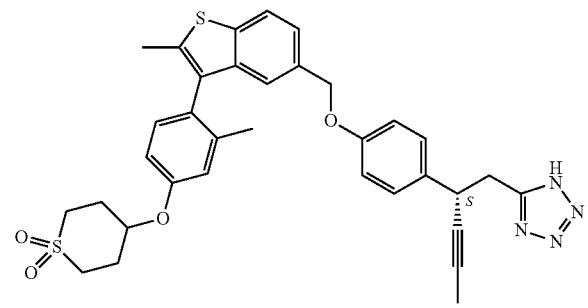

(A) Methyl 3-(4-hydroxy-2-methylphenyl)-2-methylbenzo[b]thiophene-5-carboxylate was prepared from methyl 3-bromo-2-methylbenzo[b]thiophene-5-carboxylate and (4-hydroxy-2-methylphenyl)boronic acid following General Procedure A, using $PdCl_2$(dppf).$CH_2Cl_2$ as the palladium catalyst. MS: mass calcd. for $C_{18}H_{16}O_3S$: 312.39, found 313.2 $[M+H]^+$, 335.1 $[M+Na]^+$.

(B) Methyl 3-(4-((1,1-dioxidotetrahydro-2H-thiopyran-4-yl)oxy)-2-methylphenyl)-2-methylbenzo[b]thiophene-5-carboxylate was prepared from methyl 3-(4-hydroxy-2-methylphenyl)-2-methylbenzo[b]thiophene-5-carboxylate and 4-hydroxytetrahydro-2H-thiopyran 1,1-dioxide following General Procedure B using $PPh_3$ and DBAD. MS: mass calcd. for $C_{23}H_{24}O_5S_2$: 444.57, found 445.0 $[M]^+$, 467.1 $[M+Na]^+$.

(C) To an ice-cooled solution of methyl 3-(4-((1,1-dioxidotetrahydro-2H-thiopyran-4-yl)oxy)-2-methylphenyl)-2-methylbenzo[b]thiophene-5-carboxylate (290 mg; 0.65 mmol) in dry DCM (3 mL) under argon was added DIBAL-H (1M in DCM, 2 mL; 2 mmol). After stirring for 0.5 h, the mixture was poured into a vigorously stirring mixture of sodium potassium tartrate (1M in water, 8 mL) and DCM (5 mL) and stirring was continued for 1 h. The two phases were separated, and the aqueous phase was extracted with DCM (10 mL×2). The combined organic extracts were dried ($Na_2SO_4$), filtered and concentrated under reduced pressure to afford 4-(4-(5-(hydroxymethyl)-2-methylbenzo[b]thiophen-3-yl)-3-methylphenoxy)tetrahydro-2H-thiopyran 1,1-dioxide (265 mg, 98%). LC/MS: mass calcd. for $C_{22}H_{24}O_4S_2$: 416.56, found 399.1 [M−OH]$^+$, 439.0 [M+Na]$^+$.

(D) 4-(4-(5-(Chloromethyl)-2-methylbenzo[b]thiophen-3-yl)-3-methylphenoxy)-tetrahydro-2H-thiopyran 1,1-dioxide was prepared from 4-(4-(5-(hydroxymethyl)-2-methylbenzo[b]thiophen-3-yl)-3-methylphenoxy)tetrahydro-2H-thiopyran 1,1-dioxide following General Procedure D. $^1$H NMR (CDCl$_3$) δ 7.78 (d, J=8.6 Hz, 1H), 7.29-7.34 (m, 1H), 7.14 (s, 1H), 7.11 (d, J=8.1 Hz, 1H), 6.93 (d, J=2.5 Hz, 1H), 6.85 (dd, J=8.1, 2.5 Hz, 1H), 4.72 (br. s., 1H), 4.61 (s, 2H), 3.42-3.55 (m, 2H), 2.99 (d, J=13.1 Hz, 2H), 2.50-2.60 (m, 2H), 2.36-2.48 (m, 2H), 2.34 (s, 3H), 2.04 (s, 3H).

(E) (3S)-Methyl 3-(4-((3-(4-((1,1-dioxidotetrahydro-2H-thiopyran-4-yl)oxy)-2-methylphenyl)-2-methylbenzo[b]thiophen-5-yl)methoxy)phenyl)hex-4-ynoate was prepared from 4-(4-(5-(chloromethyl)-2-methylbenzo[b]thiophen-3-yl)-3-methylphenoxy)-tetrahydro-2H-thiopyran 1,1-dioxide and (3S)-methyl 3-(4-hydroxyphenyl)hex-4-ynoate (prepared as described in WO 2005086661) following General Procedure E. $^1$H NMR (CDCl$_3$) δ 7.80 (d, J=8.6 Hz, 1H), 7.36 (d, J=8.6 Hz, 1H), 7.22-7.28 (m, 2H), 7.17 (s, 1H), 7.11 (d, J=8.6 Hz, 1H), 6.80-6.93 (m, 4H), 5.02 (s, 2H), 4.71 (br. s., 1H), 3.99-4.08 (m, 1H), 3.65 (s, 3H), 3.43-3.54 (m, 2H), 2.93-3.03 (m, 2H), 2.70-2.79 (m, 1H), 2.59-2.68 (m, 1H), 2.49-2.59 (m, 2H), 2.36-2.47 (m, 2H), 2.34 (s, 3H), 2.02 (s, 3H), 1.82 (d, J=2.5 Hz, 3H).

(F) (3S)-3-[4-[[3-[4-(1,1-Dioxothian-4-yl)oxy-2-methylphenyl]-2-methyl-benzo[b]thiophen-5-yl]methoxy]phenyl]hex-4-ynoic acid was prepared from (3S)-methyl 3-(4-((3-(4-((1,1-dioxidotetrahydro-2H-thiopyran-4-yl)oxy)-2-methylphenyl)-2-methylbenzo[b]thiophen-5-yl)methoxy)phenyl)hex-4-ynoate following General Procedure C, using NaOH as base and 2M citric acid for reaction acidification. $^1$H NMR (CDCl$_3$) δ 7.79 (d, J=8.1 Hz, 1H), 7.35 (d, J=8.1 Hz, 1H), 7.28 (s, 1H), 7.17 (s, 1H), 7.11 (d, J=8.1 Hz, 1H), 6.80-6.93 (m, 5H), 5.02 (s, 2H), 4.71 (br. s., 1H), 3.99-4.08 (m, 1H), 3.42-3.55 (m, 2H), 2.93-3.04 (m, 2H), 2.73-2.83 (m, 1H), 2.63-2.73 (m, 1H), 2.48-2.59 (m, 2H), 2.35-2.46 (m, 2H), 2.34 (s, 3H), 2.02 (s, 3H), 1.82 (d, J=2.53 Hz, 3H). LC/MS: mass calcd. for $C_{34}H_{34}O_6S_2$: 602.77, found 603.1 [M]$^+$, 625.2 [M+Na]$^+$.

(G) (3S)-3-[4-[[3-[4-(1,1-Dioxothian-4-yl)oxy-2-methylphenyl]-2-methyl-benzo[b]thiophen-5-yl]methoxy]phenyl]hex-4-ynoyl chloride was prepared from (3S)-3-[4-[[3-[4-(1,1-Dioxothian-4-yl)oxy-2-methyl-phenyl]-2-methyl-benzo[b]thiophen-5-yl]methoxy]phenyl]hex-4-ynoic acid following General Procedure G, using thionyl chloride as the chlorinating agent.

(H) (3S)-3-[4-[[3-[4-(1,1-Dioxothian-4-yl)oxy-2-methylphenyl]-2-methyl-benzo[b]thiophen-5-yl]methoxy]phenyl]hex-4-ynamide was prepared from (3S)-3-[4-[[3-[4-(1,1-dioxothian-4-yl)oxy-2-methyl-phenyl]-2-methyl-benzo[b]thiophen-5-yl]methoxy]phenyl]hex-4-ynoyl chloride following General Procedure Ha. LC/MS: mass calcd. for $C_{34}H_{35}NO_5S_2$: 601.20, found: 602.0 [M+H]$^+$.

(I) (3S)-3-[4-[[3-[4-(1,1-Dioxothian-4-yl)oxy-2-methylphenyl]-2-methyl-benzo[b]thiophen-5-yl]methoxy]phenyl]hex-4-ynenitrile was prepared from (3S)-3-[4-[[3-[4-(1,1-Dioxothian-4-yl)oxy-2-methyl-phenyl]-2-methyl-benzo[b]thiophen-5-yl]methoxy]phenyl]hex-4-ynamide following General Procedure I. LC/MS: mass calcd. for $C_{34}H_{33}NO_4S_2$: 583.18, found: 601.1 [M+NH$_4$]$^+$.

(J) 4-(4-(5-((2S)-1-(1H-Tetrazol-5-yl)pent-3-yn-2-yl)phenoxy)methyl)-2-methylbenzo[b]thiophen-3-yl)-3-methylphenoxy)tetrahydro-2H-thiopyran 1,1-dioxide (Cpd 18) was prepared from (3S)-3-[4-[[3-[4-(1,1-dioxothian-4-yl)oxy-2-methyl-phenyl]-2-methyl-benzo[b]thiophen-5-yl]methoxy]phenyl]hex-4-ynenitrile following General Procedure J, using Workup 2. Additional purification of the product was carried out by preparative HPLC on a Waters SunFire™ Prep C18, 5μ column (19×100 mm) using an acetonitrile/water (0.05% NH$_4$CO$_3$) gradient (30-85%). $^1$H NMR (CD$_3$OD) δ 7.77 (d, J=8.1 Hz, 1H), 7.31 (d, J=8.1 Hz, 1H), 7.15 (d, J=8.4 Hz, 2H), 6.91-7.08 (m, 4H), 6.80 (d, J=8.4 Hz, 2H), 5.02 (s, 2H), 4.75-4.77 (m, 1H), 3.99-4.02 (m, 1H), 3.02-3.36 (m, 6H), 2.34-2.42 (m, 4H), 2.29 (s, 3H), 1.93 (s, 3H), 1.73 (d, J=1.5 Hz, 3H). LC/MS: mass calcd. for $C_{34}H_{34}N_4O_4S_2$: 626.20, found: 627.3 [M±H]$^+$.

Example 19

5-((2S)-2-(4-((2-Methyl-3-(2-methylphenyl)benzo[b]thiophen-5-yl)methoxy)phenyl)pent-3-ynyl)-1H-tetrazole, Cpd 19

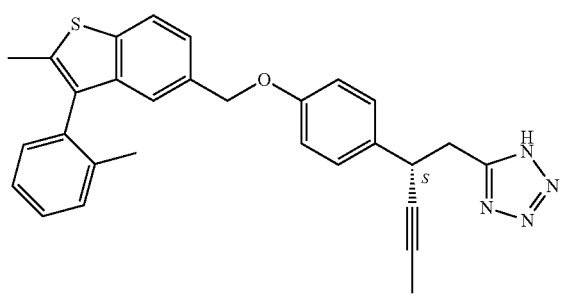

(A) Methyl 2-methyl-3-(2-methylphenyl)benzo[b]thiophene-5-carboxylate was prepared from methyl 3-bromo-2-methylbenzo[b]thiophene-5-carboxylate and 2-methylphenylboronic acid following General Procedure A, using PdCl$_2$(dppf).CH$_2$Cl$_2$ as the palladium catalyst. LC/MS: mass calcd. for $C_{18}H_{16}O_2S$: 296.09, found: 297.1 [M+H]$^+$.

(B) To a solution of methyl 2-methyl-3-(2-methylphenyl)benzo[b]thiophene-5-carboxylate (300 mg, 1.01 mmol) in THF (10 mL) cooled in an ice-water bath was added LiAlH$_4$ (1 M in THF, 2.02 mL) drop-wise under argon. The mixture was stirred at 0° C. for 1 h before warming up to rt. satd. NH$_4$Cl solution was added to quench the reaction. The mixture was extracted with EtOAc (2×50 mL). The organic layer was washed with brine, then dried over Na$_2$SO$_4$, filtered and concentrated to afford (2-methyl-3-(2-methylphenyl)benzo[b]thiophen-5-yl)methanol, which was used in the next step without further purification. LC/MS: mass calcd. for $C_{17}H_{16}O_2S$: 268.09, found: 251.1 [M−OH]$^+$.

(C) 5-(Chloromethyl)-2-methyl-3-(2-methylphenyl)benzo[b]thiophene was prepared from (2-methyl 3-(2-methylphenyl)benzo[b]thiophen-5-yl)methanol following General Procedure D.

(D) Ethyl (3S)-3-(4-((2-methyl-3-(2-methylphenyl)benzo[b]thiophen-5-yl)methoxy)phenyl)hex-4-ynoate was prepared from 5-(chloromethyl)-2-methyl-3-(2-methylphenyl)benzo[b]thiophene and (3S)-ethyl 3-(4-hydroxyphenyl)hex-4-ynoate (available from Synnovator, Inc., Research Triangle Park, N.C.; Cat. # PB05708) following General Procedure E, at a reaction temperature of 50° C. for 6 h. LC/MS: mass calcd. for $C_{31}H_{30}O_3S$: 482.19, found: 483.2 [M+H]$^+$.

(E) (3S)-3-(4-((2-Methyl-3-(2-methylphenyl)benzo[b]thiophen-5-yl)methoxy)phenyl)hex-4-ynoic acid was prepared from ethyl (3S)-3-(4-((2-methyl-3-(2-methylphenyl)

benzo[b]thiophen-5-yl)methoxy)phenyl)hex-4-ynoate following General Procedure C, using EtOH in place of MeOH, and 1N aq NaOH as the base. LC/MS: mass calcd. for $C_{29}H_{26}O_3S$: 454.16, found: 477.1 [M+Na]$^+$.

(F) (3S)-3-(4-((2-methyl-3-(2-methylphenyl)benzo[b]thiophen-5-yl)methoxy)phenyl)hex-4-ynoyl chloride was prepared from (3S)-3-(4-((2-methyl-3-(2-methylphenyl)benzo[b]thiophen-5-yl)methoxy)phenyl)hex-4-ynoic acid following General Procedure G.

(G) (3S)-3-(4-((2-Methyl-3-(2-methylphenyl)benzo[b]thiophen-5-yl)methoxy)phenyl)hex-4-ynamide was prepared from (3S)-3-(4-((2-methyl-3-(2-methylphenyl)benzo[b]thiophen-5-yl)methoxy)phenyl)hex-4-ynoyl chloride following General Procedure Hb. LC/MS: mass calcd. for $C_{29}H_{27}NO_2S$: 453.18, found: 454.2 [M+H]$^+$.

(H) (3S)-3-(4-((2-Methyl-3-(2-methylphenyl)benzo[b]thiophen-5-yl)methoxy)phenyl)hex-4-ynenitrile was prepared from (3S)-3-(4-((2-methyl-3-(2-methylphenyl)benzo[b]thiophen-5-yl)methoxy)phenyl)hex-4-ynamide following General Procedure I. LC/MS: mass calcd. for $C_{29}H_{25}NOS$: 435.17, found: 458.1 [M+Na]$^+$.

(I) (2S)-5-(2-(4-((2-Methyl-3-(2-methylphenyl)benzo[b]thiophen-5-yl)methoxy)phenyl)pent-3-yn-1-yl)-1H-tetrazole (Cpd 19) was prepared from (3S)-3-(4-((2-methyl-3-(2-methylphenyl)benzo[b]thiophen-5-yl)methoxy)phenyl)hex-4-ynenitrile following General Procedure J, using preparative HPLC for product purification: Phenomenex C18 5 μm column, 30×100 mm, 40%-100% MeCN/H$_2$O (0.1% TFA v/v) over 18 min. $^1$H NMR (CDCl$_3$) δ 7.80 (d, J=8.6 Hz, 1H), 7.32-7.40 (m, 3H), 7.25-7.32 (m, 1H), 7.14-7.24 (m, 4H), 6.87 (d, J=8.6 Hz, 2H), 5.01 (s, 2H), 4.05 (t, J=5.6 Hz, 1H), 3.30-3.47 (m, 2H), 2.34 (s, 3H), 2.05 (s, 3H), 1.84 (d, J=2.5 Hz, 3H). LC/MS: mass calcd. for $C_{29}H_{26}N_4OS$: 478.18, found: 501.1 [M+Na]$^+$.

Example 20

(2S)-5-(2-(4-((3-(2,6-Dimethylphenyl)benzo[b]thiophen-5-yl)methoxy)phenyl)pent-3-yn-1-yl)-1H-tetrazole, Cpd 20

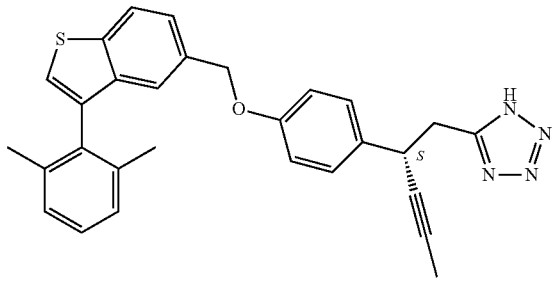

(A) 5-Hydroxymethyl-3-(2,6-dimethylphenyl)benzo[b]thiophene was prepared from 3-bromo-5-hydroxymethyl-benzothiophene (from Example 1A) and 2,6-dimethylphenylboronic acid following General Procedure A, using PdCl$_2$(dppf).CH$_2$Cl$_2$ as the palladium catalyst and Cs$_2$CO$_3$ in place of K$_2$CO$_3$. LC/MS: mass calcd. for $C_{17}H_{16}OS$: 268.37, found 251.0 [M−17]$^+$.

(B) 5-Chloromethyl-3-(2,6-dimethylphenyl)benzo[b]thiophene was prepared from 5-hydroxymethyl-3-(2,6-dimethylphenyl)benzo[b]thiophene following General Procedure D.

(C) (3S)-Methyl 3-(4-((3-(2,6-dimethylphenyl)benzo[b]thiophen-5-yl)methoxy)phenyl)hex-4-ynoate was prepared from 5-chloromethyl-3-(2,6-dimethylphenyl)benzo[b]-thiophene and (3S)-methyl 3-(4-hydroxyphenyl)hex-4-ynoate (prepared as described in WO 2005086661) following General Procedure E using DMF as solvent and stirring over night at 40° C. LC/MS: mass calcd. for $C_{30}H_{28}O_3S$: 468.61, found 469.0 [M]$^+$.

(D) (3S)-3-(4-((3-(2,6-Dimethylphenyl)benzo[b]thiophen-5-yl)methoxy)phenyl)hex-4-ynoic acid was prepared from (3S)-methyl 3-(4-((3-(2,6-dimethylphenyl)benzo[b]thiophen-5-yl)methoxy)phenyl)hex-4-ynoate following General Procedure C, using LiOH as base and 1N HCl for reaction acidification. $^1$H NMR (DMSO-d$_6$) δ 8.08 (d, J=8.3 Hz, 1H), 7.63 (s, 1H), 7.48 (d, J=8.1 Hz, 1H), 7.12-7.36 (m, 6H), 6.87 (d, J=8.5 Hz, 2H), 5.14 (s, 2H), 3.85-4.03 (m, 1H), 2.31-2.44 (m, 2H), 1.93 (s, 6H), 1.76 (d, J=2.3 Hz, 3H) LC/MS: mass calcd. for $C_{29}H_{26}O_3S$: 454.58, found 453.1 [M−H]$^-$.

(E) (3S)-3-(4-((3-(2,6-Dimethylphenyl)benzo[b]thiophen-5-yl)methoxy)phenyl)hex-4-ynoyl chloride was prepared from (3S)-3-(4-((3-(2,6-dimethylphenyl)benzo[b]thiophen-5-yl)methoxy)phenyl)hex-4-ynoic acid following General Procedure G, using thionyl chloride as the chlorinating agent.

(F) (3S)-3-(4-((3-(2,6-Dimethylphenyl)benzo[b]thiophen-5-yl)methoxy)phenyl)hex-4-ynamide was prepared from (3S)-3-(4-((3-(2,6-dimethylphenyl)benzo[b]thiophen-5-yl)methoxy)phenyl)hex-4-ynoyl chloride following General Procedure Ha. LC/MS: mass calcd. for $C_{29}H_{27}NO_2S$: 453.18, found 454.0 [M+H]$^+$.

(G) (3S)-3-(4-((3-(2,6-Dimethylphenyl)benzo[b]thiophen-5-yl)methoxy)phenyl)hex-4-ynenitrile was prepared from (3S)-3-(4-((3-(2,6-dimethylphenyl)benzo[b]thiophen-5-yl)methoxy)phenyl)hex-4-ynamide following General Procedure I. LC/MS: mass calcd. for $C_{29}H_{25}NOS$: 435.17, found 453.0 [M+NH$_4$]$^+$.

(H) (2S)-5-(2-(4-((3-(2,6-Dimethylphenyl)benzo[b]thiophen-5-yl)methoxy)phenyl)pent-3-yn-1-yl)-1H-tetrazole (Cpd 20) was prepared from (3S)-3-(4-((3-(2,6-dimethylphenyl)benzo[b]thiophen-5-yl)methoxy)phenyl)hex-4-ynenitrile following General Procedure J, using Workup 2. Additional purification of the product was carried out by preparative HPLC on a Waters SunFire™ Prep C18, 5μ column (19×100 mm) using an acetonitrile/water (0.05% NH$_4$HCO$_3$) gradient (35-85%). $^1$H NMR (CDCl$_3$) δ 7.92 (d, J=8.4 Hz, 1H), 7.44 (d, J=7.6 Hz, 1H), 7.14-7.25 (m, 7H), 6.86 (d, J=7.2 Hz, 2H), 5.02 (s, 2H), 4.03-4.05 (m, 1H), 3.32-3.34 (m, 2H), 1.99 (s, 6H), 1.80 (s, 3H). LC/MS: mass calcd. for $C_{29}H_{26}N_4OS$: 478.18, found 479.2[M+H]$^+$.

Example 21

(2S)-5-(5-((4-(1-(1H-Tetrazol-5-yl)pent-3-yn-2-yl)phenoxy)methyl)benzo[b]thiophen-3-yl)-2-(2-methoxyethoxy)-4-methylpyridine, Cpd 21

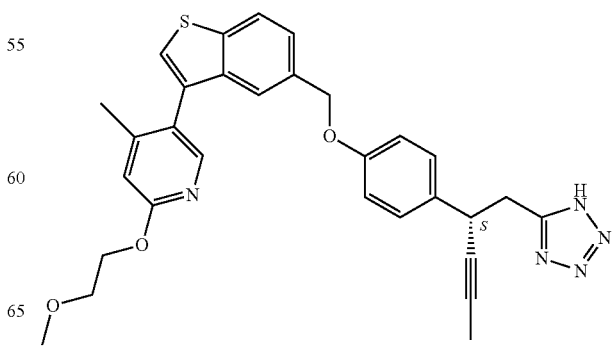

(A) To a solution of 2-methoxyethan-1-ol (1.82 g, 24 mmol) in anhydrous THF (20 mL) was added NaH (60% wt in mineral oil; 960 mg, 24 mmol) in portions. After stirring at rt for 30 min, the mixture was cooled to 0° C. and a solution of 2,5-dibromo-4-methylpyridine (2 g, 8 mmol) in THF (10 mL) was added in drop-wise fashion. The resultant mixture was then heated at 80° C. overnight. The reaction was then quenched by the addition of satd. aq. NH$_4$Cl (100 mL) and the mixture was extracted with EtOAc (2×100 mL). The combined organic extracts were dried (Na$_2$SO$_4$) and concentrated under reduced pressure. The residue obtained was purified by silica gel chromatography (0-10% EtOAc/ petroleum ether) to afford 5-bromo-2-(2-methoxyethoxy)-4-methylpyridine (1.2 g, 61% yield) as a light yellow oil. LC/MS: mass calcd. for C$_9$H$_{12}$BrNO$_2$: 246.10, found: 246.0 [M]$^+$, 248.0 [M+2]$^+$.

(B) 2-(2-Methoxyethoxy)-4-methyl-5-(4,4,5,5-tetramethyl-1,3,2-dioxaborolan-2-yl)pyridine was prepared from 5-bromo-2-(2-methoxyethoxy)-4-methylpyridine and bis(pinacolato)diboron following General Procedure A, using PdCl$_2$(dppf).CH$_2$Cl$_2$ as the palladium catalyst, KOAc in place of K$_2$CO$_3$ and DMSO as reaction solvent at a reaction temperature of 85° C. overnight. LC/MS: mass calcd. for C$_{15}$H$_{24}$BNO$_4$: 293.17, found: 294.1 [M+H]$^+$.

(C) (3S)-Ethyl 3-(4-((3-(6-(2-methoxyethoxy)-4-methylpyridin-3-yl)benzo[b]thiophen-5-yl)methoxy)phenyl)hex-4-ynoate was prepared from 2-(2-methoxyethoxy)-4-methyl-5-(4,4,5,5-tetramethyl-1,3,2-dioxaborolan-2-yl)pyridine and (3S)-ethyl 3-(4-((3-bromobenzo[b]thiophen-5-yl)methoxy)phenyl)hex-4-ynoate (from Example 7B) following General Procedure A, using PdCl$_2$(dppf).CH$_2$Cl$_2$ as the palladium catalyst and Cs$_2$CO$_3$ in place of K$_2$CO$_3$. LC/MS: mass calcd. for C$_{32}$H$_{33}$NO$_5$S: 543.67, found: 544.2 [M+H]$^+$.

(D) (3S)-3-(4-((3-(6-(2-Methoxyethoxy)-4-methylpyridin-3-yl)benzo[b]thiophen-5-yl)methoxy)phenyl)hex-4-ynoic acid was prepared from (3S)-ethyl 3-(4-((3-(6-(2-methoxyethoxy)-4-methylpyridin-3-yl)benzo[b]thiophen-5-yl)methoxy)phenyl)hex-4-ynoate following General Procedure C, using LiOH as base, EtOH in place of MeOH and 1N HCl for reaction acidification. $^1$H NMR (DMSO-d$_6$) δ 12.23 (br. s, 1H), 8.08 (d, J=8.1 Hz, 1H), 8.02 (s, 1H), 7.77 (s, 1H), 7.50 (d, J=1.2 Hz, 1H), 7.48 (s, 1H), 7.24 (d, J=8.7 Hz, 2H), 6.92 (d, J=8.4 Hz, 2H), 6.87 (s, 1H), 5.18 (s, 2H), 4.41-4.44 (m, 2H), 3.89-3.94 (m, 1H), 3.66 (t, J=4.8 Hz, 2H), 3.33 (s, 3H), 2.58 (d, J=7.5 Hz, 2H), 2.04 (s, 3H), 1.76 (d, J=2.4 Hz, 3H). LC/MS: mass calcd. for C$_{30}$H$_{29}$NO$_5$S: 515.62, found: 516.2 [M+H]$^+$.

(E) (3S)-3-(4-((3-(6-(2-Methoxyethoxy)-4-methylpyridin-3-yl)benzo[b]thiophen-5-yl)methoxy)phenyl)hex-4-ynoyl chloride was prepared from (3S)-3-(4-((3-(6-(2-methoxyethoxy)-4-methylpyridin-3-yl)benzo[b]thiophen-5-yl)methoxy)phenyl)hex-4-ynoic acid following General Procedure G, using oxalyl chloride as the chlorinating agent.

(F) (3S)-3-(4-((3-(6-(2-Methoxyethoxy)-4-methylpyridin-3-yl)benzo[b]thiophen-5-yl)methoxy)phenyl)hex-4-ynamide was prepared from (3S)-3-(4-((3-(6-(2-methoxyethoxy)-4-methylpyridin-3-yl)benzo[b]thiophen-5-yl)methoxy)phenyl)hex-4-ynoyl chloride following General Procedure Ha, and used directly without further characterization.

(G) (3S)-3-(4-((3-(6-(2-Methoxyethoxy)-4-methylpyridin-3-yl)benzo[b]thiophen-5-yl)methoxy)phenyl)hex-4-ynenitrile was prepared from (3S)-3-(4-((3-(6-(2-methoxyethoxy)-4-methylpyridin-3-yl)benzo[b]thiophen-5-yl)methoxy)phenyl)hex-4-ynamide following General Procedure I, and used directly without further characterization.

(H) (2S)-5-(5-((4-(1-(1H-Tetrazol-5-yl)pent-3-yn-2-yl)phenoxy)methyl)benzo[b]thiophen-3-yl)-2-(2-methoxyethoxy)-4-methylpyridine (Cpd 21) was prepared from (3S)-3-(4-((3-(6-(2-methoxyethoxy)-4-methylpyridin-3-yl)benzo[b]thiophen-5-yl)methoxy)phenyl)hex-4-ynenitrile following General Procedure J, using Workup 2. $^1$H NMR (CD$_3$OD) δ 7.98-7.80 (m, 2H), 7.55 (s, 1H), 7.51 (d, J=1.2 Hz, 1H), 7.49 (d, J=1.2 Hz, 1H), 7.23-7.25 (m, 2H), 6.92-6.94 (m, 2H), 6.86 (s, 1H), 5.18 (s, 2H), 4.49 (dd, J=3.6, 4.8 Hz, 2H), 4.05-4.10 (m, 1H), 3.80 (dd, J=3.2, 6.0 Hz, 2H), 3.46 (s, 3H), 3.27-3.33 (m, 2H), 2.09 (s, 3H), 1.80 (d, J=2.4 Hz, 3H). LC/MS: mass calcd. for C$_{30}$H$_{29}$N$_5$O$_3$S: 539.20, found 540.3 [M+H]$^+$.

Example 22

(2S)-5-(2-(4-((3-(1-Methyl-1H-pyrazol-5-yl)benzo[b]thiophen-5-yl)methoxy)phenyl)pent-3-yn-1-yl)-1H-tetrazole, Cpd 22

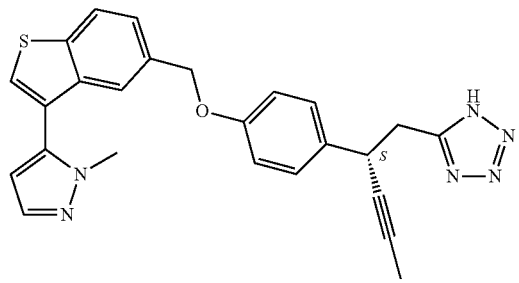

(A) (3S)-Ethyl 3-(4-((3-(1-methyl-1H-pyrazol-5-yl)benzo[b]thiophen-5-yl)methoxy)phenyl)hex-4-ynoate was prepared from (3S)-ethyl 3-(4-((3-bromobenzo[b]thiophen-5-yl)methoxy)phenyl)hex-4-ynoate (from Example 7B) and 1-methyl-1H-pyrazol-5-ylboronic acid following General Procedure A using PdCl$_2$(dppf).CH$_2$Cl$_2$ as the palladium catalyst and Cs$_2$CO$_3$ in place of K$_2$CO$_3$. LC/MS: mass calcd. for C$_{27}$H$_{26}$N$_2$O$_3$S: 458.17, found: 459.2 [M+H]$^+$.

(B) (3S)-3-(4-((3-(1-Methyl-1H-pyrazol-5-yl)benzo[b]thiophen-5-yl)methoxy)phenyl)hex-4-ynoic acid was prepared from (3S)-ethyl 3-(4-((3-(1-methyl-1H-pyrazol-5-yl)benzo[b]thiophen-5-yl)methoxy)phenyl)hex-4-ynoate following General Procedure C, using LiOH as base, EtOH in place of MeOH and 1N HCl for reaction acidification. $^1$H NMR (DMSO-d$_6$) δ 12.20 (br. s, 1H), 8.11 (d, J=8.4 Hz, 1H), 8.06 (s, 1H), 7.74 (s, 1H), 7.59-7.60 (m, 1H), 7.53 (dd, J=8.4, 1.2 Hz, 1H), 7.26 (d, J=8.6 Hz, 2H), 6.95 (d, J=8.7 Hz, 2H), 6.49 (d, J=1.8 Hz, 1H), 5.23 (s, 2H), 3.91-3.96 (m, 1H), 3.78 (s, 3H), 2.58 (d, J=7.6 Hz, 2H), 1.77 (s, 3H). LC/MS: mass calcd. for C$_{25}$H$_{22}$N$_2$O$_3$S: 430.13, found: 431.1 [M+H]$^+$.

(C) (3S)-3-(4-((3-(1-Methyl-1H-pyrazol-5-yl)benzo[b]thiophen-5-yl)methoxy)phenyl)hex-4-ynoyl chloride was prepared from (3S)-3-(4-((3-(1-methyl-1H-pyrazol-5-yl)benzo[b]thiophen-5-yl)methoxy)phenyl)hex-4-ynoic acid following General Procedure G, using oxalyl chloride as the chlorinating agent.

(D) (3S)-3-(4-((3-(1-Methyl-1H-pyrazol-5-yl)benzo[b]thiophen-5-yl)methoxy)phenyl)hex-4-ynamide was prepared from (3S)-3-(4-((3-(1-methyl-1H-pyrazol-5-yl)benzo[b]thiophen-5-yl)methoxy)phenyl)hex-4-ynoyl chloride following General Procedure Ha (inverse addition). LC/MS: mass calcd. for C$_{25}$H$_{23}$N$_3$O$_2$S: 429.15, found 430.2 [M+H]$^+$.

(E) (3S)-3-(4-((3-(1-Methyl-1H-pyrazol-5-yl)benzo[b]thiophen-5-yl)methoxy)phenyl)hex-4-ynenitrile was prepared from (3S)-3-(4-((3-(1-methyl-1H-pyrazol-5-yl)benzo[b]thiophen-5-yl)methoxy)phenyl)hex-4-ynamide following General Procedure I. LC/MS: mass calcd. for $C_{25}H_{21}N_3OS$: 411.14, found 412.0 [M+H]$^+$.

(F) (2S)-5-(2-(4-((3-(1-Methyl-1H-pyrazol-5-yl)benzo[b]thiophen-5-yl)methoxy)phenyl)pent-3-yn-1-yl)-1H-tetrazole (Cpd 22) was prepared from (3S)-3-(4-((3 (1-methyl-1H-pyrazol-5-yl)benzo[b]thiophen-5-yl)methoxy)phenyl) hex-4-ynenitrile following General Procedure J, using Workup 2. $^1$H NMR (CD$_3$OD) δ 8.02 (d, J=8.4 Hz, 1H), 7.83 (s, 1H), 7.64-7.69 (m, 2H), 7.53-7.56 (m, 1H), 7.25 (d, J=8.4 Hz, 2H), 6.94-6.97 (m, 2H), 6.48 (s, 1H), 5.23 (s, 2H), 4.06-4.10 (m, 1H), 3.78 (s, 3H), 3.27-3.32 (m, 2H), 1.80 (s, 3H). LC/MS: mass calcd. for $C_{25}H_{22}N_6OS$: 454.16, found 455.1 [M+H]$^+$.

Example 23

(2S)-5-(2-(4-((3-(1-Methyl-1H-1,2,4-triazol-5-yl)benzo[b]thiophen-5-yl)methoxy)phenyl)pent-3-yn-1-yl)-1H-tetrazole, Cpd 23

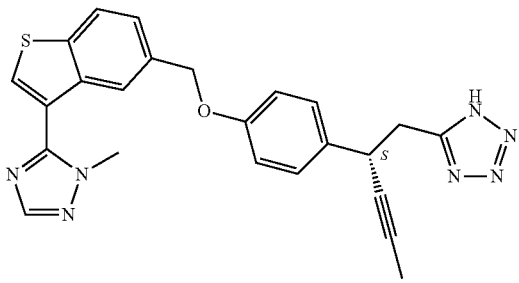

(A) (3-(2-Methyl-2H-1,2,4-triazol-3-yl)benzo[b]thiophen-5-yl)methanol was prepared from (3-(4,4,5,5-tetramethyl-1,3,2-dioxaborolan-2-yl)benzo[b]thiophen-5-yl)methanol (from Example 5A) and 5-bromo-1-methyl-1H-1,2,4-triazole following General Procedure A using PdCl$_2$(dppf).CH$_2$Cl$_2$ as the palladium catalyst and Cs$_2$CO$_3$ in place of K$_2$CO$_3$, at a reaction temperature of 80° C. overnight. LC/MS: mass calcd. for $C_{12}H_{11}N_3OS$: 245.06, found: 246.0 [M+H]$^+$.

(B) 5-(5-(Chloromethyl)benzo[b]thiophen-3-yl)-1-methyl-1H-1,2,4-triazole was prepared from (3-(2-methyl-2H-1,2,4-triazol-3-yl)benzo[b]thiophen-5-yl)methanol following General Procedure D.

(C) (3S)-Ethyl 3-(4-((3-(2-methyl-2H-1,2,4-triazol-3-yl)benzo[b]thiophen-5-yl)methoxy)phenyl)hex-4-ynoate was prepared from 5-(5-(chloromethyl)benzo[b]thiophen-3-yl)-1-methyl-1H-1,2,4-triazole and (3S)-ethyl 3-(4-hydroxyphenyl)hex-4-ynoate (available from Synnovator, Inc., Research Triangle Park, N.C.; Cat. # PB05708) following General Procedure E, at a reaction temperature of 60° C. overnight. LC/MS: mass calcd. for $C_{26}H_{25}N_3O_3S$: 459.16, found: 460.2 [M+H]$^+$.

(D) (3S)-3-(4-((3-(2-Methyl-2H-1,2,4-triazol-3-yl)benzo[b]thiophen-5-yl)methoxy)phenyl)hex-4-ynoic acid was prepared from (3S)-ethyl 3-(4-((3-(2-methyl-2H-1,2,4-triazol-3-yl)benzo[b]thiophen-5-yl)methoxy)phenyl)hex-4-ynoate following General Procedure C, using LiOH as base, EtOH in place of MeOH and 1N HCl for reaction acidification. $^1$H NMR (DMSO-d$_6$) δ 8.42 (s, 1H), 8.31 (s, 1H), 8.13-8.15 (m, 2H), 7.56 (d, J=8.4 Hz, 1H), 7.26 (d, J=8.8 Hz, 2H), 6.96 (d, J=8.8 Hz, 2H), 5.23 (s, 2H), 4.00 (s, 3H), 3.92-3.96 (m, 1H), 2.50-2.56 (m, 2H), 1.77 (d, J=2.0 Hz, 3H). LC/MS: mass calcd. for $C_{24}H_{21}N_3O_3S$: 431.13, found: 432.1 [M+H]$^+$.

(E) (3S)-3-(4-((3-(1-Methyl-1H-1,2,4-triazol-5-yl)benzo[b]thiophen-5-yl)methoxy)phenyl)hex-4-ynoyl chloride was prepared from (3S)-3-(4-((3-(1-methyl-1H-1,2,4-triazol-5-yl)benzo[b]thiophen-5-yl)methoxy)phenyl)hex-4-ynoic acid following General Procedure G, using oxalyl chloride as the chlorinating agent.

(F) (3S)-3-(4-((3-(1-Methyl-1H-1,2,4-triazol-5-yl)benzo[b]thiophen-5-yl)methoxy)phenyl)hex-4-ynamide was prepared from (3S)-3-(4-((3-(1-methyl-1H-1,2,4-triazol-5-yl)benzo[b]thiophen-5-yl)methoxy)phenyl)hex-4-ynoyl chloride following General Procedure Ha (inverse addition). LC/MS: mass calcd. for $C_{24}H_{22}N_4O_2S$: 430.15, found 431.0 [M+H]$^+$.

(G) (3S)-3-(4-((3-(1-Methyl-1H-1,2,4-triazol-5-yl)benzo[b]thiophen-5-yl)methoxy)phenyl)hex-4-ynenitrile was prepared from (3S)-3-(4-((3-(1-methyl-1H-1,2,4-triazol-5-yl)benzo[b]thiophen-5-yl)methoxy)phenyl)hex-4-ynamide following General Procedure I. LC/MS: mass calcd. for $C_{24}H_{20}N_4OS$: 412.14, found 413.2 [M+H]$^+$.

(H) (2S)-5-(2-(4-((3-(1-Methyl-1H-1,2,4-triazol-5-yl)benzo[b]thiophen-5-yl)methoxy)phenyl)pent-3-yn-1-yl)-1H-tetrazole (Cpd 23) was prepared from (3S)-3-(4-((3-(1-methyl-1H-1,2,4-triazol-5-yl)benzo[b]thiophen-5-yl)methoxy)phenyl)hex-4-ynenitrile following General Procedure J, using Workup 2. $^1$H NMR (CD$_3$OD) δ 8.14-8.19 (m, 2H), 8.04-8.06 (m, 2H), 7.58-7.60 (m, 1H), 7.23-7.26 (m, 2H), 6.95-6.99 (m, 2H), 5.24 (s, 2H), 4.06-4.10 (m, 1H), 3.98 (s, 3H), 3.27-3.32 (m, 2H), 1.81 (s, 3H). LC/MS: mass calcd. for $C_{24}H_{21}N_7OS$: 455.15, found 456.0 [M+H]$^+$.

Example 24

(2S)-2-(5-((4-(1-(1H-Tetrazol-5-yl)pent-3-yn-2-yl)phenoxy)methyl)benzo[b]thiophen-3-yl)-3-methylpyrazine, Cpd 24

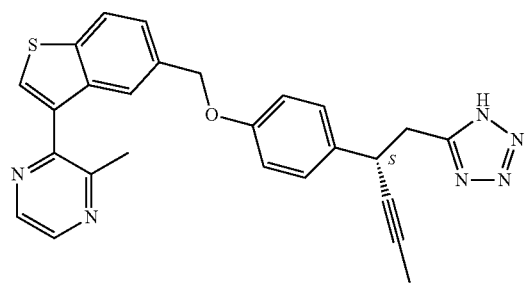

(A) (3-(3-Methylpyrazin-2-yl)benzo[b]thiophen-5-yl)methanol was prepared from (3-(4,4,5,5-tetramethyl-1,3,2-dioxaborolan-2-yl)benzo[b]thiophen-5-yl)methanol (from Example 5A) and 2-bromo-3-methylpyrazine following General Procedure A using PdCl$_2$(dppf).CH$_2$Cl$_2$ as the palladium catalyst and Cs$_2$CO$_3$ in place of K$_2$CO$_3$. LC/MS: mass calcd. for $C_{14}H_{12}N_2OS$: 256.07, found: 257.0 [M+H]$^+$.

(B) 2-(5-(Chloromethyl)benzo[b]thiophen-3-yl)-3-methylpyrazine was prepared from (3-(3-methylpyrazin-2-yl)benzo[b]thiophen-5-yl)methanol following General Procedure D.

(C) (3S)-Ethyl 3-(4-((3-(3-methylpyrazin-2-yl)benzo[b]thiophen-5-yl)methoxy)phenyl)hex-4-ynoate was prepared from 2-(5-(chloromethyl)benzo[b]thiophen-3-yl)-3-methylpyrazine and (3S)-ethyl 3-(4-hydroxyphenyl)hex-4-ynoate (available from Synnovator, Inc., Research Triangle Park, N.C.; Cat. # PB05708) following General Procedure E, at a reaction temperature of 90° C. for 1 h. LC/MS: mass calcd. for $C_{28}H_{26}N_2O_3S$: 470.17, found: 471.3 $[M+H]^+$.

(D) (3S)-3-(4-((3-(3-Methylpyrazin-2-yl)benzo[b]thiophen-5-yl)methoxy)phenyl)hex-4-ynoic acid was prepared from (3S)-ethyl 3-(4-((3-(3-methylpyrazin-2-yl)benzo[b]thiophen-5-yl)methoxy)phenyl)hex-4-ynoate following General Procedure C, using LiOH as base, EtOH in place of MeOH and 1N HCl for reaction acidification. $^1$H NMR (DMSO-$d_6$) δ 12.21 (br. s, 1H), 8.62 (dd, J=2.4, 12.0 Hz, 2H), 8.10-8.14 (m, 2H), 7.79 (d, J=0.9 Hz, 1H), 7.52 (dd, J=1.5, 8.1 Hz, 1H), 7.25 (d, J=8.7 Hz, 2H), 6.93 (d, J=8.7 Hz, 2H), 5.17 (s, 2H), 3.92-3.93 (m, 1H), 2.58 (d, J=7.5 Hz, 2H), 2.52 (s, 3H), 1.77 (d, J=2.4 Hz, 3H). LC/MS: mass calcd. for $C_{26}H_{22}N_2O_3S$: 442.13, found: 411.0 $[M-H]^-$.

(E) (3S)-3-(4-((3-(3-Methylpyrazin-2-yl)benzo[b]thiophen-5-yl)methoxy)phenyl)hex-4-ynoyl chloride was prepared from (3S)-3-(4-((3-(3-methylpyrazin-2-yl)benzo[b]thiophen-5-yl)methoxy)phenyl)hex-4-ynoic acid following General Procedure G, using oxalyl chloride as the chlorinating agent.

(F) (3S)-3-(4-((3-(3-Methylpyrazin-2-yl)benzo[b]thiophen-5-yl)methoxy)phenyl)hex-4-ynamide was prepared from (3S)-3-(4-((3-(3-methylpyrazin-2-yl)benzo[b]thiophen-5-yl)methoxy)phenyl)hex-4-ynoyl chloride following General Procedure Ha (inverse addition). LC/MS: mass calcd. for $C_{26}H_{23}N_3O_2S$: 441.15, found 442.2$[M+H]^+$.

(G) (3S)-3-(4-((3-(3-Methylpyrazin-2-yl)benzo[b]thiophen-5-yl)methoxy)phenyl)hex-4-ynenitrile was prepared from (3S)-3-(4-((3-(3-methylpyrazin-2-yl)benzo[b]thiophen-5-yl)methoxy)phenyl)hex-4-ynamide following General Procedure I. LC/MS: mass calcd. for $C_{26}H_{21}N_3OS$: 423.14, found 424.1 $[M+H]^+$.

(H) (2S)-2-(5-((4-(1-(1H-Tetrazol-5-yl)pent-3-yn-2-yl)phenoxy)methyl)benzo[b]thiophen-3-yl)-3-methylpyrazine (Cpd 24) was prepared from (3S)-3-(4-((3-(3-methylpyrazin-2-yl)benzo[b]thiophen-5-yl)methoxy)phenyl)hex-4-ynenitrile following General Procedure J, using Workup 2. $^1$H NMR (CD$_3$OD) δ 8.58-8.60 (m, 2H), 8.03 (d, J=8.4 Hz, 1H), 7.92 (s, 1H), 7.69 (s, 1H), 7.53-7.56 (m, 1H), 7.22-7.26 (m, 2H), 6.93-6.95 (m, 2H), 5.19 (s, 2H), 4.05-4.10 (m, 1H), 3.27-3.30 (m, 2H), 2.53 (s, 3H), 1.80 (s, 3H). LC/MS: mass calcd. for $C_{26}H_{22}N_6OS$: 466.16, found 467.1 $[M+H]^+$.

Example 25

(2S)-5-(5-((4-(1-(1H-Tetrazol-5-yl)pent-3-yn-2-yl)phenoxy)methyl)benzo[b]thiophen-3-yl)-4-methylpyrimidine, Cpd 25

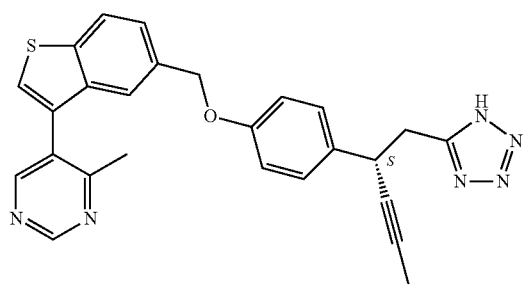

(A) (3-(4-Methylpyrimidin-5-yl)benzo[b]thiophen-5-yl)methanol was prepared from (3-(4,4,5,5-tetramethyl-1,3,2-dioxaborolan-2-yl)benzo[b]thiophen-5-yl)methanol (from Example 5A) and 5-bromo-4-methylpyrimidine following General Procedure A using PdCl$_2$(dppf).CH$_2$Cl$_2$ as the palladium catalyst and Cs$_2$CO$_3$ in place of K$_2$CO$_3$. LC/MS: mass calcd. for $C_{14}H_{12}N_2OS$: 256.07, found: 257.0 $[M+H]^+$.

(B) (3S)-Ethyl 3-(4-((3-(4-methylpyrimidin-5-yl)benzo[b]thiophen-5-yl)methoxy)phenyl)hex-4-ynoate was prepared from (3-(4-methylpyrimidin-5-yl)benzo[b]thiophen-5-yl)methanol and (3S)-ethyl 3-(4-hydroxyphenyl)hex-4-ynoate (available from Synnovator, Inc., Research Triangle Park, N.C.; Cat. # PB05708) following General Procedure B, using Bu$_3$P and ADDP at a reaction temperature of 60° C. in toluene overnight. LC/MS: mass calcd. for $C_{28}H_{26}N_2O_3S$: 470.17, found: 471.2 $[M+H]^+$.

(C) (3S)-3-(4-((3-(4-Methylpyrimidin-5-yl)benzo[b]thiophen-5-yl)methoxy)phenyl)hex-4-ynoic acid was prepared from (3S)-ethyl 3-(4-((3-(4-methylpyrimidin-5-yl)benzo[b]thiophen-5-yl)methoxy)phenyl)hex-4-ynoate following General Procedure C, using LiOH as base, EtOH in place of MeOH and 1N HCl for reaction acidification. $^1$H NMR (DMSO-$d_6$) δ 12.21 (br. s, 1H), 9.14 (s, 1H), 8.68 (s, 1H), 8.11-8.14 (m, 1H), 7.98 (s, 1H), 7.53 (d, J=5.7 Hz, 2H), 7.24 (d, J=8.7 Hz, 2H), 6.92 (d, J=8.7 Hz, 2H), 5.19 (s, 2H), 3.92-3.96 (m, 1H), 2.51-2.73 (m, 2H), 2.31 (s, 3H), 1.76 (s, 3H). LC/MS: mass calcd. for $C_{26}H_{22}N_2O_3S$: 442.14, found: 443.2 $[M+H]^+$.

(D) (3S)-3-(4-((3-(4-Methylpyrimidin-5-yl)benzo[b]thiophen-5-yl)methoxy)phenyl)hex-4-ynoyl chloride was prepared from (3S)-3-(4-((3-(4-methylpyrimidin-5-yl)benzo[b]thiophen-5-yl)methoxy)phenyl)hex-4-ynoic acid following General Procedure G, using oxalyl chloride as the chlorinating agent.

(E) (3S)-3-(4-((3-(4-Methylpyrimidin-5-yl)benzo[b]thiophen-5-yl)methoxy)phenyl)hex-4-ynamide was prepared from (3S)-3-(4-((3-(4-methylpyrimidin-5-yl)benzo[b]thiophen-5-yl)methoxy)phenyl)hex-4-ynoyl chloride following General Procedure Ha. LC/MS: mass calcd. for $C_{26}H_{23}N_3O_2S$: 441.15, found 442.0$[M+H]^+$.

(F) (3S)-3-(4-((3-(4-Methylpyrimidin-5-yl)benzo[b]thiophen-5-yl)methoxy)phenyl)hex-4-ynenitrile was prepared from (3S)-3-(4-((3-(4-methylpyrimidin-5-yl)benzo[b]thiophen-5-yl)methoxy)phenyl)hex-4-ynamide following General Procedure I. LC/MS: mass calcd. for $C_{26}H_{21}N_3OS$: 423.14, found 424.0 $[M+H]^+$.

(G) (2S)-5-(5-((4-(1-(1H-Tetrazol-5-yl)pent-3-yn-2-yl)phenoxy)methyl)benzo[b]thiophen-3-yl)-4-methylpyrimidine (Cpd 25) was prepared from (3S)-3-(4-((3-(4-methylpyrimidin-5-yl)benzo[b]thiophen-5-yl)methoxy)phenyl)hex-4-ynenitrile following General Procedure J, using Workup 2. $^1$H NMR (CD$_3$OD) δ 9.05 (s, 1H), 8.62 (s, 1H), 7.99 (d, J=8.4 Hz, 1H), 7.71 (s, 1H), 7.50 (d, J=9.0 Hz, 1H), 7.42 (s, 1H), 7.19 (d, J=8.7 Hz, 2H), 6.88 (d, J=8.4 Hz, 2H), 5.15 (s, 2H), 3.99-4.10 (m, 1H), 3.21-3.28 (m, 2H), 2.31 (s, 3H), 1.75 (s, 3H). LC/MS: mass calcd. for $C_{26}H_{22}N_6OS$: 466.16, found 467.0 $[M+H]^+$.

Example 26

(2S)-2-(5-((4-(1-(1H-Tetrazol-5-yl)pent-3-yn-2-yl)phenoxy)methyl)benzo[b]thiophen-3-yl)-5-(2-methoxyethoxy)-3-methylpyridine, Cpd 26

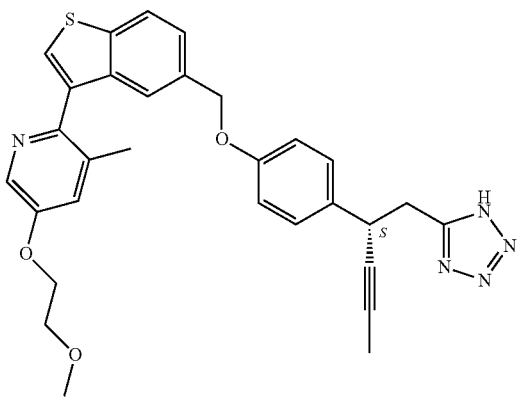

(A) A mixture of 6-bromo-5-methylpyridin-3-ol (1 g, 5.32 mmol), 1-bromo-2-methoxyethane (730 mg, 5.25 mmol) and $K_2CO_3$ (1.5 g, 10.87 mmol) in MeCN (20 mL) was stirred at rt overnight, after which the reaction was quenched by the addition of water (100 mL). The resulting solution was extracted with EtOAc (2×100 mL) and the combined organic phase was dried ($Na_2SO_4$) and concentrated under reduced pressure. The resultant residue was purified by silica gel chromatography (0-15% EtOAc/petroleum ether) to afford 2-bromo-5-(2-methoxyethoxy)-3-methylpyridine (500 mg, 38%) as colorless oil. LC/MS: mass calcd. for $C_9H_{12}BrNO_2$: 246.10, found: 246.0 $[M]^+$, 248.0 $[M+2]^+$.

(B) (3-(5-(2-Methoxyethoxy)-3-methylpyridin-2-yl)benzo[b]thiophen-5-yl)methanol was prepared from 2-bromo-5-(2-methoxyethoxy)-3-methylpyridine and (3-(4,4,5,5-tetramethyl-1,3,2-dioxaborolan-2-yl)benzo[b]thiophen-5-yl)methanol (from Example 5A) following General Procedure A, using $PdCl_2$(dppf).$CH_2Cl_2$ as the palladium catalyst, $Cs_2CO_3$ in place of $K_2CO_3$. LC/MS: mass calcd. for $C_{18}H_{19}NO_3S$: 329.41, found: 330.0$[M+H]^+$.

(C) (3S)-Ethyl 3-(4-((3-(5-(2-methoxyethoxy)-3-methylpyridin-2-yl)benzo[b]thiophen-5-yl)methoxy)phenyl)hex-4-ynoate was prepared from (3-(5-(2-methoxyethoxy)-3-methylpyridin-2-yl)benzo[b]thiophen-5-yl)methanol and (3S)-ethyl 3-(4-hydroxyphenyl)hex-4-ynoate (available from Synnovator, Inc., Research Triangle Park, N.C.; Cat. # PB05708) following General Procedure B, using $Bu_3P$ and ADDP at a reaction temperature of 50° C. in toluene for 2 h. LC/MS: mass calcd. for $C_{32}H_{33}NO_5S$: 543.67, found: 544.3 $[M+H]^+$.

(D) (3S)-3-(4-((3-(5-(2-Methoxyethoxy)-3-methylpyridin-2-yl)benzo[b]thiophen-5-yl)methoxy)phenyl)hex-4-ynoic acid was prepared from (3S)-ethyl 3-(4-((3-(5-(2-methoxyethoxy)-3-methylpyridin-2-yl)benzo[b]thiophen-5-yl)methoxy)phenyl)hex-4-ynoate following General Procedure C, using LiOH as base, EtOH in place of MeOH and 1N HCl for reaction acidification. $^1$H NMR (DMSO-$d_6$) δ 12.23 (br. s, 1H), 8.27 (s, 1H), 8.06 (d, J=8.4 Hz, 1H), 7.86 (s, 1H), 7.69 (s, 1H), 7.43-7.52 (m, 2H), 7.25 (d, J=8.7 Hz, 2H), 6.93 (d, J=8.7 Hz, 2H), 5.15 (s, 2H), 4.23-4.28 (m, 2H), 3.91-3.96 (m, 1H), 3.72 (d, J=4.5 Hz, 2H), 3.33 (s, 3H), 2.58 (d, J=7.5 Hz, 2H), 2.24 (s, 3H), 1.77 (d, J=2.4 Hz, 3H). LC/MS: mass calcd. for $C_{30}H_{29}NO_5S$: 515.62, found: 516.2 $[M+H]^+$.

(E) (3S)-3-(4-((3-(5-(2-Methoxyethoxy)-2-methylpyridin-3-yl)benzo[b]thiophen-5-yl)methoxy)phenyl)hex-4-ynoyl chloride was prepared from (3S)-3-(4-((3-(5-(2-Methoxyethoxy)-3-methylpyridin-2-yl)benzo[b]thiophen-5-yl)methoxy)phenyl)hex-4-ynoic acid following General Procedure G, using oxalyl chloride as the chlorinating agent.

(F) (3S)-3-(4-((3-(5-(2-Methoxyethoxy)-2-methylpyridin-3-yl)benzo[b]thiophen-5-yl)methoxy)phenyl)hex-4-ynamide was prepared from (3S)-3-(4-((3-(5-(2-methoxyethoxy)-3-methylpyridin-2-yl)benzo[b]thiophen-5-yl)methoxy)phenyl)hex-4-ynoyl chloride following General Procedure Ha, and was used directly without characterization.

(G) (3S)-3-(4-((3-(5-(2-Methoxyethoxy)-3-methylpyridin-2-yl)benzo[b]thiophen-5-yl)methoxy)phenyl)hex-4-ynenitrile was prepared from (3S)-3-(4-((3-(5-(2-methoxyethoxy)-2-methylpyridin-3-yl)benzo[b]thiophen-5-yl)methoxy)phenyl)hex-4-ynamide following General Procedure I. LC/MS: mass calcd. for $C_{30}H_{28}N_2O_3S$: 496.18, found: 496.8$[M+H]^+$.

(H) (2S)-2-(5-((4-(1-(1H-Tetrazol-5-yl)pent-3-yn-2-yl)phenoxy)methyl)benzo[b]thiophen-3-yl)-5-(2-methoxyethoxy)-3-methylpyridine, (Cpd 26) was prepared from (3S)-3-(4-((3-(5-(2-methoxyethoxy)-3-methylpyridin-2-yl)benzo[b]thiophen-5-yl)methoxy)phenyl)hex-4-ynenitrile following General Procedure J, using Workup 2. $^1$H NMR (CDCl$_3$) δ 8.34 (s, 1H), 7.88-7.90 (m, 1H), 7.50 (s, 1H), 7.35-7.49 (m, 3H), 6.91-6.93 (m, 2H), 6.63-6.74 (m, 2H), 5.18 (s, 2H), 4.30 (s, 2H), 3.73-3.91 (m, 3H), 3.54 (d, J=2.4 Hz, 3H), 3.14-3.18 (m, 1H), 2.91-2.98 (m, 1H), 2.29 (s, 3H), 1.84 (s, 3H). LC/MS: mass calcd. for $C_{30}H_{29}N_5O_3S$: 539.20, found: 540.1 $[M+H]^+$.

Example 27

(2S)-5-(2-(4-((3-(2,3-Dihydrobenzo[b][1,4]dioxin-5-yl)benzo[b]thiophen-5-yl)methoxy)phenyl)pent-3-yn-1-yl)-1H-tetrazole, Cpd 27

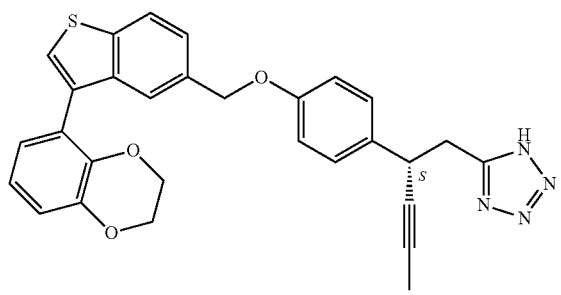

(A) (3-(2,3-Dihydrobenzo[b][1,4]dioxin-5-yl)benzo[b]thiophen-5-yl)methanol was prepared from (3-(4,4,5,5-tetramethyl-1,3,2-dioxaborolan-2-yl)benzo[b]thiophen-5-yl)methanol (from Example 5A) and 5-bromo-2,3-dihydrobenzo[b][1,4]dioxine following General Procedure A using $PdCl_2$(dppf).$CH_2Cl_2$ as the palladium catalyst and $Cs_2CO_3$ in place of $K_2CO_3$. LC/MS: mass calcd. for $C_{17}H_{14}O_3S$: 298.07, found: 281.0 $[M-OH]^+$.

(B) (3S)-Ethyl 3-(4-((3-(2,3-dihydrobenzo[b][1,4]dioxin-5-yl)benzo[b]thiophen-5-yl)methoxy)phenyl)hex-4-ynoate was prepared from (3-(2,3-dihydrobenzo[b][1,4]dioxin-5-yl)benzo[b]thiophen-5-yl)methanol and (3S)-ethyl 3-(4-hydroxyphenyl)hex-4-ynoate (available from Synnovator, Inc., Research Triangle Park, N.C.; Cat. # PB05708) following General Procedure B, using Bu$_3$P and ADDP at a reaction temperature of 60° C. in toluene overnight. LC/MS: mass calcd. for C$_{31}$H$_{28}$O$_5$S: 512.17, found: 535.1 [M+Na]$^+$.

(C) (3S)-3-(4-((3-(2,3-Dihydrobenzo[b][1,4]dioxin-5-yl)benzo[b]thiophen-5-yl)methoxy)phenyl)hex-4-ynoic acid was prepared from (3S)-ethyl 3-(4-((3-(2,3-dihydrobenzo[b][1,4]dioxin-5-yl)benzo[b]thiophen-5-yl)methoxy)phenyl)hex-4-ynoate following General Procedure C, using LiOH as base, EtOH in place of MeOH and 1N HCl for reaction acidification. $^1$H NMR (DMSO-d$_6$) δ 12.22 (br. s, 1H), 8.04 (d, J=8.4 Hz, 1H), 7.72 (s, 1H), 7.63 (s, 1H), 7.46 (d, J=8.0 Hz, 1H), 7.26 (d, J=8.4 Hz, 2H), 6.89-6.95 (m, 5H), 5.22 (s, 2H), 4.20-4.28 (m, 2H), 4.05-4.12 (s, 2H), 3.90-3.95 (m, 1H), 2.59 (d, J=7.6 Hz, 2H), 1.77 (s, 3H). LC/MS: mass calcd. for C$_{29}$H$_{24}$O$_5$S: 484.13, found: 485.2 [M+H]$^+$, 507.2 [M+Na]$^+$.

(D) (3S)-3-(4-((3-(2,3-Dihydrobenzo[b][1,4]dioxin-5-yl)benzo[b]thiophen-5-yl)methoxy)phenyl)hex-4-ynoyl chloride was prepared from (3S)-3-(4-((3-(2,3-dihydrobenzo[b][1,4]dioxin-5-yl)benzo[b]thiophen-5-yl)methoxy)phenyl)hex-4-ynoic acid following General Procedure G, using oxalyl chloride as the chlorinating agent.

(E) (3S)-3-(4-((3-(2,3-Dihydrobenzo[b][1,4]dioxin-5-yl)benzo[b]thiophen-5-yl)methoxy)phenyl)hex-4-ynamide was prepared from (3S)-3-(4-((3-(2,3-dihydrobenzo[b][1,4]dioxin-5-yl)benzo[b]thiophen-5-yl)methoxy)phenyl)hex-4-ynoyl chloride following General Procedure Ha (inverse addition). LC/MS: mass calcd. for C$_{29}$H$_{25}$NO$_4$S: 483.15, found 484.0 [M+H]$^+$.

(F) (3S)-3-(4-((3-(2,3-Dihydrobenzo[b][1,4]dioxin-5-yl)benzo[b]thiophen-5-yl)methoxy)phenyl)hex-4-ynenitrile was prepared from (3S)-3-(4-((3-(2,3-dihydrobenzo[b][1,4]dioxin-5-yl)benzo[b]thiophen-5-yl)methoxy)phenyl)hex-4-ynamide following General Procedure I, and used directly without further characterization.

(G) (2S)-5-(2-(4-((3-(2,3-Dihydrobenzo[b][1,4]dioxin-5-yl)benzo[b]thiophen-5-yl)methoxy)phenyl)pent-3-yn-1-yl)-1H-tetrazole (Cpd 27) was prepared from (3S)-3-(4-((3-(2,3-dihydrobenzo[b][1,4]dioxin-5-yl)benzo[b]thiophen-5-yl)methoxy)phenyl)hex-4-ynenitrile following General Procedure J, using Workup 1. $^1$H NMR (CD$_3$OD) δ 7.90 (d, J=8.3 Hz, 1H), 7.60 (d, J=1.6 Hz, 1H), 7.48 (s, 1H), 7.37-7.44 (m, 1H), 7.17-7.25 (m, 2H), 6.85-6.92 (m, 5H), 5.17 (s, 2H), 4.13-4.22 (m, 2H), 3.94-4.11 (m, 3H), 3.21 (dd, J=7.8, 2.5 Hz, 2H), 1.75 (d, J=2.3 Hz, 3H). LC/MS: mass calcd. for C$_{29}$H$_{24}$N$_4$O$_3$S: 508.16, found 509.0 [M+H]$^+$.

Example 28

(2S)-1-(4-(5-((4-(1-(1H-tetrazol-5-yl)pent-3-yn-2-yl)phenoxy)methyl)benzo[b]thiophen-3-yl)indolin-1-yl)propan-1-one, Cpd 28

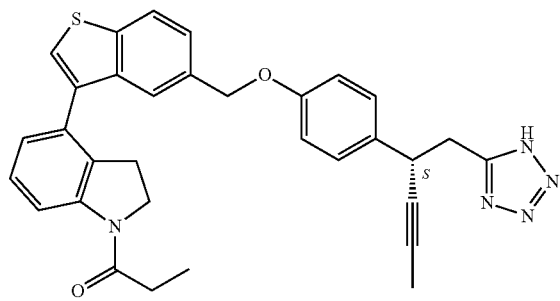

(A) To a solution of 4-bromoindoline (200 mg, 1.01 mmol) in DCM (5 mL) was added propionyl chloride (99 mg, 1.07 mmol) and triethylamine (204 mg, 2.02 mmol). The resulting solution was stirred at rt for 2 h. The reaction mixture was poured into of satd. aq NH$_4$Cl (50 mL) and the resulting mixture was extracted with DCM (3×50 mL). The combined organic extracts were dried (Na$_2$SO$_4$), filtered and concentrated to afford 1-(4-bromoindolin-1-yl)propan-1-one (240 mg, 93.3%), as a white solid. LC/MS: mass calcd. for C$_{11}$H$_{12}$BrNO: 253.01, found: 253.9, 255.9 [M+H, M+H+2]$^+$.

(B) 1-(4-(5-(Hydroxymethyl)benzo[b]thiophen-3-yl)indolin-1-yl)propan-1-one was prepared from (3-(4,4,5,5-tetramethyl-1,3,2-dioxaborolan-2-yl)benzo[b]thiophen-5-yl)methanol (from Example 5A) and 1-(4-bromoindolin-1-yl)propan-1-one following General Procedure A, using PdCl$_2$(dppf).CH$_2$Cl$_2$ as the palladium catalyst and Cs$_2$CO$_3$ as the base. LC/MS: mass calcd. for C$_{20}$H$_{19}$NO$_2$S: 337.11, found: 338.05 [M+H]$^+$.

(C) 1-(4-(5-(Chloromethyl)benzo[b]thiophen-3-yl)indolin-1-yl)propan-1-one was prepared from 1-(4-(5-(hydroxymethyl)benzo[b]thiophen-3-yl)indolin-1-yl)propan-1-one following General Procedure D. LC/MS: mass calcd. for C$_{20}$H$_{18}$ClNOS: 355.08, found: 356.0 [M+H]$^+$.

(D) Ethyl (3S)-3-(4-((3-(1-propionylindolin-4-yl)benzo[b]thiophen-5-yl)methoxy)phenyl)hex-4-ynoate was prepared from 1-(4-(5-(chloromethyl)benzo[b]thiophen-3-yl)indolin-1-yl)propan-1-one and (3S)-ethyl 3-(4-hydroxyphenyl)hex-4-ynoate (available from Synnovator, Inc., Research Triangle Park, N.C.; Cat. # PB05708) following General Procedure E, at a reaction temperature of 60° C. LC/MS: mass calcd. for C$_{34}$H$_{33}$NO$_4$S: 551.21, found: 552.2 [M+H]$^+$.

(E) (3S)-3-(4-((3-(1-Propionylindolin-4-yl)benzo[b]thiophen-5-yl)methoxy)phenyl)hex-4-ynoic acid was prepared from ethyl (3S)-3-(4-((3-(1-propionylindolin-4-yl)benzo[b]thiophen-5-yl)methoxy)phenyl)hex-4-ynoate following General Procedure C, using LiOH as base, EtOH in place of MeOH and 1N HCl for reaction acidification. LC/MS: mass calcd. for C$_{32}$H$_{29}$NO$_4$S: 523.18, found: 524.3 [M+H]$^+$.

(F) (3S)-3-(4-((3-(1-Propionylindolin-4-yl)benzo[b]thiophen-5-yl)methoxy)phenyl)hex-4-ynoyl chloride was prepared from (3S)-3-(4-((3-(1-propionylindolin-4-yl)benzo[b]thiophen-5-yl)methoxy)phenyl)hex-4-ynoic acid following General Procedure G.

(G) (3S)-3-(4-((3-(1-Propionylindolin-4-yl)benzo[b]thiophen-5-yl)methoxy)phenyl)hex-4-ynamide was prepared from (3S)-3-(4-((3-(1-propionylindolin-4-yl)benzo[b]thiophen-5-yl)methoxy)phenyl)hex-4-ynoyl chloride following General Procedure H$_a$. LC/MS: mass calcd. for C$_{32}$H$_{30}$N$_2$O$_3$S: 522.20, found: 523.2 [M+H]$^+$.

(H) (3S)-3-(4-((3-(1-Propionylindolin-4-yl)benzo[b]thiophen-5-yl)methoxy)phenyl)hex-4-ynenitrile was prepared from (3S)-3-(4-((3-(1-propionylindolin-4-yl)benzo[b]thiophen-5-yl)methoxy)phenyl)hex-4-ynamide following General Procedure I. LC/MS: mass calcd. for C$_{32}$H$_{28}$N$_2$O$_2$S: 504.19, found: 505.0 [M+H]$^+$.

(I) (2S)-1-(4-(5-((4-(1-(1H-Tetrazol-5-yl)pent-3-yn-2-yl)phenoxy)methyl)benzo[b]thiophen-3-yl)indolin-1-yl)propan-1-one was prepared from (3S)-3-(4-((3-(1-propionylindolin-4-yl)benzo[b]thiophen-5-yl)methoxy)phenyl)hex-4-ynenitrile following General Procedure J, using Workup 2. Additional purification of the product was carried out by preparative HPLC on a Waters SunFire™ Prep C18, 5μ column (19×100 mm) using an acetonitrile/water (0.05% NH$_4$HCO$_3$) gradient (35-85%). $^1$H NMR (CDCl$_3$) δ 8.32 (d, J=7.8 Hz, 1H), 7.93 (d, J=8.1 Hz, 1H), 7.21-7.56 (m, 6H), 7.06-7.09 (m, 1H), 6.89-6.91 (m, 2H), 5.14-5.21 (m, 2H), 3.98-4.07 (m, 3H), 3.31-3.35 (m, 2H), 2.96-3.05 (m, 2H), 2.47-2.50 (m, 2H), 1.87 (s, 3H), 1.26-1.29 (m, 3H). LC/MS: mass calcd. for $C_{32}H_{29}N_5O_2S$: 547.20, found: 548.0 $[M+H]^+$.

Example 29

(2S)—N-(3-(5-((4-(1-(1H-tetrazol-5-yl)pent-3-yn-2-yl)phenoxy)methyl)benzo[b]thiophen-3-yl)-4-methylphenyl)methanesulfonamide, Cpd 29

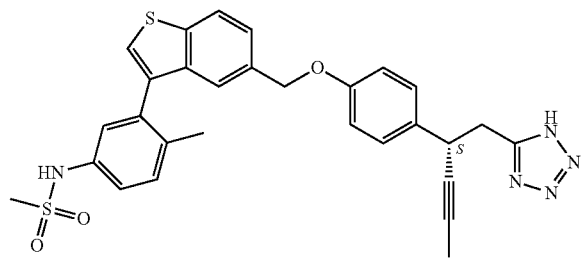

(A) (3-(5-Amino-2-methylphenyl)benzo[b]thiophen-5-yl)methanol was prepared from 3-bromo-4-methylaniline and (3-(4,4,5,5-tetramethyl-1,3,2-dioxaborolan-2-yl)benzo[b]thiophen-5-yl)methanol (from Example 5A) following General Procedure A, using $PdCl_2(dppf).CH_2Cl_2$ as the palladium catalyst and $Cs_2CO_3$ in place of $K_2CO_3$. LC/MS: mass calcd. for $C_{16}H_{15}NOS$: 269.36, found: 270.1 $[M+H]^+$.

(B) (3S)-Ethyl 3-(4-((3-(5-amino-2-methylphenyl)benzo[b]thiophen-5-yl)methoxy)phenyl)hex-4-ynoate was prepared from (3-(5-amino-2-methylphenyl)benzo[b]thiophen-5-yl)methanol and (3S)-ethyl 3-(4-hydroxyphenyl)hex-4-ynoate (available from Synnovator, Inc., Research Triangle Park, N.C.; Cat. # PB05708) following General Procedure B, using $Bu_3P$ and ADDP at a reaction temperature of 60° C. for 1 h. LC/MS: mass calcd. for $C_{30}H_{29}NO_3S$: 483.62, found: 484.0 $[M]^+$.

(C) To an ice-cooled solution of (3S)-ethyl 3-(4-((3-(5-amino-2-methylphenyl)benzo[b]thiophen-5-yl)methoxy)phenyl)hex-4-ynoate (200 mg, 0.41 mmol) and pyridine (0.07 mL, 0.83 mmol) in DCM (2 mL) was added MSCl (0.05 mL, 0.62 mmol) and the resultant solution was stirred overnight at rt. Water (5 mL) was added and the mixture was extracted with DCM (5 mL). The organic extracts were washed with 1N HCl (3×5 mL), dried ($Na_2SO_4$) and concentrated under reduced pressure. The residue thus obtained was purified by silica gel chromatography (0-20% EtOAc/petroleum ether) to afford (3S)-ethyl 3-(4-((3-(2-methyl-5-(methylsulfonamido)phenyl)benzo[b]thiophen-5-yl)methoxy)phenyl)hex-4-ynoate as a light yellow oil (200 mg, 78% yield). LC/MS: mass calcd. for $C_{31}H_{31}NO_5S_2$: 561.71, found: 562.1 $[M]^+$.

(D) (3S)-3-(4-((3-(2-Methyl-5-(methylsulfonamido)phenyl)benzo[b]thiophen-5-yl)methoxy)phenyl)hex-4-ynoic acid was prepared from (3S)-ethyl 3-(4-((3-(2-methyl-5-(methylsulfonamido)phenyl)benzo[b]thiophen-5-yl)methoxy)phenyl)hex-4-ynoate following General Procedure C, using LiOH as base, EtOH in place of MeOH and 1N HCl for reaction acidification. $^1H$ NMR (DMSO-$d_6$) δ 8.06 (d, J=8.4 Hz, 1H), 7.79 (s, 1H), 7.56 (s, 1H), 7.44-7.49 (m, 1H), 7.41 (d, J=8.4 Hz, 1H), 7.23-7.30 (m, 3H), 7.17 (d, J=1.6 Hz, 1H), 6.92 (d, J=8.8 Hz, 2H), 5.16 (s, 2H), 3.90-3.94 (m, 1H), 2.67 (s, 3H), 2.56-2.61 (m, 2H), 2.34 (s, 3H), 1.79 (s, 3H). LC/MS: mass calcd. for $C_{29}H_{27}NO_5S_2$: 533.66, found: 550.9 $[M+NH_3]^+$.

(E) (3S)-3-(4-((3-(2-Methyl-5-(methylsulfonamido)phenyl)benzo[b]thiophen-5-yl)methoxy)phenyl)hex-4-ynamide was prepared by the HATU-mediated coupling of (3S)-3-(4-((3-(2-methyl-5-(methylsulfonamido)phenyl)benzo[b]thiophen-5-yl)methoxy)phenyl)hex-4-ynoic acid and $NH_4Cl$, following the procedure described in Example 6E. LC/MS: mass calcd. for $C_{29}H_{28}N_2O_4S_2$: 532.15, found: 533.2 $[M+H]^+$.

(F) (3S)-3-(4-((3-(2-Methyl-5-(methylsulfonamido)phenyl)benzo[b]thiophen-5-yl)methoxy)phenyl)hex-4-ynenitrile was prepared from (3S)-3-(4-((3-(2-methyl-5-(methylsulfonamido)phenyl)benzo[b]thiophen-5-yl)methoxy)phenyl)hex-4-ynamide following General Procedure I, and was used directly without further characterization.

(G) (2S)—N-(3-(5-((4-(1-(1H-Tetrazol-5-yl)pent-3-yn-2-yl)phenoxy)methyl)benzo[b]thiophen-3-yl)-4-methylphenyl)methanesulfonamide (Cpd 29) was prepared from (3S)-3-(4-((3-(2-methyl-5-(methylsulfonamido)phenyl)benzo[b]thiophen-5-yl)methoxy)phenyl)hex-4-ynenitrile following General Procedure J, using Workup 2. $^1H$ NMR (CD$_3$OD) δ 7.94 (d, J=8.0 Hz, 1H), 7.60 (s, 1H), 7.53 (d, J=1.6 Hz, 1H), 7.44-7.46 (m, 2H), 7.26-7.28 (m, 1H) 7.17-7.20 (m, 3H), 6.84-6.86 (m, 2H), 5.12 (s, 2H), 4.02-4.06 (m, 1H), 3.12-3.24 (m, 2H), 2.52 (s, 3H), 2.36 (s, 3H), 1.74 (d, J=2.4 Hz, 3H). LC/MS: mass calcd. for $C_{29}H_{27}N_5O_3S_2$: 557.16, found: 558.2 $[M+H]^+$.

Example 30

(2S)-5-(2-(4-((3-(2,2-Dimethylchroman-5-yl)benzo[b]thiophen-5-yl)methoxy)phenyl)pent-3-yn-1-yl)-1H-tetrazole, Cpd 30

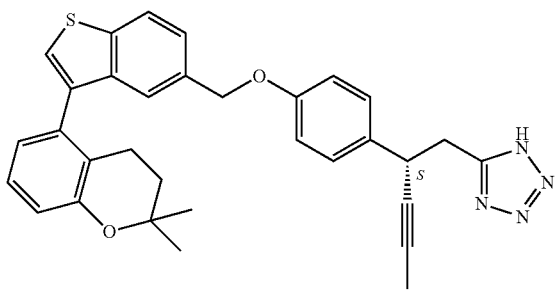

(A) To a solution of 1,3-cyclohexanedione (1.12 g, 9.99 mmol) and 1,2-ethanediammoniumacetate (1.8 g, 9.99 mmol) in MeOH (30 mL) was added 3-methylbut-2-enal (0.84 g, 9.99 mmol) in drop-wise fashion, and the resulting mixture was stirred at rt for 2 h. Water (30 mL) was added and the mixture was extracted with DCM (3×30 mL). The combined organic extracts were dried ($Na_2SO_4$) and concentrated under reduced pressure. The residue thus obtained was purified by silica gel chromatography (0-30% EtOAc/petroleum ether) to afford 2,2-dimethyl-7,8-dihydro-2H-chromen-5(6H)-one (1 g, 56%) as a yellow liquid. LC/MS: mass calcd. for $C_{11}H_{14}O_2$: 178.10, found 179.2 $[M+H]^+$.

(B) A mixture of 2,2-dimethyl-7,8-dihydro-2H-chromen-5(6H)-one (1 g, 5.6 mmol) and DDQ (2.55 g, 11.23 mmol) in 1,4-dioxane (20 mL) was stirred at 110° C. for 24 h. After cooling to rt, the reaction solution was filtered through diatomaceous earth and concentrated under reduced pressure. Purification of the resultant residue by silica gel chromatography (0-10% EtOAc/petroleum ether) afforded 2,2-dimethyl-2H-chromen-5-ol (300 mg, 30%) as a red solid. LC/MS: mass calcd. for $C_{11}H_{12}O_2$: 176.08, found 177.2 $[M+H]^+$.

(C) A solution of 2,2-dimethyl-2H-chromen-5-ol (300 mg, 1.7 mmol) in MeOH (10 mL) was hydrogenated (3 atm) over Pd/C (10%, wt. %; 100 mg) for 2 h. The reaction was filtered and the filtrate was concentrated under reduced pressure to afford 2,2-dimethylchroman-5-ol (280 mg, 92%) as a yellow oil. LC/MS: mass calcd. for $C_{11}H_{14}O_2$: 178.10, found 179.2 $[M+H]^+$.

(D) To an ice-cooled solution of 2,2-dimethylchroman-5-ol (280 mg, 1.57 mmol) and TEA (476 mg, 1.88 mmol) in DCM (10 mL) was added trifluoromethanesulfonic anhydride (530 mg, 1.879 mmol) in portion-wise fashion. After stirring for 1 h at rt, water (20 mL) was added and the mixture was extracted with EtOAc (3×30 mL). The combined organic extracts were dried ($Na_2SO_4$) and concentrated under reduced pressure. The residue thus obtained was purified by silica gel chromatography (0-10% EtOAc/petroleum ether) to afford 2,2-dimethylchroman-5-yl trifluoromethanesulfonate (310 mg, 64%) as a white solid. $^1$H NMR ($CDCl_3$) δ 7.14 (t, J=8.1 Hz, 1H), 6.78-6.82 (m, 2H), 2.81 (t, J=6.6 Hz, 2H), 1.83, (t, J=6.6 Hz, 2H), 1.36 (s, 6H).

(E) (3-(2,2-Dimethylchroman-5-yl)benzo[b]thiophen-5-yl)methanol was prepared from 2,2-dimethylchroman-5-yl trifluoromethanesulfonate and (3-(4,4,5,5-tetramethyl-1,3,2-dioxaborolan-2-yl)benzo[b]thiophen-5-yl)methanol (from Example 5A) following General Procedure A, using $PdCl_2$(dppf).$CH_2Cl_2$ as the palladium catalyst and $Cs_2CO_3$ in place of $K_2CO_3$. LC/MS: mass calcd. for $C_{20}H_{20}O_2S$: 324.12, found 307.1 $[M-OH]^+$.

(F) 5-(5-(Chloromethyl)benzo[b]thiophen-3-yl)-2,2-dimethylchroman was prepared from (3-(2,2-dimethylchroman-5-yl)benzo[b]thiophen-5-yl)methanol following General Procedure D.

(G) (3S)-Ethyl 3-(4-((3-(2,2-dimethylchroman-5-yl)benzo[b]thiophen-5-yl)methoxy)phenyl)hex-4-ynoate was prepared from 5-(5-(chloromethyl)benzo[b]thiophen-3-yl)-2,2-dimethylchroman and (3S)-ethyl 3-(4-hydroxyphenyl)hex-4-ynoate (available from Synnovator, Inc., Research Triangle Park, N.C.; Cat. # PB05708) following General Procedure E at a reaction temperature of 40° C. LC/MS: mass calcd. for $C_{34}H_{34}O_4S$: 538.22, found: 556.2 $[M+NH_4]^+$.

(H) (3S)-3-(4-((3-(2,2-Dimethylchroman-5-yl)benzo[b]thiophen-5-yl)methoxy)phenyl)hex-4-ynoic acid was prepared from (3S)-ethyl 3-(4-((3-(2,2-dimethylchroman-5-yl)benzo[b]thiophen-5-yl)methoxy)phenyl)hex-4-ynoate following General Procedure C, using LiOH as base, EtOH in place of MeOH and 1N HCl for reaction acidification. $^1$H NMR ($CD_3OD$) δ 7.91-7.95 (m, 1H), 7.37-7.45 (m, 3H), 7.24 (d, J=8.7 Hz, 2H), 7.15 (t, J=8.1 Hz, 1H), 6.78-6.88 (m, 4H), 5.12 (s, 2H), 3.92-4.02 (m, 1H), 2.58-2.62 (m, 2H), 2.40 (t, J=6.6 Hz, 2H), 1.79 (s, 3H), 1.63 (t, J=6.6 Hz, 2H), 1.30 (s, 6H). LC/MS: mass calcd. for $C_{32}H_{30}O_4S$: 510.19, found: 528.1 $[M+NH_4]^+$.

(I) (3S)-3-(4-((3-(2,2-Dimethylchroman-5-yl)benzo[b]thiophen-5-yl)methoxy)phenyl)hex-4-ynoyl chloride was prepared from (3S)-3-(4-((3-(2,2-dimethylchroman-5-yl)benzo[b]thiophen-5-yl)methoxy)phenyl)hex-4-ynoic acid following General Procedure G, using oxalyl chloride as the chlorinating agent.

(J) (3S)-3-(4-((3-(2,2-dimethylchroman-5-yl)benzo[b]thiophen-5-yl)methoxy)phenyl)hex-4-ynamide was prepared from (3S)-3-(4-((3-(2,2-dimethylchroman-5-yl)benzo [b]thiophen-5-yl)methoxy)phenyl)hex-4-ynoyl chloride following General Procedure Ha. LC/MS: mass calcd. for $C_{32}H_{31}NO_3S$: 509.20, found 510.0 $[M+H]^+$.

(K) (3S)-3-(4-((3-(2,2-dimethylchroman-5-yl)benzo[b]thiophen-5-yl)methoxy)phenyl)hex-4-ynenitrile was prepared from (3S)-3-(4-((3-(2,2-dimethylchroman-5-yl)benzo[b]thiophen-5-yl)methoxy)phenyl)hex-4-ynamide following General Procedure I. LC/MS: mass calcd. for $C_{32}H_{29}NO_2S$: 491.19, found 492.0 $[M+H]^+$, 509.1 $[M+NH_4]^+$.

(L) (2S)-5-(2-(4-((3-(2,2-dimethylchroman-5-yl)benzo[b]thiophen-5-yl)methoxy)phenyl)pent-3-yn-1-yl)-1H-tetrazole (Cpd 30) was prepared from (3S)-3-(4-((3-(2,2-dimethylchroman-5-yl)benzo[b]thiophen-5-yl)methoxy)phenyl)hex-4-ynenitrile following General Procedure J, using Workup 2. $^1$H NMR ($CD_3OD$) δ 7.93 (d, J=8.1 Hz, 1H), 7.41-7.45 (m, 3H), 7.15-7.20 (m, 3H), 6.78-6.86 (m, 4H), 5.11 (s, 2H), 4.03 (br. s, 1H), 3.14-3.19 (m, 2H), 2.38-2.42 (m, 2H), 1.74 (s, 3H), 1.63 (t, J=6.9 Hz, 2H) 1.30 (s, 6H). LC/MS: mass calcd. for $C_{32}H_{30}N_4O_2S$: 534.21, found 535.0 $[M+H]^+$.

Example 31

3-(4-(5-((4-((2S)-1-(1H-Tetrazol-5-yl)pent-3-yn-2-yl)phenoxy)methyl)benzo[b]thiophen-3-yl)-3-methylphenoxy)propane-1,2-diol, Cpd 31

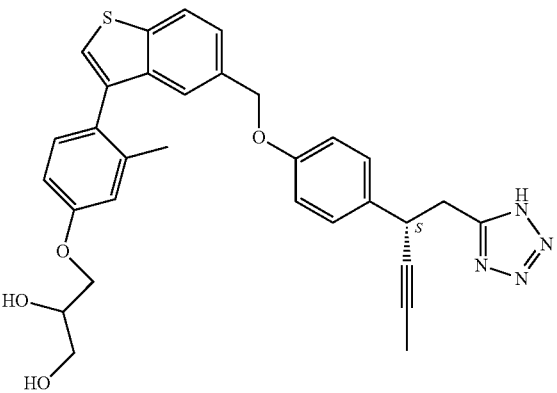

(A) 4-((4-Bromo-3-methylphenoxy)methyl)-2,2-dimethyl-1,3-dioxolane was prepared from 4-bromo-3-methylphenol and (2,2-dimethyl-1,3-dioxolan-4-yl)methanol following General Procedure B using $PPh_3$ and ADDP in toluene (in place of THF) at 60° C. $^1$H NMR ($CDCl_3$) δ 7.38 (d, J=8.8 Hz, 1H), 6.80 (d, J=2.8 Hz, 1H), 6.62 (dd, J=3.2, 8.8 Hz, 1H), 4.42-4.48 (m, 1H), 4.13-4.17 (m, 1H), 3.99-4.02 (m, 1H), 3.86-3.91 (m, 2H), 2.35 (s, 3H), 1.48 (s, 3H), 1.40 (s, 3H).

(B) 2-(4-((2,2-Dimethyl-1,3-dioxolan-4-yl)methoxy)-2-methylphenyl)-4,4,5,5-tetramethyl-1,3,2-dioxaborolane was prepared from 4-((4-bromo-3-methylphenoxy)methyl)-2,2-dimethyl-1,3-dioxolane and bis(pinacolato)diboron following General Procedure A, using $PdCl_2$(dppf).$CH_2Cl_2$ as the palladium catalyst and $Cs_2CO_3$ in place of $K_2CO_3$ and a reaction temperature of 85° C. overnight. $^1$H NMR ($CDCl_3$) δ 7.70 (d, J=8.0 Hz, 1H), 6.69-6.72 (m, 2H), 4.45-4.48 (m, 1H), 4.14-4.18 (m, 1H), 4.05-4.08 (m, 1H), 3.87-3.96 (m, 2H), 2.51 (s, 3H), 1.46 (s, 3H), 1.40 (s, 3H), 1.32 (s, 12H).

(C) 3-(4-((2,2-Dimethyl-1,3-dioxolan-4-yl)methoxy)-2-methylphenyl)benzo[b]thiophene-5-carbaldehyde was prepared from 2-(4-((2,2-dimethyl-1,3-dioxolan-4-yl)

methoxy)-2-methylphenyl)-4,4,5,5-tetramethyl-1,3,2-dioxaborolane and 3-bromobenzo[b]thiophene-5-carbaldehyde (from Example 4A) following General Procedure A, using PdCl$_2$(dppf).CH$_2$Cl$_2$ as the palladium catalyst and Cs$_2$CO$_3$ in place of K$_2$CO$_3$. $^1$H NMR: (CDCl$_3$) δ 10.02 (s, 1H), 8.02-8.04 (m, 1H), 7.89-7.90 (m, 2H), 7.37 (s, 1H), 7.20-7.26 (m, 1H), 6.82-7.00 (m, 2H), 4.50-4.53 (m, 1H), 4.14-4.24 (m, 2H), 3.93-4.08 (m, 2H), 2.15 (s, 3H), 1.48-1.50 (m, 3H), 1.42-1.43 (m, 3H).

(D) (3-(4-((2,2-Dimethyl-1,3-dioxolan-4-yl)methoxy)-2-methylphenyl)benzo[b]thiophen-5-yl)methanol was prepared from 3-(4-((2,2-dimethyl-1,3-dioxolan-4-yl)methoxy)-2-methylphenyl)benzo[b]thiophene-5-carbaldehyde following General Procedure F. LC/MS: mass calcd. for C$_{22}$H$_{24}$O$_4$S: 384.49, found: 367.1 [M−OH]$^+$.

(E) 4-((4-(5-(Chloromethyl)benzo[b]thiophen-3-yl)-3-methylphenoxy)methyl)-2,2-dimethyl-1,3-dioxolane was prepared from (3-(4-((2,2-dimethyl-1,3-dioxolan-4-yl)methoxy)-2-methylphenyl)benzo[b]thiophen-5-yl)methanol following General Procedure D.

(F) (3S)-Ethyl 3-(4-((3-(4-((2,2-dimethyl-1,3-dioxolan-4-yl)methoxy)-2-methylphenyl)benzo[b]thiophen-5-yl)methoxy)phenyl)hex-4-ynoate was prepared from 4-((4-(5-(chloromethyl)benzo[b]thiophen-3-yl)-3-methylphenoxy)methyl)-2,2-dimethyl-1,3-dioxolane and (3S)-ethyl 3-(4-hydroxyphenyl)hex-4-ynoate (available from Synnovator, Inc., Research Triangle Park, N.C.; Cat. # PB05708) following General Procedure E. LC/MS: mass calcd. for C$_{36}$H$_{38}$O$_6$S: 598.75, found: 599.2 [M+H]$^+$.

(G) A solution of (3S)-ethyl 3-(4-((3-(4-((2,2-dimethyl-1,3-dioxolan-4-yl)methoxy)-2-methylphenyl)benzo[b]thiophen-5-yl)methoxy)phenyl)hex-4-ynoate (200 mg, 0.33 mmol) in THF (4 mL) was treated with 2N HCl (4 mL) and the resulting solution was stirred at 60° C. for 30 min. Water (10 mL) was then added and the mixture was extracted with EtOAc (3×10 mL). The combined organic extracts were dried (Na$_2$SO$_4$) and concentrated under reduced pressure. Purification of the resultant residue by silica gel chromatography (0-50% EtOAc/petroleum ether) afforded (3S)-ethyl 3-(4-((3-(4-(2,3-dihydroxypropoxy)-2-methylphenyl)benzo[b]thiophen-5-yl)methoxy)phenyl)hex-4-ynoate (140 mg, 75% yield) as a colorless oil. LC/MS: mass calcd. for C$_{33}$H$_{34}$O$_6$S: 558.68, found: 559.2 [M+H]$^+$.

(H) (3S)-3-(4-((3-(4-(2,3-Dihydroxypropoxy)-2-methylphenyl)benzo[b]thiophen-5-yl)methoxy)phenyl)hex-4-ynoic acid was prepared from (3S)-ethyl 3-(4-((3-(4-(2,3-dihydroxypropoxy)-2-methylphenyl)benzo[b]thiophen-5-yl)methoxy)phenyl)hex-4-ynoate following General Procedure C using LiOH as base, EtOH in place of MeOH and 1N HCl for reaction acidification. $^1$H NMR (DMSO-d6) δ 8.06 (d, J=8.4 Hz, 1H), 7.65 (s, 1H), 7.47 (d, J=8.4 Hz, 1H), 7.42 (s, 1H), 7.23-7.25 (m, 2H), 7.16 (d, J=8.4 Hz, 1H), 6.86-6.95 (m, 4H), 5.17 (s, 2H), 4.98-5.02 (m, 1H), 4.06-4.07 (m, 1H), 4.03-4.07 (m, 1H), 3.82-3.93 (m, 3H), 3.46-3.47 (m, 2H), 2.63-2.67 (m, 2H), 2.06 (s, 3H), 1.76 (s, 3H). LC/MS: mass calcd. for C$_{31}$H$_{30}$O$_6$S: 530.63, found: 529.2 [M−H]$^-$.

(I) (3S)-3-(4-((3-(4-(2,3-Dihydroxypropoxy)-2-methylphenyl)benzo[b]thiophen-5-yl)methoxy)phenyl)hex-4-ynamide was prepared by the HATU-mediated coupling of (3S)-3-(4-((3-(4-(2,3-dihydroxypropoxy)-2-methylphenyl)benzo[b]thiophen-5-yl)methoxy)phenyl)hex-4-ynoic acid and NH$_4$Cl following the procedure described in Example 6E. LC/MS: mass calcd. for C$_{31}$H$_{31}$NO$_5$S: 529.19, found: 530.2 [M+H]$^+$.

(J) (3S)-3-(4-((3-(4-(2,3-Dihydroxypropoxy)-2-methylphenyl)benzo[b]thiophen-5-yl)methoxy)phenyl)hex-4-ynenitrile was prepared along with 3-(4-(5-((4-((3S)-1-cyanopent-3-yn-2-yl)phenoxy)methyl)benzo[b]thiophen-3-yl)-3-methylphenoxy)-2-hydroxypropyl 2,2,2-trifluoroacetate and 3-(4-(5-((4-((3S)-1-cyanopent-3-yn-2-yl)phenoxy)methyl)benzo[b]thiophen-3-yl)-3-methylphenoxy)propane-1,2-diyl bis(2,2,2-trifluoroacetate) from (3S)-3-(4-((3-(4-(2,3-dihydroxypropoxy)-2-methylphenyl)benzo[b]thiophen-5-yl)methoxy)phenyl)hex-4-ynamide following General Procedure I and the mixture was used in the subsequent reaction.

(K) 3-(4-(5-((4-((2S)-1-(1H-tetrazol-5-yl)pent-3-yn-2-yl)phenoxy)methyl)benzo[b]thiophen-3-yl)-3-methylphenoxy)propane-1,2-diol (Cpd 31) was prepared from the mixture of (3S)-3-(4-((3-(4-(2,3-dihydroxypropoxy)-2-methylphenyl)benzo[b]thiophen-5-yl)methoxy)phenyl)hex-4-ynenitrile, 3-(4-(5-((4-((3S)-1-cyanopent-3-yn-2-yl)phenoxy)methyl)benzo[b]thiophen-3-yl)-3-methylphenoxy)-2-hydroxypropyl 2,2,2-trifluoroacetate and 3-(4-(5-((4-((3S)-1-cyanopent-3-yn-2-yl)phenoxy)methyl)benzo[b]thiophen-3-yl)-3-methylphenoxy)propane-1,2-diyl bis(2,2,2-trifluoroacetate) following General Procedure J, using Workup 2. $^1$H NMR (CD$_3$OD) δ 7.93 (d, J=8.2 Hz, 1H), 7.34-7.51 (m, 3H), 7.10-7.27 (m, 3H), 6.82-6.98 (m, 4H), 5.11 (s, 2H), 3.94-4.19 (m, 4H), 3.61-3.80 (m, 2H), 3.12-3.29 (m, 2H), 2.06 (s, 3H), 1.77 (d, J=2.3 Hz, 3H). LC/MS: mass calcd. for C$_3$H$_{33}$N$_4$O$_4$S: 554.20, found: 555.25 [M+H]$^+$.

Example 32

(2S)-5-(2-(4-((3-(2-Chlorophenyl)benzo[b]thiophen-5-yl)methoxy)phenyl)pent-3-yn-1-yl)-1H-tetrazole, Cpd 32

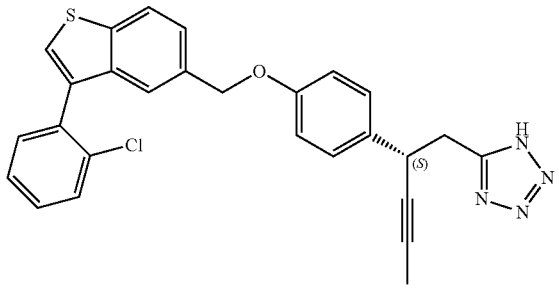

(A) 5-Hydroxymethyl-3-(2-chlorophenyl)benzo[b]thiophene was prepared from 3-bromo-5-hydroxymethylbenzothiophene (from Example 1A) and 2-chlorophenylboronic acid following General Procedure A, using PdCl$_2$(dppf).CH$_2$Cl$_2$ as the palladium catalyst and Cs$_2$CO$_3$ in place of K$_2$CO$_3$. LC/MS: mass calcd. for C$_{15}$H$_{11}$ClOS: 274.02, found 257.1 [M−OH]$^+$.

(B) 5-(Chloromethyl)-3-(2-chlorophenyl)benzo[b]thiophene was prepared from 5-hydroxymethyl-3-(2-chlorophenyl)benzo[b]thiophene following General Procedure D.

(C) (3S)-3-(4-((3-(2-Chlorophenyl)benzo[b]thiophen-5-yl)methoxy)phenyl)hex-4-ynenitrile was prepared from 5-(chloromethyl)-3-(2-chlorophenyl)benzo[b]thiophene and (3S)-3-(4-hydroxyphenyl)hex-4-ynenitrile (from Example 2G) following General Procedure E, using DMF as solvent and K$_2$CO$_3$ in place of Cs$_2$CO$_3$ at a reaction temperature of 60° C. for 3 h. LC/MS: mass calcd. for C$_{27}$H$_{20}$ClNOS: 441.09, found: 441.9 [M+H]$^+$.

(D) (2S)-5-(2-(4-((3-(2-Chlorophenyl)benzo[b]thiophen-5-yl)methoxy)phenyl)pent-3-yn-1-yl)-1H-tetrazole (Cpd 32) was prepared from (3S)-3-(4-((3-(2-chlorophenyl)benzo[b]thiophen-5-yl)methoxy)phenyl)hex-4-ynenitrile following General Procedure J, using Workup 1. $^1$H NMR (DMSO-$d_6$) δ 8.06-8.12 (m, 1H), 7.85 (s, 1H), 7.61-7.69 (m, 1H), 7.44-7.54 (m, 5H), 7.19-7.25 (m, 2H), 6.87-6.97 (m, 2H), 5.16 (s, 2H), 4.02-4.18 (m, 1H), 3.20 (d, J=7.7 Hz, 2H), 1.73 (d, J=2.4 Hz, 3H). LC/MS: mass calcd. for $C_{27}H_{21}ClN_4OS$: 484.11, found: 485.0 [M+H]$^+$.

Example 33

(2S)-3-(5-((4-(1-(1H-Tetrazol-5-yl)pent-3-yn-2-yl)phenoxy)methyl)benzo[b]thiophen-3-yl)-5-(2-methoxyethoxy)-2-methylpyridine, Cpd 33

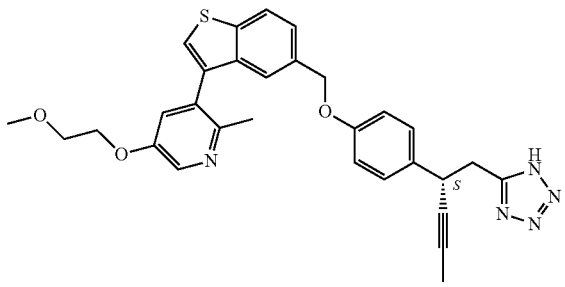

(A) 3-Bromo-5-(2-methoxyethoxy)-2-methylpyridine was prepared from 5-bromo-6-methylpyridin-3-ol and 1-bromo-2-methoxyethane following the procedure described in Example 26A. LC/MS: mass calcd. for $C_9H_{12}BrNO_2$: 246.10, found: 246.0[M]$^+$, 248.0 [M+2]$^+$.

(B) 5-(2-Methoxyethoxy)-2-methyl-3-(4,4,5,5-tetramethyl-1,3,2-dioxaborolan-2-yl)pyridine was prepared from 3-bromo-5-(2-methoxyethoxy)-2-methylpyridine and bis(pinacolato)diboron following General Procedure A, using PdCl$_2$(dppf).CH$_2$Cl$_2$ as the palladium catalyst, KOAc in place of K$_2$CO$_3$ and DMSO as reaction solvent at a reaction temperature of 85° C. overnight. LC/MS: mass calcd. for $C_{15}H_{24}BNO_4$: 293.17, found: 294.1 [M+H]$^+$.

(C) (3S)-Ethyl 3-(4-((3-(5-(2-methoxyethoxy)-2-methylpyridin-3-yl)benzo[b]thiophen-5-yl)methoxy)phenyl)hex-4-ynoate was prepared from 5-(2-methoxyethoxy)-2-methyl-3-(4,4,5,5-tetramethyl-1,3,2-dioxaborolan-2-yl)pyridine and (3S)-ethyl-3-(4-((3-bromobenzo[b]thiophen-5-yl)methoxy)phenyl)hex-4-ynoate (from Example 7B following General Procedure A, using PdCl$_2$(dppf).CH$_2$Cl$_2$ as the palladium catalyst and Cs$_2$CO$_3$ in place of K$_2$CO$_3$. LC/MS: mass calcd. for $C_{32}H_{33}NO_5S$: 543.67, found: 544.2 [M+H]$^+$.

(D) (3S)-3-(4-((3-(5-(2-Methoxyethoxy)-2-methylpyridin-3-yl)benzo[b]thiophen-5-yl)methoxy)phenyl)hex-4-ynoic acid was prepared from (3S)-ethyl 3-(4-((3-(5-(2-methoxyethoxy)-2-methylpyridin-3-yl)benzo[b]thiophen-5-yl)methoxy)phenyl)hex-4-ynoate following General Procedure C, using LiOH as base, EtOH in place of MeOH and 1N HCl for reaction acidification. $^1$H NMR (DMSO-$d_6$) δ 8.28 (d, J=3.0 Hz, 1H), 8.10 (d, J=8.4 Hz, 1H), 7.84 (s, 1H), 7.48-7.52 (m, 2H), 7.30 (d, J=2.7 Hz, 1H), 7.24 (d, J=8.7 Hz, 2H), 6.92 (d, J=8.7 Hz, 2H), 5.18 (s, 2H), 4.17-4.20 (m, 2H), 3.90-3.94 (m, 1H), 3.65-3.68 (m, 2H), 3.32 (s, 3H), 2.54-2.57 (m, 2H), 2.20 (s, 3H), 1.76 (d, J=2.4 Hz, 3H). LC/MS: mass calcd. for $C_{30}H_{29}NO_5S$: 515.62, found: 516.2 [M+H]$^+$.

(E) (3S)-3-(4-((3-(5-(2-Methoxyethoxy)-2-methylpyridin-3-yl)benzo[b]thiophen-5-yl)methoxy)phenyl)hex-4-ynoyl chloride was prepared from (3S)-3-(4-((3-(5-(2-methoxyethoxy)-2-methylpyridin-3-yl)benzo[b]thiophen-5-yl)methoxy)phenyl)hex-4-ynoic acid following General Procedure G, using oxalyl chloride as the chlorinating agent.

(F) (3S)-3-(4-((3-(5-(2-Methoxyethoxy)-2-methylpyridin-3-yl)benzo[b]thiophen-5-yl)methoxy)phenyl)hex-4-ynamide was prepared from (3S)-3-(4-((3-(5-(2-methoxyethoxy)-2-methylpyridin-3-yl)benzo[b]thiophen-5-yl)methoxy)phenyl)hex-4-ynoyl chloride following General Procedure Ha. LC/MS: mass calcd. for $C_{30}H_{30}N_2O_4S$: 514.19, found: 515.0 [M+H]$^+$.

(G) (3S)-3-(4-((3-(5-(2-methoxyethoxy)-2-methylpyridin-3-yl)benzo[b]thiophen-5-yl)methoxy)phenyl)hex-4-ynenitrile was prepared from (3S)-3-(4-((3-(5-(2-Methoxyethoxy)-2-methylpyridin-3-yl)benzo[b]thiophen-5-yl)methoxy)phenyl)hex-4-ynamide following General Procedure I. LC/MS: mass calcd. for $C_{30}H_{28}N_2O_3S$: 496.18, found: 497.0 [M+H]$^+$.

(H) (2S)-3-(5-((4-(1-(1H-Tetrazol-5-yl)pent-3-yn-2-yl)phenoxy)methyl)benzo[b]thiophen-3-yl)-5-(2-methoxyethoxy)-2-methylpyridine (Cpd 33) was prepared from (3S)-3-(4-((3-(5-(2-methoxyethoxy)-2-methylpyridin-3-yl)benzo[b]thiophen-5-yl)methoxy)phenyl)hex-4-ynenitrile following General Procedure J, using Workup 2. $^1$H NMR (CD$_3$OD) δ 8.20 (s, 1H), 7.96 (d, J=8.1 Hz, 1H), 7.58 (s, 1H), 7.47 (d, J=8.4 Hz, 1H), 7.41 (s, 1H), 7.34 (s, 1H), 7.18 (d, J=8.4 Hz, 2H), 6.87 (d, J=8.4 Hz, 2H), 5.14 (s, 2H), 4.16-4.19 (m, 2H), 4.00-4.05 (m, 1H), 3.71-3.74 (m, 2H), 3.38 (s, 3H), 3.21-3.27 (m, 2H), 2.20 (s, 3H), 1.75 (s, 3H). LC/MS: mass calcd. for $C_{30}H_{29}N_5O_3S$: 539.20, found: 540.1 [M+H]$^+$.

Example 34

5-((2S)-2-(4-((2-Bromo-3-(2-methylphenyl)benzo[b]thiophen-5-yl)methoxy)phenyl)pent-3-ynyl)-1H-tetrazole, Cpd 34

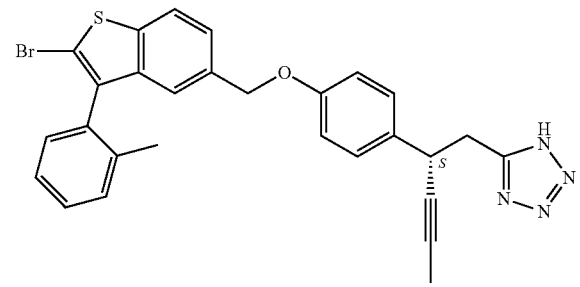

(A) To an ice-cooled solution of tert-butyldimethyl 3-((2-methylphenyl)benzo[b]thiophen-5-yl)methoxy)silane (400 mg, 0.27 mmol; from Example 2A) in DMF (10 mL) was added NBS (193 mg, 1.08 mmol) and the resultant mixture was stirred at 0° C. for 2 h. Water (30 mL) was then added and the mixture was extracted with EtOAc (3×30 mL). The combined organic extracts were dried (Na$_2$SO$_4$), concentrated under reduced pressure and the residue that was obtained was purified by silica gel chromatography (0-30% EtOAc/petroleum ether) to afford (2-bromo-3-(2-methylphenyl)benzo[b]thiophen-5-yl)methanol (200 mg, 55%) as a colorless oil. LC/MS: mass calcd. for $C_{16}H_{13}BrOS$: 331.99, found: 315.0, 317.0 [M–OH]$^+$, [M+2-OH]$^+$.

(B) 2-Bromo-5-(chloromethyl)-3-(2-methylphenyl)benzo[b]thiophene was prepared from (2-bromo-3-(2-methylphenyl)benzo[b]thiophen-5-yl)methanol following General Procedure D.

(C) (3S)-3-(4-((2-Bromo-3-(2-methylphenyl)benzo[b]thiophen-5-yl)methoxy)phenyl)hex-4-ynenitrile was prepared from 2-bromo-5-(chloromethyl)-3-(2-methylphenyl)benzo[b]thiophene and (3S)-3-(4-hydroxyphenyl)hex-4-ynenitrile (from Example 2G) following General Procedure E, at a reaction temperature of 60° C. overnight. LC/MS: mass calcd. for $C_{28}H_{22}BrNOS$: 499.06, found: 516.9, 518.9 $[M+NH_4]^+$, $[M+2+NH_4]^+$.

(D) 5-((2S)-2-(4-((2-Bromo-3-(2-methylphenyl)benzo[b]thiophen-5-yl)methoxy)phenyl)pent-3-ynyl)-1H-tetrazole (Cpd 34) was prepared from (3S)-3-(4-((2-bromo-3-(2-methylphenyl)benzo[b]thiophen-5-yl)methoxy)phenyl)hex-4-ynenitrile following General Procedure J, using Workup 2. $^1$H NMR (CD$_3$OD) δ 7.86 (d, J=8.4 Hz, 1H), 7.46 (d, J=8.4 Hz, 1H), 7.31-7.37 (m, 3H), 7.14-7.21 (m, 4H), 6.87 (d, J=8.4 Hz, 2H), 5.09 (s, 2H), 4.05 (br. s, 1H), 3.25 (d, J=7.2 Hz, 2H), 2.02 (s, 3H), 1.77 (s, 3H). LC/MS: mass calcd. for $C_{28}H_{23}BrN_4OS$: 542.08, found: 542.9, 544.9 $[M+H]^+$, $[M+2+H]^+$.

Example 35

5-((2S)-2-(4-((2-Iodo-3-(2-methylphenyl)benzo[b]thiophen-5-yl)methoxy)phenyl)pent-3-ynyl)-1H-tetrazole, Cpd 35

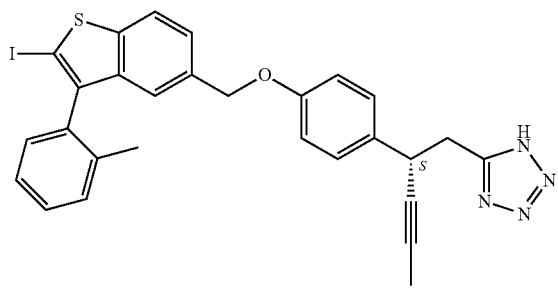

(A) To a cooled (−78° C.) solution of tert-butyldimethyl-(3-(2-methylphenyl)benzo[b]thiophen-5-yl)methoxy)silane (400 mg, 0.27 mmol; from Example 2A) in THF (15 mL), maintained under an inert nitrogen atmosphere, was added LDA (2M in THF; 0.54 mL, 1.08 mmol) and the resultant mixture was stirred at −78° C. for 0.5 h. A solution of iodine (415 mg, 1.64 mmol) in THF was then added and the resultant mixture was stirred at −78° C. for 2 h. The reaction was then quenched by the addition of satd. aq NaCl (30 mL) and the mixture was extracted with EtOAc (3×30 mL). The combined organic extracts were dried (Na$_2$SO$_4$), concentrated under reduced pressure and the residue that was obtained was purified by silica gel chromatography (0-10% EtOAc/petroleum ether) to afford tert-butyl((2-iodo-3-(2-methylphenyl)benzo[b]thiophen-5-yl)methoxy)dimethylsilane (360 mg, 67%) as a yellow oil. LC/MS: mass calcd. for $C_{22}H_{27}IOSSi$: 494.06, found: 362.8 $[M-OTBS]^+$.

(B) (2-Iodo-3-(2-methylphenyl)benzo[b]thiophen-5-yl)methanol was prepared from tert-butyldimethyl-((2-iodo-3-(2-methylphenyl)benzo[b]thiophen-5-yl)methoxy)silane following the procedure described in Example 2C. LC/MS: mass calcd. for $C_{16}H_{13}IOS$: 379.97, found: 362.7 $[M-OH]^+$.

(C) 2-Iodo-5-(chloromethyl)-3-(2-methylphenyl)benzo[b]thiophene was prepared from (2-iodo-3-(2-methylphenyl)benzo[b]thiophen-5-yl)methanol following General Procedure D.

(D) (3S)-3-(4-((2-Iodo-3-(2-methylphenyl)benzo[b]thiophen-5-yl)methoxy)phenyl)hex-4-ynenitrile was prepared from 2-iodo-5-(chloromethyl)-3-(2-methylphenyl)benzo[b]thiophene and (3S)-3-(4-hydroxyphenyl)hex-4-ynenitrile (from Example 2G) following General Procedure E, using K$_2$CO$_3$ in place of Cs$_2$CO$_3$ and a reaction temperature of 60° C. overnight. LC/MS: mass calcd. for $C_{28}H_{22}INOS$: 547.05, found: 564.9 $[M+NH_4]^+$.

(E) 5-((2S)-2-(4-((2-Iodo-3-(2-methylphenyl)benzo[b]thiophen-5-yl)methoxy)phenyl)pent-3-ynyl)-1H-tetrazole (Cpd 35) was prepared from (3S)-3-(4-((2-iodo-3-(2-methylphenyl)benzo[b]thiophen-5-yl)methoxy)phenyl)hex-4-ynenitrile following General Procedure J, using Workup 2. $^1$H NMR (CD$_3$OD) δ 7.84 (d, J=8.4 Hz, 1H), 7.27-7.45 (m, 4H), 7.16-7.20 (m, 3H), 7.08 (d, J=7.2 Hz, 1H), 6.84 (d, J=8.8 Hz, 2H), 5.04 (s, 2H), 4.04 (br. s, 1H), 3.24 (d, J=7.2 Hz, 2H), 1.96 (s, 3H), 1.77 (s, 3H). LC/MS: mass calcd. for $C_{28}H_{23}IN_4OS$: 590.06, found: 590.9 $[M+H]^+$.

Example 36

5-((2S)-2-(4-((2-Trifluoromethyl-3-(2-methylphenyl)benzo[b]thiophen-5-yl)methoxy)phenyl)pent-3-ynyl)-1H-tetrazole, Cpd 36

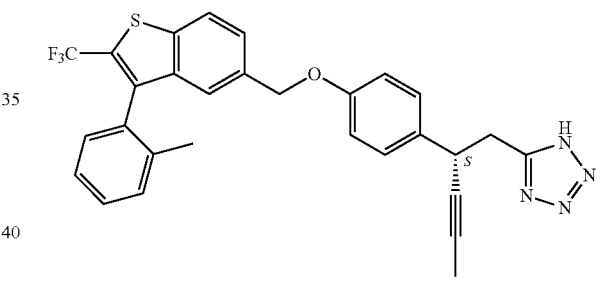

(A) To a cooled (−78° C.) solution of tert-butyldimethyl-((3-(2-methylphenyl)benzo[b]thiophen-5-yl)methoxy)silane (300 mg, 0.814 mmol; from Example 2A) in THF (8 mL), maintained under an inert nitrogen atmosphere, was added n-BuLi (2.5M in hexanes; 0.65 mL, 1.63 mmol) in drop-wise fashion and the resultant mixture was stirred at −78° C. for 10 min. A solution of triisopropoxyborane (612 mg, 3.26 mmol) in THF (2 mL) was then added in drop-wise fashion and the resultant mixture was stirred at −78° C. for 30 min, then at rt for 1 h. The reaction was then quenched by the addition of water (10 mL) and the mixture was extracted with EtOAc (3×10 mL). The combined organic extracts were dried (Na$_2$SO$_4$) and concentrated under reduced pressure to afford 5-((tert-butyldimethylsilyloxy)methyl)-3-(2-methylphenyl)benzo[b]thiophen-2-ylboronic acid (250 mg, 74%) as colorless oil. LC/MS: mass calcd. for $C_{22}H_{29}BO_3SSi$: 412.17, found: 411.1 $[M-H]^-$.

(B) To an ice-cooled mixture of 5-((tert-butyldimethylsilyloxy)methyl)-3-(2-methylphenyl)benzo[b]thiophen-2-ylboronic acid (250 mg, 0.606 mmol), sodium trifluoromethanesulfinate (284 mg, 1.820 mmol), copper(I) chloride (60 mg, 0.606 mmol), DCM (5 mL), MeOH (5 mL) and water (4 mL) was added 2-hydroperoxy-2-methylpropane (273 mg, 3.029 mmol) in drop-wise fashion. After stirring at rt overnight, water (15 mL) was added and the mixture was extracted with EtOAc (3×15 mL). The combined organic extracts were dried (Na$_2$SO$_4$), concentrated under reduced pressure and the residue that was obtained was purified by silica gel chromatography (0-5% EtOAc/petroleum ether) to afford tert-butyldimethyl((2-trifluoromethyl-3-(2-methylphenyl)benzo[b]thiophen-5-yl)methoxy)silane (200 mg, 75%) as a colorless oil. LC/MS: mass calcd. for C$_{23}$H$_{27}$F$_3$OSSi: 436.15, found: 305.1 [M−OTBS]$^+$.

(C) (3-(2-Methylphenyl)-2-(trifluoromethyl)benzo[b]thiophen-5-yl)methanol was prepared from tert-butyldimethyl((2-trifluoromethyl-3-(2-methylphenyl)benzo[b]thiophen-5-yl)methoxy)silane following the procedure described in Example 2C. LC/MS: mass calcd. for C$_{17}$H$_{13}$F$_3$OS: 322.06, found: 305.1 [M−OH]$^+$.

(D) 5-(Chloromethyl)-3-(2-methylphenyl)-2-(trifluoromethyl)benzo[b]thiophene was prepared from (3-(2-methylphenyl)-2-(trifluoromethyl)benzo[b]thiophen-5-yl)methanol following General Procedure D.

(E) (3S)-3-(4-((3-(2-Methylphenyl)-2-(trifluoromethyl)benzo[b]thiophen-5-yl)methoxy)phenyl)hex-4-ynenitrile was prepared from 5-(chloromethyl)-3-(2-methylphenyl)-2-(trifluoromethyl)benzo[b]thiophene and (3S)-3-(4-hydroxyphenyl)hex-4-ynenitrile (from Example 2G) following General Procedure E, at a reaction temperature of 60° C. overnight. LC/MS: mass calcd. for C$_{29}$H$_{22}$F$_3$NOS: 489.14, found: 507.0[M+NH$_4$]$^+$.

(F) 5-((2S)-2-(4-((2-Trifluoromethyl-3-(2-methylphenyl)benzo[b]thiophen-5-yl)methoxy)phenyl)pent-3-ynyl)-1H-tetrazole (Cpd 36) was prepared from (3S)-3-(4-((3-(2-methylphenyl)-2-(trifluoromethyl)benzo[b]thiophen-5-yl)methoxy)phenyl)hex-4-ynenitrile following General Procedure J, using Workup 2. Additional purification of the product was carried out by preparative HPLC on a Waters SunFire™ Prep C18, 5μ column (19×100 mm) using an acetonitrile/water (0.05% NH$_4$HCO$_3$) gradient (45-85%). $^1$H NMR (DMSO-d$_6$) δ 8.02-8.25 (m, 1H), 7.66-7.69 (m, 1H), 7.33-7.51 (m, 3H), 7.20-7.25 (m, 4H), 6.86-6.94 (m, 2H), 5.12-5.16 (m, 2H), 4.08-4.09 (m, 1H), 3.21 (d, J=7.8 Hz, 2H), 1.92-2.02 (m, 3H), 1.73 (d, J=1.5 Hz, 3H). LC/MS: mass calcd. for C$_{29}$H$_{23}$F$_3$N$_4$OS: 532.15, found: 533.0 [M+H]$^+$.

Example 37

(2S)-5-(2-(4-((3-Cyclopropyl-2-(trifluoromethyl)benzo[b]thiophen-5-yl)methoxy)phenyl)pent-3-yn-1-yl)-1H-tetrazole, Cpd 37

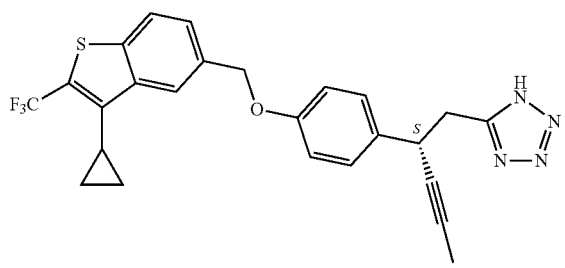

(A) To a solution of (3S)-3-(4-hydroxyphenyl)hex-4-ynoic acid (200 mg, 0.98 mmol) in THF (6 mL) was added tetrabutylammonium hydroxide (40% in water, 1.45 mL, 2.23 mmol) and H$_2$O (0.9 mL). After stirring at rt for 5 min, NaI (40 mg, 0.267 mmol) was added, followed by addition of a solution of 1-(chloromethyl)-4-methoxybenzene (0.12 mL, 0.89 mmol) in THF (4 mL) and stirring was continued for 18 h. The reaction was quenched by addition of 1N HCl and the mixture was extracted with EtOAc (2×20 mL). The combined organic extracts were washed with brine, dried (Na$_2$SO$_4$) and concentrated under reduced pressure to afford (3S)-3-(4-((4-methoxybenzyl)oxy)phenyl)hex-4-ynoic acid, which was used directly without further purification. LC/MS: mass calcd. for C$_{20}$H$_{20}$O$_4$: 324.14, found: 347.1 [M+Na]$^+$.

(B) To a solution of (3S)-3-(4-((4-methoxybenzyl)oxy)phenyl)hex-4-ynoic acid (300 mg, 0.93 mmol) in DMF (4 mL) was added 3-aminopropionitrile (130 mg, 1.85 mmol), HATU (527 mg, 1.39 mmol), and DIEA (0.478 mL, 2.78 mmol) and the resulting mixture was stirred at rt for 2 h. EtOAc (50 mL) was then added, and the organic phase was washed successively with satd. aq NaHCO$_3$, 1N HCl and brine (3×50 mL). The organic phase was dried (Na$_2$SO$_4$) and concentrated under reduced pressure and the residue thus obtained was purified by silica gel chromatography (20-80% EtAOc/heptanes) to afford (3S)—N-(2-cyanoethyl)-3-(4-((4-methoxybenzyl)oxy)phenyl)hex-4-ynamide (200 mg, 57%) as a white solid. LC/MS: mass calcd. for C$_{23}$H$_{24}$N$_2$O$_3$: 376.18, found: 377.2 [M+H]$^+$.

(C) To the suspension of (3S)—N-(2-cyanoethyl)-3-(4-((4-methoxybenzyl)oxy)phenyl)hex-4-ynamide (200 mg, 0.53 mmol) in DCM (10 mL) was added pyridine (0.256 mL, 3.19 mmol) and PCl$_5$ (166 mg, 0.80 mmol) and the resultant mixture was stirred at 40° C. for 3 h. After cooling to rt, TMSN$_3$ (0.282 mL, 2.13 mmol) was added and the mixture was stirred at rt overnight. The reaction was quenched by the careful addition of satd. aq NaHCO$_3$ (20 mL) was added slowly and after stirring for 15 min, the mixture was diluted with DCM (200 mL). The organic phase was then washed successively with 0.1N HCl and brine, dried (Na$_2$SO$_4$) and concentrated under reduced pressure. The residue thus obtained was purified by silica gel chromatography (0-50% EtOAc/heptanes) to afford (2S)-3-(5-(2-(4-((4-methoxybenzyl)oxy)phenyl)pent-3-yn-1-yl)-1H-tetrazol-1-yl)propanenitrile (147 mg, 69%) as a yellow solid. LC/MS: mass calcd. for C$_{23}$H$_{23}$N$_5$O$_2$: 401.19, found: 402.1 [M+H]$^+$.

(D) To a solution of (2S)-3-(5-(2-(4-((4-methoxybenzyl)oxy)phenyl)pent-3-yn-1-yl)-1H-tetrazol-1-yl)propanenitrile (147 mg, 0.366 mmol) in DCM (2 mL) was added TFA (1 mL) and the mixture was stirred at rt for 6 h. The reaction was then concentrated under reduced pressure, and the residue was re-dissolved in EtOAc (20 mL). The solution was washed successively with satd. aq NaHCO$_3$ and brine, dried (Na$_2$SO$_4$) and concentrated under reduced pressure. The resultant residue was purified by silica gel chromatography (0-60% EtOAc/heptanes) to afford (2S)-3-(5-(2-(4-hydroxyphenyl)pent-3-yn-1-yl)-1H-tetrazol-1-yl)propanenitrile (43 mg, 42%) as a colorless oil. $^1$H NMR (CDCl$_3$) δ 7.06 (d, J=8.6 Hz, 2H), 6.75-6.81 (m, 2H), 4.03-4.16 (m, 3H), 3.39 (dd, J=14.1, 7.1 Hz, 1H), 3.21 (dd, J=14.4, 7.8 Hz, 1H), 2.76-2.87 (m, 1H), 2.64-2.75 (m, 1H), 1.84 (d, J=2.0 Hz, 3H). LC/MS: mass calcd. for C$_{15}$H$_{15}$N$_5$O: 281.13, found: 282.1 [M+H]$^+$.

(E) Methyl 3-cyclopropylbenzo[b]thiophene-5-carboxylate was prepared from methyl 3-bromobenzo[b]thiophene-5-carboxylate and cyclopropylboronic acid following General Procedure A, using PdCl$_2$(dppf).CH$_2$Cl$_2$ as the palladium catalyst. LC/MS: mass calcd. for C$_{13}$H$_{12}$O$_2$S: 232.06, found: 233.1 [M+H]$^+$.

(F) To a solution of methyl 3-cyclopropylbenzo[b]thiophene-5-carboxylate (200 mg, 0.861 mmol) in AcOH (3 mL) was added Br$_2$ (88.8 μL, 1.72 mmol) in DCM (3 mL) and the mixture was stirred at rt for 20 min. Water (50 mL) was added, followed by 5% aq $Na_2S_2O_3$ solution (10 mL). The mixture was then extracted with EtOAc (2×50 mL) and the combined organic extracts were washed successively with satd. aq $NaHCO_3$ and brine, then dried ($Na_2SO_4$) and concentrated under reduced pressure. Purification of the resultant residue by silica gel chromatography (0-10% EtOAc/heptane) afforded methyl 2-bromo-3-cyclopropylbenzo[b]thiophene-5-carboxylate (222 mg, 83%) as an off-white solid. $^1$H NMR ($CDCl_3$) δ 8.58 (d, J=1.0 Hz, 1H), 7.96 (dd, 1.5 Hz, 1H), 7.70 (d, J=8.1 Hz, 1H), 3.97 (s, 3H), 1.82 (tt, J=8.5, 5.4 Hz, 1H), 1.09-1.15 (m, 2H), 0.82-0.88 (m, 2H).

(G) To a solution of methyl 2-bromo-3-cyclopropylbenzo[b]thiophene-5-carboxylate (200 mg, 0.643 mmol), NaI (193 mg, 1.29 mmol) and CuI (245 mg, 1.29 mmol) in DMF (5 mL) was added methyl 2,2-difluoro-2-(fluorosulfonyl)acetate (0.409 mL, 3.21 mmol) in a drop-wise fashion under argon and the mixture was stirred at 105° C. for 2 d. After cooling to rt, the mixture was filtered through a pad of diatomaceous earth, which was further washed with EtOAc. The combined filtrate was washed successively with water and brine and the organic phase was dried ($Na_2SO_4$) and concentrated under reduced pressure. The resultant residue was purified by silica gel chromatography (0-10% EtOAc/heptanes) to afford methyl 3-cyclopropyl-2-iodobenzo[b]thiophene-5-carboxylate as the major product (200 mg, 87%). $^1$H NMR ($CDCl_3$) δ 8.65 (d, J=1.5 Hz, 1H), 7.95 (dd, 1.5 Hz, 1H), 7.75 (d, J=8.1 Hz, 1H), 3.97 (s, 3H), 1.78-1.90 (m, 1H), 1.14-1.21 (m, 2H), 0.79-0.86 (m, 2H).

(H) To a solution of methyl 3-cyclopropyl-2-iodobenzo[b]thiophene-5-carboxylate (200 mg, 0.558 mmol) and CuI (213 mg, 1.12 mmol) in DMF (4 mL) was added methyl 2,2-difluoro-2-(fluorosulfonyl)acetate (0.355 mL, 2.79 mmol) in a drop-wise fashion under argon and the mixture was stirred at 150° C. (sealed tube) in a microwave reactor for 1 h. After cooling to rt, the mixture was filtered through a pad of diatomaceous earth, which was further washed with EtOAc. The combined filtrate was washed successively with water and brine and the organic phase was dried ($Na_2SO_4$) and concentrated under reduced pressure. The resultant residue was purified by silica gel chromatography (0-10% EtOAc/heptanes) to afford methyl 3-cyclopropyl-2-(trifluoromethyl)benzo[b]thiophene-5-carboxylate (128 mg, 76%). $^1$H NMR ($CDCl_3$) δ 8.77 (d, J=1.5 Hz, 1H), 8.10 (dd, J=8.6, 1.5 Hz, 1H), 7.88 (d, J=8.6 Hz, 1H), 3.99 (s, 3H), 2.01 (ddt, J=7.2, 3.7, 1.6 Hz, 1H), 1.15-1.22 (m, 2H), 0.86-0.92 (m, 2H).

(I) To an ice-cooled solution of methyl 3-cyclopropyl-2-(trifluoromethyl)benzo[b]thiophene-5-carboxylate (128 mg, 0.426 mmol) in THF (5 mL) was added $LiAlH_4$ (1 M in THF, 0.639 mL) in drop-wise fashion under argon and the mixture was stirred at 0° C. for 1 h. The reaction was quenched by the addition of satd. aq $NH_4Cl$ solution and the mixture was extracted with EtOAc (2×20 mL). The combined organic extracts were washed with brine, then dried ($Na_2SO_4$) and concentrated under reduced pressure. The resultant residue was purified by silica gel chromatography (0-30% EtOAc/heptane) to give 3-cyclopropyl-2-(trifluoromethyl)benzo[b]thiophen-5-yl)methanol (72 mg, 62%) as a white solid. $^1$H NMR ($CDCl_3$) δ 8.07 (s, 1H), 7.81 (d, J=8.1 Hz, 1H), 7.46 (dd, J=8.6, 1.5 Hz, 1H), 4.85 (s, 2H), 1.92-2.02 (m, 1H), 1.82 (br. s, 1H), 1.09-1.15 (m, 2H), 0.83-0.89 (m, 2H).

(J) (2S)-3-(5-(2-(4-((3-Cyclopropyl-2-(trifluoromethyl)benzo[b]thiophen-5-yl)methoxy)phenyl)pent-3-yn-1-yl)-1H-tetrazol-1-yl)propanenitrile was prepared from 3-cyclopropyl-2-(trifluoromethyl)benzo[b]thiophen-5-yl)methanol and (2S)-3-(5-(2-(4-hydroxyphenyl)pent-3-yn-1-yl)-1H-tetrazol-1-yl)propanenitrile (from Step D) following General Procedure B, using ADDP and $Bu_3P$ at a reaction temperature of 60° C. for 3 h. LC/MS: mass calcd. for $C_{28}H_{24}F_3N_5OS$: 535.17, found: 536.2 [M+H]$^+$.

(K) To a solution of (2S)-3-(5-(2-(4-((3-cyclopropyl-2-(trifluoromethyl)benzo[b]thiophen-5-yl)methoxy)phenyl)pent-3-yn-1-yl)-1H-tetrazol-1-yl)propanenitrile (60 mg, 0.112 mmol) in THF (1 mL) and i-PrOH (0.5 mL) was added 1N NaOH (1 mL) and the mixture was stirred at rt for 1 h. The organic solvent was evaporated and the aqueous solution was acidified with 2M aq citric acid and extracted with EtOAc (2×10 mL). The combined organic extracts were washed with brine, dried ($Na_2SO_4$) and concentrated. The resultant residue was purified by silica gel chromatography (20-100% EtOAc/heptane) to afford (2S)-5-(2-(4-((3-cyclopropyl-2-(trifluoromethyl)benzo[b]thiophen-5-yl)methoxy)phenyl)pent-3-yn-1-yl)-1H-tetrazole (43 mg, 80%) as a white solid. $^1$H NMR ($CDCl_3$) δ 8.09 (s, 1H), 7.81 (d, J=8.1 Hz, 1H), 7.48 (dd, 1.5 Hz, 1H), 7.27 (d, J=7.8 Hz, 2H), 6.93 (d, J=7.8 Hz, 2H), 5.14 (s, 2H), 4.08-4.18 (m, 1H), 3.37-3.51 (m, 2H), 1.91-2.01 (m, 1H), 1.82 (d, J=2.5 Hz, 3H), 1.05-1.14 (m, 2H), 0.77-0.87 (m, 2H). LC/MS: mass calcd. for $C_{25}H_{21}F_3N_4OS$: 482.14, found: 505.2 [M+Na]$^+$.

Example 38

5-((2S)-2-(4-((2-Cyano-3-(2-methylphenyl)benzo[b]thiophen-5-yl)methoxy)phenyl)pent-3-yn-1-yl)-1H-tetrazole, Cpd 38

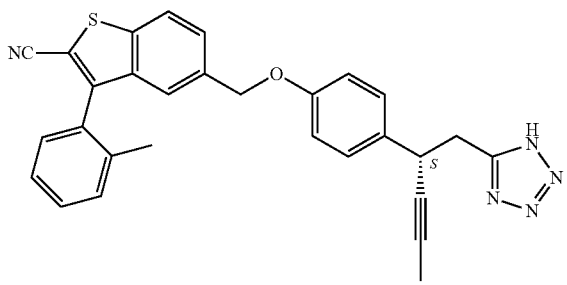

(A) To an ice-cooled solution of tert-butyldimethyl-((3-(2-methylphenyl)benzo[b]thiophen-5-yl)methoxy)silane (6 g, 16.28 mmol; from Example 2A) in DMF (50 mL) was added NBS (2.9 g, 16.3 mmol) and the resultant mixture was stirred at 0° C. for 2 h. Water (100 mL) was then added and the mixture was extracted with EtOAc (3×100 mL). The combined organic extracts were dried ($Na_2SO_4$), concentrated under reduced pressure and the residue that was obtained was purified by silica gel chromatography (0-30% EtOAc/petroleum ether) to afford ((2-bromo-3-(2-methylphenyl)benzo[b]thiophen-5-yl)methoxy)(tert-butyl)dimethylsilane (4 g, 55%) as a colorless oil. LC/MS: mass calcd. for $C_{16}H_{13}BrOS$: 331.99, found: 315.0, 317.0 [M−OTBS]$^+$, [M+2-OTBS]$^+$.

(B) A mixture of ((2-bromo-3-(2-methylphenyl)benzo[b]thiophen-5-yl)methoxy)(tert-butyl)dimethylsilane (200 mg, 0.447 mmol), zinc cyanide (105 mg, 0.894 mmol) and Pd(PPh$_3$)$_4$ (50 mg, 0.043 mmol) in DMF (10 mL) was placed under an inert atmosphere of nitrogen in a sealed tube and heated for 16 h at 100° C. After cooling to rt, water (30 mL) was added, and the mixture was extracted with EtOAc (3×30 mL). The combined organic extracts were washed with brine, dried ($Na_2SO_4$) and concentrated. The resultant residue was purified by silica gel chromatography (0-20% EtOAc/petroleum ether) to afford 5-(((tert-butyldimethylsilyloxy)-methyl)-3-(2-methylphenyl)benzo[b]thiophene-2-carbonitrile (150 mg, 48%) as a yellow oil. LC/MS: mass calcd. for $C_{23}H_{27}NOSSi$: 393.16, found: 394.0 $[M+H]^+$.

(C) 5-(Hydroxymethyl)-3-(2-methylphenyl)benzo[b]thiophene-2-carbonitrile was prepared from 5-((tert-butyldimethylsilyloxy)-methyl)-3-(2-methylphenyl)benzo[b]thiophene-2-carbonitrile following the procedure described in Example 2C. LC/MS: mass calcd. for $C_{17}H_{13}NOS$: 279.07, found: 262.0 $[M-OH]^+$.

(D) 5-((4-((2S)-1-(1-(2-Cyanoethyl)-1H-tetrazol-5-yl)pent-3-yn-2-yl)phenoxy)methyl)-3-(2-methylphenyl)benzo[b]thiophene-2-carbonitrile was prepared from 5-(hydroxymethyl)-3-(2-methylphenyl)benzo[b]thiophene-2-carbonitrile and (2S)-3-(5-(2-(4-hydroxyphenyl)pent-3-yn-1-yl)-1H-tetrazol-1-yl)propanenitrile (from Example 37D) following General Procedure B, using ADDP and $Bu_3P$ at a reaction temperature of 60° C. LC/MS: mass calcd. for $C_{32}H_{26}N_6OS$: 542.19, found: 543.0 $[M+H]^+$.

(E) 5-((2S)-2-(4-((2-Cyano-3-(2-methylphenyl)benzo[b]thiophen-5-yl)methoxy)phenyl)pent-3-yn-1-yl)-1H-tetrazole (Cpd 38) was prepared from 5-((4-((2S)-1-(1-(2-cyanoethyl)-1H-tetrazol-5-yl)pent-3-yn-2-yl)phenoxy)methyl)-3-(2-methylphenyl)benzo[b]thiophene-2-carbonitrile following the procedure described in Example 37K, using EtOH in place of i-PrOH and 1N HCl for reaction acidification. $^1$H NMR (CD$_3$OD) δ 8.02 (d, J=8.4 Hz, 1H), 7.67 (d, J=8.4 Hz, 1H), 7.33-7.47 (m, 4H), 7.23-7.26 (m, 1H), 7.18 (d, J=8.7 Hz, 2H), 6.85 (d, J=8.7 Hz, 2H), 5.17 (s, 2H), 4.02 (br. s, 1H), 3.22 (d, J=7.8 Hz, 2H), 2.05 (s, 3H), 1.75 (s, 3H). LC/MS: mass calcd. for $C_{29}H_{23}N_5OS$: 489.16, found: 490.0 $[M+H]^+$.

Example 39

(2S)-5-(2-(4-((2-(Methylsulfonyl)-3-(2-methylphenyl)benzo[b]thiophen-5-yl)methoxy)phenyl)pent-3-yn-1-yl)-1H-tetrazole, Cpd 39

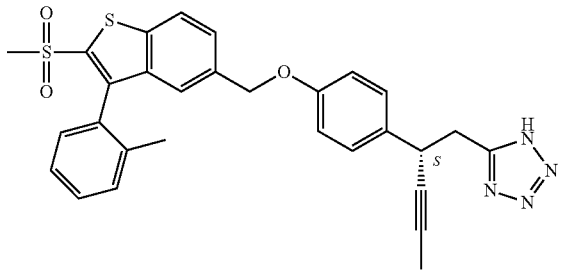

(A) A mixture of ((2-bromo-3-(2-methylphenyl)benzo[b]thiophen-5-yl)methoxy)(tert-butyl)dimethylsilane (500 mg, 1.12 mmol) (from Example 38A), sodium methanesulfinate (350 mg, 3.43 mmol), copper (I) trifluoromethanesulfonate benzene complex (110 mg, 0.22 mmol) and N,N'-dimethylethylenediamine (40 mg, 0.45 mmol) in DMSO (15 mL) was placed under an inert atmosphere of nitrogen in a sealed tube and heated for 16 h at 120° C. After cooling to rt, water (20 mL) was added, and the mixture was extracted with EtOAc (3×30 mL). The combined organic extracts were washed with brine, dried (Na$_2$SO$_4$) and concentrated. The resultant residue was purified by silica gel chromatography (0-30% EtOAc/petroleum ether) to afford tert-butyldimethyl((2-(methylsulfonyl)-3-(2-methylphenyl)benzo[b]thiophen-5-yl)methoxy)silane (80 mg, 16%) as a yellow oil. LC/MS: mass calcd. for $C_{23}H_{30}O_3S_2Si$: 446.14, found: 446.9 $[M+H]^+$.

(B) (2-(Methylsulfonyl)-3-(2-methylphenyl)benzo[b]thiophen-5-yl)methanol was prepared from tert-butyldimethyl((2-(methylsulfonyl)-3-(2-methylphenyl)benzo[b]thiophen-5-yl)methoxy)silane following the procedure described in Example 2C. LC/MS: mass calcd. for $C_{17}H_{16}O_3S_2$: 332.05, found: 332.9 $[M+H]^+$.

(C) 5-(Chloromethyl)-2-(methylsulfonyl)-3-(2-methylphenyl)benzo[b]thiophene was prepared from (2-(methylsulfonyl)-3-(2-methylphenyl)benzo[b]thiophen-5-yl)methanol following General Procedure D.

(D) (3S)-3-(4-((2-(Methylsulfonyl)-3-(2-methylphenyl)benzo[b]thiophen-5-yl)methoxy)phenyl)hex-4-ynenitrile was prepared from 5-(chloromethyl)-2-(methylsulfonyl)-3-(2-methylphenyl)benzo[b]thiophene and (3S)-3-(4-hydroxyphenyl)hex-4-ynenitrile (from Example 2G) following General Procedure E, using K$_2$CO$_3$ in place of Cs$_2$CO$_3$ and a reaction temperature of 60° C. overnight. LC/MS: mass calcd. for $C_{29}H_{25}NO_3S_2$: 499.13, found: 517.0 $[M+NH_4]^+$.

(E) (2S)-5-(2-(4-((2-(Methylsulfonyl)-3-(2-methylphenyl)benzo[b]thiophen-5-yl)methoxy)phenyl)pent-3-yn-1-yl)-1H-tetrazole (Cpd 39) was prepared from (3S)-3-(4-((2-(methylsulfonyl)-3-(2-methylphenyl)[b]thiophen-5-yl)methoxy)phenyl)hex-4-ynenitrile following General Procedure J, using Workup 2. $^1$H NMR (CD$_3$OD) δ 8.02 (d, J=8.7 Hz, 1H), 7.62 (d, J=8.4 Hz, 1H), 7.31-7.44 (m, 3H), 7.24-7.29 (m, 2H), 7.16 (d, J=8.7 Hz, 2H), 6.81 (d, J=8.7 Hz, 2H), 5.09 (s, 2H), 4.02 (br. s, 1H), 3.21 (d, J=7.5 Hz, 2H), 2.96 (s, 3H), 1.94 (s, 3H), 1.74 (s, 3H). LC/MS: mass calcd. for $C_{29}H_{26}N_4O_3S_2$: 542.14, found: 543.0 $[M+H]^+$.

Example 40

(2R)-5-(1-(1H-Tetrazol-5-yl)pent-3-yn-2-yl)-2-((3-(2-methylphenyl)benzo[b]thiophen-5-yl)methoxy)pyridine, Cpd 40

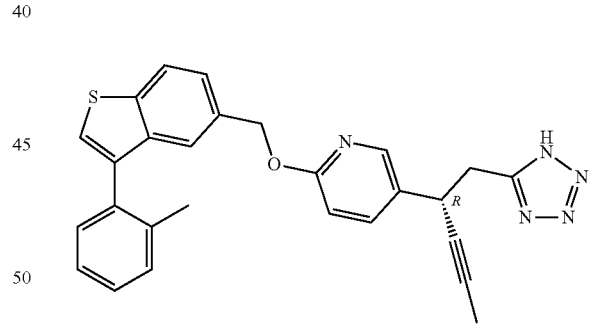

(A) A solution of 6-methoxypyridine-3-carbaldehyde (10 g, 73.00 mmol) and 2,2-dimethyl-1,3-dioxane-4,6-dione (11 g, 76.70 mmol) in water (150 mL) was stirred for 2 h at 75° C., and then cooled in a water/ice bath. The resulting solids were collected by filtration and dried in an oven under reduced pressure to provide 5-((6-methoxypyridin-3-yl)methylene)-2,2-dimethyl-1,3-dioxane-4,6-dione as a yellow powder (18 g, 99%). LC/MS: mass calcd. for $C_{13}H_{13}NO_5$: 263.25, found: 264.0 $[M+H]^+$.

(B) To a solution of bromo(prop-1-yn-1-yl)magnesium (114 mL, 57.03 mmol, 0.5 N in THF) in THF (300 mL) was added a solution of 5-((6-methoxypyridin-3-yl)methylene)-2,2-dimethyl-1,3-dioxane-4,6-dione (10 g, 38.02 mmol) in THF (100 mL) in drop-wise fashion and the resulting solution was stirred at rt overnight. The reaction was then quenched by the addition of satd. aq. NH$_4$Cl (100 mL). The resulting mixture was extracted with 300 mL of hexane (which was discarded) and the aqueous layer was collected. The pH of the aqueous layer was adjusted to 2 with 1N HCl and the resulting solution was extracted with EtOAc (3×200 mL). The combined EtOAc extracts were dried (Na$_2$SO$_4$) and concentrated under reduced pressure to provide 5-(1-(6-methoxypyridin-3-yl)but-2-ynyl)-2,2-dimethyl-1,3-dioxane-4,6-dione (10 g, 87%) as a yellow solid. LC/MS: mass calcd. for C$_{16}$H$_{17}$NO$_5$: 303.31, found: 304.0 [M+H]$^+$.

(C) A solution of 5-(1-(6-methoxypyridin-3-yl)but-2-ynyl)-2,2-dimethyl-1,3-dioxane-4,6-dione (5 g, 16.48 mmol), DMF (100 mL) and water (10 mL) was stirred overnight at 100° C. The reaction was then quenched by the addition of satd. aq. NH$_4$Cl (200 mL) and the resulting mixture was extracted with EtOAc (3×200 mL). The combined organic extracts were dried (Na$_2$SO$_4$) and concentrated under reduced pressure to provide 3-(6-methoxypyridin-3-yl)hex-4-ynoic acid (3.5 g, 97%) as a red oil, which was used directly without further purification. LC/MS: mass calcd. for C$_{12}$H$_{13}$NO$_3$: 219.24, found: 220.1 [M+H]$^+$.

(D) A solution of 3-(6-methoxypyridin-3-yl)hex-4-ynoic acid (8.8 g, 40.18 mmol), dioxane (20 mL), water (20 mL) and conc. HCl (5 mL) was stirred overnight at 100° C. After cooling to rt, the solution was neutralized to pH 5 by the addition of satd. aq. NaHCO$_3$ and the resulting mixture was extracted with EtOAc (3×100 mL). The combined organic extracts were dried (Na$_2$SO$_4$) and concentrated under reduced pressure to provide 3-(6-hydroxypyridin-3-yl)hex-4-ynoic acid (7.6 g, 92%) as a brown oil, which was used directly without further purification. LC/MS: mass calcd. for C$_{11}$H$_{11}$NO$_3$: 205.21, found: 206.0 [M+H]$^+$.

(E) A solution of 3-(6-hydroxypyridin-3-yl)hex-4-ynoic acid (8 g, 39.00 mmol) in EtOH (45 mL) was treated with conc. H$_2$SO$_4$ (2 mL) and the resultant solution was stirred for 2 h at 80° C. After cooling to rt, the solution was neutralized to pH 5 by the addition of satd. aq. NaHCO$_3$ and the resulting mixture was extracted with EtOAc (3×100 mL). The combined organic extracts were dried (Na$_2$SO$_4$) and concentrated under reduced pressure. The residue thus obtained was purified by silica gel chromatography (0-20% MeOH/DCM) to afford ethyl 3-(6-hydroxypyridin-3-yl)hex-4-ynoate (2.2 g, 24.2%). $^1$H NMR (CDCl$_3$) δ 7.46-7.53 (m, 2H), 6.57 (d, J=9.3 Hz, 1H), 4.17 (q, J=7.2 Hz, 2H), 3.88-3.94 (m, 1H), 2.55-2.71 (m, 2H), 1.82 (d, J=2.4 Hz, 3H), 1.24 (t, J=7.2 Hz, 3H).

(F) Enantiomeric resolution of ethyl 3-(6-hydroxypyridin-3-yl)hex-4-ynoate was carried out by chiral super critical fluid chromatography on a ChiralPak AS-H 5μ column (2×25 cm) using an isocratic mobile phase [EtOH (0.2% DEA)/CO$_2$ (50:50); 170 g/min] to afford (3R)-ethyl 3-(6-hydroxypyridin-3-yl)hex-4-ynoate (RT=4.15 min)$^1$H NMR (CDCl$_3$) δ 7.47-7.55 (m, 2H), 6.59 (d J=9.3 Hz, 1H), 4.09-4.19 (m, 2H), 3.89-3.95 (m, 1H), 2.70 (dd, J=7.5, 15.3 Hz, 1H), 2.59 (dd, J=7.5, 15.6 Hz, 1H), 1.82 (s, 3H), 1.25-1.27 (m, 3H) and (3S)-ethyl 3-(6-hydroxypyridin-3-yl) hex-4-ynoate (RT=5.97 min).

(G) To an ice-cooled solution of 5-hydroxymethyl-3-(2-methylphenyl)benzo[b]-thiophene (from Example 1B) (200 mg, 0.79 mmol) in DCM (20 mL) and DMF (2 mL) was added PBr$_3$ (148 μL, 1.57 mmol) in dropwise fashion. After stirring for 1 h, the mixture was neutralized to pH 6-7 with the addition of 1M aq. NaHCO$_3$, and the resulting mixture was extracted with DCM (3×10 mL). The combined organic extracts were dried (Na$_2$SO$_4$) and concentrated under reduced pressure to afford crude 5-bromomethyl-3-(2-methylphenyl)benzo[b]-thiophene, which was used directly without purification.

(H) To a solution of 5-bromomethyl-3-(2-methylphenyl) benzo[b]-thiophene from the above step in toluene (10 mL) was added (3R)-ethyl 3-(6-hydroxypyridin-3-yl)hex-4-ynoate (170 mg, 0.73 mmol) and Ag$_2$CO$_3$ (434 mg, 1.57 mmol) and the resulting mixture was stirred at 60° C. overnight. Water (20 mL) was then added and the mixture was extracted with EtOAc (3×20 mL). The combined organic extracts were concentrated under reduced pressure and the resultant residue was purified by silica gel chromatography (0-20% EtOAc/petroleum ether) to afford (3R)-ethyl 3-(6-((3-(2-methylphenyl)benzo[b]thiophen-5-yl)methoxy)pyridin-3-yl)hex-4-ynoate (80 mg, 19% yield) as colorless oil. LC/MS: mass calcd. for C$_{29}$H$_{27}$NO$_3$S: 469.60, found: 470.3 [M+H]$^+$.

(I) (3R)-3-(6-((3-(2-Methylphenyl)benzo[b]thiophen-5-yl)methoxy)pyridin-3-yl)hex-4-ynoic acid was prepared from (3R)-ethyl 3-(6-((3-(2-methylphenyl)benzo[b]thiophen-5-yl)methoxy)pyridin-3-yl)hex-4-ynoate following General Procedure C, using LiOH as base, EtOH in place of MeOH, a rt reaction temperature overnight and 1N HCl for reaction acidification. $^1$H NMR (DMSO-d$_6$) δ 8.01-8.09 (m, 2H), 7.62-7.69 (m, 2H), 7.46 (dd, J=1.5, 8.4 Hz, 1H), 7.20-7.42 (m, 5H), 6.75 (d, J=8.4 Hz, 1H), 5.38 (s, 2H), 3.95-4.05 (m, 1H), 2.40-2.50 (m, 2H), 2.06 (s, 3H), 1.75 (d, J=2.4 Hz, 3H). LC/MS: mass calcd. for C$_{27}$H$_{23}$NO$_3$S: 441.54, found: 442.0 [M+H]$^+$.

(J) (3R)-3-(6-((3-(2-Methylphenyl)benzo[b]thiophen-5-yl)methoxy)pyridin-3-yl)hex-4-ynamide was prepared from (3R)-3-(6-((3-(2-methylphenyl)benzo[b]thiophen-5-yl) methoxy)pyridin-3-yl)hex-4-ynoic acid following the procedure described in Example 6E. LC/MS: mass calcd. for C$_{27}$H$_{24}$N$_2$O$_2$S: 440.16, found: 441.2 [M+H]$^+$.

(K) (3R)-3-(6-((3-(2-methylphenyl)benzo[b]thiophen-5-yl)methoxy)pyridin-3-yl)hex-4-ynenitrile was prepared from (3R)-3-(6-((3-(2-methylphenyl)benzo[b]thiophen-5-yl)methoxy)pyridin-3-yl)hex-4-ynamide following General Procedure I. LC/MS: mass calcd. for C$_{27}$H$_{22}$N$_2$OS: 422.15, found: 423.2 [M+H]$^+$.

(L) (2R)-5-(1-(1H-Tetrazol-5-yl)pent-3-yn-2-yl)-2-((3-(2-methylphenyl)benzo[b]thiophen-5-yl)methoxy)pyridine (Cpd 40) was prepared from (3R)-3-(6-((3-(2-methylphenyl) benzo[b]thiophen-5-yl)methoxy)pyridin-3-yl)hex-4-ynenitrile following General Procedure J, using Workup 2. $^1$H NMR (CD$_3$OD) δ 8.05 (d, J=2.7 Hz, 1H), 7.96-7.88 (m, 1H), 7.70 (m, 1H), 7.49-7.18 (m, 7H), 6.81 (m, 1H), 5.40-5.34 (m, 2H), 4.21-4.11 (m, 1H), 3.31 (s, 2H), 2.08 (d, J=3.4 Hz, 3H), 1.83-1.77 (m, 3H). LC/MS: mass calcd. for C$_{27}$H$_{23}$N$_5$OS: 465.16, found: 466.2 [M+H]$^+$.

Example 41

(2R)-5-(1-(1H-Tetrazol-5-yl)pent-3-yn-2-yl)-2-((3-(4-(2-methoxyethoxy)-2-methylphenyl)benzo[b]thiophen-5-yl)methoxy)pyridine, Cpd 41

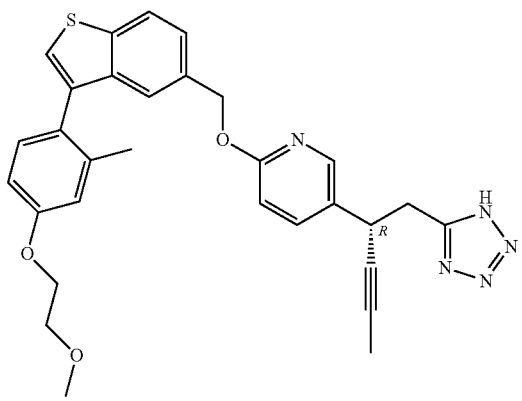

(A) 5-(Bromomethyl)-3-(4-(2-methoxyethoxy)-2-methylphenyl)benzo[b]thiophene was prepared from (3-(4-(2-Methoxyethoxy)-2-methylphenyl)benzo[b]thiophen-5-yl)methanol (from Example 8D) and PBr$_3$, following the procedure described in Example 40G, and used directly in the next step.

(B) Ethyl 3-(6-((3-(4-(2-methoxyethoxy)-2-methylphenyl)benzo[b]thiophen-5-yl)methoxy)pyridin-3-yl)hex-4-ynoate was prepared from 5-(bromomethyl)-3-(4-(2-methoxyethoxy)-2-methylphenyl)benzo[b]thiophene and ethyl 3-(6-hydroxypyridin-3-yl)hex-4-ynoate (from Example 40E) following the procedure described in Example 40H at a reaction temperature of 60° C. overnight. LC/MS: mass calcd. for C$_{32}$H$_{33}$NO$_5$S: 543.67, found: 544.4 [M+H]$^+$.

(C) 3-(6-((3-(4-(2-Methoxyethoxy)-2-methylphenyl)benzo[b]thiophen-5-yl)methoxy)pyridin-3-yl)hex-4-ynoic acid was prepared from ethyl 3-(6-((3-(4-(2-methoxyethoxy)-2-methylphenyl)benzo[b]thiophen-5-yl)methoxy)pyridin-3-yl)hex-4-ynoate following General Procedure C, using LiOH as base, EtOH in place of MeOH and 1N HCl for reaction acidification. $^1$H NMR (DMSO-d$_6$) δ 12.31 (br. s, 1H), 8.10 (d, J=2.4 Hz, 1H), 8.04 (d, J=8.4 Hz, 1H), 7.71 (dd, J=2.4, 8.4 Hz, 1H), 7.64 (s, 1H), 7.42-7.48 (m, 2H), 7.16 (d, J=8.4 Hz, 1H), 6.96 (d, J=2.4 Hz, 1H), 6.88 (dd, J=2.7, 8.4 Hz, 1H), 6.80 (d, J=8.4 Hz, 1H), 5.40 (s, 2H), 4.14-4.17 (m, 2H), 3.96-4.02 (m, 1H), 3.68-3.71 (m, 2H), 3.33 (s, 3H), 2.63-2.66 (m, 2H), 2.01 (s, 3H), 1.78 (s, 3H). LC/MS: mass calcd. for C$_{30}$H$_{29}$NO$_5$S: 515.62, found: 516.3 [M+H]$^+$.

(D) Enantiomeric resolution of 3-(6-((3-(4-(2-methoxyethoxy)-2-methylphenyl)benzo[b]-thiophen-5-yl)methoxy)pyridin-3-yl)hex-4-ynoic acid was carried out by chiral chromatography on a ChiralPak AS-H 5µ column (2×25 cm) using an isocratic mobile phase [hexane (0.1% HOAc)/EtOH (85:15); 20 mL/min] to afford (3S)-3-(6-((3-(4-(2-methoxyethoxy)-2-methylphenyl)benzo[b]thiophen-5-yl)methoxy)pyridin-3-yl)hex-4-ynoic acid (RT=8 min) and (3R)-3-(6-((3-(4-(2-methoxyethoxy)-2-methylphenyl)benzo[b]thiophen-5-yl)methoxy)pyridin-3-yl)hex-4-ynoic acid (RT=13.5 min).

(E) (3R-enantiomer): $^1$H NMR (DMSO-d$_6$) δ 8.10 (d, J=2.4 Hz, 1H), 8.04 (d, J=8.4 Hz, 1H), 7.71 (dd, J=2.4, 8.4 Hz, 1H), 7.64 (s, 1H), 7.42-7.48 (m, 2H), 7.16 (d, J=8.4 Hz, 1H), 6.96 (d, J=2.4 Hz, 1H), 6.85 (dd, J=2.7, 8.4 Hz, 1H), 6.80 (d, J=8.4 Hz, 1H), 5.40 (s, 2H), 4.14-4.17 (m, 2H), 3.96-4.02 (m, 2H), 3.68-3.71 (m, 2H), 3.33 (d, J=6.0 Hz, 3H), 2.64 (dd, J=2.1, 7.8 Hz, 2H), 2.01 (s, 3H), 1.77 (d, J=2.4 Hz, 3H). LC/MS: mass calcd. for C$_{30}$H$_{29}$NO$_5$S: 515.62, found: 514.1 [M–H]$^-$.

(F) (3R)-3-(6-((3-(4-(2-Methoxyethoxy)-2-methylphenyl)benzo[b]thiophen-5-yl)methoxy)pyridin-3-yl)hex-4-ynamide was prepared from (3R)-3-(6-((3-(4-(2-methoxyethoxy)-2-methylphenyl)benzo[b]thiophen-5-yl)methoxy)pyridin-3-yl)hex-4-ynoic acid following the procedure described in Example 6E. LC/MS: mass calcd. for C$_{30}$H$_{30}$N$_2$O$_4$S: 514.19, found: 515.3 [M+H]$^+$.

(G) (3R)-3-(6-((3-(4-(2-Methoxyethoxy)-2-methylphenyl)benzo[b]thiophen-5-yl)methoxy)pyridin-3-yl)hex-4-ynenitrile was prepared from (3R)-3-(6-((3-(4-(2-methoxyethoxy)-2-methylphenyl)benzo[b]thiophen-5-yl)methoxy)pyridin-3-yl)hex-4-ynamide following General Procedure I. LC/MS: mass calcd. for C$_{30}$H$_{28}$N$_2$O$_3$S: 496.18, found: 497.2 [M+H]$^+$.

(H) (2R)-5-(1-(1H-Tetrazol-5-yl)pent-3-yn-2-yl)-2-((3-(4-(2-methoxyethoxy)-2-methylphenyl)benzo[b]thiophen-5-yl)methoxy)pyridine (Cpd 41) was prepared from (3R)-3-(6-((3-(4-(2-methoxyethoxy)-2-methylphenyl)benzo[b]thiophen-5-yl)methoxy)pyridin-3-yl)hex-4-ynenitrile following General Procedure J, using Workup 2. $^1$H NMR (CD$_3$OD) δ 8.03 (d, J=2.5 Hz, 1H), 7.95-7.85 (m, 1H), 7.64 (m, 1H), 7.47-7.38 (m, 2H), 7.35 (s, 1H), 7.13 (d, J=8.3 Hz, 1H), 6.91 (d, J=2.6 Hz, 1H), 6.83 (m, 1H), 6.76 (d, J=8.6 Hz, 1H), 5.36 (s, 2H), 4.20-4.06 (m, 3H), 3.81-3.71 (m, 2H), 3.41 (s, 1H), 3.35-3.24 (m, 4H), 2.05 (s, 3H), 1.79 (d, J=2.4 Hz, 3H). LC/MS: mass calcd. for C$_{30}$H$_{29}$N$_5$O$_3$S: 539.20, found: 540.25 [M+H]$^+$.

Example 42

(2R)-5-(1-(1H-Tetrazol-5-yl)pent-3-yn-2-yl)-2-((3-(3-(2-methoxyethoxy)-2-methylphenyl)benzo[b]thiophen-5-yl)methoxy)pyridine, Cpd 42

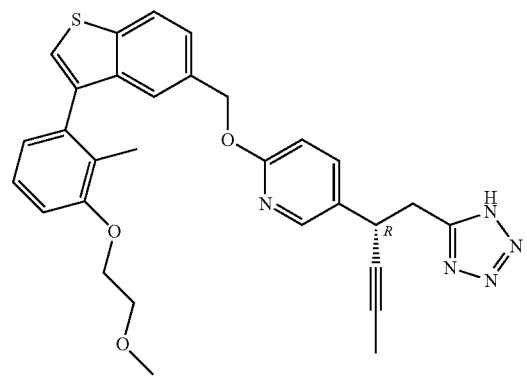

(A) (3-(3-(2-Methoxyethoxy)-2-methylphenyl)benzo[b]thiophen-5-yl)methanol was prepared from 1-Bromo-3-(2-methoxyethoxy)-2-methylbenzene (from Example 10A) and (3-(4,4,5,5-tetramethyl-1,3,2-dioxaborolan-2-yl)benzo[b]thiophen-5-yl)methanol (from Example 5A) following General Procedure A using PdCl$_2$(dppf).CH$_2$Cl$_2$ as the palladium catalyst and Cs$_2$CO$_3$ in place of K$_2$CO$_3$. LC/MS: mass calcd. for C$_{19}$H$_{20}$O$_3$S: 428.43, found: 311.1 [M–OH]$^+$.

(B) 5-(Bromomethyl)-3-(3-(2-methoxyethoxy)-2-methylphenyl)benzo[b]thiophene was prepared from (3-(3-(2-methoxyethoxy)-2-methylphenyl)benzo[b]thiophen-5-yl)methanol following the procedure described in Example 40G and used directly in the following reaction.

(C) (3R)-Ethyl 3-(6-((3-(3-(2-methoxyethoxy)-2-methylphenyl)benzo[b]thiophen-5-yl)methoxy)pyridin-3-yl)hex-4-ynoate was prepared from 5-(bromomethyl)-3-(3-(2-methoxyethoxy)-2-methylphenyl)benzo[b]thiophene and (3R)-ethyl 3-(6-hydroxypyridin-3-yl)hex-4-ynoate (from Example 40F), following the procedure described in Example 40H. LC/MS: mass calcd. for C$_{32}$H$_{33}$NO$_5$S: 543.67, found: 544.1 [M+H]$^+$.

(D) (3R)-3-(6-((3-(3-(2-methoxyethoxy)-2-methylphenyl)benzo[b]thiophen-5-yl)methoxy)pyridin-3-yl)hex-4-ynoic acid was prepared from (3R)-ethyl 3-(6-((3-(3-(2-methoxyethoxy)-2-methylphenyl)benzo[b]thiophen-5-yl)methoxy)pyridin-3-yl)hex-4-ynoate following General Procedure C, using LiOH as base, EtOH in place of MeOH, a rt reaction temperature overnight and 2N HCl for reaction acidification. $^1$H NMR (DMSO-d$_6$) δ 8.09 (d, J=2.1 Hz, 1H), 8.04 (d, J=8.4 Hz, 1H), 7.66-7.71 (m, 2H), 7.47 (dd, J=1.5, 8.4 Hz, 1H), 7.41 (s, 1H), 7.26 (t, J=8.1 Hz, 1H), 7.06 (d, J=8.1 Hz, 1H), 6.86 (d, J=7.5 Hz, 1H), 6.77 (d, J=8.7 Hz, 1H), 5.39 (s, 2H), 4.15-4.19 (m, 2H), 3.96-4.01 (m, 1H), 3.71-3.74 (m, 2H), 3.35 (s, 3H), 2.54-2.61 (m, 2H), 1.92 (s, 3H), 1.76 (d, J=2.1 Hz, 3H). LC/MS: mass calcd. for $C_{30}H_{29}NO_5S$: 515.62, found: 514.1 [M−H]⁻.

(E) (3R)-3-(6-((3-(3-(2-Methoxyethoxy)-2-methylphenyl)benzo[b]thiophen-5-yl)methoxy)pyridin-3-yl)hex-4-ynamide was prepared from (3R)-3-(6-((3-(3-(2-methoxyethoxy)-2-methylphenyl)benzo[b]thiophen-5-yl)methoxy)pyridin-3-yl)hex-4-ynoic acid following the procedure described in Example 6E. LC/MS: mass calcd. for $C_{30}H_{30}N_2O_4S$: 514.19, found: 515.3 [M+H]⁺.

(F) (3R)-3-(6-((3-(3-(2-Methoxyethoxy)-2-methylphenyl)benzo[b]thiophen-5-yl)methoxy)pyridin-3-yl)hex-4-ynenitrile was prepared from (3R)-3-(6-((3-(3-(2-methoxyethoxy)-2-methylphenyl)benzo[b]thiophen-5-yl)methoxy)pyridin-3-yl)hex-4-ynamide following General Procedure I. LC/MS: mass calcd. for $C_{30}H_{28}N_2O_3S$: 496.18, found: 497.2 [M+H]⁺.

(G) (2R)-5-(1-(1H-Tetrazol-5-yl)pent-3-yn-2-yl)-2-((3-(3-(2-methoxyethoxy)-2-methylphenyl)benzo[b]thiophen-5-yl)methoxy)pyridine (Cpd 42) was prepared from (3R)-3-(6-((3-(3-(2-methoxyethoxy)-2-methylphenyl)benzo[b]thiophen-5-yl)methoxy)pyridin-3-yl)hex-4-ynenitrile following General Procedure J, using Workup 2. ¹H NMR (CD₃OD) δ 8.03 (d, J=2.5 Hz, 1H), 7.95-7.85 (m, 1H), 7.63-7.64 (m, 1H), 7.38-7.47 (m, 2H), 7.35 (s, 1H), 7.13 (d, J=8.3 Hz, 1H), 6.91 (d, J=2.6 Hz, 1H), 6.81-6.83 (m, 1H), 6.76 (d, J=8.6 Hz, 1H), 5.36 (s, 2H), 4.06-4.20 (m, 3H), 3.41 (s, 1H), 3.24-3.35 (m, 1H), 2.05 (s, 3H), 1.98-1.99 (m, 2H), 1.79 (d, J=2.4 Hz, 3H), 1.55-1.56 (m, 3H). LC/MS: mass calcd. for $C_{30}H_{29}N_5O_3S$: 539.20, found: 540.3 [M+H]⁺.

Example 43

(2R)-4-(4-(5-(((5-(1-(1H-Tetrazol-5-yl)pent-3-yn-2-yl)pyridin-2-yl)oxy)methyl)-benzo[b]thiophen-3-yl)-3-methylphenoxy)-2-methylbutan-2-ol, Cpd 43

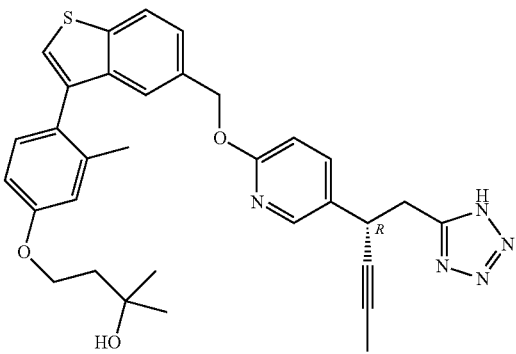

(A) To a solution of 3-bromo-5-hydroxymethylbenzothiophene (1.0 g, 4.11 mmol) (from Example 1A) in DCM (20 mL) and DMF (1 mL) was added PBr₃ (1 mL, 10.6 mmol) in drop-wise fashion, and the resultant solution was stirred at rt for 1 h. Water (40 mL) was then added and the mixture was extracted with DCM (3×40 mL). The combined organic extracts were dried (Na₂SO₄) and concentrated under reduced pressure to afford 3-bromo-5-(bromomethyl)-1-benzothiophene (1.1 g, 87%) as colorless oil, which was used directly without further purification.

(B) A mixture of 3-bromo-5-(bromomethyl)-1-benzothiophene (1.1 g, 3.59 mmol), ethyl 3-(6-hydroxypyridin-3-yl)hex-4-ynoate (880 mg, 3.77 mmol) (from Example 40E) and Ag₂CO₃ (0.79 g, 2.86 mmol) in toluene (30 mL) was stirred at 60° C. overnight. The mixture was then concentrated under reduced pressure and the resultant residue was purified directly by silica gel chromatography [EtOAc/petroleum ether (0-11%) to provide ethyl 3-[6-[(3-bromo-1-benzothiophen-5-yl)methoxy]pyridin-3-yl]hex-4-ynoate (950 mg, 58%) as light yellow oil. LC/MS: mass calcd for $C_{22}H_{20}BrNO_3S$: 458.37, found 458.2 [M]⁺, 460.2 [M+2]⁺.

(C) Ethyl 3-(6-[[3-(4-hydroxy-2-methylphenyl)-1-benzothiophen-5-yl]methoxy]pyridin-3-yl)hex-4-ynoate was prepared from ethyl 3-[6-[(3-bromo-1-benzothiophen-5-yl)methoxy]pyridin-3-yl]hex-4-ynoate and (4-hydroxy-2-methylphenyl)boronic acid following General Procedure A, using PdCl₂(dppf).CH₂Cl₂ as the palladium catalyst and Cs₂CO₃ in place of K₂CO₃. LC/MS: mass calcd for $C_{29}H_{27}NO_4S$: 485.59, found 486.2 [M+H]⁺.

(D) Ethyl 3-[6-([3-[4-(3-hydroxy-3-methylbutoxy)-2-methylphenyl]-1-benzothiophen-5-yl]methoxy)pyridin-3-yl]hex-4-ynoate was prepared from ethyl 3-(6-[[3-(4-hydroxy-2-methylphenyl)-1-benzothiophen-5-yl]methoxy]pyridin-3-yl)hex-4-ynoate and 3-methylbutane-1,3-diol following General Procedure B using PBu₃ and ADDP with toluene as solvent and a reaction temperature of 60° C. overnight. LC/MS: mass calcd. for $C_{34}H_{37}NO_5S$: 571.73, found: 572.2 [M+H]⁺.

(E) 3-[6-([3-[4-(3-Hydroxy-3-methylbutoxy)-2-methylphenyl]-1-benzothiophen-5-yl]methoxy)pyridin-3-yl]hex-4-ynoic acid was prepared from ethyl 3-[6-([3-[4-(3-hydroxy-3-methylbutoxy)-2-methylphenyl]-1-benzothiophen-5-yl]methoxy)pyridin-3-yl]hex-4-ynoate following General Procedure C, using LiOH as base, EtOH in place of MeOH, a rt reaction temperature overnight and 1N HCl for reaction acidification. Product purification was carried out by preparative HPLC on a Waters SunFire™ Prep C18, 5μ column (19×100 mm) using an acetonitrile/water (0.05% NH₄HCO₃) gradient (35-75%). ¹H NMR (DMSO-d₆) δ 8.10 (d, J=2.4 Hz, 1H), 8.03 (d, J=8.1 Hz, 1H), 7.70 (dd, J=8.4 Hz, 2.4 Hz, 1H), 7.63 (s, 1H), 7.43-7.48 (m, 2H), 7.15 (d, J=8.4 Hz, 1H), 6.93 (d, J=2.7 Hz, 1H), 6.84-6.88 (m, 1H), 6.79 (d, J=8.7 Hz, 1H), 5.40 (s, 2H), 4.14 (t, J=6.9 Hz, 2H), 3.95-4.00 (m, 1H), 2.61-2.63 (m, 2H), 2.05 (s, 3H), 1.88 (t, J=7.2 Hz, 2H), 1.77 (d, J=2.4 Hz, 3H), 1.19 (s, 6H). LC/MS: mass calcd for $C_{32}H_{33}NO_5S$: 543.67, found 544.3 [M+H]⁺.

(F) Enantiomeric resolution of 3-(6-((3-(4-(3-hydroxy-3-methylbutoxy)-2-methylphenyl)benzo[b]thiophen-5-yl)methoxy)pyridin-3-yl)hex-4-ynoic acid was carried out by chiral chromatography on a ChiralPak AS-H 5μ column (2×25 cm) using an isocratic mobile phase [hexane (0.1% HOAc)/EtOH (85:15); 20 mL/min] to afford (3S)-3-(6-((3-(4-(3-hydroxy-3-methylbutoxy)-2-methylphenyl)benzo[b]thiophen-5-yl)methoxy)pyridin-3-yl)hex-4-ynoic acid (RT=9.0 min) and (3R)-3-(6-((3-(4-(3-hydroxy-3-methylbutoxy)-2-methylphenyl)benzo[b]thiophen-5-yl)methoxy)pyridin-3-yl)hex-4-ynoic acid (RT=12.5 min).

(S-enantiomer): ¹H NMR (DMSO-d₆) δ 8.10 (d, J=2.4 Hz, 1H), 8.03 (d, J=8.1 Hz, 1H), 7.70 (dd, J=8.4, 2.4 Hz, 1H), 7.63 (s, 1H), 7.43-7.48 (m, 2H), 7.15 (d, J=8.4 Hz, 1H), 6.94 (d, J=2.7 Hz, 1H), 6.85-6.88 (m, 1H), 6.79 (d, J=8.7 Hz, 1H), 5.40 (s, 2H), 4.14 (t, J=6.9 Hz, 2H), 3.95-4.05 (m, 1H), 2.61-2.73 (m, 2H), 2.05 (s, 3H), 1.88 (t, J=7.2 Hz, 2H), 1.77 (d, J=2.4 Hz, 3H), 1.19 (s, 6H). LC/MS: mass calcd. for $C_{32}H_{33}NO_5S$: 543.67, found 541.9 [M−H]⁻.

(R-enantiomer): ¹H NMR (DMSO-d₆) δ 8.10 (d, J=2.4 Hz, 1H), 8.03 (d, J=8.1 Hz, 1H), 7.70 (dd, J=8.4, 2.4 Hz, 1H), 7.63 (s, 1H), 7.43-7.48 (m, 2H), 7.15 (d, J=8.4 Hz, 1H), 6.94 (d, J=2.7 Hz, 1H), 6.85-6.88 (m, 1H), 6.79 (d, J=8.7 Hz, 1H), 5.40 (s, 2H), 4.14 (t, J=6.9 Hz, 2H), 3.95-4.05 (m, 1H), 2.61-2.73 (m, 2H), 2.05 (s, 3H), 1.88 (t, J=7.2 Hz, 2H), 1.77 (d, J=2.4 Hz, 3H), 1.19 (s, 6H). LC/MS: mass calcd. for $C_{32}H_{33}NO_5S$: 543.67, found: 542.1 [M−H]⁻.

(G) (3R)-3-(6-((3-(4-(3-Hydroxy-3-methylbutoxy)-2-methylphenyl)benzo[b]thiophen-5-yl)methoxy)pyridin-3-yl)hex-4-ynamide was prepared from (3R)-3-(6-((3-(4-(3-hydroxy-3-methylbutoxy)-2-methylphenyl)benzo[b]thiophen-5-yl)methoxy)pyridin-3-yl)hex-4-ynoic acid following the procedure described in Example 6E. LC/MS: mass calcd. for $C_{32}H_{34}N_2O_4S$: 542.22, found: 543.3 [M+H]⁺.

(H) (3R)-3-(6-((3-(4-(3-Hydroxy-3-methylbutoxy)-2-methylphenyl)benzo[b]thiophen-5-yl)methoxy)pyridin-3-yl)hex-4-ynenitrile was prepared from (3R)-3-(6-((3-(4-(3-hydroxy-3-methylbutoxy)-2-methylphenyl)benzo[b]thiophen-5-yl)methoxy)pyridin-3-yl)hex-4-ynamide following General Procedure I. LC/MS: mass calcd. for $C_{32}H_{32}N_2O_3S$: 524.21, found: 525.3 [M+H]⁺.

(I) (2R)-4-(4-(5-(((5-(1-(1H-Tetrazol-5-yl)pent-3-yn-2-yl)pyridin-2-yl)oxy)methyl)benzo[b]thiophen-3-yl)-3-methylphenoxy)-2-methylbutan-2-ol (Cpd 43) was prepared from (3R)-3-(6-((3-(4-(3-hydroxy-3-methylbutoxy)-2-methylphenyl)benzo[b]thiophen-5-yl)methoxy)pyridin-3-yl)hex-4-ynenitrile following General Procedure J, using Workup 2. ¹H NMR (CD₃OD) δ 7.96 (d, J=2.3 Hz, 1H), 7.91 (d, J=8.3 Hz, 1H), 7.61 (dd, 2.5 Hz, 1H), 7.44 (dd, J=8.4, 1.4 Hz, 1H), 7.37-7.41 (m, 2H), 7.18-7.26 (m, 1H), 7.00 (d, J=8.1 Hz, 1H), 6.86 (d, J=7.7 Hz, 1H), 6.73 (d, J=8.6 Hz, 1H), 5.34 (s, 2H), 4.19 (dd, J=5.4, 3.9 Hz, 2H), 4.06-4.13 (m, 1H), 3.78-3.84 (m, 2H), 3.45 (s, 3H), 3.12-3.28 (m, 2H), 1.95 (s, 3H), 1.77 (d, J=2.3 Hz, 3H), 0.88 (t, J=7.3 Hz, 3H). LC/MS: mass calcd. for $C_{32}H_{33}N_5O_3S$: 567.23, found: 568.3 [M+H]⁺.

Example 44

(2S)-5-(2-(4-((2-Fluoro-3-(4-(2-methoxyethoxy)-2-methylphenyl)benzo[b]thiophen-5-yl)methoxy)phenyl)pent-3-yn-1-yl)-1H-tetrazole, Cpd 44

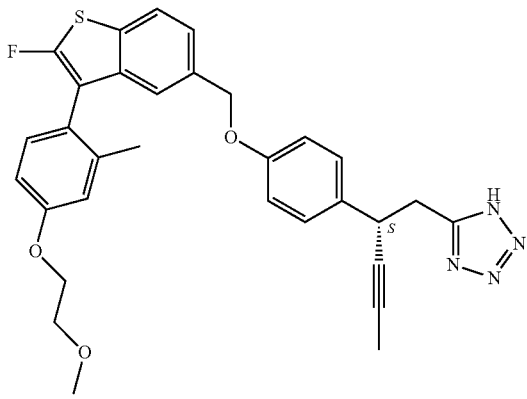

(A) A solution of (3-(4-(2-methoxyethoxy)-2-methylphenyl)benzo[b]thiophen-5-yl)methanol (from Example 8D) (1 g, 3.0 mmol), tert-butyldimethylsilyl chloride (690 mg, 4.6 mmol) and imidazole (625 mg, 9.2 mmol) in DCM (30 mL) was stirred at rt for 3 h. Water (50 mL) was added and the mixture was extracted with EtOAc (3×50 mL). The combined organic extracts were washed with brine, dried (Na₂SO₄) and concentrated. The resultant residue was purified by silica gel chromatography (0-10% EtOAc/petroleum ether) to afford of tert-butyl((3-(4-(2-methoxyethoxy)-2-methylphenyl)benzo[b]thiophen-5-yl)methoxy)dimethylsilane (1.0 g, 75%) as a colorless oil. LC/MS: mass calcd. for $C_{25}H_{34}O_3SSi$: 442.20, found: 311.1 [M−OTBS]⁺.

(B) tert-Butyl ((2-fluoro-3-(4-(2-methoxyethoxy)-2-methylphenyl)benzo[b]thiophen-5-yl)methoxy)dimethylsilane was prepared from of tert-butyl((3-(4-(2-methoxyethoxy)-2-methylphenyl)benzo[b]thiophen-5-yl)methoxy)dimethylsilane and N-fluoro-N-(phenylsulfonyl)benzenesulfonamide following the procedure described in Example 3A. LC/MS: mass calcd. for $C_{25}H_{33}FO_3SSi$: 460.19, found: 329.1 [M−OTBS]⁺.

(C) (2-Fluoro-3-(4-(2-methoxyethoxy)-2-methylphenyl)benzo[b]thiophen-5-yl)methanol was prepared from tert-butyl ((2-fluoro-3-(4-(2-methoxyethoxy)-2-methylphenyl)benzo[b]thiophen-5-yl)methoxy)dimethylsilane following the procedure described in Example 2C, and was used directly without characterization.

(D) 5-(Chloromethyl)-2-fluoro-3-(4-(2-methoxyethoxy)-2-methylphenyl)benzo[b]thiophene was prepared from (2-fluoro-3-(4-(2-methoxyethoxy)-2-methylphenyl)benzo[b]thiophen-5-yl)methanol following General Procedure D.

(E) (3S)-3-(4-((2-Fluoro-3-(4-(2-methoxyethoxy)-2-methylphenyl)benzo[b]thiophen-5-yl)methoxy)phenyl)hex-4-ynenitrile was prepared from 5-(chloromethyl)-2-fluoro-3-(4-(2-methoxyethoxy)-2-methylphenyl)benzo[b]thiophene and (3S)-3-(4-hydroxyphenyl)hex-4-ynenitrile (from Example 2G) following General Procedure E, at a reaction temperature of 60° C. overnight, and was used directly without characterization.

(F) (2S)-5-(2-(4-((2-Fluoro-3-(4-(2-methoxyethoxy)-2-methylphenyl)benzo[b]thiophen-5-yl)methoxy)phenyl)pent-3-yn-1-yl)-1H-tetrazole (Cpd 44) was prepared from (3S)-3-(4-((2-fluoro-3-(4-(2-methoxyethoxy)-2-methylphenyl)benzo[b]thiophen-5-yl)methoxy)phenyl)hex-4-ynenitrile following General Procedure J, using Workup 2. ¹H NMR (CD₃OD) δ 7.76 (d, J=8.4 Hz, 1H), 7.39 (d, J=8.4 Hz, 1H), 7.26 (s, 1H), 7.18 (d, J=8.4 Hz, 2H), 7.12 (d, J=8.4 Hz, 1H), 6.92 (s, 1H), 6.83-6.86 (m, 3H), 5.06 (s, 2H), 4.12-4.15 (m, 2H), 4.02 (br. s, 1H), 3.73-3.76 (m, 2H), 3.42 (s, 3H), 3.23 (d, J=7.2 Hz, 2H), 2.06 (s, 3H), 1.74 (s, 3H). LC/MS: mass calcd. for $C_{31}H_{29}FN_4O_3S$: 556.19, found: 557.1 [M+H]⁺.

Example 45

(2S)-5-(2-(4-((2-Chloro-3-(4-(2-methoxyethoxy)-2-methylphenyl)benzo[b]thiophen-5-yl)methoxy)phenyl)pent-3-yn-1-yl)-1H-tetrazole, Cpd 45

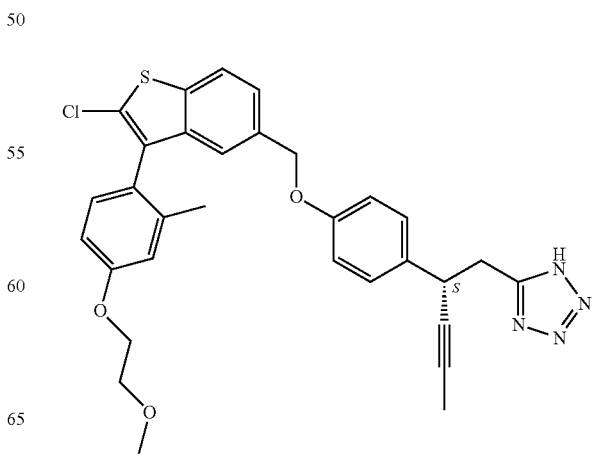

(A) tert-Butyl((2-chloro-3-(4-(2-methoxyethoxy)-2-methylphenyl)benzo[b]thiophen-5-yl)methoxy)dimethylsilane was prepared from tert-butyl((3-(4-(2-methoxyethoxy)-2-methylphenyl)benzo[b]thiophen-5-yl)methoxy)dimethylsilane (from Example 44A) and NCS following the procedure described in Example 2B. LC/MS: mass calcd. for $C_{25}H_{33}ClO_3SSi$: 476.16, found: 344.9 [M–OTBS]$^+$.

(B) (2-Chloro-3-(4-(2-methoxyethoxy)-2-methylphenyl)benzo[b]thiophen-5-yl)methanol was prepared from tert-butyl((2-chloro-3-(4-(2-methoxyethoxy)-2-methylphenyl)benzo[b]thiophen-5-yl)methoxy)dimethylsilane following the procedure described in Example 2C. LC/MS: mass calcd. for $C_{19}H_{19}ClO_3S$: 362.07, found: 344.9[M–OH]$^+$.

(C) 2-Chloro-5-(chloromethyl)-3-(4-(2-methoxyethoxy)-2-methylphenyl)benzo[b]thiophene was prepared from (2-chloro-3-(4-(2-methoxyethoxy)-2-methylphenyl)benzo[b]thiophen-5-yl)methanol following General Procedure D.

(D) (3S)-3-(4-((2-Chloro-3-(4-(2-methoxyethoxy)-2-methylphenyl)benzo[b]thiophen-5-yl)methoxy)phenyl)hex-4-ynenitrile was prepared from 2-chloro-5-(chloromethyl)-3-(4-(2-methoxyethoxy)-2-methylphenyl)benzo[b]thiophene and (3S)-3-(4-hydroxyphenyl)hex-4-ynenitrile (from Example 2G) following General Procedure E, at a reaction temperature of 60° C. overnight. LC/MS: mass calcd. for $C_{31}H_{28}ClNO_3S$: 529.15, found: 547.0 [M+NH$_4$]$^+$.

(E) (2S)-5-(2-(4-((2-Chloro-3-(4-(2-methoxyethoxy)-2-methylphenyl)benzo[b]thiophen-5-yl)methoxy)phenyl)pent-3-yn-1-yl)-1H-tetrazole (Cpd 45) was prepared from (3S)-3-(4-((2-chloro-3-(4-(2-methoxyethoxy)-2-methylphenyl)benzo[b]thiophen-5-yl)methoxy)phenyl)hex-4-ynenitrile following General Procedure J, using Workup 2. $^1$H NMR (CD$_3$OD) δ 7.80 (d, J=8.4 Hz, 1H), 7.42 (d, J=8.4 Hz, 1H), 7.16-7.19 (m, 3H), 7.05 (d, J=8.4 Hz, 1H), 6.83-6.93 (m, 4H), 5.06 (s, 2H), 4.14-4.17 (m, 2H), 4.02 (br. s, 1H), 3.74-3.77 (m, 2H), 3.42 (s, 3H), 3.22 (d, J=7.5 Hz, 2H), 1.98 (s, 3H), 1.74 (s, 3H). LC/MS: mass calcd. for $C_{31}H_{29}ClN_4O_3S$: 572.16, found: 573.0 [M+H]$^+$.

Example 46

(2S)-5-(2-(4-((3-(4-(2-Methoxyethoxy)-2-methylphenyl)-2-methylbenzo[b]thiophen-5-yl)methoxy)phenyl)pent-3-yn-1-yl)-1H-tetrazole, Cpd 46

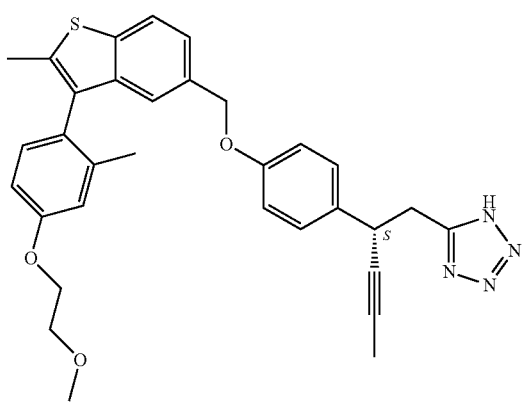

(A) To a cooled (–78° C.) solution of tert-butyl((3-(4-(2-methoxyethoxy)-2-methylphenyl)benzo[b]thiophen-5-yl)methoxy)dimethylsilane (from Example 44A) (300 mg, 0.68 mmol) in THF (10 mL), maintained under an inert atmosphere of nitrogen, was added LDA (2.0 M in THF; 0.68 mL.

1.36 mmol). Iodomethane (290 mg, 2.04 mmol) was then added and the resultant mixture was stirred at –78° C. for 2 h. The reaction was then quenched by the addition of satd. aq NaCl, and the mixture was extracted with EtOAc (3×30 mL). The combined organic extracts were washed with brine, dried (Na$_2$SO$_4$) and concentrated. The resultant residue was purified by silica gel chromatography (0-10% EtOAc/petroleum ether) to afford tert-butyl((3-(4-(2-methoxyethoxy)-2-methylphenyl)-2-methylbenzo[b]thiophen-5-yl)methoxy)dimethylsilane (220 mg, 71%) as a colorless oil. LC/MS: mass calcd. for $C_{26}H_{36}O_3SSi$: 456.22, found: 324.9 [M–OTBS]$^+$.

(B) (3-(4-(2-Methoxyethoxy)-2-methylphenyl)-2-methylbenzo[b]thiophen-5-yl)methanol was prepared from tert-butyl((3-(4-(2-methoxyethoxy)-2-methylphenyl)-2-methylbenzo[b]thiophen-5-yl)methoxy)dimethylsilane following the procedure described in Example 2C. LC/MS: mass calcd. for $C_{20}H_{22}O_3S$: 342.13, found: 325.0 [M–OH]$^+$.

(C) 5-(Chloromethyl)-3-(4-(2-methoxyethoxy)-2-methylphenyl)-2-methylbenzo[b]thiophene was prepared from (3-(4-(2-methoxyethoxy)-2-methylphenyl)-2-methylbenzo[b]thiophen-5-yl)methanol following General Procedure D.

(D) (3S)-3-(4-((3-(4-(2-Methoxyethoxy)-2-methylphenyl)-2-methylbenzo[b]thiophen-5-yl)methoxy)phenyl)hex-4-ynenitrile was prepared from 5-(chloromethyl)-3-(4-(2-methoxyethoxy)-2-methylphenyl)-2-methylbenzo[b]thiophene and (3S)-3-(4-hydroxyphenyl)hex-4-ynenitrile (from Example 2G) following General Procedure E, using K$_2$CO$_3$ in place of Cs$_2$CO$_3$ at a reaction temperature of 60° C. overnight. LC/MS: mass calcd. for $C_{32}H_{31}NO_3S$: 509.20, found: 527.1 [M+NH$_4$]$^+$.

(E) (2S)-5-(2-(4-((3-(4-(2-Methoxyethoxy)-2-methylphenyl)-2-methylbenzo[b]thiophen-5-yl)methoxy)phenyl)pent-3-yn-1-yl)-1H-tetrazole (Cpd 46) was prepared from (3S)-3-(4-((3-(4-(2-methoxyethoxy)-2-methylphenyl)-2-methylbenzo[b]thiophen-5-yl)methoxy)phenyl)hex-4-ynenitrile following General Procedure J, using Workup 2. $^1$H NMR (CD$_3$OD) δ 7.76 (d, J=8.4 Hz, 1H), 7.31 (d, J=8.1 Hz, 1H), 7.17 (d, J=8.7 Hz, 2H), 7.10 (s, 1H), 7.01 (d, J=8.4 Hz, 1H), 6.91 (s, 1H), 6.82-6.85 (m, 3H), 5.02 (s, 2H), 4.12-4.15 (m, 2H), 4.03 (br. s, 1H), 3.73-3.76 (m, 2H), 3.42 (s, 3H), 3.22 (d, J=7.5 Hz, 2H), 2.28 (s, 3H), 1.98 (s, 3H), 1.74 (s, 3H). LC/MS: mass calcd. for $C_{32}H_{32}N_4O_3S$: 552.22, found: 553.1 [M+H]$^+$.

Example 47

5-((2S)-2-(4-((3-(4-(2-Methoxyethoxy)-2-methylphenyl)-2-(trifluoromethyl)benzo[b]thiophen-5-yl)methoxy)phenyl)pent-3-yn-1-yl)-1H-tetrazole, Cpd 47

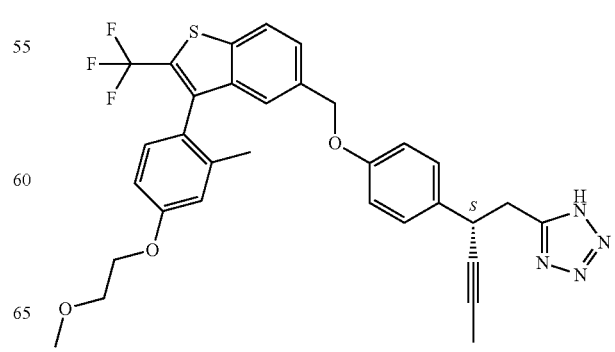

(A) To a solution of tert-butyl((3-(4-(2-methoxyethoxy)-2-methylphenyl)benzo[b]thiophen-5-yl)methoxy)dimethylsilane (Example 44A) (300 mg, 0.68 mmol) in THF (6 mL) at −78° C. was added n-BuLi (2.5 M in hexanes, 0.54 mL, 1.36 mmol) in dropwise fashion, and the resultant mixture was stirred at −78° C. for 10 min. At this time, a solution of triisopropoxyborane (510 mg, 2.71 mmol) in THF (2 mL) was added in dropwise fashion. The resultant mixture was stirred at −78° C. for 30 min and at rt for 1 h. The reaction was then quenched by the addition of water (10 mL) and the mixture was extracted with EtOAc (3×10 mL). The combined organic extracts were dried over Na$_2$SO$_4$, filtered, and the filtrate concentrated under reduced pressure to afford 5-((tert-butyldimethylsilyloxy)methyl)-3-(4-(2-methoxyethoxy)-2-methylphenyl)benzo[b]thiophen-2-ylboronic acid (250 mg) as a colorless oil, which was used in the next step without further purification. LC/MS: mass calcd. for C$_{25}$H$_{35}$BO$_5$SSi: 486.21, found: 354.9 [M−OTBS]$^+$.

(B) To an ice-cooled mixture of 5-((tert-butyldimethylsilyloxy)methyl)-3-(4-(2-methoxyethoxy)-2-methylphenyl)benzo[b]thiophen-2-ylboronic acid (250 mg, 0.51 mmol), sodium trifluoromethanesulfinate (241 mg, 1.544 mmol), copper(I) chloride (51 mg, 0.515 mmol), DCM (5 mL), MeOH (5 mL) and water (4 mL) was added 2-hydroperoxy-2-methylpropane (232 mg, 2.574 mmol) in a dropwise fashion, and the resultant mixture was stirred at rt overnight. The reaction was then quenched by the addition of water (15 mL) and the mixture was extracted with EtOAc (3×15 mL). The combined organic extracts were dried over Na$_2$SO$_4$, filtered, and the filtrate concentrated under reduced pressure. The resultant residue was purified by column chromatography on silica gel (0-10% EtOAc/petroleum ether) to afford tert-butyl((3-(4-(2-methoxyethoxy)-2-methylphenyl)-2-(trifluoromethyl)benzo[b]thiophen-5-yl)methoxy)dimethylsilane (200 mg, 76%) as a colorless oil. LC/MS: mass calcd. for C$_{26}$H$_{33}$F$_3$O$_3$SSi: 510.19, found: 378.9 [M−OTBS]$^+$.

(C) (3-(4-(2-Methoxyethoxy)-2-methylphenyl)-2-(trifluoromethyl)benzo[b]thiophen-5-yl)methanol was prepared from tert-butyl((3-(4-(2-methoxyethoxy)-2-methylphenyl)-2-(trifluoromethyl)benzo[b]thiophen-5-yl)methoxy)dimethylsilane following the procedure described in Example 2C. LC/MS: mass calcd. for C$_{20}$H$_{19}$F$_3$O$_3$S: 396.10, found: 378.8 [M−OH]$^+$.

(D) 5-(Chloromethyl)-3-(4-(2-methoxyethoxy)-2-methylphenyl)-2-(trifluoromethyl)benzo[b]thiophene was prepared from (3-(4-(2-methoxyethoxy)-2-methylphenyl)-2-(trifluoromethyl)benzo[b]thiophen-5-yl)methanol following General Procedure D.

(E) (3S)-3-(4-((3-(4-(2-Methoxyethoxy)-2-methylphenyl)-2-(trifluoromethyl)benzo[b]thiophen-5-yl)methoxy)phenyl)hex-4-ynenitrile was prepared from 5-(chloromethyl)-3-(4-(2-methoxyethoxy)-2-methylphenyl)-2-(trifluoromethyl)benzo[b]thiophene and (3S)-3-(4-hydroxyphenyl)hex-4-ynenitrile (from Example 2G) following General Procedure E, at a reaction temperature of 60° C. overnight. LC/MS: mass calcd. for C$_{32}$H$_{28}$F$_3$NO$_3$S: 563.17, found: 581.0[M+NH$_4$]$^+$.

(F) 5-((2S)-2-(4-((3-(4-(2-Methoxyethoxy)-2-methylphenyl)-2-(trifluoromethyl)benzo[b]thiophen-5-yl)methoxy)phenyl)pent-3-yn-1-yl)-1H-tetrazole (Cpd 47) was prepared from (3S)-3-(4-((3-(4-(2-methoxyethoxy)-2-methylphenyl)-2-(trifluoromethyl)benzo[b]thiophen-5-yl)methoxy)phenyl)hex-4-ynenitrile following General Procedure J, using Workup 2. Additional purification of the product was carried out by preparative HPLC on a Waters SunFire™ Prep C18, 5μ column (19×100 mm) using an acetonitrile/water (0.05% NH$_4$HCO$_3$) gradient (45-85%). $^1$H NMR (CD$_3$OD) δ 8.00 (d, J=8.4 Hz, 1H), 7.58 (d, J=8.7 Hz, 1H), 7.16-7.24 (m, 3H), 7.06 (d, J=8.4 Hz, 1H), 6.82-6.92 (m, 4H), 5.10 (s, 2H), 4.15-4.18 (m, 2H), 4.00-4.05 (m, 1H), 3.75-3.78 (m, 2H), 3.43 (s, 3H), 3.19-3.24 (m, 2H), 1.88 (d, J=3.6 Hz, 3H), 1.74-1.76 (m, 3H). LC/MS: mass calcd. for C$_{32}$H$_{29}$F$_3$N$_4$O$_3$S: 606.19, found: 606.95 [M+H]$^+$.

Example 48

1-(5-((4-((2S)-1-(1H-Tetrazol-5-yl)pent-3-yn-2-yl)phenoxy)methyl)benzo[b]thiophen-3-yl)-2-methylpiperidine, Cpd 48

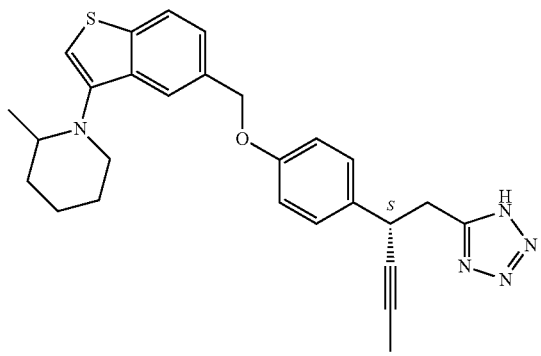

(A) To a solution of methyl 3-bromobenzo[b]thiophene-5-carboxylate (8.0 g, 29.5 mmol) in DCM (50 mL) and TFA (50 mL) was added H$_2$O$_2$ (30% in water; 3.35 mL, 29.5 mmol). After the mixture was stirred at rt overnight, water (100 mL) was added and the mixture was extracted with DCM (3×100 mL). The combined organic extracts were washed with brine, dried (Na$_2$SO$_4$) and concentrated under reduced pressure. The resultant residue was purified by silica gel chromatography (0-35% EtOAc/petroleum ether) to afford methyl 3-bromobenzo[b]thiophene-5-carboxylate 1,1-dioxide (7.5 g, 84%) as a light yellow solid. LC/MS: mass calcd. for C$_{10}$H$_7$BrO$_4$S: 301.92, found: 302.0, 304.0 [M, M+2]$^+$.

(B) To a solution of methyl 3-bromobenzo[b]thiophene-5-carboxylate 1,1-dioxide (700 mg, 2.31 mmol) in toluene (10 mL) was added 2-methylpiperidine (914 mg, 9.22 mmol) and the resulting mixture was stirred at 120° C. overnight. After cooling to rt, water (70 mL) was added and the mixture was extracted with EtOAc (3×70 mL). The combined organic extracts were dried (Na$_2$SO$_4$), concentrated under reduced pressure and the resultant residue was purified by silica gel chromatography (0-40% EtOAc/petroleum ether) to afford methyl 3-(2-methylpiperidin-1-yl)benzo[b]thiophene-5-carboxylate 1,1-dioxide (600 mg, 48%) as light yellow oil. LC/MS: mass calcd. for C$_{16}$H$_{19}$NO$_4$S: 321.10, found: 322.0 [M+H]$^+$.

(C) To an ice-cooled solution of methyl 3-(2-methylpiperidin-1-yl)benzo[b]thiophene-5-carboxylate 1,1-dioxide (600 mg, 1.87 mmol) in THF (10 mL) under argon was added diisobutylaluminum hydride (1 M in DCM; 11.2 mL, 11.2 mmol) in drop-wise fashion. After stirring at rt for 4 h, satd. aq potassium sodium tartrate solution (60 mL) was added to quench the reaction and the mixture was extracted with EtOAc (3×60 mL). The combined organic extracts were washed with brine, dried ($Na_2SO_4$) and concentrated under reduced pressure. The resultant residue was purified by silica gel chromatography (0-25% EtOAc/heptane) to give (3-(2-methylpiperidin-1-yl)benzo[b]thiophen-5-yl) methanol (280 mg, 55%) as light yellow oil. LC/MS: mass calcd. for $C_{15}H_{19}NOS$: 261.12, found: 262.1 $[M+H]^+$.

(D) Ethyl (3S)-3-(4-((3-(2-methylpiperidin-1-yl)benzo[b]thiophen-5-yl)methoxy)phenyl)hex-4-ynoate was prepared from (3-(2-methylpiperidin-1-yl)benzo[b]thiophen-5-yl) methanol and (3S)-ethyl 3-(4-hydroxyphenyl)hex-4-ynoate (available from Synnovator, Inc., Research Triangle Park, N.C.; Cat. # PB05708) following General Procedure B, using ADDP and $Bu_3P$ at a reaction temperature of 60° C. for 1 h. LC/MS: mass calcd. for $C_{29}H_{33}NO_3S$: 475.22, found: 476.2 $[M+H]^+$.

(E) (3S)-3-(4-((3-(2-Methylpiperidin-1-yl)benzo[b]thiophen-5-yl)methoxy)phenyl)hex-4-ynoic acid was prepared from ethyl (3S)-3-(4-((3-(2-methylpiperidin-1-yl)benzo[b]thiophen-5-yl)methoxy)phenyl)hex-4-ynoate following General Procedure C, using EtOH in place of MeOH, and LiOH (10 eq.) as base. LC/MS: mass calcd. for $C_{27}H_{29}NO_3S$: 447.19, found: 448.1 $[M+H]^+$.

(F) (3S)—N-(2-Cyanoethyl)-3-(4-((3-(2-methylpiperidin-1-yl)benzo[b]thiophen-5-yl)methoxy)phenyl)hex-4-ynamide was prepared from (3S)-3-(4-((3-(2-methylpiperidin-1-yl)benzo[b]thiophen-5-yl)methoxy)phenyl)hex-4-ynoic acid following the method described in Example 37B. LC/MS: mass calcd. for $C_{30}H_{33}N_3O_2S$: 499.23, found: 500.3 $[M+H]^+$.

(G) 3-(5-((2S)-2-(4-((3-(2-Methylpiperidin-1-yl)benzo[b]thiophen-5-yl)methoxy)phenyl)pent-3-yn-1-yl)-1H-tetrazol-1-yl)propanenitrile was prepared from (3S)—N-(2-Cyanoethyl)-3-(4-((3-(2-methylpiperidin-1-yl)benzo[b]thiophen-5-yl)methoxy)phenyl)hex-4-ynamide following the method described in Example 37C. LC/MS: mass calcd. for $C_{30}H_{32}N_6OS$: 524.24, found: 525.3 $[M+H]^+$.

(H) 1-(5-((4-((2S)-1-(1H-Tetrazol-5-yl)pent-3-yn-2-yl) phenoxy)methyl)benzo[b]thiophen-3-yl)-2-methylpiperidine (Cpd 48) was prepared from 3-(5-((2S)-2-(4-((3-(2-methylpiperidin-1-yl)benzo[b]thiophen-5-yl)methoxy) phenyl)pent-3-yn-1-yl)-1H-tetrazol-1-yl)propanenitrile following the method described in Example 37K. Product purification was carried out by preparative HPLC (Phenomenex C18 column, 5 µm, 100×30 mm, 20-70% MeCN/$H_2O$ (0.1% TFA v/v) over 16 min). Product-containing fractions were pooled, and partially concentrated to remove the organic solvent. The remaining aqueous solution was neutralized with satd. aq $NaHCO_3$ and extracted with EtOAc. The combined organic extracts were washed with brine, dried ($Na_2SO_4$) and concentrated to provide the title compound as a white solid. $^1H$ NMR ($CDCl_3$) δ 11.84 (br. s, 1H), 7.79 (s, 1H), 7.75 (dd, J=8.1, 2.0 Hz, 1H), 7.35 (d, J=8.1 Hz, 1H), 7.18 (br. d, J=8.6 Hz, 2H), 6.86 (d, J=8.1 Hz, 2H), 6.78 (d, J=3.0 Hz, 1H), 5.10 (s, 2H), 4.02-4.09 (m, 1H), 3.45 (br. s, 1H), 3.22-3.38 (m, 3H), 2.68-2.80 (m, 1H), 1.90-1.98 (m, 1H), 1.64-1.80 (m, 3H), 1.48-1.58 (m, 2H), 0.06 (dd, J=6.6, 1.0 Hz, 3H). LC/MS: mass calcd. for $C_{27}H_{29}N_5OS$: 471.21, found: 472.2 $[M+H]^+$.

Example 49

(2S)-5-((4-(1-(1H-Tetrazol-5-yl)pent-3-yn-2-yl)phenoxy)methyl)-3-(2-methylphenyl)thieno[2,3-b]pyridine, Cpd 49

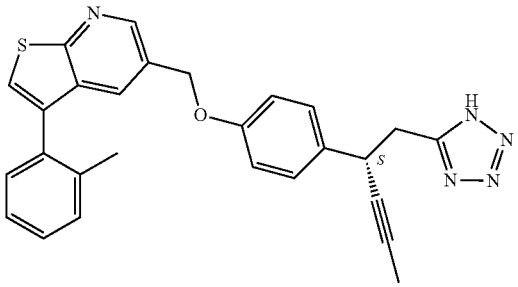

(A) To a solution of 5-bromo-2-fluoronicotinaldehyde (6.0 g, 29.4 mmol) and ethyl 2-mercaptoacetate (4.2 g, 34.9 mmol) in THF (10 mL) was added NaH (60% in mineral oil, 2.4 g, 60.0 mmol,) in portions at 0° C. The reaction mixture was refluxed for 3 h, then cooled to rt, and quenched with water (100 mL). The resulting solution was extracted with EtOAc (3×100 mL) and the combined organic extracts were dried ($Na_2SO_4$), filtered and concentrated under reduced pressure. The resultant residue was purified by silica gel chromatography (0-10% EtOAc/petroleum ether) to afford ethyl 5-bromothieno[2,3-b]pyridine-2-carboxylate (2.4 g, 28% yield), as light yellow oil. LC/MS: mass calcd. for $C_{10}H_8BrNO_2S$: 284.95, found: 285.9, 287.9 $[M+H, M+H+2]^+$.

(B) 5-Bromothieno[2,3-b]pyridine-2-carboxylic acid was prepared from ethyl 5-bromothieno[2,3-b]pyridine-2-carboxylate following General Procedure C, using EtOH in place of MeOH, and LiOH as base. After the acidification step with 1N HCl, the precipitates were collected by filtration and dried under vacuum. LC/MS: mass calcd. for $C_8H_4BrNO_2S$: 256.91, found: 257.8, 259.8 $[M+H, M+H+2]^+$.

(C) To a solution of 5-bromothieno[2,3-b]pyridine-2-carboxylic acid (6.6 g, 25.6 mmol) in DMA (50 mL) was added DBU (12.8 g, 84.1 mmol) and the resulting mixture was stirred at 150° C. overnight. After cooling to rt, the reaction was quenched with $H_2O$ (100 mL) and the resulting mixture was extracted with EtOAc (3×100 mL). The combined organic extracts were dried ($Na_2SO_4$), filtered and concentrated under reduced pressure. The residue thus obtained was purified by silica gel chromatography (0-10% EtOAc/petroleum ether) to afford 5-bromothieno[2,3-b] pyridine (3.3 g, 60%), as a white solid. LC/MS: mass calcd. for $C_7H_4BrNS$: 212.92, found: 213.8, 215.8 $[M+H, M+H+2]^+$.

(D) To an ice-cooled solution of 5-bromothieno[2,3-b] pyridine (2.9 g, 13.5 mmol) in THF (30 mL) was added isopropylmagnesium chloride-lithium chloride complex (1.3M in THF; 31 mL, 40.3 mmol) in a drop-wise fashion with stirring at 0° C. After stirring overnight at rt, the reaction was quenched by addition of DMF (3 mL) and the resulting mixture was extracted with EtOAc (3×100 mL). The combined organic extracts were dried ($Na_2SO_4$), filtered and concentrated under reduced pressure. The residue thus obtained was purified by silica gel chromatography (0-10% EtOAc/petroleum ether) to afford thieno[2,3-b]pyridine-5- carbaldehyde (1.5 g, 67%), as light yellow oil. LC/MS: mass calcd. for $C_8H_5NOS$: 163.01, found: 163.8 $[M+H]^+$.

(E) To a solution of thieno[2,3-b]pyridine-5-carbaldehyde (1.4 g, 8.58 mmol) in $CHCl_3$ (30 mL) under nitrogen was added bromine (5.5 g, 34.4 mmol) and the resulting solution was stirred at 70° C. overnight. After cooling to rt, the reaction was quenched with $H_2O$ (50 mL) and the resulting mixture was extracted with EtOAc (3×100 mL). The combined organic extracts were dried ($Na_2SO_4$), filtered and concentrated under reduced pressure. The residue thus obtained was purified by silica gel chromatography (0-10% EtOAc/petroleum ether) to afford 3-bromothieno[2,3-b]pyridine-5-carbaldehyde (500 mg, 19%), as light yellow oil. LC/MS: mass calcd. for $C_8H_4BrNOS$: 240.92, found: 241.8, 243.8 $[M+H, M+H+2]^+$.

(F) (3-Bromothieno[2,3-b]pyridin-5-yl)methanol was prepared from 3-bromothieno[2,3-b]pyridine-5-carbaldehyde following General Procedure F. LC/MS: mass calcd. for $C_8H_6BrNOS$: 242.94, found: 243.9, 245.9 $[M+H, M+H+2]^+$.

(G) (3S)-3-(4-((3-Bromothieno[2,3-b]pyridin-5-yl)methoxy)phenyl)hex-4-ynenitrile was prepared from (3-bromothieno[2,3-b]pyridin-5-yl)methanol and (3S)-3-(4-hydroxyphenyl)hex-4-ynenitrile (from Example 2G) following General Procedure B, using ADDP and $Bu_3P$ at a reaction temperature of 60° C. for 2 h. LC/MS: mass calcd. for $C_{20}H_{15}BrN_2OS$: 410.01, found: 411.2, 413.2 $[M+H, M+H+2]^+$.

(H) (3S)-3-(4-((3-(2-Methylphenyl)thieno[2,3-b]pyridin-5-yl)methoxy)phenyl)hex-4-ynenitrile was prepared from (3S)-3-(4-((3-bromothieno[2,3-b]pyridin-5-yl)methoxy)phenyl)hex-4-ynenitrile and 2-methylphenylboronic acid following General Procedure A, using $PdCl_2(dppf).CH_2Cl_2$ as the palladium catalyst and $Cs_2CO_3$ as the base. LC/MS: mass calcd. for $C_{27}H_{22}N_2OS$: 422.15, found: 423.3 $[M+H]^+$.

(I) (2S)-5-((4-(1-(1H-Tetrazol-5-yl)pent-3-yn-2-yl)phenoxy)methyl)-3-(2-methylphenyl)thieno[2,3-b]pyridine (Cpd 49) was prepared from (3S)-3-(4-((3-(2-methylphenyl)thieno[2,3-b]pyridin-5-yl)methoxy)phenyl)hex-4-ynenitrile following General Procedure J, using Workup 1. $^1H$ NMR (DMSO-$d_6$) δ 8.71 (d, J=1.6 Hz, 1H), 7.89 (s, 1H), 7.84 (d, J=1.6 Hz, 1H), 7.25-7.42 (m, 4H), 7.24 (d, J=8.4 Hz, 2H), 6.95 (d, J=8.4 Hz, 2H), 5.24 (s, 2H), 4.08-4.10 (m, 1H), 3.22 (d, J=7.6 Hz, 2H), 2.19 (s, 3H), 1.74 (d, J=2.0 Hz, 3H). LC/MS: mass calcd. for $C_{27}H_{23}N_5OS$: 465.16, found: 466.05 $[M+H]^-$.

Example 50

(2S)-5-((4-(1-(1H-Tetrazol-5-yl)pent-3-yn-2-yl)phenoxy)methyl)-3-(4-methoxy-2-methylphenyl)thieno[2,3-b]pyridine, Cpd 50

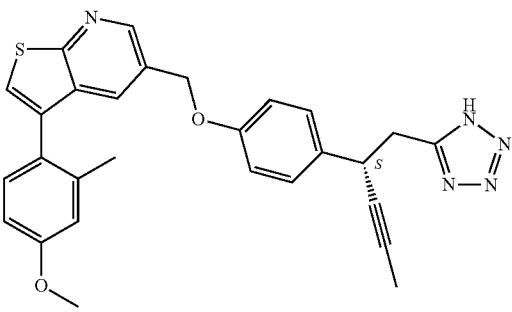

(A) (3S)-3-(4-((3-(4-Methoxy-2-methylphenyl)thieno[2,3-b]pyridin-5-yl)methoxy)phenyl)hex-4-ynenitrile was prepared from (3S)-3-(4-((3-bromothieno[2,3-b]pyridin-5-yl)methoxy)phenyl)hex-4-ynenitrile (from Example 49G) and 4-methoxy-2-methylphenylboronic acid following General Procedure A, using $PdCl_2(dppf).CH_2Cl_2$ as the palladium catalyst and $Cs_2CO_3$ as the base. LC/MS: mass calcd. for $C_{28}H_{24}N_2O_2S$: 452.16, found: 453.2 $[M+H]^+$.

(B) (2S)-5-((4-(1-(1H-Tetrazol-5-yl)pent-3-yn-2-yl)phenoxy)methyl)-3-(4-methoxy-2-methylphenyl)thieno[2,3-b]pyridine was prepared from (3S)-3-(4-((3-(4-methoxy-2-methylphenyl)thieno[2,3-b]pyridin-5-yl)methoxy)phenyl)hex-4-ynenitrile following General Procedure J, using Workup 1. $^1H$ NMR (DMSO-$d_6$) δ 8.69 (d, J=2.0 Hz, 1H), 7.80-7.83 (m, 2H), 7.19-7.24 (m, 3H), 6.88-6.97 (m, 4H), 5.23 (s, 2H), 4.05-4.12 (m, 1H), 3.81 (s, 3H), 3.05-3.15 (m, 2H), 2.10 (s, 3H), 1.73 (d, J=2.0 Hz, 3H). LC/MS: mass calcd. for $C_{28}H_{25}N_5O_2S$: 495.17, found: 496.1 $[M+H]^+$.

Example 51

(2S)-5-((4-(1-(1H-Tetrazol-5-yl)pent-3-yn-2-yl)phenoxy)methyl)-3-(2-methylphenyl)thieno[2,3-c]pyridine, Cpd 51

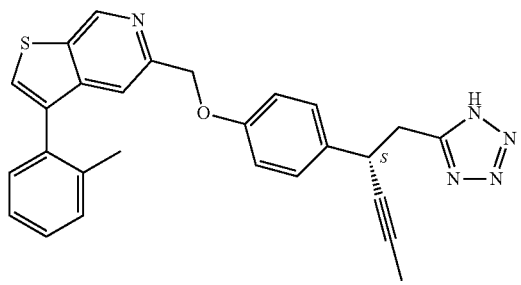

(A) A solution of methyl 2-acetamido-2-(dimethoxyphosphoryl)acetate (8.45 g, 35.3 mmol) and DBU (5.38 g, 35.3 mmol) in DCM (50 mL) was added in drop-wise fashion to an ice-cooled solution of 2,3-thiophene dicarboxaldehyde (4.5 g, 32.1 mmol) in DCM (150 mL). After stirring at 0° C. for 1 h, the mixture was allowed to stir at rt overnight. The reaction was then concentrated under reduced pressure and the resultant residue was purified by silica gel chromatography (0-50% EtOAc/petroleum ether) to afford of methyl thieno[2,3-c]pyridine-5-carboxylate (3.3 g, 54%), as a white solid. LC/MS: mass calcd. for $C_9H_7NO_2S$: 193.02, found: 193.9 $[M+H]^+$.

(B) To a solution of methyl thieno[2,3-c]pyridine-5-carboxylate (3.1 g, 16.0 mmol) in $CHCl_3$ (100 mL) was added bromine (7.7 g, 48.1 mmol) and the resulting solution was stirred at 70° C. overnight. After cooling to rt, the reaction was quenched with 10% aq. $Na_2S_2O_3$ (50 mL) and the resulting mixture was extracted with EtOAc (3×100 mL). The combined organic extracts were dried ($Na_2SO_4$), filtered and concentrated under reduced pressure. The residue thus obtained was purified by silica gel chromatography (0-50% EtOAc/petroleum ether) to afford methyl 3-bromothieno[2,3-c]pyridine-5-carboxylate (3.8 g, 87%), as an off-white solid. LC/MS: mass calcd. for $C_9H_6BrNO_2S$: 270.93, found: 271.9, 274.0 $[M+H, M+H+2]^+$.

(C) To a cooled (−30° C.) solution of methyl 3-bromothieno[2,3-c]pyridine-5-carboxylate (3.6 g, 13.2 mmol) in THF (100 mL) under an inert nitrogen atmosphere was added diisobutylaluminum hydride (1 M in hexane; 66 mL, 66 mmol) in drop-wise fashion. After stirring at rt for 1 h, the reaction was quenched by the addition of 1M aq. potassium sodium tartrate solution (50 mL). The mixture was extracted with EtOAc (3×100 mL) and the combined organic extracts were dried ($Na_2SO_4$), filtered and concentrated under reduced pressure. The resultant residue was purified by silica gel chromatography (0-50% EtOAc/heptane) to give (3-bromothieno[2,3-c]pyridin-5-yl)methanol (1.5 g, 45%), as yellow oil. LC/MS: mass calcd. for $C_8H_6BrNOS$: 242.94, found: 243.8, 245.8 [M+H, M+H+2]$^+$.

(D) (3S)-3-(4-((3-Bromothieno[2,3-c]pyridin-5-yl)methoxy)phenyl)hex-4-ynenitrile was prepared from (3-bromothieno[2,3-c]pyridin-5-yl)methanol and (3S)-3-(4-hydroxyphenyl)hex-4-ynenitrile (from Example 2G) following General Procedure B, using ADDP and $Bu_3P$ at a reaction temperature of 60° C. overnight. LC/MS: mass calcd. for $C_{20}H_{15}BrN_2OS$: 410.01, found: 411.2, 413.1 [M+H, M+H+2]$^+$.

(E) (3S)-3-(4-((3-(2-Methylphenyl)thieno[2,3-c]pyridin-5-yl)methoxy)phenyl)hex-4-ynenitrile was prepared from (3S)-3-(4-((3-bromothieno[2,3-c]pyridin-5-yl)methoxy)phenyl)hex-4-ynenitrile and 2-methylphenylboronic acid following General Procedure A, using $PdCl_2(dppf) \cdot CH_2Cl_2$ as the palladium catalyst and $Cs_2CO_3$ as the base. LC/MS: mass calcd. for $C_{27}H_{22}N_2OS$: 422.15, found: 423.2 [M+H]$^+$.

(F) (2S)-5-((4-(1-(1H-Tetrazol-5-yl)pent-3-yn-2-yl)phenoxy)methyl)-3-(2-methylphenyl)thieno[2,3-c]pyridine (Cpd 51) was prepared from (3S)-3-(4-((3-(2-methylphenyl)thieno[2,3-c]pyridin-5-yl)methoxy)phenyl)hex-4-ynenitrile following General Procedure J, using Workup 1. $^1$H NMR (DMSO-$d_6$) δ 9.32 (s, 1H), 8.06 (s, 1H), 7.34-7.43 (m, 3H), 7.27-7.34 (m, 1H), 7.22 (m, 3H), 6.87-6.94 (m, 2H), 5.24 (s, 2H), 4.07-4.11 (m, 1H), 3.21 (d, J=7.8 Hz, 2H), 2.01 (s, 3H), 1.71 (d, J=2.4 Hz, 3H). LC/MS: mass calcd. for $C_{27}H_{23}N_5OS$: 465.16, found: 466.2 [M+H]$^+$.

Example 52

(2S)-5-((4-(1-(1H-Tetrazol-5-yl)pent-3-yn-2-yl)phenoxy)methyl)-3-(4-methoxy-2-methylphenyl)thieno[2,3-c]pyridine, Cpd 52

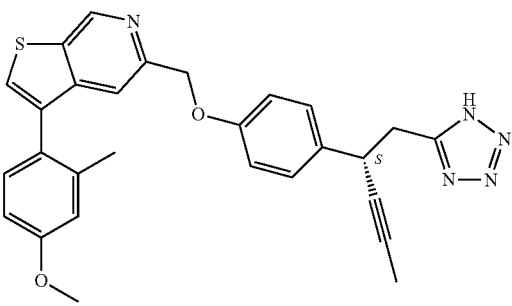

(A) (3S)-3-(4-((3-(4-Methoxy-2-methylphenyl)thieno[2,3-c]pyridin-5-yl)methoxy)phenyl)hex-4-ynenitrile was prepared from (3S)-3-(4-((3-bromothieno[2,3-c]pyridin-5-yl)methoxy)phenyl)hex-4-ynenitrile (from Example 51D) and 4-methoxy-2-methylphenylboronic acid following General Procedure A, using $PdCl_2(dppf) \cdot CH_2Cl_2$ as the palladium catalyst and $Cs_2CO_3$ as the base. LC/MS: mass calcd. for $C_{28}H_{24}N_2O_2S$: 452.16, found: 453.4 [M+H]$^+$.

(B) (2S)-5-((4-(1-(1H-Tetrazol-5-yl)pent-3-yn-2-yl)phenoxy)methyl)-3-(4-methoxy-2-methylphenyl)thieno[2,3-c]pyridine (Cpd 52) was prepared from (3S)-3-(4-((3-(4-methoxy-2-methylphenyl)thieno[2,3-c]pyridin-5-yl)methoxy)phenyl)hex-4-ynenitrile following General Procedure J, using Workup 1. $^1$H NMR (DMSO-$d_6$) δ 9.30 (d, J=1.0 Hz, 1H), 8.00 (s, 1H), 7.42 (d, J=1.0 Hz, 1H), 7.20-7.26 (m, 2H), 7.15 (d, J=8.4 Hz, 1H), 6.90-6.97 (m, 3H), 6.87-6.97 (m, 1H), 5.24 (s, 2H), 4.08-4.09 (m, 1H), 3.80 (s, 3H), 3.21 (d, J=7.7 Hz, 2H), 2.01 (s, 3H), 1.72 (d, J=2.4 Hz, 3H). LC/MS: mass calcd. for $C_{28}H_{25}N_5O_2S$: 495.17, found: 496.2 [M+H]$^+$.

Example 53

(2S)-5-((4-(1-(1H-Tetrazol-5-yl)pent-3-yn-2-yl)phenoxy)methyl)-3-(2-methylphenyl)thieno[3,2-b]pyridine, Cpd 53

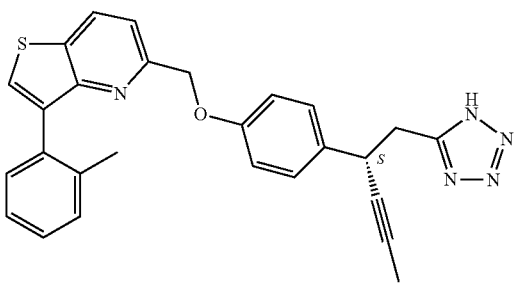

(A) A mixture of 5-chlorothieno[3,2-b]pyridine (1.8 g, 10.6 mmol), $PdCl_2(dppf) \cdot CH_2Cl_2$ (866 mg, 1.06 mmol) and $Et_3N$ (3 mL) in MeOH (15 mL) was stirred overnight at 110° C. under an atmosphere of CO (g) (60 atm). After cooling to rt, the reaction was quenched by the addition of satd. aq $NH_4Cl$ (50 mL) and the resulting solution was extracted with EtOAc (3×50 mL). The combined organic extracts were dried ($Na_2SO_4$), filtered and concentrated under reduced pressure. The resultant residue was purified by silica gel chromatography (0-25% EtOAc/petroleum ether) to afford methyl thieno[3,2-b]pyridine-5-carboxylate (1.7 g, 82%), as a yellow solid. LC/MS: mass calcd. for $C_9H_7NO_2S$: 193.02, found: 193.8 [M+H]$^+$.

(B) Methyl 3-bromothieno[3,2-b]pyridine-5-carboxylate was prepared from methyl thieno[3,2-b]pyridine-5-carboxylate following the methods described in Example 51B. LC/MS: mass calcd. for $C_9H_6BrNO_2S$: 270.93, found: 271.8, 273.8 [M+H, M+H+2]$^+$.

(C) (3-Bromothieno[3,2-b]pyridin-5-yl)methanol was prepared from methyl 3-bromothieno[3,2-b]pyridine-5-carboxylate following the methods described in Example 51C. LC/MS: mass calcd. for $C_8H_6BrNOS$: 242.94, found: 243.8, 245.8 [M+H, M+H+2]$^+$.

(D) (3S)-3-(4-((3-Bromothieno[3,2-b]pyridin-5-yl)methoxy)phenyl)hex-4-ynenitrile was prepared from (3-bromothieno[3,2-b]pyridin-5-yl)methanol and (3S)-3-(4-hydroxyphenyl)hex-4-ynenitrile (from Example 2G) following General Procedure B, using ADDP and $Bu_3P$ at a reaction temperature of 60° C. overnight. LC/MS: mass calcd. for $C_{20}H_{15}BrN_2OS$: 410.01, found: 412.8 [M+H+2]$^+$.

(E) (3S)-3-(4-((3-(2-Methylphenyl)thieno[3,2-b]pyridin-5-yl)methoxy)phenyl)hex-4-ynenitrile was prepared from (3S)-3-(4-((3-bromothieno[3,2-b]pyridin-5-yl)methoxy)phenyl)hex-4-ynenitrile and 2-methylphenylboronic acid following General Procedure A, using $PdCl_2(dppf) \cdot CH_2Cl_2$ as the palladium catalyst and $Cs_2CO_3$ as the base. LC/MS: mass calcd. for $C_{27}H_{22}N_2OS$: 422.15, found: 423.2 [M+H]$^+$.

(F) (2S)-5-((4-(1-(1H-Tetrazol-5-yl)pent-3-yn-2-yl)phenoxy)methyl)-3-(2-methylphenyl)thieno[3,2-b]pyridine (Cpd 53) was prepared from (3S)-3-(4-((3-(2-methylphenyl)thieno[3,2-b]pyridin-5-yl)methoxy)phenyl)hex-4-ynenitrile following General Procedure J, using Workup 1. $^1$H NMR (DMSO-$d_6$) δ 8.57 (d, J=8.3 Hz, 1H), 8.10 (s, 1H), 7.54 (d, J=8.4 Hz, 1H), 7.21-7.37 (m, 6H), 6.94-7.01 (m, 2H), 5.20 (s, 2H), 4.05-4.14 (m, 1H), 3.22 (d, J=7.7 Hz, 2H), 2.16 (s, 3H), 1.74 (d, J=2.4 Hz, 3H). LC/MS: mass calcd. for $C_{27}H_{23}N_5OS$: 465.16, found: 466.2 [M+H]$^+$.

Example 54

(2S)-5-((4-(1-(1H-Tetrazol-5-yl)pent-3-yn-2-yl)phenoxy)methyl)-3-(4-methoxy-2-methylphenyl)thieno[3,2-b]pyridine, Cpd 54

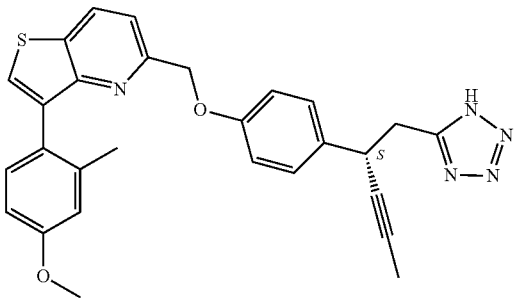

(A) (3S)-3-(4-((3-(4-Methoxy-2-methylphenyl)thieno[3,2-b]pyridin-5-yl)methoxy)phenyl)hex-4-ynenitrile was prepared from (3S)-3-(4-((3-bromothieno[3,2-b]pyridin-5-yl)methoxy)phenyl)hex-4-ynenitrile (from Example 53D) and 4-methoxy-2-methylphenylboronic acid following General Procedure A, using PdCl$_2$(dppf).CH$_2$Cl$_2$ as the palladium catalyst and Cs$_2$CO$_3$ as the base. LC/MS: mass calcd. for $C_{28}H_{24}N_2O_2S$: 452.16, found: 453.2 [M+H]$^+$.

(B) (2S)-5-((4-(1-(1H-Tetrazol-5-yl)pent-3-yn-2-yl)phenoxy)methyl)-3-(4-methoxy-2-methylphenyl)thieno[3,2-b]pyridine (Cpd 54) was prepared from (3S)-3-(4-((3-(4-methoxy-2-methylphenyl)thieno[3,2-b]pyridin-5-yl)methoxy)phenyl)hex-4-ynenitrile following General Procedure J, using Workup 1. $^1$H NMR (DMSO-$d_6$) δ 8.54 (d, J=8.4 Hz, 1H), 8.03 (s, 1H), 7.52 (d, J=8.4 Hz, 1H), 7.22-7.24 (m, 3H), 6.95-6.98 (m, 2H), 6.92 (d, J=2.7 Hz, 1H), 6.85 (dd, J=8.4, 2.7 Hz, 1H), 5.20 (s, 2H), 4.01-4.18 (m, 1H), 3.80 (s, 3H), 3.20 (d, J=7.7 Hz, 2H), 2.14 (s, 3H), 1.73 (d, J=2.4 Hz, 3H). LC/MS: mass calcd. for $C_{28}H_{25}N_5O_2S$: 495.17, found: 496.3 [M+H]$^+$.

Example 55

(2S)-5-(2-(4-((3-Cyclohexylbenzo[b]thiophen-5-yl)methoxy)phenyl)pent-3-yn-1-yl)-1H-tetrazole, Cpd 55

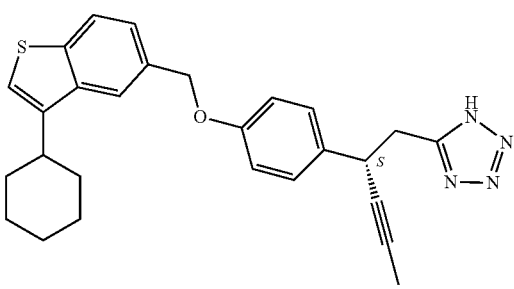

(A) (3S)-3-(4-((3-Bromobenzo[b]thiophen-5-yl)methoxy)phenyl)hex-4-ynenitrile was prepared from (3-bromobenzo[b]thiophen-5-yl)methanol (from Example 1A) and (3S)-3-(4-hydroxyphenyl)hex-4-ynenitrile (from Example 2G) following General Procedure B, using ADDP and Bu$_3$P, at a reaction temperature of 60° C. overnight. $^1$H NMR (DMSO-$d_6$) δ 8.02-8.15 (m, 2H), 7.81-7.88 (m, 1H), 7.56 (dd, J=8.3, 1.6 Hz, 1H), 7.28-7.41 (m, 2H), 7.00-7.09 (m, 2H), 5.29 (s, 2H), 3.94-4.16 (m, 1H), 2.84-3.03 (m, 2H), 1.85 (d, J=2.4 Hz, 3H).

(B) To an ice-cooled solution of (3S)-3-(4-((3-bromobenzo[b]thiophen-5-yl)methoxy)phenyl)hex-4-ynenitrile (500 mg, 1.22 mmol) in THF (2 ml) was added PdCl$_2$(dppf).CH$_2$Cl$_2$ (100 mg, 0.123 mmol), followed by the addition of cyclohexylzinc (II) bromide (0.5M in THF; 7.3 mL, 3.65 mmol). After stirring at 60° C. for 2 h, the reaction was quenched with water (20 mL) and the resulting mixture was extracted with EtOAc (3×20 mL). The combined organic extracts were concentrated under reduced pressure and the resultant residue was purified by silica gel chromatography (0-40% EtOAc/petroleum ether) to afford (3S)-3-(4-((3-cyclohexylbenzo[b]thiophen-5-yl)methoxy)phenyl)hex-4-ynenitrile (130 mg, 15%), as a yellow oil. LC/MS: mass calcd. for $C_{27}H_{27}NOS$: 413.18, found: 414.4 [M+H]$^+$.

(C) (2S)-5-(2-(4-((3-Cyclohexylbenzo[b]thiophen-5-yl)methoxy)phenyl)pent-3-yn-1-yl)-1H-tetrazole (Cpd 55) was prepared from (3S)-3-(4-((3-cyclohexylbenzo[b]thiophen-5-yl)methoxy)phenyl)hex-4-ynenitrile following General Procedure J, using Workup 2. Additional purification of the product was carried out by preparative HPLC on a Waters SunFire™ Prep C18, 5µ column (19×100 mm) using an acetonitrile/water (0.05% TFA) gradient (55-75%). $^1$H NMR (DMSO-$d_6$) δ 7.96 (d, J=8.3 Hz, 1H), 7.91 (d, J=1.6 Hz, 1H), 7.42 (d, J=9.7 Hz, 2H), 7.24-7.26 (m, 2H), 6.97-6.99 (m, 2H), 5.21 (s, 2H), 3.96-4.10 (m, 1H), 3.23 (d, J=7.8 Hz, 2H), 2.85-2.93 (m, 1H), 1.96-1.98 (m, 2H), 1.62-1.89 (m, 6H), 1.43-1.49 (m, 4H), 1.25-1.28 (m, 1H). LC/MS: mass calcd. for $C_{27}H_{28}N_4OS$: 456.20, found: 457.5 [M+H]$^+$.

Example 56

(2S)-5-(2-(4-((3-Cyclopentylbenzo[b]thiophen-5-yl)methoxy)phenyl)pent-3-yn-1-yl)-1H-tetrazole, Cpd 56

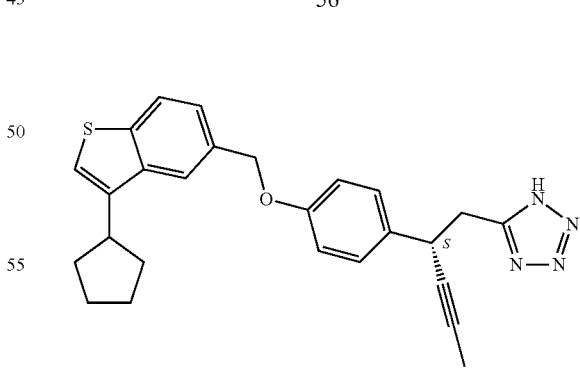

(A) (3S)-3-(4-((3-Cyclopentylbenzo[b]thiophen-5-yl)methoxy)phenyl)hex-4-ynenitrile was prepared from (3S)-3-(4-((3-bromobenzo[b]thiophen-5-yl)methoxy)phenyl)hex-4-ynenitrile (from Example 55A) and cyclopentylzinc (II) bromide using the methods described in Example 55B. LC/MS: mass calcd. for $C_{26}H_{25}NOS$: 399.17, found: 422.3 [M+Na]$^+$.

(B) (2S)-5-(2-(4-((3-Cyclopentylbenzo[b]thiophen-5-yl)methoxy)phenyl)pent-3-yn-1-yl)-1H-tetrazole (Cpd 56) was prepared from (3S)-3-(4-((3-cyclopentylbenzo[b]thiophen-5-yl)methoxy)phenyl)hex-4-ynenitrile following General Procedure J, using Workup 2. Additional purification of the product was carried out by preparative HPLC on a Waters SunFire™ Prep C18, 5μ column (19×100 mm) using an acetonitrile/water (0.05% TFA) gradient (55-75%). $^1$H NMR (DMSO-$d_6$) δ 7.92-7.97 (m, 2H), 7.43 (d, J=9.5 Hz, 2H), 7.25 (d, J=8.2 Hz, 2H), 6.97 (d, J=8.2 Hz, 2H), 5.21 (s, 2H), 4.05-4.16 (m, 1H), 3.23-3.25 (m, 1H), 1.54-1.77 (m, 9H). LC/MS: mass calcd. for $C_{26}H_{26}N_4OS$: 442.18, found: 443.4 [M+H]$^+$.

Example 57

(2S)-5-(2-(4-((3-Cyclopropylbenzo[b]thiophen-5-yl)methoxy)phenyl)pent-3-yn-1-yl)-1H-tetrazole, Cpd 57

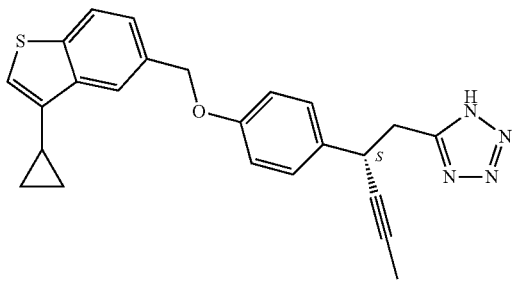

(A) (3S)-3-(4-((3-Cyclopropylbenzo[b]thiophen-5-yl)methoxy)phenyl)hex-4-ynenitrile was prepared from (3S)-3-(4-((3-bromobenzo[b]thiophen-5-yl)methoxy)phenyl)hex-4-ynenitrile (from Example 55A) and 2-cyclopropyl-4,4,5,5-tetramethyl-1,3,2-dioxaborolane following General Procedure A, using PdCl$_2$(dppf).CH$_2$Cl$_2$ as the palladium catalyst and Cs$_2$CO$_3$ as the base. $^1$H NMR (CDCl$_3$) δ 7.89-8.03 (m, 1H), 7.84 (d, J=8.0 Hz, 1H), 7.39-7.49 (m, 1H), 7.30-7.37 (m, 2H), 6.94-7.05 (m, 3H), 5.20 (s, 2H), 3.90-3.96 (m, 1H), 2.72 (dd, J=6.7, 2.2 Hz, 2H), 2.03-2.06 (m, 1H), 1.89 (d, J=2.4 Hz, 3H), 0.95-1.00 (m, 2H), 0.68-0.74 (m, 2H).

(B) (2S)-5-(2-(4-((3-Cyclopropylbenzo[b]thiophen-5-yl)methoxy)phenyl)pent-3-yn-1-yl)-1H-tetrazole (Cpd 57) was prepared from (3S)-3-(4-((3-cyclopropylbenzo[b]thiophen-5-yl)methoxy)phenyl)hex-4-ynenitrile following General Procedure J, using Workup 2. Additional purification of the product was carried out by preparative HPLC on a Waters SunFire™ Prep C18, 5μ column (19×100 mm) using an acetonitrile/water (0.05% TFA) gradient (55-75%). $^1$H NMR (DMSO-$d_6$) δ 8.03 (d, J=1.8 Hz, 1H), 7.95 (d, J=8.3 Hz, 1H), 7.45 (dd, J1=8.2 Hz, J2=1.6 Hz, 1H), 7.29 (s, 1H), 7.20-7.22 (m, 2H), 6.93-6.95 (m, 2H), 5.20 (s, 2H), 4.06-4.08 (m, 1H), 3.07-3.12 (m, 1H), 2.96-3.07 (m, 1H), 2.09-2.15 (m, 1H), 1.73 (d, J=2.4 Hz, 3H), 0.98-1.17 (m, 2H), 0.95-0.97 (m, 2H). LC/MS: mass calcd. for $C_{24}H_{22}N_4OS$: 414.15, found: 415.3 [M+H]$^+$.

Examples 58 and 59

(2S)-5-(2-(4-((3-Isopropylbenzo[b]thiophen-5-yl)methoxy)phenyl)pent-3-yn-1-yl)-1H-tetrazole, Cpd 58 and (2S)-5-(2-(4-((3-Propylbenzo[b]thiophen-5-yl)methoxy)phenyl)pent-3-yn-1-yl)-1H-tetrazole, Cpd 59

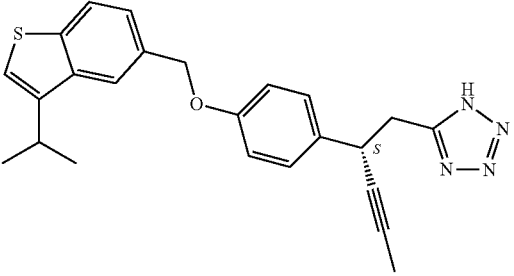

Cpd 58

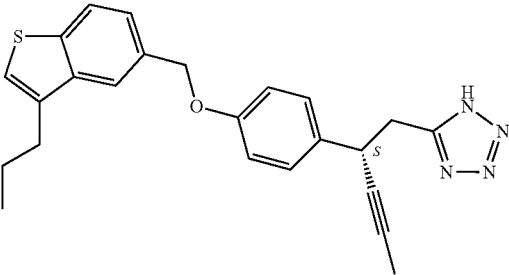

Cpd 59

(A) (3S)-3-(4-((3-Isopropylbenzo[b]thiophen-5-yl)methoxy)phenyl)hex-4-ynenitrile and (3S)-3-(4-((3-propylbenzo[b]thiophen-5-yl)methoxy)phenyl)hex-4-ynenitrile were obtained as a mixture from (3S)-3-(4-((3-bromobenzo[b]thiophen-5-yl)methoxy)phenyl)hex-4-ynenitrile (from Example 55A) and isopropylzinc (II) bromide using the methods described in Example 55B. They were carried forward to next step as an unseparated mixture.

(B) (2S)-5-(2-(4-((3-Isopropylbenzo[b]thiophen-5-yl)methoxy)phenyl)pent-3-yn-1-yl)-1H-tetrazole (Cpd 58) and (2S)-5-(2-(4-((3-propylbenzo[b]thiophen-5-yl)methoxy)phenyl)pent-3-yn-1-yl)-1H-tetrazole (Cpd 59) were prepared from a mixture of (3S)-3-(4-((3-isopropylbenzo[b]thiophen-5-yl)methoxy)phenyl)hex-4-ynenitrile and (3S)-3-(4-((3-propylbenzo[b]thiophen-5-yl)methoxy)phenyl)hex-4-ynenitrile, following General Procedure J, using Workup 2. Additional purification of the products were carried out by preparative HPLC on a Waters SunFire™ Prep C18, 5μ column (19×100 mm) using an acetonitrile/water (0.05% TFA) gradient (55-75%). Cpd 58: $^1$H NMR (DMSO-$d_6$) δ 7.97 (d, J=8.3 Hz, 1H), 7.91 (d, J=1.6 Hz, 1H), 7.40-7.46 (m, 2H), 7.22-7.28 (m, 2H), 6.96-7.02 (m, 2H), 5.21 (s, 2H), 4.08-4.12 (m, 1H), 3.16-3.37 (m, 3H), 1.74 (d, J=2.4 Hz, 3H), 1.31 (d, J=6.8 Hz, 6H). LC/MS: mass calcd. for $C_{24}H_{24}N_4OS$: 416.17, found: 417.3 [M+H]t Cpd 59: $^1$H NMR (DMSO-$d_6$) δ 7.97 (d, J=8.3 Hz, 1H), 7.83-7.92 (m, 1H), 7.36-7.51 (m, 2H), 7.20-7.30 (m, 2H), 6.93-7.04 (m, 2H), 5.20 (s, 2H), 4.08-4.12 (m, 1H), 3.24 (d, J=7.7 Hz, 2H), 2.79 (t, J=7.6 Hz, 2H), 1.63-1.78 (m, 5H), 0.96 (t, J=7.3 Hz, 3H). LC/MS: mass calcd. for $C_{24}H_{24}N_4OS$: 416.17, found: 417.3 [M+H]$^+$.

Example 60

(2S)-5-(2-(4-(Benzo[b]thiophen-5-ylmethoxy)phenyl)pent-3-yn-1-yl)-1H-tetrazole, Cpd 60

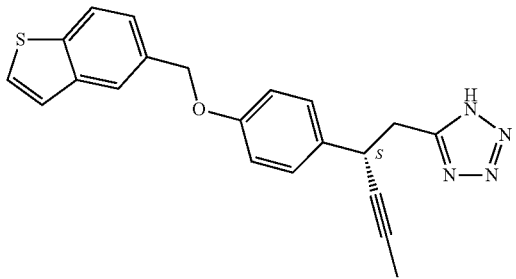

(A) (3S)-3-(4-(Benzo[b]thiophen-5-yl)methoxy)phenyl)hex-4-ynenitrile was prepared from benzo[b]thiophen-5-ylmethanol and (3S)-3-(4-hydroxyphenyl)hex-4-ynenitrile (from Example 2G) following General Procedure B, using ADDP and Bu$_3$P at a reaction temperature of 60° C. overnight, and was used in the next step without characterization.

(B) (2S)-5-(2-(4-(Benzo[b]thiophen-5-ylmethoxy)phenyl)pent-3-yn-1-yl)-1H-tetrazole (Cpd 60) was prepared from (3S)-3-(4-(benzo[b]thiophen-5-yl)methoxy)phenyl)hex-4-ynenitrile following General Procedure J, using Workup 1. $^1$H NMR (DMSO-d$_6$) δ 8.01 (d, J=8.3 Hz, 1H), 7.92-7.97 (m, 1H), 7.78 (d, J=5.4 Hz, 1H), 7.46 (dd, J=5.4, 0.8 Hz, 1H), 7.42 (dd, J=8.4, 1.6 Hz, 1H), 7.21-7.28 (m, 2H), 6.94-7.01 (m, 2H), 5.19 (s, 2H), 4.07-4.11 (m, 1H), 3.22 (d, J=7.7 Hz, 2H), 1.73 (d, J=2.4 Hz, 3H). LC/MS: mass calcd. for $C_{21}H_{18}N_4OS$: 374.12, found: 375.0 [M+H]$^+$.

Example 61

(2RS)-5-(2-(4-((3-(2-Methylphenyl)benzo[b]thiophen-5-yl)methoxy)phenyl)pent-3-yn-1-yl)-1H-tetrazole, Cpd 61

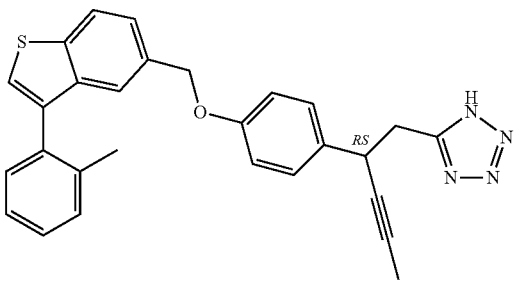

(A) 5-(Chloromethyl)-3-(2-methylphenyl)benzo[b]thiophene was prepared from (3-(2-methylphenyl)benzo[b]thiophen-5-yl)methanol (from Example 1B) following General Procedure D. LC/MS: mass calcd. for $C_{16}H_{13}ClS$: 272.04, found: 273.0 [M+H]$^+$.

(B) (3RS)-Methyl 3-(4-((3-(2-Methylphenyl)benzo[b]thiophen-5-yl)methoxy)phenyl)hex-4-ynoate was prepared from 5-(chloromethyl)-3-(2-methylphenyl)benzo[b]thiophene and methyl 3-(4-hydroxyphenyl)hex-4-ynoate (available from Oxchem Corporation, Irwindale, Calif., catalog #AX8267763) following General Procedure E, at a reaction temperature of 40° C. LC/MS: mass calcd. for $C_{29}H_{26}O_3S$: 454.16, found: 477.1 [M+Na]$^+$.

(C) (3RS)-3-(4-((3-(2-Methylphenyl)benzo[b]thiophen-5-yl)methoxy)phenyl)hex-4-ynoic acid was prepared from (3RS)-methyl 3-(4-((3-(2-methylphenyl)benzo[b]thiophen-5-yl)methoxy)phenyl)hex-4-ynoate following General Procedure C, using 1N aq NaOH as the base and at a reaction temperature of 35° C. LC/MS: mass calcd. for $C_{28}H_{24}O_3S$: 440.14, found: 463.2 [M+Na]$^+$.

(D) (3RS)-3-(4-((3-(2-Methylphenyl)benzo[b]thiophen-5-yl)methoxy)phenyl)hex-4-ynoyl chloride was prepared from (3RS)-3-(4-((3-(2-methylphenyl)benzo[b]thiophen-5-yl)methoxy)phenyl)hex-4-ynoic acid following General Procedure G.

(E) (3RS)-3-(4-((3-(2-Methylphenyl)benzo[b]thiophen-5-yl)methoxy)phenyl)hex-4-ynamide was prepared from (3RS)-3-(4-((3-(2-methylphenyl)benzo[b]thiophen-5-yl)methoxy)phenyl)hex-4-ynoyl chloride following General Procedure Hb. LC/MS: mass calcd. for $C_{28}H_{25}NO_2S$: 439.16, found: 440.2 [M+H]$^+$.

(F) (3RS)-3-(4-((3-(2-Methylphenyl)benzo[b]thiophen-5-yl)methoxy)phenyl)hex-4-ynenitrile was prepared from (3RS)-3-(4-((3-(2-methylphenyl)benzo[b]thiophen-5-yl)methoxy)phenyl)hex-4-ynamide following General Procedure I. LC/MS: mass calcd. for $C_{28}H_{23}NOS$: 421.15, found: 444.1 [M+Na]$^+$.

(G) (2RS)-5-(2-(4-((3-(2-Methylphenyl)benzo[b]thiophen-5-yl)methoxy)phenyl)pent-3-yn-1-yl)-1H-tetrazole (Cpd 61) was prepared from (3RS)-3-(4-((3-(2-methylphenyl)benzo[b]thiophen-5-yl)methoxy)phenyl)hex-4-ynenitrile following General Procedure J, and was purified by preparative HPLC (Phenomenex C18 column, 5 μm, 100×30 mm, 20-70% MeCN/H$_2$O (0.1% TFA v/v) over 18 min). $^1$H NMR (CDCl$_3$) δ 7.93 (d, J=8.6 Hz, 1H), 7.43-7.48 (m, 2H), 7.31-7.36 (m, 3H), 7.27-7.31 (m, 2H), 7.21-7.25 (m, 2H), 6.86-6.93 (m, 2H), 5.07 (s, 2H), 4.05 (ddd, J=8.2, 5.4, 2.5 Hz, 1H), 3.40-3.47 (m, 1H), 3.31-3.39 (m, 1H), 2.15 (s, 3H), 1.88 (d, J=2.5 Hz, 3H). LC/MS: mass calcd. for $C_{28}H_{24}N_4OS$: 464.17, found: 465.1 [M+H]$^+$.

Example 62

(2R)-5-(2-(4-((3-(2-Methylphenyl)benzo[b]thiophen-5-yl)methoxy)phenyl)pent-3-yn-1-yl)-1H-tetrazole, Cpd 62

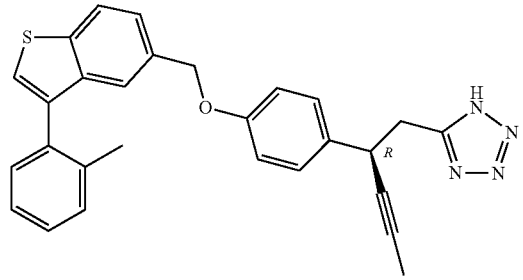

(A) (3R)-3-(4-((3-(2-Methylphenyl)benzo[b]thiophen-5-yl)methoxy)phenyl)hex-4-ynoic acid was prepared from (3RS)-3-(4-((3-(2-methylphenyl)benzo[b]thiophen-5-yl)

methoxy)phenyl)hex-4-ynoic acid (from Example 61C) through a chiral HPLC separation (Chiralcel OJ-H 250×4.6 mm I.D., 5 μm column; Mobile phase: 40% of methanol (0.05% DEA) in CO$_2$, Flow rate: 2.5 mL/min; Column temp: 35° C.). LC/MS: mass calcd. for C$_{28}$H$_{24}$O$_3$S: 440.14, found: 463.2 [M+Na]$^+$.

(B) (3R)-3-(4-((3-(2-Methylphenyl)benzo[b]thiophen-5-yl)methoxy)phenyl)hex-4-ynamide was prepared from (3R)-3-(4-((3-(2-methylphenyl)benzo[b]thiophen-5-yl)methoxy)phenyl)hex-4-ynoic acid following General Procedures G and H$_b$. LC/MS: mass calcd. for C$_{28}$H$_{25}$NO$_2$S: 439.16, found: 440.2 [M+H]$^+$.

(C) (3R)-3-(4-((3-(2-Methylphenyl)benzo[b]thiophen-5-yl)methoxy)phenyl)hex-4-ynenitrile was prepared from (3R)-3-(4-((3-(2-methylphenyl)benzo[b]thiophen-5-yl)methoxy)phenyl)hex-4-ynamide following General Procedures I. LC/MS: mass calcd. for C$_{28}$H$_{23}$NOS: 421.15, found: 444.1 [M+Na]$^+$.

(D) (2R)-5-(2-(4-((3-(2-Methylphenyl)benzo[b]thiophen-5-yl)methoxy)phenyl)pent-3-yn-1-yl)-1H-tetrazole (Cpd 62) was prepared from (3R)-3-(4-((3-(2-methylphenyl)benzo[b]thiophen-5-yl)methoxy)phenyl)hex-4-ynenitrile following General Procedure J, and was purified by preparative HPLC (Phenomenex C18 column, 5 μm, 100×30 mm, 20-70% MeCN/H$_2$O (0.1% TFA v/v) over 18 min). $^1$H NMR (CDCl$_3$) δ: 7.93 (d, J=8.6 Hz, 1H), 7.43-7.48 (m, 2H), 7.31-7.36 (m, 3H), 7.27-7.31 (m, 2H), 7.21-7.25 (m, 2H), 6.86-6.93 (m, 2H), 5.07 (s, 2H), 4.05 (ddd, J=8.2, 5.4, 2.5 Hz, 1H), 3.40-3.47 (m, 1H), 3.31-3.39 (m, 1H), 2.15 (s, 3H), 1.88 (d, J=2.5 Hz, 3H). LC/MS: mass calcd. for C$_{28}$H$_{24}$N$_4$OS: 464.17, found: 465.1 [M+H]$^+$.

Example 63

(2S)-5-(2-(4-((7-Methyl-3-(2-methylphenyl)benzo[b]thiophen-5-yl)methoxy)phenyl)pent-3-yn-1-yl)-1H-tetrazole, Cpd 63

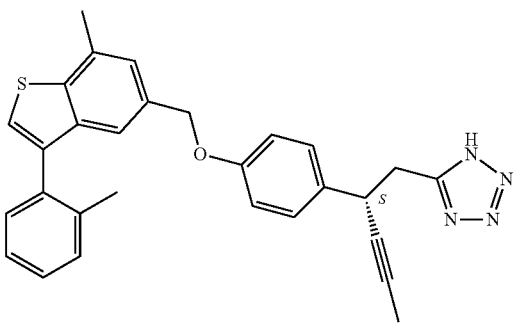

(A) To an ice-cooled solution of 3-thiopheneacetic acid (2.0 g, 14.1 mmol) and acetic anhydride (5.19 mL, 54.9 mmol) in ethyl ether (8 mL) was added boron trifluoride diethyl etherate (2.65 mL, 21.1 mmol) in drop-wise fashion over 15 min. The reaction mixture was then warmed to rt over 1 h, and was stirred at rt for 2.5 d. The reaction was quenched with water, and the mixture was extracted with EtOAc. The combined organic extracts were washed successively with satd. aq NaHCO$_3$, water and brine, and then dried (MgSO$_4$) filtered and concentrated under reduced pressure. The resultant residue was purified by silica gel chromatography (20-80% EtOAc/heptanes) to afford 7-methyl-5H-thieno[2,3-c]pyran-5-one (2.34 g, 51%). LC/MS: mass calcd. for C$_8$H$_6$O$_2$S: 166.01, found: 167.1 [M+H]$^+$.

(B) A suspension of 7-methyl-5H-thieno[2,3-c]pyran-5-one (1.19 g, 7.16 mmol) in ethyl propiolate (2.77 mL, 27.2 mmol) and toluene (10 mL) was distributed in 4 separate vials under N$_2$, each one of which was heated under microwave irritation at 180° C. for 1 h. The mixtures were combined and concentrated under reduced pressure. The resulting residue was purified by silica gel chromatography (10-60% EtOAc/heptanes) to afford ethyl 7-methylbenzo[b]thiophene-5-carboxylate (0.38 g, 24% yield). LC/MS: mass calcd. for C$_{12}$H$_{12}$O$_2$S: 220.06, found: 221.1 [M+H]$^+$.

(C) To a solution of ethyl 7-methylbenzo[b]thiophene-5-carboxylate (0.38 g, 1.73 mmol) in AcOH (10 mL) was added Br$_2$ (0.1 mL, 1.90 mmol) in drop-wise fashion over 5 min. After stirring at rt for 2.5 h, the reaction was quenched with water and the mixture was extracted with EtOAc. The combined organic extracts were washed successively with 10% aq Na$_2$S$_2$O$_3$, and satd. aq NaHCO$_3$, and then dried (MgSO$_4$), filtered and concentrated under reduced pressure. The resulting residue was purified by silica gel chromatography (5-20% EtOAc/heptanes) to afford ethyl 3-bromo-7-methylbenzo[b]thiophene-5-carboxylate (0.15 g, 29% yield). LC/MS: mass calcd. for C$_{12}$H$_{11}$BrO$_2$S: 297.97, found: 300.1 [M+2]$^+$.

(D) Ethyl 7-methyl-3-(2-methylphenyl)benzo[b]thiophene-5-carboxylate was prepared from ethyl 3-bromo-7-methylbenzo[b]thiophene-5-carboxylate and 2-methylphenylboronic acid following General Procedure A, using PdCl$_2$(PPh$_3$)$_2$ as the palladium catalyst and Na$_2$CO$_3$ as the base. LC/MS: mass calcd. for C$_{19}$H$_{18}$O$_2$S: 310.10, found: 311.1 [M+H]$^+$.

(E) To a cold (−78° C.) solution of ethyl 7-methyl-3-(2-methylphenyl)benzo[b]thiophene-5-carboxylate (0.46 g, 1.49 mmol) in DCM (40 mL) was added diisobutylaluminum hydride (1 M in toluene, 10 mL) in drop-wise fashion under a nitrogen atmosphere. After stirring at −78° C. for 1 h, the reaction was quenched with 2N aq HCl. The mixture was warmed to rt and extracted with DCM. The combined organic extracts were dried (MgSO$_4$), filtered and concentrated under reduced pressure. The resultant residue was purified by silica gel chromatography (10-25% EtOAc/heptanes) to afford (7-methyl-3-(2-methylphenyl)benzo[b]thiophen-5-yl)methanol (0.32 g, 80% yield). LC/MS: mass calcd. for C$_{17}$H$_{16}$OS: 268.09, found: 251.1 [M−OH]$^+$.

(F) (3S)-3-(4-((7-Methyl-3-(2-methylphenyl)benzo[b]thiophen-5-yl)methoxy)phenyl)hex-4-ynenitrile was prepared from (7-methyl-3-(2-methylphenyl)benzo[b]thiophen-5-yl)methanol and (3S)-3-(4-hydroxyphenyl)hex-4-ynenitrile (from Example 2G) following General Procedure B, using ADDP and Bu$_3$P, at a reaction temperature of 60° C. for 4 h. LC/MS: mass calcd. for C$_{29}$H$_{25}$NOS: 435.17, found: 458.3 [M+Na]$^+$.

(G) (2S)-5-(2-(4-((7-Methyl-3-(2-methylphenyl)benzo[b]thiophen-5-yl)methoxy)phenyl)pent-3-yn-1-yl)-1H-tetrazole (Cpd 63) was prepared from (3S)-3-(4-((7-methyl-3-(2-methylphenyl)benzo[b]thiophen-5-yl)methoxy)phenyl)hex-4-ynenitrile following General Procedure J, using Workup 2. $^1$H NMR (CDCl$_3$) δ 7.27-7.36 (m, 7H), 7.23 (d, J=8.6 Hz, 2H), 6.91 (d, J=8.6 Hz, 2H), 5.06 (s, 2H), 3.99-4.08 (m, 1H), 3.38-3.47 (m, 1H), 3.29-3.38 (m, 1H), 2.64 (s, 3H), 2.16 (s, 3H), 1.90 (d, J=2.0 Hz, 3H) LC/MS: mass calcd. for C$_{29}$H$_{26}$N$_4$OS: 478.18, found: 479.2 [M+H]$^+$.

Example 64

(2S)-5-(2-(4-((3-Butyl-7-methylbenzo[b]thiophen-5-yl)methoxy)phenyl)pent-3-yn-1-yl)-1H-tetrazole, Cpd 64

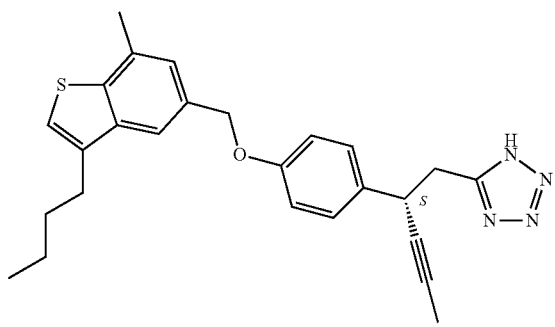

(A) (3-Bromo-7-methylbenzo[b]thiophen-5-yl)methanol was prepared from ethyl 3-bromo-7-methylbenzo[b]thiophene-5-carboxylate (from Example 63C) following the procedure described in Example 371. LC/MS: mass calcd. for $C_{10}H_9BrOS$: 255.96, found: 238.9, 240.9 [M−OH, M−OH+2]$^+$.

(B) (2S)-3-(5-(2-(4-((3-Bromo-7-methylbenzo[b]thiophen-5-yl)methoxy)phenyl)pent-3-yn-1-yl)-1H-tetrazol-1-yl)propanenitrile was prepared from (3-bromo-7-methylbenzo[b]thiophen-5-yl)methanol and (2S)-3-(5-(2-(4-hydroxyphenyl)pent-3-yn-1-yl)-1H-tetrazol-1-yl)propanenitrile (from Example 37D) following the General Procedure B, using ADDP and Bu$_3$P, at a reaction temperature of 60° C. for 2 h. LC/MS: mass calcd. for $C_{25}H_{22}BrN_5OS$: 519.07, found: 520.2 [M+H]$^+$.

(C) To a solution of (2S)-3-(5-(2-(4-((3-bromo-7-methylbenzo[b]thiophen-5-yl)methoxy)phenyl)pent-3-yn-1-yl)-1H-tetrazol-1-yl)propanenitrile (30 mg, 0.058 mmol), butylzinc bromide (0.35 mL, 0.173 mmol) and PdCl$_2$(dppf).CH$_2$Cl$_2$ (4.7 mg, 0.006 mmol) in 1,4-dioxane (1.2 mL) was bubbled N$_2$ for 5 min and the mixture was then stirred overnight at 60° C. After cooling to rt, 1N aq NaOH (0.6 mL) and MeOH (0.15 mL) were added, and the mixture was stirred at rt for 30 min. The mixture was then acidified with 2N aq HCl and extracted with DCM. The combined organic extracts were dried (MgSO$_4$), filtered and concentrated under reduced pressure and the resultant residue was purified by preparative HPLC [Phenomenex C18 column, 5 μm, 30×100 mm, 20%-100% MeCN/H$_2$O (0.1% TFA v/v)] to afford (2S)-5-(2-(4-((3-butyl-7-methylbenzo[b]thiophen-5-yl)methoxy)phenyl)pent-3-yn-1-yl)-1H-tetrazole (Cpd 64) (5.9 mg, 23% yield). $^1$H NMR (CDCl$_3$) δ 7.64 (s, 1H), 7.24-7.30 (m, 2H), 7.23 (s, 1H), 7.11 (s, 1H), 6.98 (br. d, J=8.6 Hz, 2H), 5.15 (s, 2H), 4.06 (br. s, 1H), 3.40-3.49 (m, 1H), 3.31-3.40 (m, 1H), 2.84 (br. t, J=7.6 Hz, 2H), 2.57 (s, 3H), 1.90 (s, 3H), 1.73 (dt, J=15.2, 7.6 Hz, 3H), 1.43 (dq, J=15.0, 7.3 Hz, 3H), 0.96 (t, J=7.3 Hz, 3H). LC/MS: mass calcd. for $C_{26}H_{28}N_4OS$: 444.20, found: 445.2 [M+H]$^+$.

Example 65

(2S)-5-(2-(4-((3-Cyclopentyl-7-methylbenzo[b]thiophen-5-yl)methoxy)phenyl)pent-3-yn-1-yl)-1H-tetrazole, Cpd 65

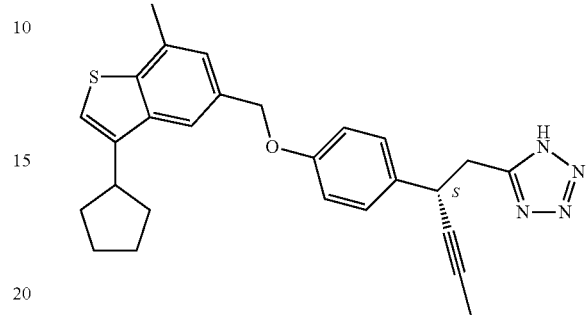

(2S)-5-(2-(4-((3-Cyclopentyl-7-methylbenzo[b]thiophen-5-yl)methoxy)phenyl)pent-3-yn-1-yl)-1H-tetrazole (Cpd 65) was prepared from (2S)-3-(5-(2-(4-((3-bromo-7-methylbenzo[b]thiophen-5-yl)methoxy)phenyl)pent-3-yn-1-yl)-1H-tetrazol-1-yl)propanenitrile (from Example 64B) and cyclopentylzinc bromide following the procedure described in Example 64C. $^1$H NMR (CDCl$_3$) δ 7.69 (s, 1H), 7.19-7.30 (m, 3H), 7.12 (s, 1H), 6.97 (br. d, J=8.1 Hz, 2H), 5.14 (s, 2H), 4.07 (br. s, 1H), 3.29-3.49 (m, 3H), 2.57 (s, 3H), 2.10-2.22 (m, 2H), 1.89 (s, 3H), 1.64-1.86 (m, 6H). LC/MS: mass calcd. for $C_{27}H_{28}N_4OS$: 456.20, found: 457.2 [M+H]$^+$.

Example 66

(2S)-5-(2-(4-((3-Cyclohexyl-7-methylbenzo[b]thiophen-5-yl)methoxy)phenyl)pent-3-yn-1-yl)-1H-tetrazole, Cpd 66

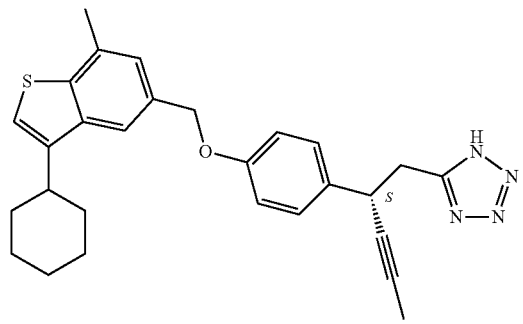

(2S)-5-(2-(4-((3-Cyclohexyl-7-methylbenzo[b]thiophen-5-yl)methoxy)phenyl)pent-3-yn-1-yl)-1H-tetrazole (Cpd 66) was prepared from (2S)-3-(5-(2-(4-((3-bromo-7-methylbenzo[b]thiophen-5-yl)methoxy)phenyl)pent-3-yn-1-yl)-1H-tetrazol-1-yl)propanenitrile (from Example 64B) and cyclohexylzinc bromide following the procedure described in Example 64C. $^1$H NMR (CDCl$_3$) δ 7.66 (s, 1H), 7.24-7.30 (m, 2H), 7.22 (s, 1H), 7.10 (s, 1H), 6.98 (d, J=8.6 Hz, 2H), 5.15 (s, 2H), 4.07 (br. s, 1H), 3.51-3.51 (m, 1H), 3.31-3.48 (m, 2H), 2.90 (br. d, J=7.6 Hz, 1H), 2.57 (s, 3H), 2.07 (br.

d, J=8.1 Hz, 2H), 1.75-1.93 (m, 7H), 1.20-1.55 (m, 4H). LC/MS: mass calcd. for $C_{28}H_{30}N_4OS$: 470.21, found: 471.2 $[M+H]^+$.

Example 67

(2S)-5-(2-(4-((7-Chloro-3-(2-methylphenyl)benzo[b]thiophen-5-yl)methoxy)phenyl)pent-3-yn-1-yl)-1H-tetrazole, Cpd 67

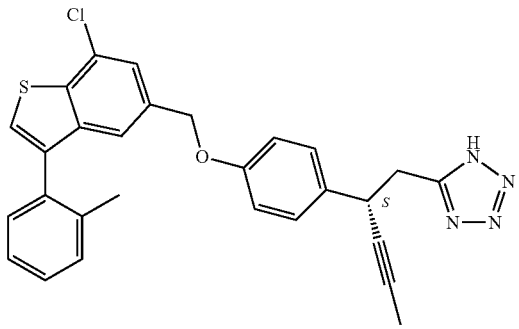

(A) A mixture of 4-bromo-2-chlorobenzenethiol (4.1 g, 18.3 mmol), bromoacetaldehyde diethyl acetal (3.03 mL, 20.2 mmol) and $K_2CO_3$ (5.07 g, 36.7 mmol) in acetone (27 mL) was stirred at 60° C. for 3 h. The mixture was filtered, and the precipitates were washed with acetone. The combined filtrate was concentrated, and the resulting residue was purified by silica gel chromatography (2-8% EtOAc/heptanes) to afford (4-bromo-2-chlorophenyl)(2,2-diethoxyethyl)sulfane (5.67 g, 91% yield). $^1$H NMR (CDCl$_3$) δ 7.52 (d, J=1.5 Hz, 1H), 7.31-7.36 (m, 1H), 7.23-7.28 (m, 1H), 4.67 (t, J=5.6 Hz, 1H), 3.64-3.75 (m, 2H), 3.49-3.62 (m, 2H), 3.13 (d, J=5.6 Hz, 2H), 1.20 (t, J=7.1 Hz, 6H).

(B) To a solution of (4-bromo-2-chlorophenyl)(2,2-diethoxyethyl)sulfane (1.56 g, 4.59 mmol) in p-xylene (78 mL) was added phosphoric acid (85% in water, 0.31 mL, 4.59 mmol) and the resulting mixture was stirred overnight at 180° C. with azeotropic removal of EtOH (Dean-Stark trap). After cooling to rt, water was added to quench the reaction, and the mixture was extracted with EtOAc/ether. The combined organic extracts were washed successively with satd. aq NaHCO$_3$ and brine, dried (MgSO$_4$) and concentrated. The residue thus obtained was purified by silica gel chromatography (100% heptanes) to afford 5-bromo-7-chlorobenzo[b]thiophene (0.41 g, 36% yield). $^1$H NMR (CDCl$_3$) δ 7.87 (s, 1H), 7.53 (d, J=5.6 Hz, 1H), 7.48 (s, 1H), 7.31 (d, J=5.6 Hz, 1H).

(C) A mixture of 5-bromo-7-chlorobenzo[b]thiophene (0.41 g, 1.66 mmol), zinc cyanide (214 mg, 1.82 mmol) and Pd(PPh$_3$)$_4$ (191 mg, 0.166 mmol) in DMF (3 mL) was stirred at 120° C. under N$_2$ overnight. After cooling to rt, the mixture was filtered and the inorganics were washed with EtOAc. The combined organic filtrate was washed successively with water and brine, dried (MgSO$_4$) and concentrated under reduced pressure. The residue thus obtained was purified by silica gel chromatography (3-15% EtOAc/heptanes) to afford 7-chlorobenzo[b]thiophene-5-carbonitrile (0.20 g, 62.7% yield). $^1$H NMR (CDCl$_3$) δ 8.07 (s, 1H), 7.68 (d, J=5.6 Hz, 1H), 7.58 (s, 1H), 7.47 (d, J=5.6 Hz, 1H).

(D) 3-Bromo-7-chlorobenzo[b]thiophene-5-carboxamide was prepared from 7-chlorobenzo[b]thiophene-5-carbonitrile following the procedure described in Example 63C (but at a reaction temperature of 95° C.), and was used in the next step without further purification.

(E) 7-Chloro-3-(2-methylphenyl)benzo[b]thiophene-5-carboxamide was prepared from 3-bromo-7-chlorobenzo[b]thiophene-5-carboxamide and 2-methylphenylboronic acid following General Procedure A, using PdCl$_2$(PPh$_3$)$_2$ as the palladium catalyst and Na$_2$CO$_3$ as the base. LC/MS: mass calcd. for $C_{16}H_{12}ClNOS$: 301.03, found: 302.0 $[M+H]^+$.

(F) A mixture of 7-chloro-3-(2-methylphenyl)benzo[b]thiophene-5-carboxamide (100 mg, 0.331 mmol), di-tert-butyl dicarbonate (152 mg, 0.696 mmol) and DMAP (4 mg, 0.033 mmol) in acetonitrile (8 mL) was stirred at rt for 3 h. The solution was concentrated, and the resulting residue was purified by silica gel chromatography (5-15% EtOAc/heptanes) to afford di-tert-butyl (7-chloro-3-(2-methylphenyl)benzo[b]thiophene-5-carbonyl)dicarbamate (130 mg, 78% yield). $^1$H NMR (CDCl$_3$) δ 7.80 (d, J=4.0 Hz, 2H), 7.45 (s, 1H), 7.32-7.41 (m, 2H), 7.21-7.32 (m, 2H), 2.14 (s, 3H), 1.37 (s, 18H).

(G) To a solution of di-tert-butyl (7-chloro-3-(2-methylphenyl)benzo[b]thiophene-5-carbonyl)dicarbamate (130 mg, 0.26 mmol) in EtOH (5 mL) was added NaBH$_4$ (20 mg, 0.52 mmol) and the mixture was stirred at rt for 3 d. The reaction was quenched by the addition of water and 1N HCl, and the mixture was extracted with DCM. The combined organic extracts were dried (MgSO$_4$), concentrated under reduced pressure and the resultant residue was purified by silica gel chromatography (5-20% EtOAc/heptanes) to afford (7-chloro-3-(2-methylphenyl)benzo[b]thiophen-5-yl)methanol (42 mg, 56% yield). LC/MS: mass calcd. for $C_{16}H_{13}ClOS$: 288.04, found: 271.0 $[M-OH]^+$.

(H) (2S)-3-(5-(2-(4-((7-Chloro-3-(2-methylphenyl)benzo[b]thiophen-5-yl)methoxy)phenyl)pent-3-yn-1-yl)-1H-tetrazol-1-yl)propanenitrile was prepared from (7-chloro-3-(2-methylphenyl)benzo[b]thiophen-5-yl)methanol and (2S)-3-(5-(2-(4-hydroxyphenyl)pent-3-yn-1-yl)-1H-tetrazol-1-yl)propanenitrile (from Example 37D) following the General Procedure B, using ADDP and Bu$_3$P, at a reaction temperature of 60° C. for 3 h. LC/MS: mass calcd. for $C_{31}H_{26}ClN_5OS$: 551.15, found: 552.2 $[M+H]^+$.

(I) To a solution of (2S)-3-(5-(2-(4-((7-chloro-3-(2-methylphenyl)benzo[b]thiophen-5-yl)methoxy)phenyl)pent-3-yn-1-yl)-1H-tetrazol-1-yl)propanenitrile (68 mg, 0.123 mmol), in THF (2 mL) and MeOH (0.5 mL) was added 1N aq NaOH (1 mL) and the mixture was stirred at rt for 2 h. The mixture was then acidified with 1N aq HCl and extracted with DCM. The combined organic extracts were dried (MgSO$_4$), concentrated under reduced pressure and the resultant residue was purified by preparative HPLC [Phenomenex C18 column, 5 μm, 30×100 mm, 40%-100% MECN/H$_2$O (0.1% TFA v/v)] to afford (2S)-5-(2-(4-((7-chloro-3-(2-methylphenyl)benzo[b]thiophen-5-yl)methoxy)phenyl)pent-3-yn-1-yl)-1H-tetrazole (Cpd 67) (38 mg, 62% yield). $^1$H NMR (CDCl$_3$) δ 7.49 (s, 1H), 7.32-7.40 (m, 4H), 7.20-7.30 (m, 4H), 6.89 (d, J=8.6 Hz, 2H), 5.06 (s, 2H), 4.05 (br. d, J=5.6 Hz, 1H), 3.40-3.49 (m, 1H), 3.30-3.39 (m, 1H), 2.14 (s, 3H), 1.89 (d, J=2.0 Hz, 3H). LC/MS: mass calcd. for C$_{28}$H$_{23}$ClN$_4$OS: 498.13, found: 499.1 [M+H]$^+$.

Example 68

(2S)-5-(2-(4-((7-Chloro-3-(4-methoxy-2-methylphenyl)benzo[b]thiophen-5-yl)methoxy)phenyl)pent-3-yn-1-yl)-1H-tetrazole, Cpd 68

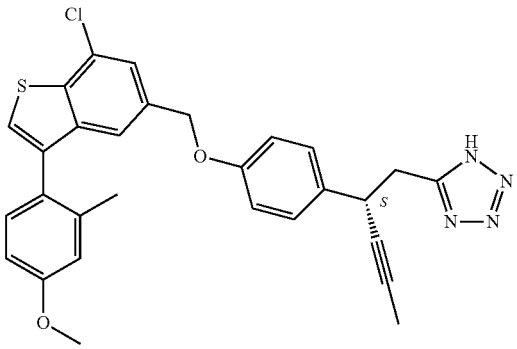

(A) 7-Chloro-3-(4-methoxy-2-methylphenyl)benzo[b]thiophene-5-carboxamide was prepared from 3-bromo-7-chlorobenzo[b]thiophene-5-carboxamide (from Example 67E) and 4-methoxy-2-methylphenylboronic acid following General Procedure A, using PdCl$_2$(PPh$_3$)$_2$ as the palladium catalyst and Na$_2$CO$_3$ as the base. LC/MS: mass calcd. for C$_{17}$H$_{14}$ClNO$_2$S: 331.04, found: 332.1 [M+H]$^+$.

(B) Di-tert-butyl (7-chloro-3-(4-methoxy-2-methylphenyl)benzo[b]thiophene-5-carbonyl)dicarbamate was prepared from 7-chloro-3-(4-methoxy-2-methylphenyl)benzo[b]thiophene-5-carboxamide following the procedure described in Example 67F. $^1$H NMR (CDCl$_3$) δ 7.80 (s, 2H), 7.41 (s, 1H), 7.15 (d, J=8.1 Hz, 1H), 6.88 (d, J=2.0 Hz, 1H), 6.83 (dd, 2.5 Hz, 1H), 3.88 (s, 3H), 2.12 (s, 3H), 1.37 (s, 18H).

(C) (7-Chloro-3-(4-methoxy-2-methylphenyl)benzo[b]thiophen-5-yl)methanol was prepared from di-tert-butyl (7-chloro-3-(4-methoxy-2-methylphenyl)benzo[b]thiophene-5-carbonyl)dicarbamate following the procedure described in Example 67G. LC/MS: mass calcd. for C$_{17}$H$_{15}$ClO$_2$S: 318.05, found: 301.0 [M−OH]$^+$.

(D) (2S)-3-(5-(2-(4-((7-Chloro-3-(4-methoxy-2-methylphenyl)benzo[b]thiophen-5-yl)methoxy)phenyl)pent-3-yn-1-yl)-1H-tetrazol-1-yl)propanenitrile was prepared from (7-chloro-3-(4-methoxy-2-methylphenyl)benzo[b]thiophen-5-yl)methanol and (2S)-3-(5-(2-(4-hydroxyphenyl)pent-3-yn-1-yl)-1H-tetrazol-1-yl)propanenitrile (from Example 37D) following the General Procedure B, using ADDP and Bu$_3$P, at a reaction temperature of 60° C. for 3 h. LC/MS: mass calcd. for C$_{32}$H$_{28}$ClN$_5$O$_2$S: 581.17, found: 582.2 [M+H]$^+$.

(E) (2S)-5-(2-(4-((7-Chloro-3-(4-methoxy-2-methylphenyl)benzo[b]thiophen-5-yl)methoxy)phenyl)pent-3-yn-1-yl)-1H-tetrazole (Cpd 68) was prepared from (2S)-3-(5-(2-(4-((7-chloro-3-(4-methoxy-2-methylphenyl)benzo[b]thiophen-5-yl)methoxy)phenyl)pent-3-yn-1-yl)-1H-tetrazol-1-yl)propanenitrile following the procedure described in Example 67I. $^1$H NMR (CDCl$_3$) δ 7.48 (d, J=1.0 Hz, 1H), 7.35 (d, J=1.0 Hz, 1H), 7.33 (s, 1H), 7.21-7.25 (m, 2H), 7.19 (d, J=8.1 Hz, 1H), 6.85-6.92 (m, 3H), 6.83 (dd, J=8.3, 2.8 Hz, 1H), 5.05 (s, 2H), 4.06 (ddd, J=8.1, 5.6, 2.5 Hz, 1H), 3.86 (s, 3H), 3.39-3.47 (m, 1H), 3.30-3.39 (m, 1H), 2.12 (s, 3H), 1.88 (d, J=2.0 Hz, 3H). LC/MS: mass calcd. for C$_{29}$H$_{25}$ClN$_4$O$_2$S: 528.14, found: 529.2 [M+H]$^+$.

Example 69

(2S)-5-(2-(4-((7-Fluoro-3-(2-methylphenyl)benzo[b]thiophen-5-yl)methoxy)phenyl)pent-3-yn-1-yl)-1H-tetrazole, Cpd 69

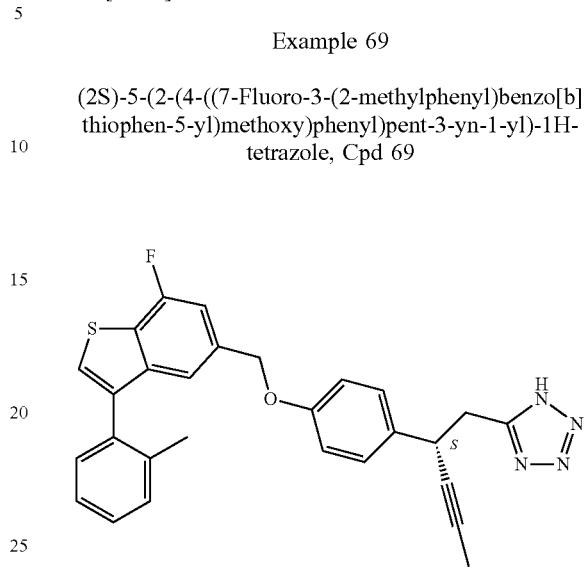

(A) (4-Bromo-2-fluorophenyl)(2,2-diethoxyethyl)sulfane was prepared from 4-bromo-2-fluorobenzenethiol following the procedure described in Example 67A. $^1$H NMR (CDCl$_3$) δ 7.29-7.34 (m, 1H), 7.20-7.28 (m, 2H), 4.62 (t, J=5.6 Hz, 1H), 3.61-3.70 (m, 2H), 3.48-3.57 (m, 2H), 3.07 (d, J=5.6 Hz, 2H), 1.18 (t, J=7.1 Hz, 6H).

(B) To a solution of (4-bromo-2-fluorophenyl)(2,2-diethoxyethyl)sulfane (7.84 g, 24.3 mmol) in toluene (60 mL) was added polyphosphoric acid (26.4 g, 243 mmol) and the mixture was refluxed for 4 h. The mixture was poured into ice-water, stirred for 30 min and extracted with toluene. The combined organic extracts were washed successively with aq. NaHCO$_3$ and brine, dried (Na$_2$SO$_4$) and concentrated under reduced pressure. The resultant residue was purified by silica gel chromatography (2-8% EtOAc/heptanes) to afford 5-bromo-7-fluorobenzo[b]thiophene (1.05 g, 18.7% yield). $^1$H NMR (CDCl$_3$) δ 7.77 (s, 1H), 7.52 (d, J=5.6 Hz, 1H), 7.28-7.32 (m, 1H), 7.20 (d, J=9.1 Hz, 1H).

(C) 7-Fluorobenzo[b]thiophene-5-carbonitrile was prepared from 5-bromo-7-fluorobenzo[b]thiophene following the procedure described in Example 67C. $^1$H NMR (CDCl$_3$) δ 7.97 (s, 1H), 7.66 (d, J=5.1 Hz, 1H), 7.43-7.48 (m, 1H), 7.27 (d, J=9.1 Hz, 1H).

(D) To a solution of 7-fluorobenzo[b]thiophene-5-carbonitrile (200 mg, 1.13 mmol) in AcOH (4 mL) was added Br$_2$ (198 mg, 1.24 mmol) in drop-wise fashion. The mixture was stirred at 90° C. overnight, and was then concentrated under reduced pressure. The resulting residue was purified by silica gel chromatography (3-15% EtOAc/heptanes) to afford compound A: 3-bromo-7-fluorobenzo[b]thiophene-5-carbonitrile (89 mg, 30.8% yield) and compound B: 3-bromo-7-fluorobenzo[b]thiophene-5-carboxamide (100 mg, 32% yield). Compound A: $^1$H NMR (CDCl$_3$) δ 7.97 (s, 1H), 7.65 (s, 1H), 7.36 (d, J=9.1 Hz, 1H). Compound B: LC/MS: mass calcd. for C$_9$H$_5$BrFNOS: 272.93, found: 273.9 [M+H]$^+$.

(E) 7-Fluoro-3-(2-methylphenyl)benzo[b]thiophene-5-carbonitrile was prepared from 3-bromo-7-fluorobenzo[b]thiophene-5-carbonitrile and 2-methylphenylboronic acid following General Procedure A, using PdCl$_2$(PPh$_3$)$_2$ as the palladium catalyst and Na$_2$CO$_3$ as the base. LC/MS: mass calcd. for C$_{16}$H$_{10}$FNS: 267.05, found: 268.0 [M+H]$^+$.

(F) To a cooled (−78° C.) solution of 7-fluoro-3-(2-methylphenyl)benzo[b]thiophene-5-carbonitrile (90 mg, 0.71 mmol) in DCM (5 mL) under an inert nitrogen atmosphere was added diisobutylaluminum hydride (1 M in toluene; 0.71 mL, 0.71 mmol) in a drop-wise fashion. After stirring at −78° C. for 1 h and then at rt for an additional hour, the reaction was quenched with 2N aq HCl and extracted with DCM. The combined organic extracts were dried (MgSO$_4$) and concentrated under reduced pressure. The resultant residue was re-dissolved in EtOH (3 mL) and treated with NaBH$_4$ (25 mg, 0.67 mmol). After stirring at rt for 3 d, the reaction was quenched by the addition of water and 1N aq HCl. The mixture was extracted with DCM and the combined organic extracts were dried (MgSO$_4$) and concentrated under reduced pressure. The residue thus obtained was purified by silica gel chromatography (15-30% EtOAc/heptanes) to afford (7-fluoro-3-(2-methylphenyl) benzo[b]thiophen-5-yl)methanol (31 g, 33.8%). LC/MS: mass calcd. for C$_{16}$H$_{13}$FOS: 272.07, found: 255.1 [M−OH]$^+$.

(G) (2S)-3-(5-(2-(4-((7-Fluoro-3-(2-methylphenyl)benzo[b]thiophen-5-yl)methoxy)phenyl)pent-3-yn-1-yl)-1H-tetrazol-1-yl)propanenitrile was prepared from (7-fluoro-3-(2-methylphenyl)benzo[b]thiophen-5-yl)methanol and (2S)-3-(5-(2-(4-hydroxyphenyl)pent-3-yn-1-yl)-1H-tetrazol-1-yl)propanenitrile (from Example 37D) following the General Procedure B, using ADDP and Bu$_3$P, at a reaction temperature of 60° C. for 3 h. LC/MS: mass calcd. for C$_{31}$H$_{26}$FN$_5$OS: 535.18, found: 536.2 [M+H]$^+$.

(H) (2S)-5-(2-(4-((7-Fluoro-3-(2-methylphenyl)benzo[b]thiophen-5-yl)methoxy)phenyl)pent-3-yn-1-yl)-1H-tetrazole (Cpd 69) was prepared from (2S)-3-(5-(2-(4-((7-fluoro-3-(2-methylphenyl)benzo[b]thiophen-5-yl)methoxy) phenyl)pent-3-yn-1-yl)-1H-tetrazol-1-yl)propanenitrile following the procedure described in Example 67I. $^1$H NMR (CDCl$_3$) δ 7.21-7.38 (m, 8H), 7.18 (d, J=10.1 Hz, 1H), 6.87 (d, J=8.6 Hz, 2H), 5.05 (s, 2H), 4.07 (br. s, 1H), 3.40-3.48 (m, 1H), 3.32-3.40 (m, 1H), 2.14 (s, 3H), 1.86 (s, 3H). LC/MS: mass calcd. for C$_{28}$H$_{23}$FN$_4$OS: 482.16, found: 483.3 [M+H]$^+$.

Example 70

(2S)-5-(2-(4-((7-Fluoro-3-(4-methoxy-2-methylphenyl)benzo[b]thiophen-5-yl)methoxy)phenyl)pent-3-yn-1-yl)-1H-tetrazole, Cpd 70

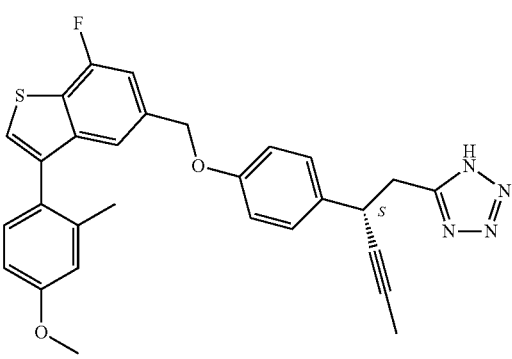

(A) 7-Fluoro-3-(4-methoxy-2-methylphenyl)benzo[b]thiophene-5-carboxamide was prepared from 3-bromo-7-fluorobenzo[b]thiophene-5-carboxamide (from Example 69D, Compound B) and 4-methoxy-2-methylphenylboronic acid following General Procedure A, using PdCl$_2$(PPh$_3$)$_2$ as the palladium catalyst and Na$_2$CO$_3$ as the base. LC/MS: mass calcd. for C$_{17}$R$_4$FNO$_2$S: 315.07, found: 316.0 [M+H]$^+$.

(B) Di-tert-butyl (7-fluoro-3-(4-methoxy-2-methylphenyl)benzo[b]thiophene-5-carbonyl)dicarbamate was prepared from 7-fluoro-3-(4-methoxy-2-methylphenyl)benzo[b]thiophene-5-carboxamide following the procedure described in Example 67F. $^1$H NMR (CDCl$_3$) δ: 7.70 (s, 1H), 7.51 (d, J=10.1 Hz, 1H), 7.38 (s, 1H), 7.15 (d, J=8.1 Hz, 1H), 6.89 (d, J=2.0 Hz, 1H), 6.83 (dd, J=8.6, 2.5 Hz, 1H), 3.88 (s, 3H), 2.12 (s, 3H), 1.37 (s, 18H).

(C) (7-Fluoro-3-(4-methoxy-2-methylphenyl)benzo[b]thiophen-5-yl)methanol was prepared from di-tert-butyl (7-fluoro-3-(4-methoxy-2-methylphenyl)benzo[b]thiophene-5-carbonyl)dicarbamate following the procedure described in Example 67G. LC/MS: mass calcd. for C$_{17}$H$_{15}$FO$_2$S: 302.08, found: 285.1 [M−OH]$^+$.

(D) (2S)-3-(5-(2-(4-((7-Fluoro-3-(4-methoxy-2-methylphenyl)benzo[b]thiophen-5-yl)methoxy)phenyl)pent-3-yn-1-yl)-1H-tetrazol-1-yl)propanenitrile was prepared from (7-fluoro-3-(4-methoxy-2-methylphenyl)benzo[b]thiophen-5-yl)methanol and (2S)-3-(5-(2-(4-hydroxyphenyl)pent-3-yn-1-yl)-1H-tetrazol-1-yl)propanenitrile (from Example 37D) following the General Procedure B, using ADDP and Bu$_3$P, at a reaction temperature of 60° C. for 3 h. LC/MS: mass calcd. for C$_{32}$H$_{28}$FN$_5$O$_2$S: 565.19, found: 566.2 [M+H]$^+$.

(E) (2S)-5-(2-(4-((7-Fluoro-3-(4-methoxy-2-methylphenyl)benzo[b]thiophen-5-yl)methoxy)phenyl)pent-3-yn-1-yl)-1H-tetrazole (Cpd 70) was prepared from (2S)-3-(5-(2-(4-((7-fluoro-3-(4-methoxy-2-methylphenyl)benzo[b]thiophen-5-yl)methoxy)phenyl)pent-3-yn-1-yl)-1H-tetrazol-1-yl)propanenitrile following the procedure described in Example 67I. $^1$H NMR (CDCl$_3$) δ 7.29 (s, 1H), 7.21-7.25 (m, 3H), 7.13-7.21 (m, 2H), 6.84-6.90 (m, 3H), 6.82 (dd, J=8.1, 2.5 Hz, 1H), 5.04 (s, 2H), 4.08 (ddd, J=8.3, 5.8, 2.5 Hz, 1H), 3.86 (s, 3H), 3.32-3.46 (m, 2H), 2.12 (s, 3H), 1.82 (d, J=2.5 Hz, 3H). LC/MS: mass calcd. for C$_{29}$H$_{25}$FN$_4$O$_2$S: 512.17, found: 513.2 [M+H]$^+$.

BIOLOGICAL EXAMPLES

In Vitro Assay

GPR40 Calcium Flux Assay

Compounds were tested in a calcium flux assay using transfected HEK293 cells stably expressing either human GPR40 or rat GPR40. Human GPR40 expressing cells were cultured in DMEM-High Glucose media supplemented with 10% fetal bovine serum, 1× L-Glutamine, 1× Penicillin/Streptomycin and 500 μg/mL G418. Rat GPR40 expressing cells were cultured in DMEM-High Glucose media supplemented with 10% fetal bovine serum and 1 μg/mL puromycin. Cells were plated into poly-D-lysine coated 384-well plates and cultured overnight in a 37° C. humidified tissue culture incubator under 5% CO$_2$/90% O$_2$ atmosphere. On the day of the experiment, the culture media was replaced with assay buffer (HBSS, 20 mM HEPES, 0.1% BSA) and the cells incubated at 37° C. for 1 h. Calcium-sensitive fluorescent dye (Fluo 8 No-Wash Calcium Dye, ABD Bioquest) was then added and the cells incubated for another 30 min at 37° C. followed by 15 min at room temperature while protected from the light. The cell plate and a plate of diluted compounds of Formula (I) were loaded into a fluorescent plate reader that added compounds onto the cells while measuring the fluorescence intensity of each well. The plate reader recorded fluorescence intensity at 1 second intervals for 8 min and provided the data for analysis in an Excel format. $EC_{50}$ values were calculated using Prism (GraphPad) software. Resultant mean data are shown in Table 2.

TABLE 2

$Ca^{2+}$ Mobilization Data

| Cpd No | hGPR40 $Ca^{2+}$ Assay $EC_{50}$ (μM) |
|---|---|
| 1 | 0.002 |
| 2 | 0.02; 0.013 |
| 3 | 0.022; 0.008 |
| 4 | 0.02 |
| 5 | 0.065 |
| 6 | 0.19 |
| 7 | 0.17 |
| 8 | 0.009 |
| 9 | 0.27 |
| 10 | 0.054 |
| 11 | 0.088 |
| 12 | 0.028; 0.03 |
| 13 | 0.013 |
| 14 | 0.13 |
| 15 | 0.085 |
| 16 | 0.023 |
| 17 | 0.097 |
| 18 | 0.08 |
| 19 | 0.028 |
| 20 | 0.024 |
| 21 | 0.051 |
| 22 | 0.067 |
| 23 | 1.74 |
| 24 | 0.55 |
| 25 | 0.037 |
| 26 | 0.034 |
| 27 | 0.061 |
| 28 | 0.027 |
| 29 | 0.42 |
| 30 | 0.43 |
| 31 | 0.029 |
| 32 | 0.011 |
| 33 | 0.008 |
| 34 | 0.019 |
| 35 | 0.028 |
| 36 | 0.015 |
| 37 | 0.59 |
| 38 | 0.016 |
| 39 | 0.67 |
| 40 | 0.058 |
| 41 | 0.019 |
| 42 | 0.12 |
| 43 | 0.13 |
| 44 | 0.018 |
| 45 | 0.039 |
| 46 | 0.047 |
| 47 | 0.013 |
| 48 | 0.083 |
| 49 | 0.010 |
| 50 | 0.052 |
| 51 | 0.003 |
| 52 | 0.001 |
| 53 | 0.17 |
| 54 | 0.18 |
| 55 | 0.11 |
| 56 | 0.054 |
| 57 | 0.86 |

TABLE 2-continued $Ca^{2+}$ Mobilization Data

| Cpd No | hGPR40 $Ca^{2+}$ Assay $EC_{50}$ (μM) |
|---|---|
| 58 | 0.1 |
| 59 | 0.13 |
| 60 | 0.11 |
| 61 | 0.034 |
| 62 | 0.91 |
| 63 | 0.13 |
| 64 | 0.33 |
| 65 | 0.44 |
| 66 | 1.12 |
| 67 | 0.063 |
| 68 | 0.025 |
| 69 | 0.023 |
| 70 | 0.01 |

In-Vivo Assay

Oral Glucose Tolerance Test

Male SD rats (200-250 g) were housed 2 per cage in a temperature-controlled room with a 12-hour light/dark cycle. They were allowed ad libitum access to water and fed with normal rodent chow. The night before the oral glucose tolerance test (oGTT), the rats were transferred to clean cages and fasted overnight. On the morning of the oGTT, the rats were weighed and randomized into groups based on fasted blood glucose and body weight. Rats were dosed with vehicle (0.5% methocel) or compounds (10 mg/kg, po) thirty to forty min prior to the oGTT (glucose, 2 g/kg, po). Blood was collected from the tail vein at 0, 10, 30, 60 and 120 minutes after glucose challenge to measure blood glucose; plasma was used to determine insulin levels. The area under the curve for blood glucose excursion was calculated from t=0 to t=120 minutes. Percent lowering of glucose was calculated from the AUC data with respect to the vehicle-treated group. Resultant data are shown in Table 3.

TABLE 3

| Cpd No. | Percent Lowering of Glucose (AUC compound vs. AUC Vehicle) |
|---|---|
| 1 | 81% |
| 12 | 101% |
| 16 | 105% |
| 44 | 91% |
| 47 | 91% |

Note:
AUC = Integrated area under the glucose excursion curve from t = 0 to t = 120 minutes.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

What is claimed is:

1. A compound of Formula (I)

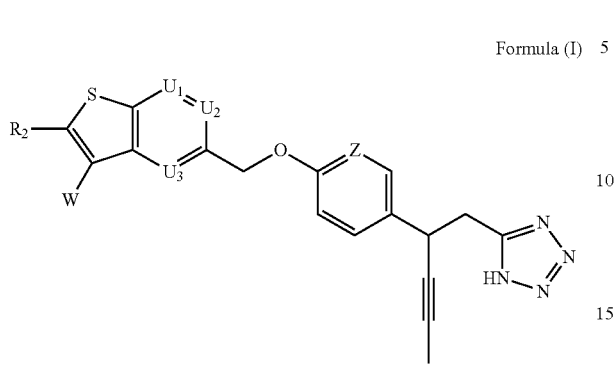

Formula (I)

wherein
U₁ is N or C(R₁), wherein R₁ is selected from the group consisting of hydrogen, fluoro, chloro, or methyl;
U₂ and U₃ are independently selected from CH or N, such that only up to one of U₁, U₂, and U₃ is N in any instance;
R₂ is selected from the group consisting of hydrogen, methyl, chloro, fluoro, bromo, iodo, trifluoromethyl, cyano, and C₁₋₄alkylsulfonyl;
W is selected from the group consisting of
i) hydrogen;

ii) 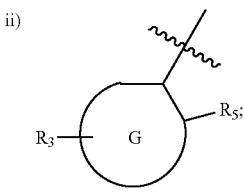

wherein ring G is selected from the group consisting of phenyl, pyridyl, pyrazinyl, and pyrimidinyl; and, when ring G is phenyl, substituents R₃ and R₅ are optionally taken together with the atoms to which they are attached to form an unsubstituted or substituted bicyclic ring system selected from
dihydrobenzo[b][1,4]dioxin-5-yl, 2,2,-dimethylchroman-5-yl, or (1-ethylcarboxy-indolin-4-yl);
wherein R₃ is selected from the group consisting of hydrogen, chloro, C₁₋₄alkyl, 1,1-dioxidotetrahydro-2H-thiopyran-4-yl, 1,1-dioxido-3,6-dihydro-2H-thiopyran-4-yl, C₁₋₃alkylsulfonyl, C₁₋₃alkylsulfonylamino, and —OR₄;
wherein R₄ is
i) C₁₋₈alkyl optionally independently substituted with one or two C₁₋₃alkoxy or hydroxy substituents;
ii) 4-hydroxy-1,1-dioxidotetrahydro-2H-thiopyran-4-ylmethyl;
iii) 1,1-dioxidotetrahydro-2H-thiopyran-4-yl;
iv) tetrahydro-2H-pyran-4-yl;
v) C₁₋₃alkylsulfonylpropyl;
or
vi) (3-methyl-1,1-dioxidothietan-3-yl)methyl;
wherein R₅ is methyl, bromo, chloro, or trifluoromethyl;

iii) C₃₋₈cycloalkyl;

iv) 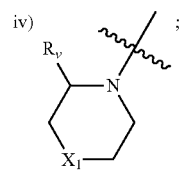

wherein X₁ is selected from the group consisting of CH₂, O, S, NH, and N(C₁₋₄alkyl); and wherein R_v is hydrogen or methyl;

v) 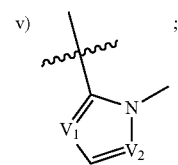

wherein V₁ and V₂ are independently selected from CH or N;
and
vi) C₁₋₆alkyl;
Z is CH or N;
or an enantiomer, diastereomer, or pharmaceutically acceptable salt form thereof.

2. The compound of claim 1 wherein U₁ is N or C(R₁), wherein R₁ is hydrogen, fluoro, or chloro.

3. The compound of claim 1 wherein U₂ and U₃ are independently selected from CH or N, such that only up to one of U₁, U₂, and U₃ is N in any instance.

4. The compound of claim 3 wherein U₂ is independently selected from CH or N; and U₃ is CH, such that only one of U₁ and U₂ is N in any instance.

5. The compound of claim 1 wherein R₂ is selected from the group consisting of hydrogen, chloro, fluoro, bromo, iodo, methyl, methanesulfonyl, trifluoromethyl, and cyano.

6. The compound of claim 5 wherein R₂ is selected from the group consisting of hydrogen, methyl, chloro, fluoro, bromo, iodo, trifluoromethyl, and cyano.

7. The compound of claim 6 wherein R₂ is selected from the group consisting of hydrogen, chloro, fluoro, bromo, trifluoromethyl, and cyano.

8. The compound of claim 1 wherein W is selected from the group consisting of i) 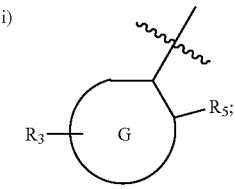

wherein ring G is selected from the group consisting of phenyl, pyridyl, and pyrimidinyl; and, when ring G is phenyl, substituents R₃ and R₅ are optionally taken together with the atoms to which they are attached to form an unsubstituted or substituted bicyclic ring system selected from dihydrobenzo[b][1,4]dioxin-5-yl, or (1-ethylcarboxy-indolin-4-yl);

wherein R₃ is selected from the group consisting of hydrogen, chloro, $C_{1-4}$alkyl, 1,1-dioxido-3,6-dihydro-2H-thiopyran-4-yl, and —OR₄;
wherein R₄ is
i) $C_{1-8}$alkyl independently substituted with one or two $C_{1-3}$alkoxy or hydroxy substituents;
ii) 1,1-dioxidotetrahydro-2H-thiopyran-4-yl;
iii) $C_{1-3}$alkylsulfonylpropyl; or
iv) (3-methyl-1,1-dioxidothietan-3-yl)methyl;
  wherein R₅ is methyl, bromo, chloro, or trifluoromethyl;
ii) $C_{5-8}$cycloalkyl;

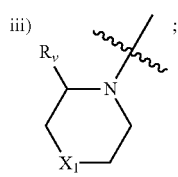

wherein X₁ is selected from the group consisting of CH₂, O, S, NH, and N($C_{1-4}$alkyl); and wherein $R_\nu$ is hydrogen or methyl;

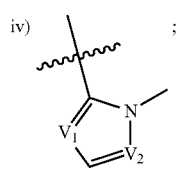

wherein V₁ and V₂ are independently selected from CH or N; and
v) $C_{1-6}$alkyl.

9. The compound of claim 8 wherein W is selected from the group consisting of

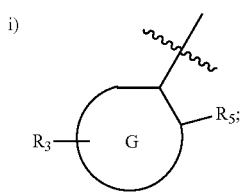

wherein ring G is selected from the group consisting of phenyl, pyridyl, and pyrimidinyl; and, when ring G is phenyl, substituents R₃ and R₅ are optionally taken together with the atoms to which they are attached to form an unsubstituted or substituted bicyclic ring system selected from dihydrobenzo[b][1,4]dioxin-5-yl, or (1-ethylcarboxy-indolin-4-yl);
  wherein R₃ is selected from the group consisting of hydrogen, chloro, $C_{1-4}$alkyl, 1,1-dioxido-3,6-dihydro-2H-thiopyran-4-yl, and —OR₄;
  wherein R₄ is
  i) $C_{1-6}$alkyl independently substituted with one or two $C_{1-3}$alkoxy substituents;

ii) 1,1-dioxidotetrahydro-2H-thiopyran-4-yl;
iii) $C_{1-3}$alkylsulfonylpropyl; or
iv) (3-methyl-1,1-dioxidothietan-3-yl)methyl;
  wherein R₅ is methyl, bromo, chloro, or trifluoromethyl;

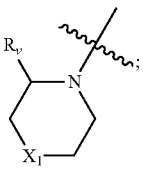

wherein X₁ is selected from the group consisting of CH₂, O, S, NH, and N($C_{1-4}$alkyl); and wherein $R_\nu$ is hydrogen or methyl;
and

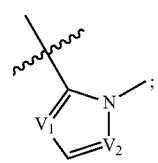

wherein V₁ is independently selected from CH or N, and V₂ is CH.

10. The compound of claim 9 wherein W is selected from the group consisting of

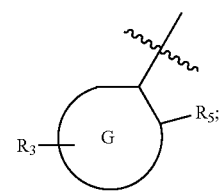

wherein ring G is selected from the group consisting of phenyl and pyridyl; and, when ring G is phenyl, substituents R₃ and R₅ are optionally taken together with the atoms to which they are attached to form (1-ethylcarboxy-indolin-4-yl);
  wherein R₃ is selected from the group consisting of hydrogen, and —OR₄;
  wherein R₄ is
  i) $C_{1-6}$alkyl independently substituted with one or two $C_{1-3}$alkoxy substituents;
  ii) $C_{1-3}$alkylsulfonylpropyl; or
  iii) (3-methyl-1,1-dioxidothietan-3-yl)methyl;
  wherein R₅ is methyl, bromo, chloro, or trifluoromethyl.

11. The compound of claim 1 wherein W is selected from the group consisting of 2-methylphenyl, 2-bromophenyl, 2-chloro-5-methylpyridin-4-yl, 2-methyl-4-(4-hydroxy-1,1-dioxidotetrahydro-2H-thiopyran-4-yl)methoxyphenyl, 2-methyl-4-(3-methyl-3-hydroxybutoxy)phenyl, 2-methyl-4-(2-methoxyethoxy)phenyl, 2-methyl-4-(tetrahydro-2H-pyran-4-yloxy)phenyl, 2-methyl-3-(2-methoxyethoxy)phenyl, 2-methylpyridin-3-yl, 2-methyl-4-(3-methyl-1,1-dioxidothietan-3-yl)methoxy)phenyl, 2-trifluoromethylphenyl, 2-methyl-4-(methyl sulfonyl)phenyl, 2-methyl-5-(2-methoxyethoxy)phenyl, 2-methyl-4-(3-methanesulfonylpropyloxy)phenyl, 2-methyl-4-(1,1-dioxidotetrahydro-2H-thiopyran-4-yl)phenyl, 2-methyl-4-(1,1-dioxidotetrahydro-2H-thiopyran-4-yloxy)phenyl, 2,6-dimethylphenyl, 2-(2-methoxyethoxy)-4-methylpyridin-5-yl, 1-methyl-1H-pyrazol-5-yl, 1-methyl-1H-1,2,4-triazol-5-yl, 4-methylpyrimidin-5-yl, 5-(2-methoxyethoxy)-3-methylpyridin-2-yl, dihydrobenzo[b][1,4]dioxin-5-yl, 1-(ethylcarboxy)-indolin-4-yl, 2-methyl-5-(methanesulfonylamino)phenyl, 2,2,-dimethylchroman-5-yl, 2-methyl-4-(2,3-dihydroxy-propyloxy)phenyl, 2-chlorophenyl, 5-(2-methoxyethoxy)-2-methylpyridin-3-yl, cyclopropyl, cyclohexyl, cyclopentyl, isopropyl, 2-methylpiperidin-1-yl, 2-methyl-4-methoxyphenyl, n-propyl, hydrogen, and n-butyl.

12. A compound of Formula (I)

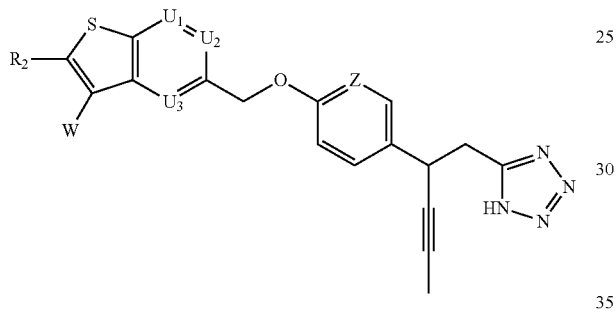

Formula (I)

wherein
- $U_1$ is N or $C(R_1)$, wherein $R_1$ is hydrogen, fluoro, or chloro;
- $U_2$ and $U_3$ are independently selected from CH or N, such that only up to one of $U_1$, $U_2$, and $U_3$ is N in any instance;
- $R_2$ is selected from the group consisting of hydrogen, methyl, chloro, fluoro, bromo, iodo, trifluoromethyl, and cyano;
- W is selected from the group consisting of i)

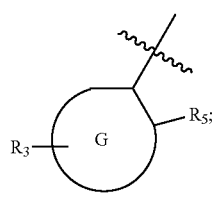

wherein ring G is selected from the group consisting of phenyl, pyridyl, and pyrimidinyl; and, when ring G is phenyl, substituents $R_3$ and $R_5$ are optionally taken together with the atoms to which they are attached to form an unsubstituted or substituted bicyclic ring system selected from dihydrobenzo[b][1,4]dioxin-5-yl, or (1-ethylcarboxy-indolin-4-yl);
wherein $R_3$ is selected from the group consisting of hydrogen, chloro, $C_{1-4}$alkyl, 1,1-dioxido-3,6-dihydro-2H-thiopyran-4-yl, and —$OR_4$;

wherein $R_4$ is
- i) $C_{1-8}$alkyl independently substituted with one or two $C_{1-3}$alkoxy or hydroxy substituents;
- ii) 1,1-dioxidotetrahydro-2H-thiopyran-4-yl;
- iii) $C_{1-3}$ alkylsulfonylpropyl;
  or
- iv) (3-methyl-1,1-dioxidothietan-3-yl)methyl;
wherein $R_5$ is methyl, bromo, chloro, or trifluoromethyl;
ii) $C_{5-8}$cycloalkyl;

iii)

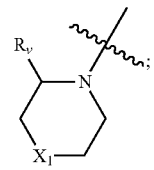

wherein $X_1$ is selected from the group consisting of $CH_2$, O, S, NH, and $N(C_{1-4}$alkyl); and wherein $R_y$ is hydrogen or methyl;

iv)

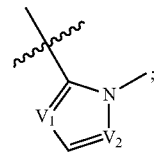

wherein $V_1$ and $V_2$ are independently selected from CH or N;
and
v) $C_{1-6}$alkyl;
Z is CH or N;
or an enantiomer, diastereomer, or pharmaceutically acceptable salt form thereof.

13. A compound of Formula (I)

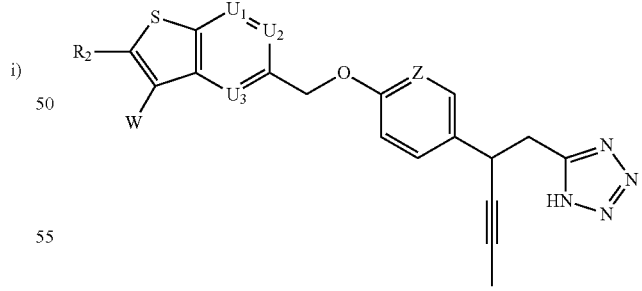

Formula (I)

wherein
- $U_1$ is N or $C(R_1)$, wherein $R_1$ is hydrogen, fluoro, or chloro;
- $U_2$ is independently selected from CH or N;
- $U_3$ is CH, such that only one of $U_1$ and $U_2$ is N in any instance;
- $R_2$ is selected from the group consisting of hydrogen, methyl, chloro, fluoro, bromo, iodo, trifluoromethyl, and cyano;

W is selected from the group consisting of

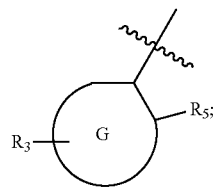

wherein ring G is selected from the group consisting of phenyl, pyridyl, and pyrimidinyl; and, when ring G is phenyl, substituents $R_3$ and $R_5$ are optionally taken together with the atoms to which they are attached to form an unsubstituted or substituted bicyclic ring system selected from dihydrobenzo[b][1,4]dioxin-5-yl, or (1-ethylcarboxy-indolin-4-yl);

wherein $R_3$ is selected from the group consisting of hydrogen, chloro, $C_{1-4}$alkyl, 1,1-dioxido-3,6-dihydro-2H-thiopyran-4-yl, and —$OR_4$;

wherein $R_4$ is ii) $C_{1-6}$alkyl independently substituted with one or two $C_{1-3}$alkoxy substituents;

iii) 1,1-dioxidotetrahydro-2H-thiopyran-4-yl;

iv) $C_{1-3}$alkylsulfonylpropyl;

or v) (3-methyl-1,1-dioxidothietan-3-yl)methyl;

wherein $R_5$ is methyl, bromo, chloro, or trifluoromethyl;

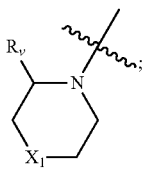

wherein $X_1$ is selected from the group consisting of $CH_2$, O, S, NH, and $N(C_{1-4}alkyl)$; and wherein $R_v$ is hydrogen or methyl;

and

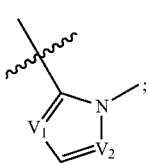

wherein $V_1$ is independently selected from CH or N, and $V_2$ is CH;

Z is CH or N;

or an enantiomer, diastereomer, or pharmaceutically acceptable salt form thereof.

14. A compound of Formula (I)

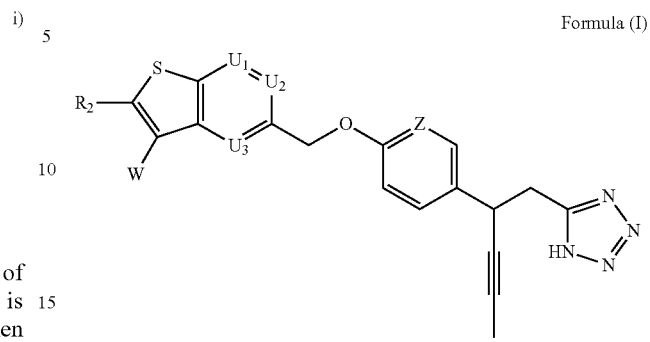

Formula (I)

wherein $U_1$ is N or $C(R_1)$, wherein $R_1$ is hydrogen, fluoro, or chloro;

$U_2$ is independently selected from CH or N;

$U_3$ is CH, such that only one of $U_1$ and $U_2$ is N in any instance;

$R_2$ is selected from the group consisting of hydrogen, chloro, fluoro, bromo, trifluoromethyl, and cyano;

W is selected from the group consisting of

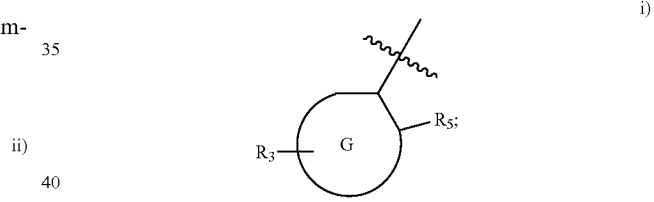

wherein ring G is selected from the group consisting of phenyl and pyridyl; and, when ring G is phenyl, substituents $R_3$ and $R_5$ are optionally taken together with the atoms to which they are attached to form (1-ethylcarboxy-indolin-4-yl);

wherein $R_3$ is selected from the group consisting of hydrogen, and —$OR_4$;

wherein $R_4$ is i) $C_{1-6}$alkyl independently substituted with one or two $C_{1-3}$alkoxy substituents;

ii) $C_{1-3}$alkylsulfonylpropyl;

or iii) (3-methyl-1,1-dioxidothietan-3-yl)methyl;

wherein $R_5$ is methyl, bromo, chloro, or trifluoromethyl;

Z is CH or N;

or an enantiomer, diastereomer, or pharmaceutically acceptable salt form thereof.

15. A compound of Formula (I)

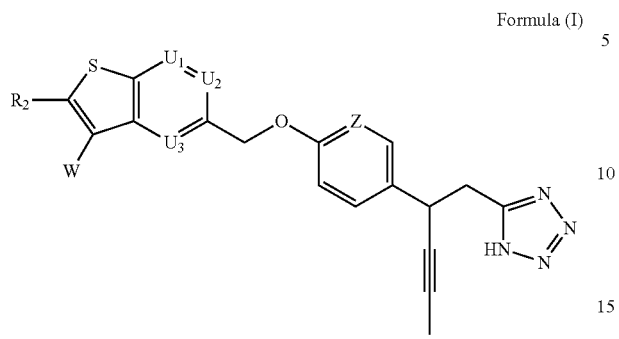

Formula (I)

wherein
- $U_1$ is N or $C(R_1)$, wherein $R_1$ is hydrogen, methyl, fluoro, or chloro;
- $U_2$ is independently selected from CH or N;
- $U_3$ is CH or N, such that only one of $U_1$ and $U_2$ is N in any instance;
- $R_2$ is selected from the group consisting of hydrogen, chloro, fluoro, bromo, iodo, methyl, methanesulfonyl, trifluoromethyl, and cyano;
- W is selected from the group consisting of 2-methylphenyl, 2-bromophenyl, 2-chloro-5-methylpyridin-4-yl, 2-methyl-4-(4-hydroxy-1,1-dioxidotetrahydro-2H-thiopyran-4-yl)methoxyphenyl, 2-methyl-4-(3-methyl-3-hydroxybutoxy)phenyl, 2-methyl-4-(2-methoxyethoxy)phenyl, 2-methyl-4-(tetrahydro-2H-pyran-4-yloxy)phenyl, 2-methyl-3-(2-methoxyethoxy)phenyl, 2-methylpyridin-3-yl, 2-methyl-4-(3-methyl-1,1-dioxidothietan-3-yl)methoxy)phenyl, 2-trifluoromethylphenyl, 2-methyl-4-(methyl sulfonyl)phenyl, 2-methyl-5-(2-methoxyethoxy)phenyl, 2-methyl-4-(3-methanesulfonylpropyloxy)phenyl, 2-methyl-4-(1,1-dioxidotetrahydro-2H-thiopyran-4-yl)phenyl, 2-methyl-4-(1,1-dioxidotetrahydro-2H-thiopyran-4-yloxy)phenyl, 2,6-dimethylphenyl, 2-(2-methoxyethoxy)-4-methylpyridin-5-yl, 1-methyl-1H-pyrazol-5-yl, 1-methyl-1H-1,2,4-triazol-5-yl, 4-methylpyrimidin-5-yl, 5-(2-methoxyethoxy)-3-methylpyridin-2-yl, dihydrobenzo[b][1,4]dioxin-5-yl, 1-(ethylcarboxy)-indolin-4-yl, 2-methyl-5-(methanesulfonylamino)phenyl, 2,2,-dimethylchroman-5-yl, 2-methyl-4-(2,3-dihydroxy-propyloxy)phenyl, 2-chlorophenyl, 5-(2-methoxyethoxy)-2-methylpyridin-3-yl, cyclopropyl, cyclohexyl, cyclopentyl, isopropyl, 2-methylpiperidin-1-yl, 2-methyl-4-methoxyphenyl, n-propyl, hydrogen, and n-butyl;
- Z is CH or N;

or an enantiomer, diastereomer, or pharmaceutically acceptable salt form thereof.

16. A compound of Formula (I)

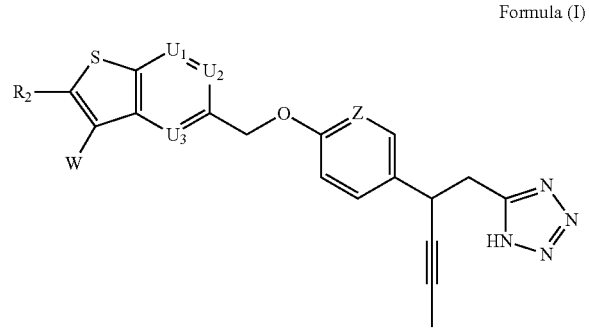

Formula (I)

selected from the group consisting of
- (2S)-5-(2-(4-((3-(2-Methylphenyl)benzo[b]thiophen-5-yl)methoxy)phenyl)pent-3-yn-1-yl)-1H-tetrazole;
- 5-((2S)-2-(4-((2-Chloro-3-(2-methylphenyl)benzo[b]thiophen-5-yl)methoxy)phenyl)pent-3-ynyl)-1H-tetrazole;
- 5-((2S)-2-(4-((2-Fluoro-3-(2-methylphenyl)benzo[b]thiophen-5-yl)methoxy)phenyl)pent-3-ynyl)-1H-tetrazole;
- (2S)-5-(2-(4-((3-(2-Bromophenyl)benzo[b]thiophen-5-yl)methoxy)phenyl)pent-3-yn-1-yl)-1H-tetrazole;
- (2S)-4-(5-((4-(1-(1H-tetrazol-5-yl)pent-3-yn-2-yl)phenoxy)methyl)benzo[b]thiophen-3-yl)-2-chloro-5-methylpyridine;
- (2S)-4-((4-(5-((4-(1-(1H-Tetrazol-5-yl)pent-3-yn-2-yl)phenoxy)methyl)benzo[b]thiophen-3-yl)-3-methylphenoxy)methyl)-4-hydroxytetrahydro-2H-thiopyran 1,1-dioxide;
- (2S)-4-(4-(5-((4-(1-(1H-Tetrazol-5-yl)pent-3-yn-2-yl)phenoxy)methyl)benzo[b]thiophen-3-yl)-3-methylphenoxy)-2-methylbutan-2-ol;
- (2S)-5-(2-(4-((3-(4-(2-Methoxyethoxy)-2-methylphenyl)benzo[b]thiophen-5-yl)methoxy)phenyl)pent-3-yn-1-yl)-1H-tetrazole;
- (2S)-5-(2-(4-((3-(2-Methyl-4-((tetrahydro-2H-pyran-4-yl)oxy)phenyl)benzo[b]thiophen-5-yl)methoxy)phenyl)pent-3-yn-1-yl)-1H-tetrazole;
- (2S)-5-(2-(4-((3-(3-(2-Methoxyethoxy)-2-methylphenyl)benzo[b]thiophen-5-yl)methoxy)phenyl)pent-3-yn-1-yl)-1H-tetrazole;
- (2S)-3-(5-((4-(1-(1H-Tetrazol-5-yl)pent-3-yn-2-yl)phenoxy)methyl)benzo[b]thiophen-3-yl)-2-methylpyridine;
- (2S)-3-((4-(5-((4-(1-(1H-Tetrazol-5-yl)pent-3-yn-2-yl)phenoxy)methyl)benzo[b]thiophen-3-yl)-3-methylphenoxy)methyl)-3-methylthietane 1,1-dioxide;
- (2S)-5-(2-(4-((3-(2-(Trifluoromethyl)phenyl)benzo[b]thiophen-5-yl)methoxy)phenyl)pent-3-yn-1-yl)-1H-tetrazole;
- (2S)-5-(2-(4-((3-(2-Methyl-4-(methylsulfonyl)phenyl)benzo[b]thiophen-5-yl)methoxy)phenyl)pent-3-yn-1-yl)-1H-tetrazole;
- (2S)-5-(2-(4-((3-(5-(2-Methoxyethoxy)-2-methylphenyl)benzo[b]thiophen-5-yl)methoxy)phenyl)pent-3-yn-1-yl)-1H-tetrazole;
- (2S)-5-(2-(4-((3-(2-Methyl-4-(3-(methylsulfonyl)propoxy)phenyl)benzo[b]thiophen-5-yl)methoxy)phenyl)pent-3-yn-1-yl)-1H-tetrazole;
- (2S)-4-(4-(5-((4-(1-(1H-Tetrazol-5-yl)pent-3-yn-2-yl)phenoxy)methyl)benzo[b]thiophen-3-yl)-3-methylphenyl)tetrahydro-2H-thiopyran 1,1-dioxide;

4-(4-(5-((4-((2S)-1-(1H-Tetrazol-5-yl)pent-3-yn-2-yl)
phenoxy)methyl)-2-methylbenzo[b]thiophen-3-yl)-3-
methylphenoxy)tetrahydro-2H-thiopyran 1,1-dioxide;
5-((2S)-2-(4-((2-Methyl-3-(2-methylphenyl)benzo[b]
thiophen-5-yl)methoxy)phenyl)pent-3-ynyl)-1H-tetra-
zole;
(2S)-5-(2-(4-((3-(2,6-Dimethylphenyl)benzo[b]thiophen-
5-yl)methoxy)phenyl)pent-3-yn-1-yl)-1H-tetrazole;
(2S)-5-(5-((4-(1-(1H-Tetrazol-5-yl)pent-3-yn-2-yl)phe-
noxy)methyl)benzo[b]thiophen-3-yl)-2-(2-methoxy-
ethoxy)-4-methylpyridine;
(2S)-5-(2-(4-((3-(1-Methyl-1H-pyrazol-5-yl)benzo[b]
thiophen-5-yl)methoxy)phenyl)pent-3-yn-1-yl)-1H-
tetrazole;
(2S)-5-(2-(4-((3-(1-Methyl-1H-1,2,4-triazol-5-yl)benzo
[b]thiophen-5-yl)methoxy)phenyl)pent-3-yn-1-yl)-1H-
tetrazole;
(2S)-2-(5-((4-(1-(1H-Tetrazol-5-yl)pent-3-yn-2-yl)phe-
noxy)methyl)benzo[b]thiophen-3-yl)-3-methylpyra-
zine;
(2S)-5-(5-((4-(1-(1H-Tetrazol-5-yl)pent-3-yn-2-yl)phe-
noxy)methyl)benzo[b]thiophen-3-yl)-4-methylpyrimi-
dine;
(2S)-2-(5-((4-(1-(1H-Tetrazol-5-yl)pent-3-yn-2-yl)phe-
noxy)-methyl)benzo[b]thiophen-3-yl)-5-(2-methoxy-
ethoxy)-3-methylpyridine;
(2S)-5-(2-(4-((3-(2,3-Dihydrobenzo[b][1,4]dioxin-5-yl)
benzo[b]thiophen-5-yl)methoxy)phenyl)pent-3-yn-1-
yl)-1H-tetrazole;
(2S)-1-(4-(5-((4-(1-(1H-tetrazol-5-yl)pent-3-yn-2-yl)phe-
noxy)methyl)benzo[b]thiophen-3-yl)indolin-1-yl)pro-
pan-1-one;
(2S)—N-(3-(5-((4-(1-(1H-tetrazol-5-yl)pent-3-yn-2-yl)
phenoxy)methyl)benzo[b]thiophen-3-yl)-4-methylphe-
nyl)methanesulfonamide;
(2S)-5-(2-(4-((3-(2,2-dimethylchroman-5-yl)benzo[b]
thiophen-5-yl)methoxy)phenyl)pent-3-yn-1-yl)-1H-
tetrazole;
3-(4-(5-((4-((2S)-1-(1H-Tetrazol-5-yl)pent-3-yn-2-yl)
phenoxy)methyl)benzo[b]thiophen-3-yl)-3-methylphe-
noxy)propane-1,2-diol;
(2S)-5-(2-(4-((3-(2-Chlorophenyl)benzo[b]thiophen-5-
yl)methoxy)phenyl)pent-3-yn-1-yl)-1H-tetrazole;
(2S)-3-(5-((4-(1-(1H-Tetrazol-5-yl)pent-3-yn-2-yl)phe-
noxy)methyl)benzo[b]thiophen-3-yl)-5-(2-methoxy-
ethoxy)-2-methylpyridine;
5-((2S)-2-(4-((2-Bromo-3-(2-methylphenyl)benzo[b]
thiophen-5-yl)methoxy)phenyl)pent-3-ynyl)-1H-tetra-
zole;
5-((2S)-2-(4-((2-Iodo-3-(2-methylphenyl)benzo[b]thio-
phen-5-yl)methoxy)phenyl)pent-3-ynyl)-1H-tetrazole;
5-((2S)-2-(4-((2-Trifluoromethyl-3-(2-methylphenyl)
benzo[b]thiophen-5-yl)methoxy)phenyl)pent-3-ynyl)-
1H-tetrazole;
(2S)-5-(2-(4-((3-Cyclopropyl-2-(trifluoromethyl)benzo
[b]thiophen-5-yl)methoxy)phenyl)pent-3-yn-1-yl)-1H-
tetrazole;
5-((2S)-2-(4-((2-Cyano-3-(2-methylphenyl)benzo[b]thio-
phen-5-yl)methoxy)phenyl)pent-3-yn-1-yl)-1H-tetra-
zole;
(2S)-5-(2-(4-((2-(Methyl sulfonyl)-3-(2-methylphenyl)
benzo[b]thiophen-5-yl)methoxy)phenyl)pent-3-yn-1-
yl)-1H-tetrazole;
(2R)-5-(1-(1H-Tetrazol-5-yl)pent-3-yn-2-yl)-2-((3-(2-
methylphenyl)benzo[b]thiophen-5-yl)methoxy)pyri-
dine;
(2R)-5-(1-(1H-Tetrazol-5-yl)pent-3-yn-2-yl)-2-((3-(4-(2-
methoxyethoxy)-2-methylphenyl)benzo[b]thiophen-5-
yl)methoxy)pyridine;
(2R)-5-(1-(1H-Tetrazol-5-yl)pent-3-yn-2-yl)-2-((3-(3-(2-
methoxyethoxy)-2-methylphenyl)benzo[b]thiophen-5-
yl)methoxy)pyridine;
(2R)-4-(4-(5-(((5-(1-(1H-Tetrazol-5-yl)pent-3-yn-2-yl)
pyridin-2-yl)oxy)methyl)-benzo[b]thiophen-3-yl)-3-
methylphenoxy)-2-methylbutan-2-ol;
(2S)-5-(2-(4-((2-Fluoro-3-(4-(2-methoxyethoxy)-2-meth-
ylphenyl)benzo[b]thiophen-5-yl)methoxy)phenyl)
pent-3-yn-1-yl)-1H-tetrazole;
(2S)-5-(2-(4-((2-Chloro-3-(4-(2-methoxyethoxy)-2-
methylphenyl)benzo[b]thiophen-5-yl)methoxy)phe-
nyl)pent-3-yn-1-yl)-1H-tetrazole;
(2S)-5-(2-(4-((3-(4-(2-Methoxyethoxy)-2-methylphe-
nyl)-2-methylbenzo[b]thiophen-5-yl)methoxy)phenyl)
pent-3-yn-1-yl)-1H-tetrazole;
5-((2S)-2-(4-((3-(4-(2-Methoxyethoxy)-2-methylphe-
nyl)-2-(trifluoromethyl)benzo[b]thiophen-5-yl)
methoxy)phenyl)pent-3-yn-1-yl)-1H-tetrazole;
1-(5-((4-((2S)-1-(1H-Tetrazol-5-yl)pent-3-yn-2-yl)phe-
noxy)methyl)benzo[b]thiophen-3-yl)-2-methylpiperi-
dine;
(2S)-5-((4-(1-(1H-Tetrazol-5-yl)pent-3-yn-2-yl)phenoxy)
methyl)-3-(2-methylphenyl)thieno[2,3-b]pyridine;
(2S)-5-((4-(1-(1H-Tetrazol-5-yl)pent-3-yn-2-yl)phenoxy)
methyl)-3-(4-methoxy-2-methylphenyl)thieno[2,3-b]
pyridine;
(2S)-5-((4-(1-(1H-Tetrazol-5-yl)pent-3-yn-2-yl)phenoxy)
methyl)-3-(2-methylphenyl)thieno[2,3-c]pyridine;
(2S)-5-((4-(1-(1H-Tetrazol-5-yl)pent-3-yn-2-yl)phenoxy)
methyl)-3-(4-methoxy-2-methylphenyl)thieno[2,3-c]
pyridine;
(2S)-5-((4-(1-(1H-Tetrazol-5-yl)pent-3-yn-2-yl)phenoxy)
methyl)-3-(2-methylphenyl)thieno[3,2-b]pyridine;
(2S)-5-((4-(1-(1H-Tetrazol-5-yl)pent-3-yn-2-yl)phenoxy)
methyl)-3-(4-methoxy-2-methylphenyl)thieno[3,2-b]
pyridine;
(2S)-5-(2-(4-((3-Cyclohexylbenzo[b]thiophen-5-yl)
methoxy)phenyl)pent-3-yn-1-yl)-1H-tetrazole;
(2S)-5-(2-(4-((3-Cyclopentylbenzo[b]thiophen-5-yl)
methoxy)phenyl)pent-3-yn-1-yl)-1H-tetrazole;
(2S)-5-(2-(4-((3-Cyclopropylbenzo[b]thiophen-5-yl)
methoxy)phenyl)pent-3-yn-1-yl)-1H-tetrazole;
(2S)-5-(2-(4-((3-Isopropylbenzo[b]thiophen-5-yl)
methoxy)phenyl)pent-3-yn-1-yl)-1H-tetrazole;
(2S)-5-(2-(4-((3-Propylbenzo[b]thiophen-5-yl)methoxy)
phenyl)pent-3-yn-1-yl)-1H-tetrazole;
(2S)-5-(2-(4-(Benzo[b]thiophen-5-ylmethoxy)phenyl)
pent-3-yn-1-yl)-1H-tetrazole;
(2RS)-5-(2-(4-((3-(2-Methylphenyl)benzo[b]thiophen-5-
yl)methoxy)phenyl)pent-3-yn-1-yl)-1H-tetrazole;
(2R)-5-(2-(4-((3-(2-Methylphenyl)benzo[b]thiophen-5-
yl)methoxy)phenyl)pent-3-yn-1-yl)-1H-tetrazole;
(2S)-5-(2-(4-((7-Methyl-3-(2-methylphenyl)benzo[b]
thiophen-5-yl)methoxy)phenyl)pent-3-yn-1-yl)-1H-
tetrazole;
(2S)-5-(2-(4-((3-Butyl-7-methylbenzo[b]thiophen-5-yl)
methoxy)phenyl)pent-3-yn-1-yl)-1H-tetrazole;
(2S)-5-(2-(4-((3-Cyclopentyl-7-methylbenzo[b]thiophen-
5-yl)methoxy)phenyl)pent-3-yn-1-yl)-1H-tetrazole;
(2S)-5-(2-(4-((3-Cyclohexyl-7-methylbenzo[b]thiophen-
5-yl)methoxy)phenyl)pent-3-yn-1-yl)-1H-tetrazole;
(2S)-5-(2-(4-((7-Chloro-3-(2-methylphenyl)benzo[b]
thiophen-5-yl)methoxy)phenyl)pent-3-yn-1-yl)-1H-
tetrazole;

(2S)-5-(2-(4-((7-Chloro-3-(4-methoxy-2-methylphenyl)benzo[b]thiophen-5-yl)methoxy)phenyl)pent-3-yn-1-yl)-1H-tetrazole;

(2S)-5-(2-(4-((7-Fluoro-3-(2-methylphenyl)benzo[b]thiophen-5-yl)methoxy)phenyl)pent-3-yn-1-yl)-1H-tetrazole;

(2S)-5-(2-(4-((7-Fluoro-3-(4-methoxy-2-methylphenyl)benzo[b]thiophen-5-yl)methoxy)phenyl)pent-3-yn-1-yl)-1H-tetrazole or a pharmaceutically acceptable salt form thereof.

17. A pharmaceutical composition comprising a compound of claim 1 or 16 and at least one of a pharmaceutically acceptable carrier, a pharmaceutically acceptable excipient, and a pharmaceutically acceptable diluent.

18. The pharmaceutical composition of claim 17, wherein the composition is a solid oral dosage form.

19. The pharmaceutical composition of claim 17, wherein the composition is a syrup, an elixir or a suspension.

* * * * *